(12) United States Patent
Maddocks

(10) Patent No.: US 12,109,184 B2
(45) Date of Patent: Oct. 8, 2024

(54) PERSONALIZED METHODS OF TREATING CANCER

(71) Applicants: CANCER RESEARCH TECHNOLOGY LIMITED, London (GB); Faeth Therapeutics, Inc., Austin, TX (US)

(72) Inventor: Oliver D.K. Maddocks, Glasgow (GB)

(73) Assignees: Faeth Therapeutics, Inc., Austin, TX (US); Cancer Research Technology Limited, London (GB)

( * ) Notice: Subject to any disclaimer, the term of this patent is extended or adjusted under 35 U.S.C. 154(b) by 0 days.

(21) Appl. No.: 17/338,283

(22) Filed: Jun. 3, 2021

(65) Prior Publication Data
US 2022/0054444 A1 Feb. 24, 2022

Related U.S. Application Data

(60) Provisional application No. 63/034,679, filed on Jun. 4, 2020.

(51) Int. Cl.
*A61K 31/198* (2006.01)
*A61P 35/00* (2006.01)

(52) U.S. Cl.
CPC ............ *A61K 31/198* (2013.01); *A61P 35/00* (2018.01)

(58) Field of Classification Search
CPC ........ A61K 31/198; A61K 45/06; A61P 35/00
See application file for complete search history.

(56) References Cited

U.S. PATENT DOCUMENTS

| 3,832,465 | A | 8/1974 | Ghadimi |
| 4,734,401 | A | 3/1988 | Blouin |
| 4,988,724 | A | 1/1991 | Ajani et al. |
| 6,218,420 | B1 | 4/2001 | Dioguardi |
| 6,713,501 | B1 | 3/2004 | Walser |
| 10,973,251 | B1 | 4/2021 | Li et al. |
| 11,241,407 | B2 | 2/2022 | Li et al. |
| 2003/0129262 | A1 | 7/2003 | Epner et al. |
| 2006/0280840 | A1 | 12/2006 | Robertson |
| 2007/0270355 | A1 | 11/2007 | Garcia et al. |
| 2007/0286909 | A1 | 12/2007 | Smith et al. |
| 2008/0317886 | A1 | 12/2008 | Sparkman |
| 2011/0118528 | A1 | 5/2011 | Longo et al. |
| 2011/0153221 | A1 | 6/2011 | Stefanon et al. |
| 2013/0123363 | A1 | 5/2013 | Uesugi et al. |
| 2014/0087970 | A1 | 3/2014 | Possemato et al. |
| 2014/0100357 | A1 | 4/2014 | Miao et al. |
| 2014/0170259 | A1 | 6/2014 | Poels et al. |
| 2014/0363417 | A1 | 12/2014 | Cheng et al. |
| 2015/0315561 | A1 | 11/2015 | Schabbauer et al. |
| 2017/0143025 | A1 | 5/2017 | Rason et al. |
| 2020/0230092 | A1 | 7/2020 | Maddocks et al. |
| 2022/0117943 | A1 | 4/2022 | Maddocks |
| 2022/0193447 | A1 | 6/2022 | Maddocks et al. |
| 2022/0400730 | A1 | 12/2022 | Li et al. |
| 2023/0277492 | A1 | 9/2023 | Maddocks et al. |

FOREIGN PATENT DOCUMENTS

| EP | 4190173 A1 | 6/2023 | |
| JP | 2005289938 A | 10/2005 | |
| JP | 2014512803 A | 5/2014 | |
| WO | WO-9802441 A2 | 1/1998 | |
| WO | WO-0114387 A1 | 3/2001 | |
| WO | WO-2006043090 A1 | 4/2006 | |
| WO | WO-2009077766 A1 | 6/2009 | |
| WO | WO-2010075007 A3 | 11/2010 | |
| WO | WO-2011092469 A1 | 8/2011 | |
| WO | WO-2011143579 A2 | 11/2011 | |
| WO | WO-2012116229 A2 | 8/2012 | |
| WO | WO-2014049566 A2 | 4/2014 | |
| WO | WO-2015075483 A1 | 5/2015 | |
| WO | WO-2016130918 A1 | 8/2016 | |
| WO | WO-2017053328 A1 | 3/2017 | |
| WO | WO-2017144877 A1 | 8/2017 | |
| WO | WO-2018071873 A2 | 4/2018 | |
| WO | WO-2019092455 A1 * | 5/2019 | ........... A23L 33/175 |
| WO | WO-2019118549 A1 | 6/2019 | |
| WO | WO-2019211605 A1 | 11/2019 | |
| WO | WO-2021016132 A1 | 1/2021 | |
| WO | WO-2021247724 A1 | 12/2021 | |
| WO | WO-2021247923 A1 | 12/2021 | |
| WO | WO-2022015951 A2 | 1/2022 | |
| WO | WO-2022132981 A1 | 6/2022 | |
| WO | WO-2023130140 A2 | 7/2023 | |

OTHER PUBLICATIONS

Walpole et al (BMC Public Health, 2012; 12: 439 (Year: 2012).*
Snezhkina et al (Snezhkina, Anastasiya V., et al. Oxidative medicine and cellular longevity 2016) (Year: 2016).*
Dredge et al (Cancer Chemothe Pharmacol (2009) 65:191-195 (Year: 2009).*
Zhang, Nature Metabolism, 2020, vol. 2 (Year: 2020).*
Nature, Reviews|Cancer vol. 18, Nov. 2018 (Year: 2018).*
Cavuoto, Cancer Treatment Reviews, 2012, 38, 726-736 (Year: 2012).*
Doxsee, The Prostate, 2007, 67:162-171 (Year: 2007).*
Butler, Trends in Endocrinology and Metabolism, 2021, vol. 32, No. 6 (Year: 2021).*
Dredge, K et al. The polyamine analog PG11047 potentiates the antitumor activity of cisplatin and bevacizumab in preclinical models of lung and prostate cancer. Cancer Chemother Pharmacol 65, 191-195 (2009).

(Continued)

*Primary Examiner* — Susanna Moore
*Assistant Examiner* — Luisalberto Gonzalez
(74) *Attorney, Agent, or Firm* — Cooley LLP

(57) ABSTRACT

Disclosed herein are dietary compositions that are substantially devoid of at least cysteine or a salt thereof for use in treating a cancer. The dietary compositions and methods of the disclosure can be used to treat cancers that are MTAP-deficient, alone or in combination with a cancer therapy.

19 Claims, 58 Drawing Sheets

Specification includes a Sequence Listing.

(56) References Cited

OTHER PUBLICATIONS

International Search Report and Written Opinion issued in PCT/2021/35780 on Oct. 1, 2021.

Snezhkina, A.V. et al. The Dysregulation of Polyamine Metabolism in Colorectal Cancer Is Associated with Overexpression of c-Myc and C/EBPβ rather than Enterotoxigenic Bacteroides fragilis Infection. Oxid Med Cell Longev. 2016;.

Finkelstein et al., Methionine metabolism in mammals. The methionine-sparing effect of cystine. J Biol Chem. 263(24):11750-11754 (1998).

PCT/US2021/035780 International Preliminary Report on Patentability (Chapter I) dated Dec. 6, 2022.

Final Office Action mailed on Nov. 24, 2023, for U.S. Appl. No. 18/174,706, filed Feb. 27, 2023, 13 pages.

International Search Report and Written Opinion, PCT/GB2017/050458, mailed Jul. 18, 2017, 20 pages.

Notice of Allowance mailed on Jan. 4, 2024, for U.S. Appl. No. 15/999,666, filed Aug. 20, 2018, 12 pages.

Extended European Search Report mailed on Feb. 1, 2024, for EP Application No. 23151551.1, 27 pages.

Fu et al., "Specific amino acid dependency regulates invasiveness and viability of androgen-independent prostate cancer cells" Nutr Cancer. (2003) 45(1):60-73.

Ge et al., "Activation of caspases and cleavage of Bid are required for tyrosine and phenylalanine deficiency-induced apoptosis of human A375 melanoma cells" Arch Biochem Biophys. (2002) Jul. 1; 403(1):50-58.

Yan et al., "Effects of complex unbalanced amino acids on tumors in mice bearing liver cancer H22" Chinese Journal of Clinical Oncology (2011) 38(3):134-137.

Adams et al., "The c-myc oncogene driven by immunoglobulin enhancers induces lymphoid malignancy in transgenic mice" Nature (1985) 318:533-538.

Amelio et al., "Serine and glycine metabolism in cancer" Trends Biochem Sci. (2014) Apr.; 39(4):191-198.

Anonymous. ClinicalTrials.gov Archive. NCT02337894 on Jan. 13, 2015.Retrived from the Internet: https://clinicaltrails.gov/archive/NCT. Retrieved on Apr. 2, 2017. 5 pages.

Badgley et al., "Absract A41: Leveraging metabolic dependencies in cancer: Cystein addiction in pancreatic cancer cells" Mol Cancer Research (2016) 14(1_Supp): A41, 4 pages.

Barker et al., "Crypt stem cells as the cells-of-origin of intestinal cancer" Nature (2009) 457:608-611.

Bartlett, David L., et al., "Effect of growth hormone and protein intake on tumor growth and host cachexia", Surgery, 1995, vol. 117, No. 3, pp. 260-267.

Bassiri et al., "Translational development of difluoromethylornithine (DFMO) for the treatment of neuroblastoma" Transl Pediatr. (2015) Jul.; 4(3):226-238.

Bertino et al., "Targeting tumors that lack methylthioadenosine phosphorylase (MTAP) activity: current strategies" Cancer Biol Ther. (2011) Apr. 1; 11(7):627-632.

Blau et al., eds., "Laboratory Guide to the Methods in Biochemical Genetics" (2008) Berlin Heidelberg, Germany: Springer Verlag. p. 74. 59 pages.

Bunz F et al. "Requirement for p53 and p21 to sustain G2 arrest after DNA damage", Science. Nov. 1998: 282:1497-1501.

CAS Registry No. 1036730-42-3, STN entry date: Jul. 28, 2008, Pidilizumab, 1 page.

CAS Registry No. 1374853-91-4, STN entry date: May 31, 2012, Pembrolizumab, 1 page.

CAS Registry No. 1380723-44-3, STN entry date: Jul. 3, 2012, Atezolizumab, 1 page.

CAS Registry No. 1428935-60-7, STN entry date: Apr. 23, 2013, Durvalumab, 1 page.

CAS Registry No. 1537032-82-8, STN entry date: Feb. 4, 2014, Avelumab, 1 page.

CAS Registry No. 1801342-60-8, STN entry date: Aug. 4, 2015, Cemiplimab, 1 page.

CAS Registry No. 477202-00-9, dated Dec. 19, 2002, 1 page.

CAS Registry No. 70052-12-9, STN entry date: Nov. 16, 1984, Eflornithine, 2 pages.

CAS Registry No. 946414-94-4, STN entry date: Sep. 7, 2007, Nivolumab, 1 page.

CAS Registry No. 96020-91-6, STN entry date: Apr. 21, 1985, Ornithine, 1 page.

Commisso et al., "Macropinocytosis of protein is an amino acid supply route in Ras-transformed cells" Nature (2013) 497:633-637.

Corsetti et al., "Protect and Counter-attack: Nutritional Supplementation with Essential Amino acid Ratios Reduces Doxorubicin-induced Cardiotoxicity in vivo and promote Cancer Cell Death in vitro" J. Cytol. Histol. (2015) 6:5, 1000354, 2 pages.

Donehower, et al. "Mice deficient for p53 are developmentally normal but susceptible to spontaneous tumours", Nature, Mar. 19, 1992, pp. 215-221, vol. 356.

Erdman et al., "Dietary Reference Intakes for Water, Potassium, Sodium, Chloride, and Sulfate" Institute of Medicine, Feb. 11, 2004, 4 pages.

Extended European Search Report mailed on Sep. 18, 2023, for EP Application No. 23166882.3, 11 pages.

Faubert et al., "Stable isotope tracing to assess tumor metabolism in vivo" Nat Protoc. (2021) Nov.; 16(11):5123-5145.

Fiatarone et al., "Exercise training and nutritional supplementation for physical frailty in very elderly people" N. Engl. J. Med. (1994) Jun. 23; 330(25):1769-75.

Fiatarone Singh et al., "The effect of oral nutritional supplements on habitual dietary quality and quantity in frail elders" J. Nutr. Health Aging (2000) 4(1):5-12.

Final Office Action mailed on Sep. 2, 2022, for U.S. Appl. No. 15/999,666, filed Aug. 20, 2018, 13 pages.

Final Office Action mailed on Sep. 22, 2021, for U.S. Appl. No. 15/999,666, filed Aug. 20, 2018, 11 pages.

Geck et al., "Nonessential amino acid metabolism in breast cancer" Advances in Biological Regulation (2016) 62:11-17.

Gravel et al., "Serine deprivation enhances antineoplastic activity of biguanides" Cancer Res. (2014) Dec. 15; 74(24):7521-7533.

Harenza et al., "Transcriptomic profiling of 39 commonly-used neuroblastoma cell lines" Sci Data. (2017) Mar. 28: 4:170033. 8 pages.

Hingorani et al., "Trp53R172H and KrasG12D cooperate to promote chromosomal instability and widely metastatic pancreatic ductal adenocarcinoma in mice" Cancer Cell (2005) 7:469-483.

Hirakawa et al., "Comparative utilization of a crystalline amino acid diet and a methionine-fortified casein diet by young rats and mice" Nutr Res (1984) 4(5):891-895.

Hogarty et al., "ODC1 is a critical determinant of MYCN oncogenesis and a therapeutic target in neuroblastoma" Cancer Res. (2008) Dec. 1; 68(23): 9735-9745.

Holbert et al., "Polyamines in cancer: integrating organismal metabolism and antitumour immunity" Nat Rev Cancer.(2022) Aug.; 22(8):467-480.

Hui et al., "Glucose feeds the TCA cycle via circulating lactate" Nature. (2017) Nov. 2; 551(7678):115-118.

Hui et al., "Quantitative Fluxomics of Circulating Metabolites" Cell Metab. (2020) Oct. 6; 32(4):676-688. e4.

Institute of Medicine, "Dietary Reference Intakes for Energy, Carbohydrate, Fiber, Fat, Fatty Acids, Cholesterol, Protein and Amino Acids" Chapters 6, 7, and 8, Sep. 2002, 323 pages.

International Search Report and Written Opinion for PCT/US2021/021148 Jul. 28, 2021, 12 pages.

International Search Report and Written Opinion mailed on Apr. 11, 2022, for PCT/US2021/063639, filed on Dec. 15, 2021, 8 pages.

International Search Report and Written Opinion mailed on Jun. 26, 2023, for PCT/US2023/60025, filed on Jan. 3, 2023, 9 pages.

International Search Report and Written Opinion issued in PCT/US2021/035476 on Oct. 12, 2021. 10 pages.

Kocak et al., "Hox-C9 activates the intrinsic pathway of apoptosis and is associated with spontaneous regression in neuroblastoma" Cell Death Dis. (2013) Apr. 11; 4(4):e586. 11 pages.

Kshattry S. et al. "Abstract 367: Assessing the therapeutic efficacy of Cyst(e)inase to induce oxidative stress mediated cytotoxicity in pancreatic cancer cells" Experimental and Molecular Therapeutics, 4 pages, 2016.

(56) References Cited

OTHER PUBLICATIONS

Labadie et al., "Reimagining IDO Pathway Inhibition in Cancer Immunotherapy via Downstream Focus on the Tryptophan-Kynurenine-Aryl Hydrocarbon Axis" Clin Cancer Res. (2019) Mar. 1; 25(5):1462-1471.

Labuschagne CF et al. "Serine, but not glycine, supports one-carbon metabolism and proliferation of cancer cells", Cell Reports 7. 1248-1258, May 22, 2014.

Lancha et al., "Effect of aspartate, asparagine, and carnitine supplementation in the diet on metabolism of skeletal muscle during a moderate exercise" Physiol Behav. (1995) Feb.; 57(2):367-71.

Lewis et al., "A subset analysis of a phase II trial evaluating the use of DFMO as maintenance therapy for high-risk neuroblastoma" Int J Cancer. (2020) Dec. 1; 147(11):3152-3159.

Liberzon et al., "Molecular signatures database (MSigDB) 3.0" Bioinformatics. (2011) Jun. 15; 27(12):1739-1740.

Locasale, "Serine, glycine and one-carbon units: cancer metabolism in full circle" Nat Rev Cancer. (2013) Aug.; 13(8):572-583.

Logiudice et al., "Alpha-Difluoromethylornithine, an Irreversible Inhibitor of Polyamine Biosynthesis, as a Therapeutic Strategy against Hyperproliferative and Infectious Diseases" Med Sci (Basel). (2018) Feb. 8; 6(1):12. 17 pages.

Lopez-Lazaro M, "Selective amino acid restriction therapy (SAART);a non-pharmacological strategy against all types of cancer cells" .Oncoscience (2015) 2(10):857-866.

Maddocks Odk et al., "Serine metabolism supports the methionine cycle and DNR/RNA methylation through de novo ATP synthesis in cancer cells" Molecular Cell. 2016; 61: 210-221.

Maddocks Odk et al., "Serine starvation induces stress and p53-dependent metabolic remodeling in cancer cells" Nature, Dec. 2013; 493(7433): 542-546.

McCormack et al. "Oral nutritional supplement fortified with beta-alanine improves physical working capacity in older adults: a randomized, placebo-controlled study." Experimental Gerontology 48(9) 2013:933-939.

Miyo, M. et al., "Metabolic Adaptation to Nutritional Stress in Human Colorectal Cancer" Scientific Reports (2016) vol. 6, No. 1, 38415, 13 pages.

Morton et al., "Mutant p53 drives metastasis and overcomes growth arrest/senescence in pancreatic cancer" PNAS USA (2010) 107:246-251.

Moser et al., "A dominant mutation that predisposes to multiple intestinal neoplasia in the mouse" Science (1990) 322-324.

NAS. IOM. Food and Nutrition Board, "Dietary Reference Intakes: RDA and AI for Vitamins and Elements" (2017) 3 pages.

Non-Final Office Action mailed on Jul. 7, 2023, for U.S. Appl. No. 18/174,706, filed Feb. 27, 2023, 13 pages.

Non-Final Office Action mailed on Mar. 18, 2021, for U.S. Appl. No. 15/999,666, filed Aug. 20, 2018, 8 pages.

Non-Final Office Action mailed on May 10, 2023, for U.S. Appl. No. 15/999,666, filed Aug. 20, 2018, 12 pages.

Okada, Kenzo, et al., "Tumor glutamine level is negatively correlated with tumor weight in tumor-bearing rats administered a glutamine antagonist and a new imbalanced amino acid solution", Journal of Clinical Biochemistry and Nutrition, 1992, vol. 12, No. 3, pp. 183-191.

Paddon-Jones et al., "Amino acid ingestion improves muscle protein synthesis in the young and elderly" Am J Physiol Endocrinol Metab. (2004) Mar.; 286(3):E321-E328.

Paddon-Jones et al., "Differential stimulation of muscle protein synthesis in elderly humans following isocaloric ingestion of amino acids or whey protein" Experimental Gerontology. (2006) Feb. 1; 41(2):215-9.

Partial European Search Report mailed on Sep. 20, 2023, for EP Application No. EP 23151551.1, 23 pages.

Polet F et al., "Reducing the serine availability complements the inhibition of the glutamine metabolism to block leukemia cell growth" Oncotarget Jan. 2016;7(2):1765-1776.

Possemato et al., "Functional genomics reveal that the serine synthesis pathway is essential in breast cancer" Nature (2011) Aug. 18; 476(7360):346-350.

Ran et al., "Genome engineering using the CRISPR-Cas9 system" Nat Protoc. (2013) Nov.; 8(11):2281-2308.

Rose WC et al., "Growth on diets devoid of glycine, serine, and cystine, and low in choline" J Biol Chem. (1952) 194:321-328.

Rounbehler et al., "Targeting ornithine decarboxylase impairs development of MYCN-amplified neuroblastoma" Cancer Res. (2009) Jan. 15; 69(2):547-553.

Sahu et al., "Proline Starvation Induces Unresolved ER Stress and Hinders mTORC1-Dependent Tumorigenesis" Cell Metabolism (2016) 24:753-761.

Search Report, Intellectual Property Office, United Kingdom Application No. GB1609441.9, Mar. 1, 2017,5 pages.

Sholler et al., "A Phase I Trial of DFMO Targeting Polyamine Addiction in Patients with Relapsed/Refractory Neuroblastoma" PLoS One. (2015) May 27;10(5):e0127246. 20 pages.

Sholler et al., "Maintenance DFMO Increases Survival in High Risk Neuroblastoma" Sci Rep. (2018) Sep. 27; 8(1):14445. 9 pages.

Soldin et al., "Pediatric reference ranges" 3rd ed., Washington: AACC Press, (1999) pp. 11-20.

Solerte et al., "Metabolic effects of orally administered amino acid mixture in elderly subjects with poorly controlled type 2 diabetes mellitus" Am J Cardiol. (2004) Apr. 22; 93(8A):23A-29A.

Su et al., "Metabolite Spectral Accuracy on Orbitraps" Anal Chem. (2017) Jun. 6; 89(11):5940-5948.

Su et al., "Multiple intestinal neoplasia caused by a mutation in the murine homolog of the APC gene" Science (1992) 256:668-670.

Tang et al., "Cystine Deprivation Triggers Programmed Necrosis in VHL-Deficient Renal Cell Carcinomas" Cancer Res. (2016) Apr. 1; 76(7):1892-1903.

Trumbo et al., "Dietary reference intakes for energy, carbohydrate, fiber, fat, fatty acids, cholesterol, protein and amino acids" J Am Diet Assoc. (2002) Nov.; 102(11):1621-1630.

Uniprot P01137, Sep. 13, 2023, 14 pages.
Uniprot P14784, Sep. 13, 2023, 7 pages.
Uniprot P16410, Sep. 13, 2023, 11 pages.
Uniprot P25942, Sep. 13, 2023, 8 pages.
Uniprot P43489, Sep. 13, 2023, 6 pages.
Uniprot Q07011, Sep. 13, 2023, 6 pages.
Uniprot Q15116, Sep. 13, 2023, 9 pages.
Uniprot Q495A1, Sep. 13, 2023, 5 pages.
Uniprot Q5ZPR3, Sep. 13, 2023, 9 pages.
Uniprot Q8TDQ0, Sep. 13, 2023, 9 pages.
Uniprot Q9H7M9, Sep. 13, 2023, 7 pages.
Uniprot Q9NZQ7, Sep. 13, 2023, 9 pages.
Uniprot Q9Y6W8, Sep. 13, 2023, 4 pages.

Vigneron AM et al., "Cytoplasmic ASPP1 inhibits apoptosis through the control of YAP" Genes & Development. (2010) 24:2430-2439.

Wang et al., "Peak Annotation and Verification Engine for Untargeted LC-MS Metabolomics" Anal Chem. (2019) Feb. 5; 91(3):1838-1846.

Weiss et al. "Targeted Expression of MYCN Causes Neuroblastoma in Transgenic Mice", The EMBO Journal (1997), 16(11): 2985-2995.

Wernerman, J., "Clinical use of glutamine supplementation" J Nutr. (2008) Oct.; 138(10):2040S-2044S.

Wu et al., "Dietary protein intake and human health" Food Funct. (2016) Mar.; 7(3):1251-1265.

Ying et al., "Oncogenic Kras maintains pancreatic tumors through regulation of anabolic glucose metabolism" Cell (2012) 149:656-670.

Zhang et al., "Application of Holistic Liquid Chromatography-High Resolution Mass Spectrometry Based Urinary Metabolomics for Prostate Cancer Detection and Biomarker Discovery" PLoS One (2013) 8(6):e65880, 10 pages.

Zhang et al., "Polyamine pathway activity promotes cysteine essentiality in cancer cells" Nature Metabolism (2020) 2:1062-1076, 27 pages.

Zhang W. et al., "Stromal control of cystine metabolism promotes cancer cell survival in chronic lymphocytic leukaemia" Nature Cell Biology, 14(3):276-286 (2012).

(56) References Cited

OTHER PUBLICATIONS

Non-Final Office Action mailed on Mar. 29, 2024, for U.S. Appl. No. 17/337,077, filed Jun. 2, 2021, 14 pages.
Notice of Allowance mailed on Apr. 12, 2024, for U.S. Appl. No. 15/999,666, filed Aug. 20, 2018, 11 pages.
Notice of Allowance mailed on May 9, 2024, for U.S. Appl. No. 15/999,666, filed Aug. 20, 2018, 9 pages.
Tajan et al., "Serine synthesis pathway inhibition cooperates with dietary serine and glycine limitation for cancer therapy" Nat Commun. (2021) Jan. 14; 12(1):366. 16 pages.
Yan et al., "Effects of complex unbalanced amino acids on tumors in mice bearing liver cancer H22" Chinese Journal of Clinical Oncology (2011) 38(3):134-137 (with full English Translation). 8 total pages.
Bonfili et al., "Essential amino acid mixtures drive cancer cells to apoptosis through proteasome inhibition and autophagy activation" FEBS J. (2017) Jun.; 284(11):1726-1737.
Extended European Search Report mailed on Jun. 3, 2024, for EP Application No. 21816784.9, 10 pages.
Extended European Search Report mailed on Jun. 12, 2024, for EP Application No. 21818131.1, 10 pages.
Hamad et al., "Amino Acids Diets as Model for Investigating Cancer Induced by Acrylamide Produced during Wrong Food Cooking" SOJ Biochem (2018) 4(1): 1-14.
Tajan et al., "Dietary Approaches to Cancer Therapy" Cancer Cell. (2020) Jun. 8; 37(6):767-785.
Non-Final Office Action for U.S. Appl. No. 18/174,706 mailed Jul. 18, 2024, 20 pages.

\* cited by examiner

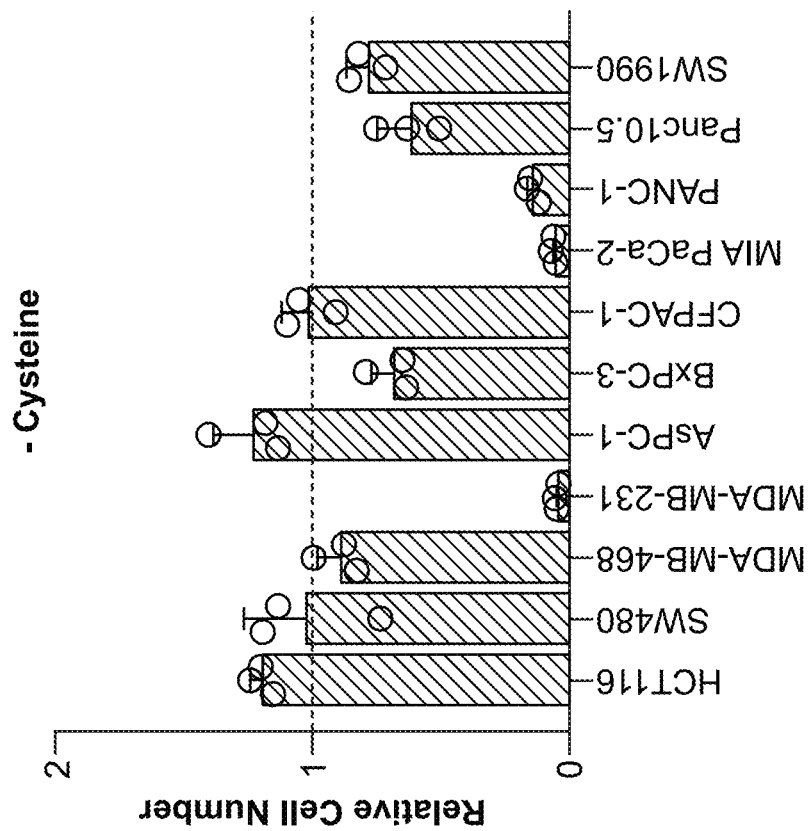
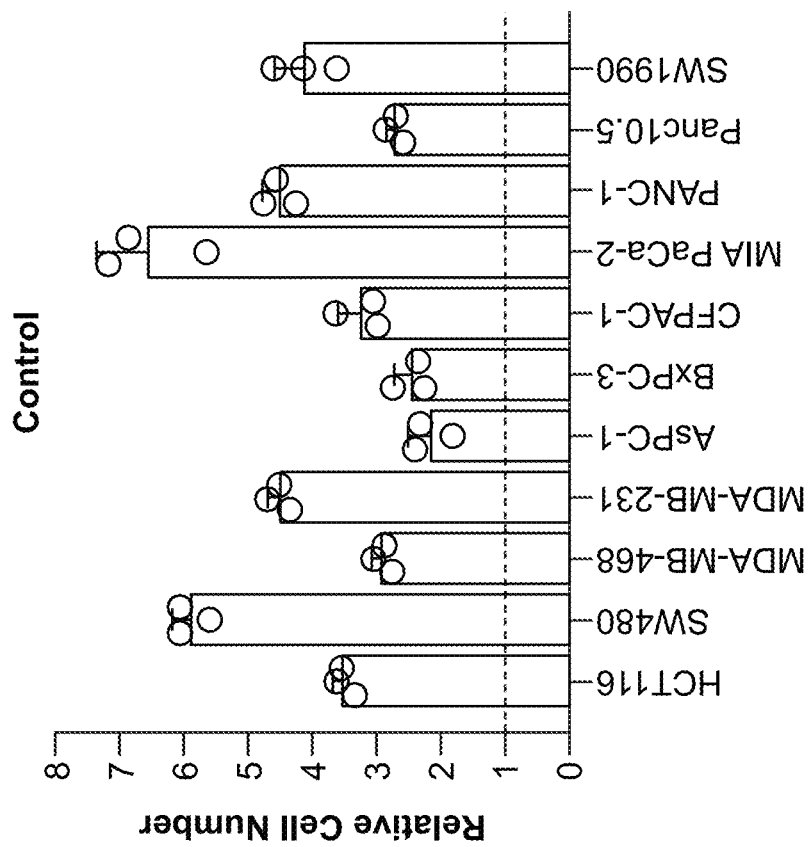
FIG. 1

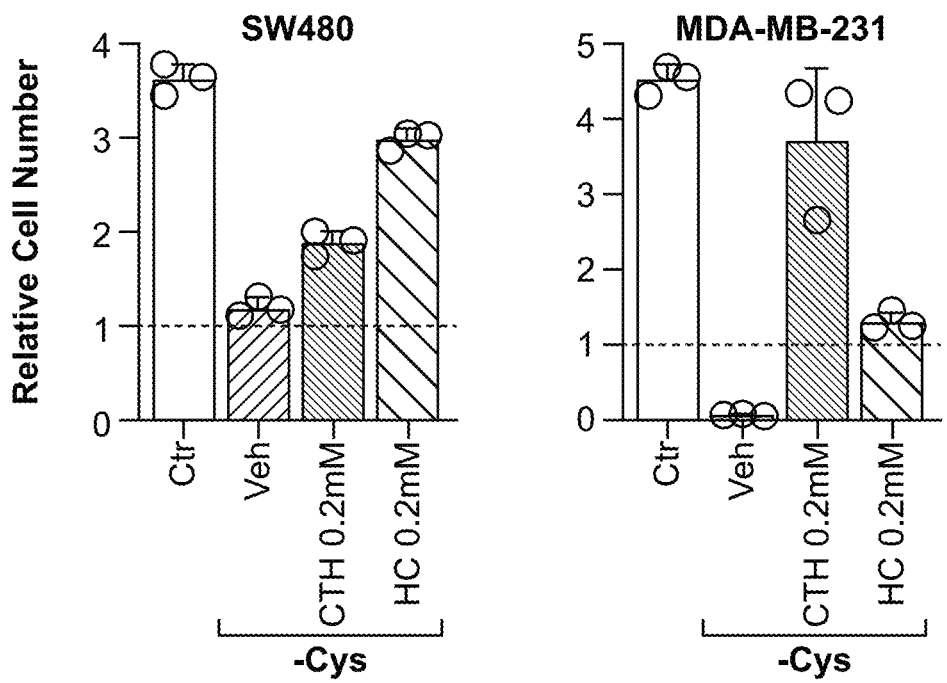
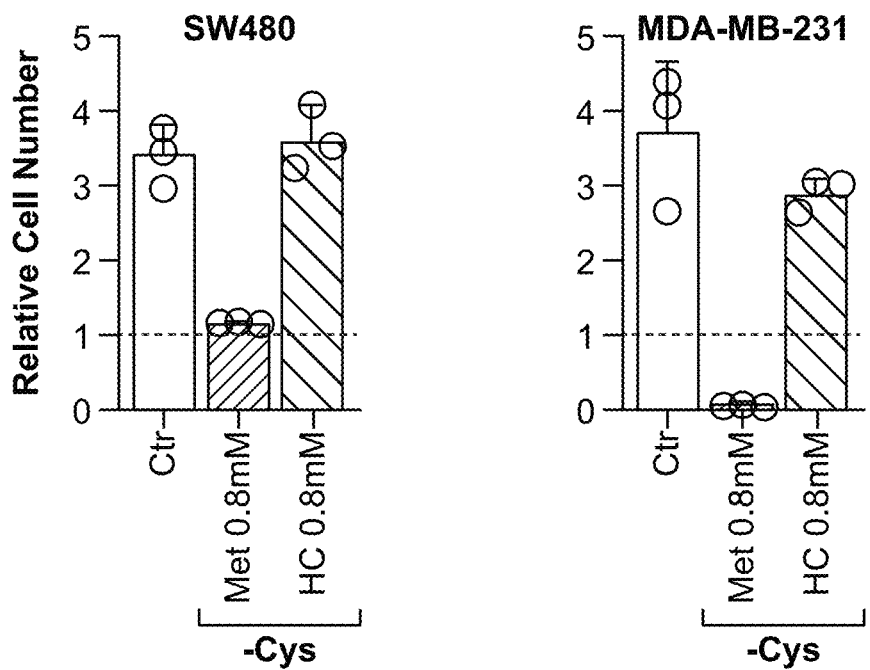
FIG. 7

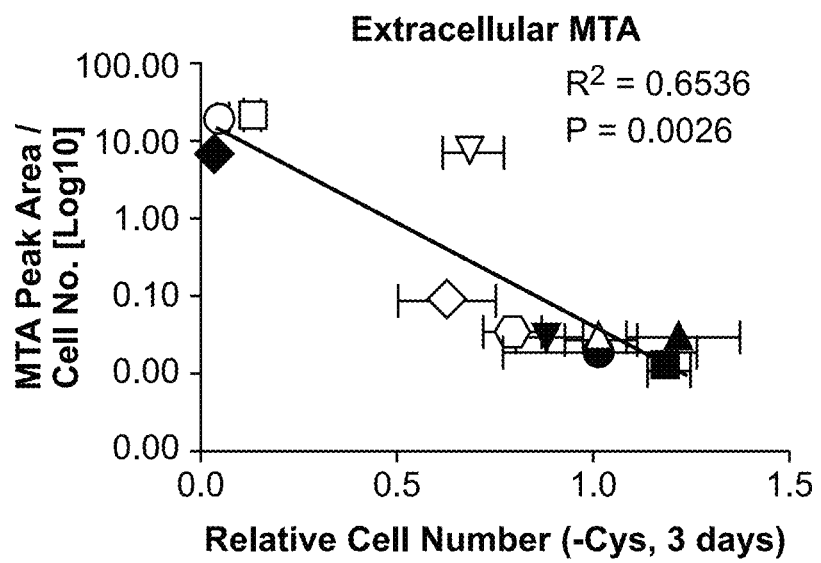
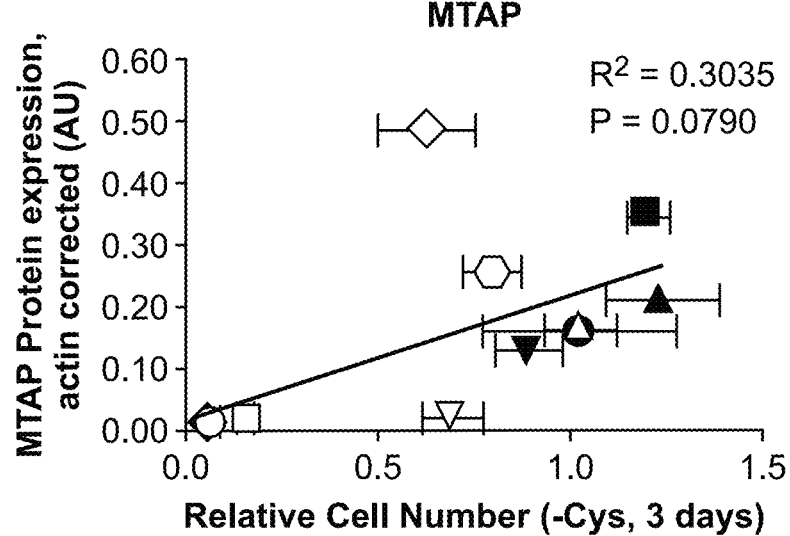
FIG. 9

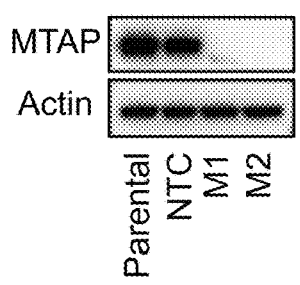
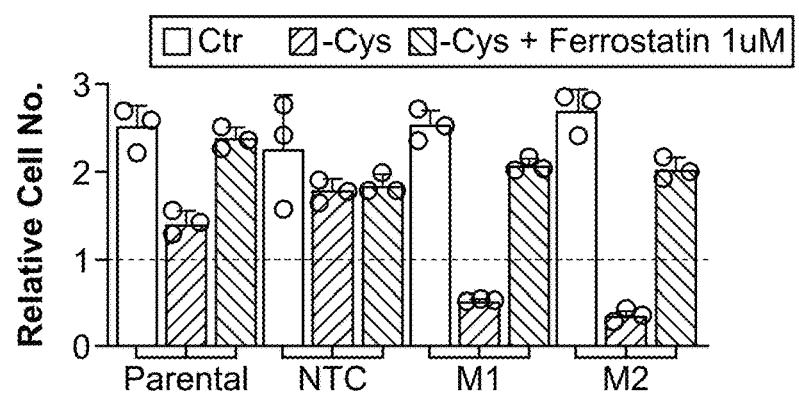
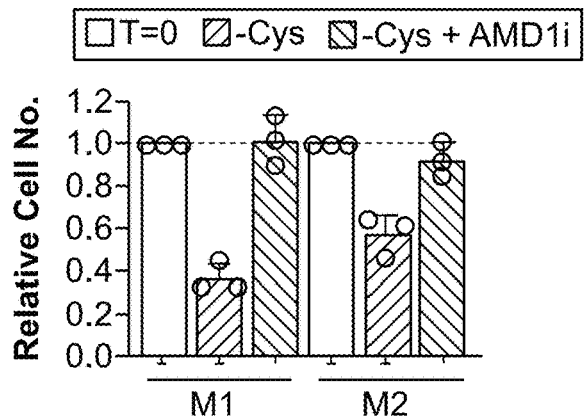
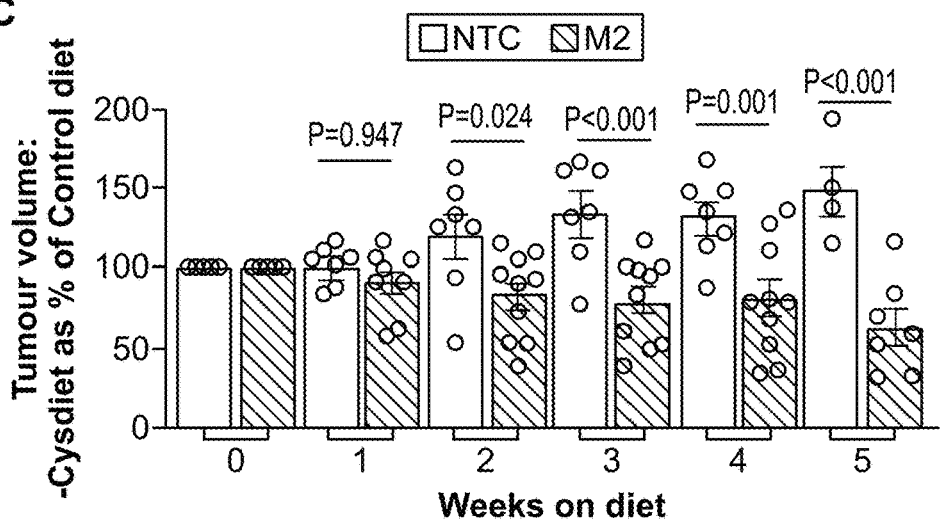
FIG. 18

| | Correlation Coefficient ($R^2$) | | Correlation Coefficient ($R^2$) |
|---|---|---|---|
| Extracellular MTA (Ctr) | 0.65356 | Gamma-L-Glutamyl-L-cysteine (Ctr) | 0.07006 |
| MTA (Ctr) | 0.54847 | Steady state ROS (Ctr) | 0.06295 |
| OOC1 + AMD1 (Ctr) | 0.53198 | GPX4 expression (-Cys) | 0.05780 |
| MTA (-Cys) | 0.52529 | Cysteine (Ctr/T=0) | 0.05364 |
| Decarboxy-SAM (Ctr) | 0.44628 | Cystine (Ctr) | 0.04219 |
| AMD1 (Ctr) | 0.39630 | GSH (-Cys) | 0.03399 |
| GPX4 inh ML210 IC50 | 0.37674 | GPX4 expression (Ctr) | 0.03213 |
| Cystathionine (Ctr) | 0.32260 | Methionine (-Cys) | 0.03105 |
| MTAP (Ctr) | 0.30353 | PUFA-PL 4 double bonds (Ctr) | 0.02890 |
| OOC1 + AMD1 (-Cys) | 0.24305 | Cysteine (-Cys 90 min) | 0.02801 |
| GPX4 inh RSL3 IC50 | 0.22142 | OOC1 (-Cys) | 0.02713 |
| CBS + CSE (-Cys) | 0.20996 | Methionine (Ctr) | 0.02620 |
| Cystathionine (-Cys) | 0.20373 | Cysteine half-life (-Cys) | 0.02450 |
| Homocysteine (Ctr) | 0.18489 | NADP+NaDPH (Ctr) | 0.01696 |
| GSSG (-Cys) | 0.17667 | PUFA-PL 3 double bonds (Ctr) | 0..01665 |
| Homocysteine (-Cys) | 0.17151 | GSH/GSSH (-Cys) | 0.01658 |
| MTAP (-Cys) | 0.16189 | NADP+ (Ctr) | 0.01438 |
| SAH (Ctr) | 0.16099 | SAM (-Cys) | 0.01374 |
| AHCY (-Cys) | 0.15003 | PUFA-PL > 2 double bonds (Ctr) | 0.01145 |
| Gamma-L-Glutamyl-L-cysteine (-Cys) | 0.14256 | AHCY (Ctr) | 0.01140 |
| Cysteine (-Cys) | 0.13364 | NADPH (Ctr) | 0.00688 |
| CBS (-Cys) | 0.12728 | Cystine (-Cys) | 0.00493 |
| CSE (-Cys) | 0.11978 | PUFA-PL 2 double bonds | 0.00476 |
| CBS (Ctr) | 0.11676 | GSH (Ctr) | 0.00384 |
| SAM (Ctr) | 0.11044 | Iron uptake (Ctr) | 0.00370 |
| Cysteine (-Cys 15 min) | 0.10409 | OOC1 (Ctr) | 0.00179 |
| AMD (-Cys) | 0.10250 | GSH/GSSG (Ctr) | 0.00036 |
| Cysteine (-Cys 45 min) | 0.10077 | CSE (Ctr) | 0.00022 |
| Cysteine (Ctr) | 0.09721 | SAH (-Cys) | 0.00010 |
| Malonyldialdehyde (MDA) stain (Ctr) | 0.09399 | Decarboxy-SAM (-Cys) | 0.00005 |
| CBS + CSE (Ctr) | 0.09222 | | |
| GSSG (Ctr) | 0.07798 | | |

FIG. 27

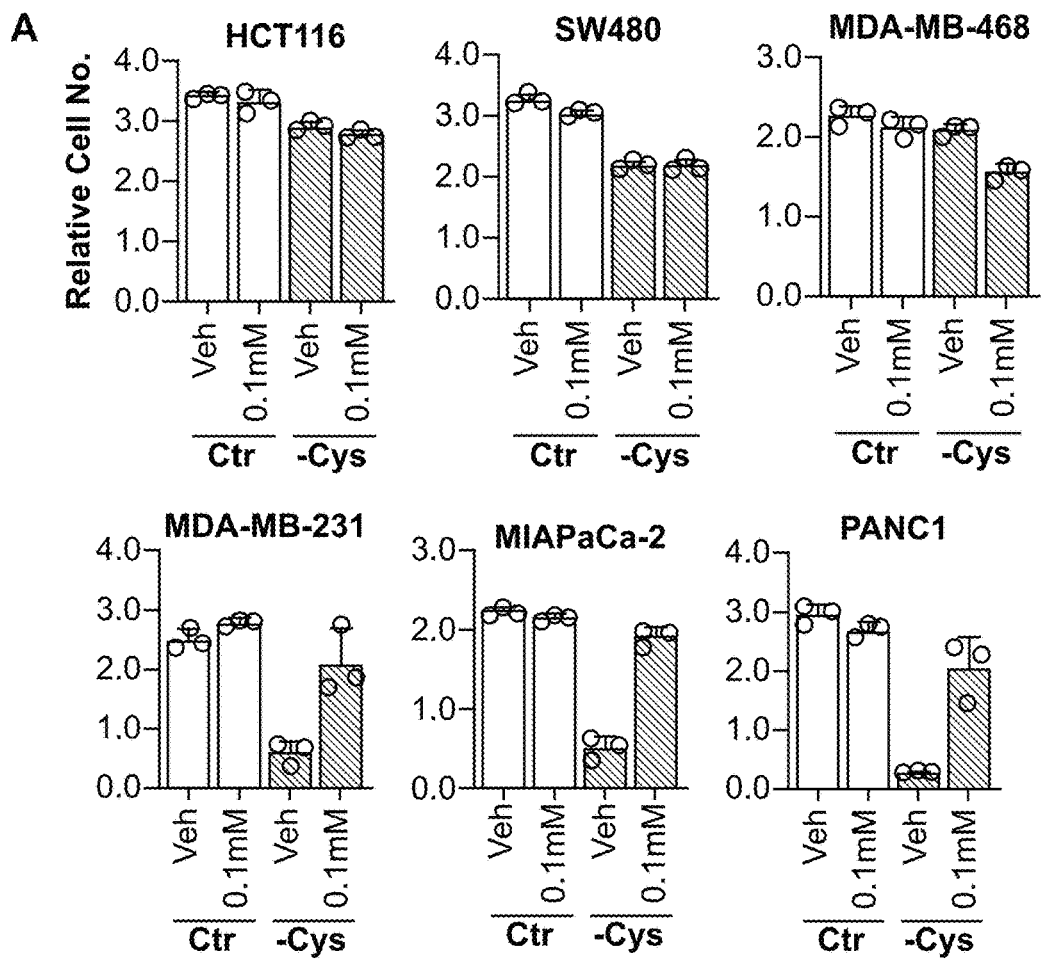
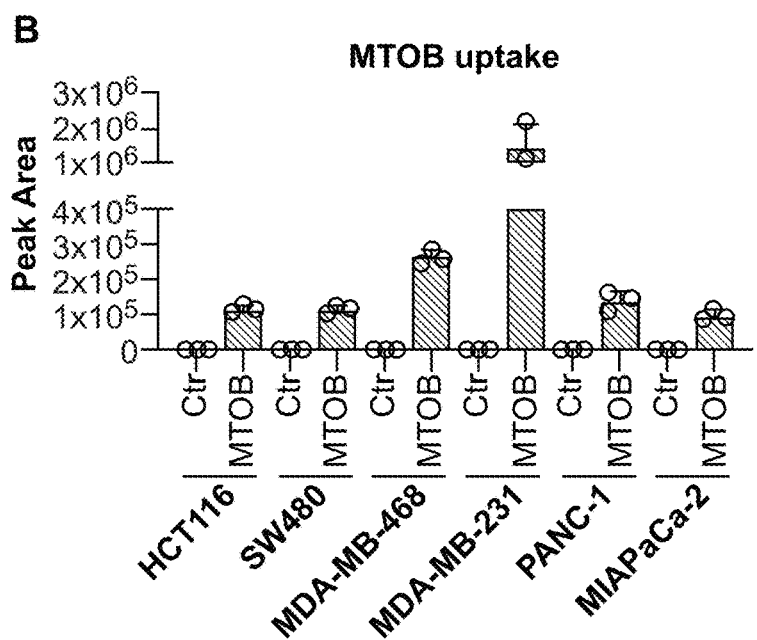
FIG. 32

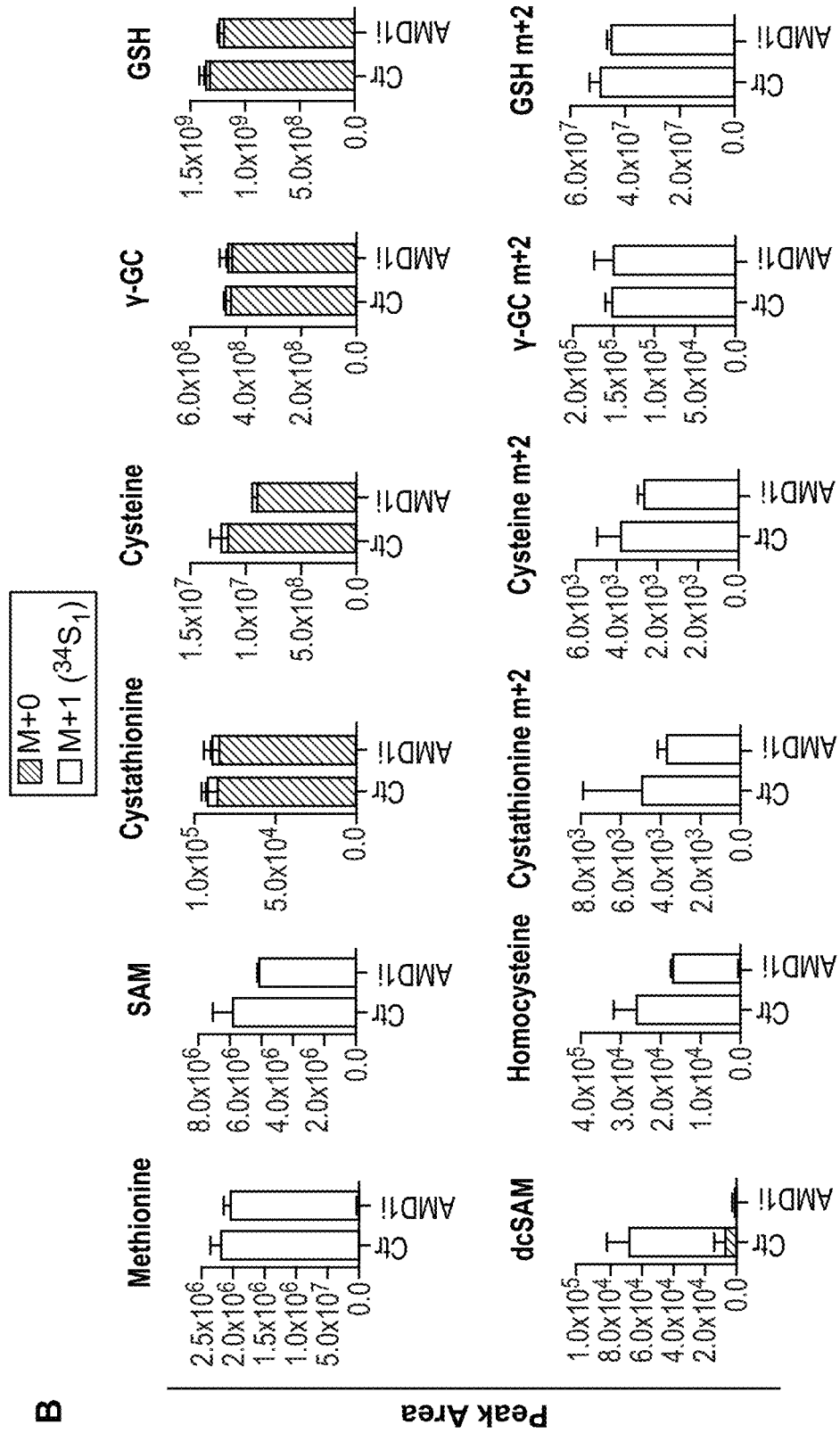
FIG. 33 (Cont. 1)

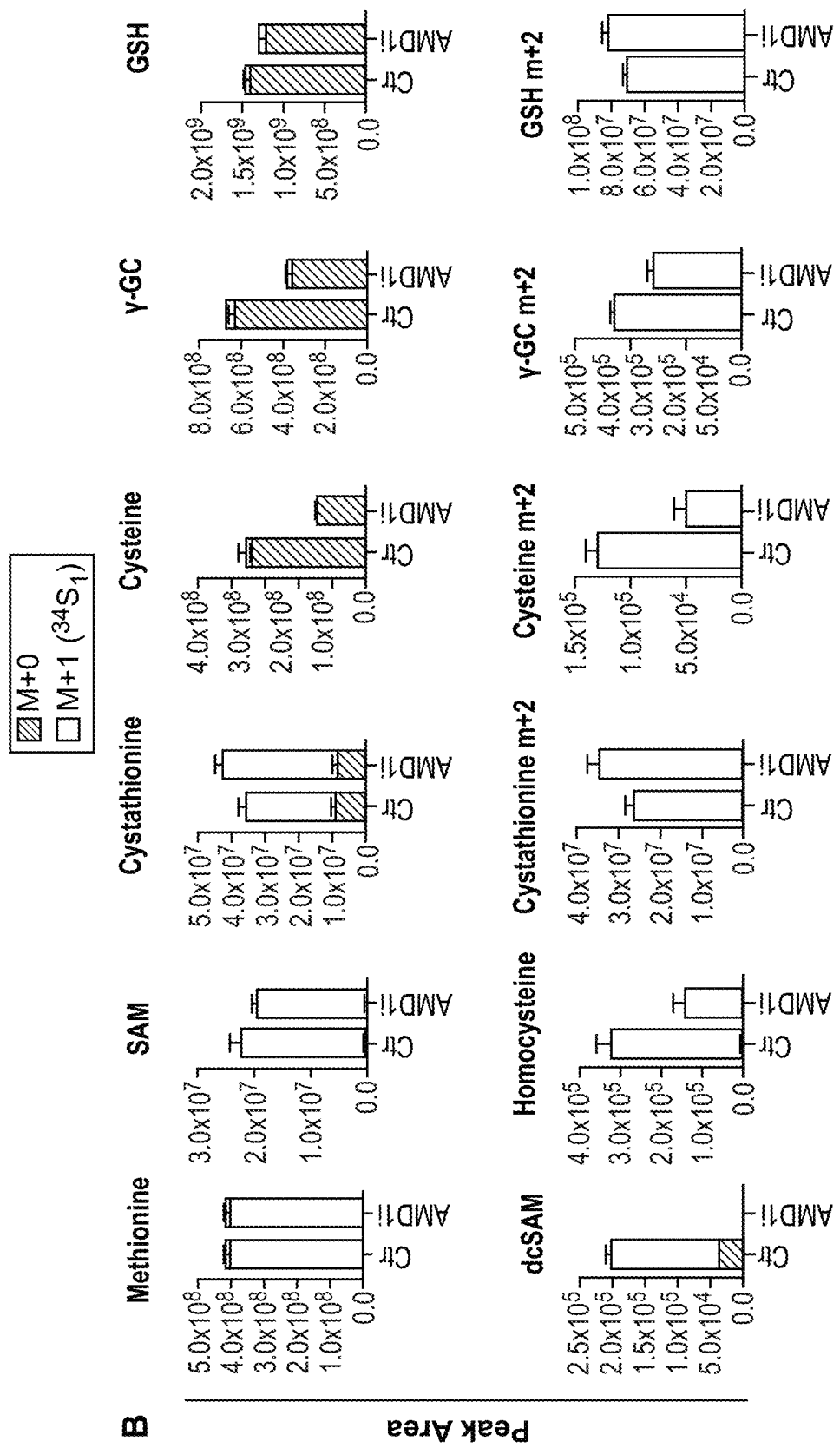
FIG. 33 (Cont. 2)

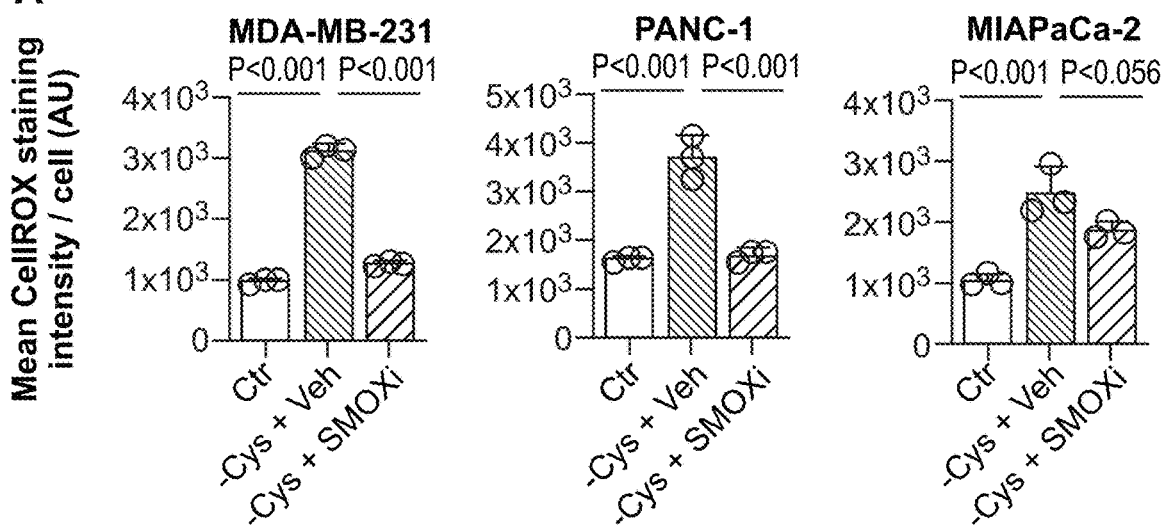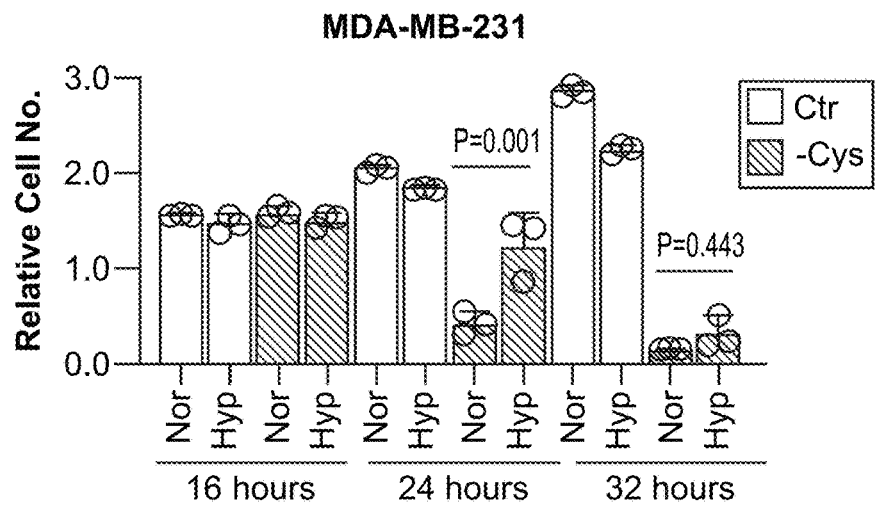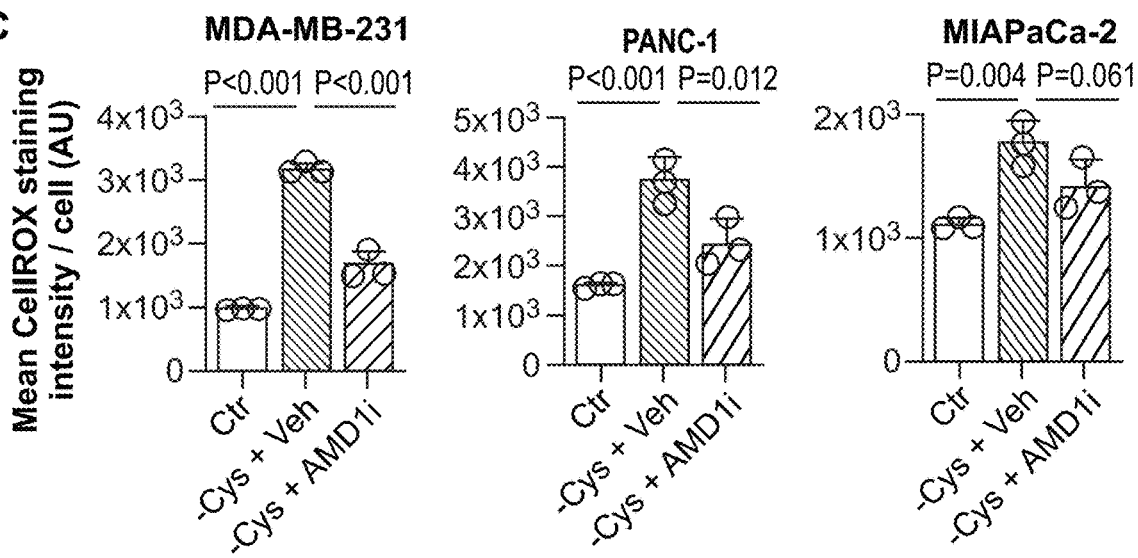
FIG. 35

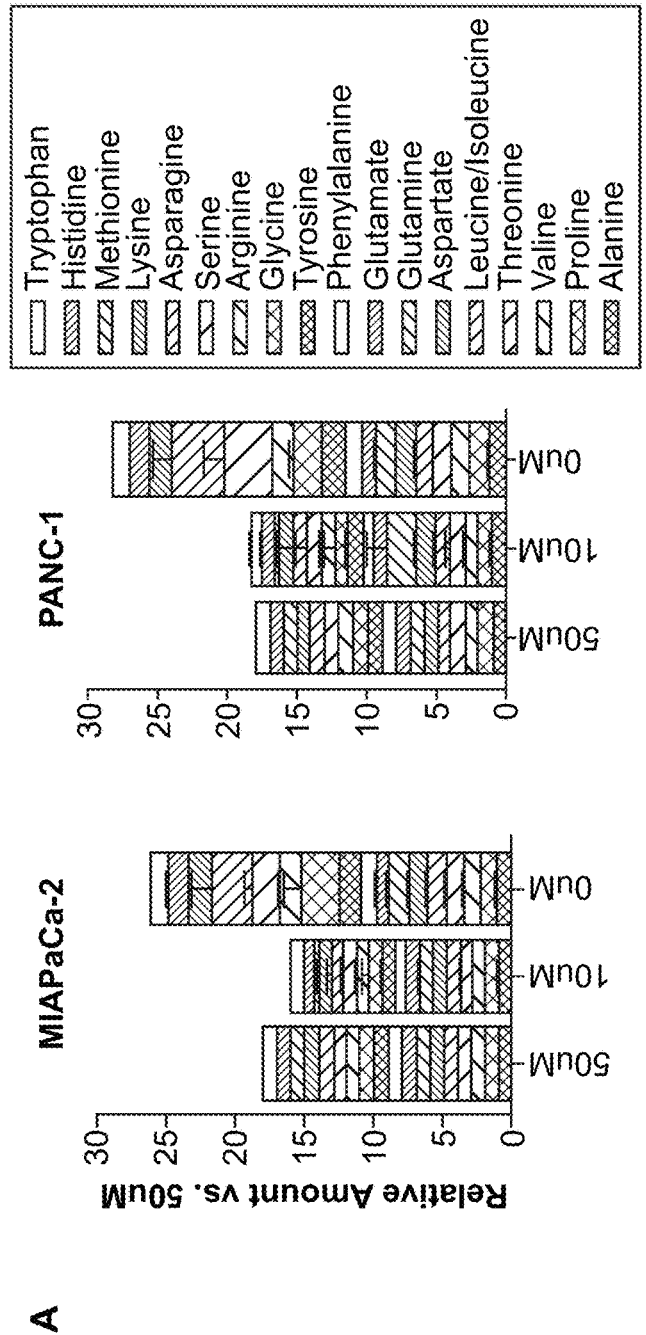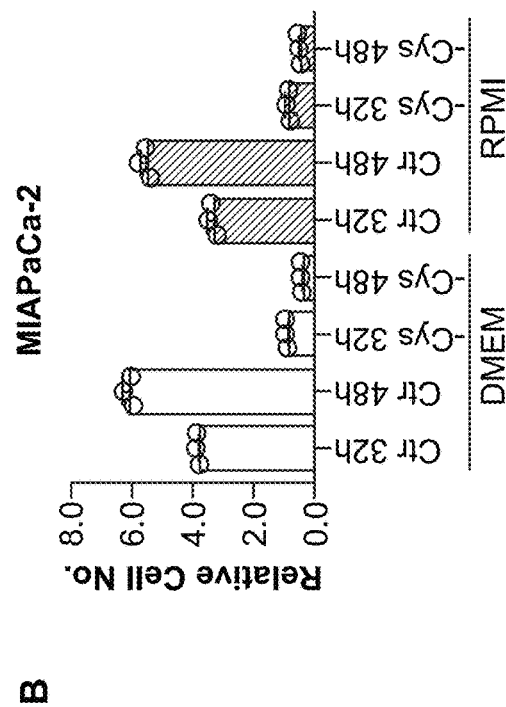
FIG. 39

PERSONALIZED METHODS OF TREATING CANCER

CROSS-REFERENCE

This application claims the benefit of U.S. Provisional Application No. 63/034,679, filed Jun. 4, 2020, which is incorporated herein by reference.

SEQUENCE LISTING

The instant application contains a Sequence Listing which has been submitted electronically in ASCII format and is hereby incorporated by reference in its entirety. Said ASCII copy, created on Jun. 3, 2021, is named 57630-705.201_SL.txt and is 965 bytes in size.

BACKGROUND

Cancer cells acquire metabolic adaptations that support enhanced rates of growth and proliferation of the cancer cells. Specifically, cancer cells have high demands for non-essential amino acids, which non-essential amino acids are precursors for anabolic and anti-oxidant pathways that support cell survival and proliferation. Amino acid withdrawal may impede cancer cell proliferation and lead to cell death.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

In some embodiments, disclosed herein is a method for treating a cancer in a subject in need thereof, the method comprising administering to the subject a therapeutically-effective amount of a dietary product, wherein the dietary product comprises at most about 0.5% (w/w) of cysteine or cystine, and wherein the dietary product comprises at least about 7.5% (w/w) of at least one essential amino acid selected from the group consisting of: methionine, histidine, isoleucine, leucine, lysine, phenylalanine, threonine, tryptophan, and valine, wherein the subject is undergoing a cancer therapy for the cancer, wherein the administering the dietary product to the subject increases efficacy of the cancer therapy in the subject by at least about 10% as compared to an efficacy of the cancer therapy in a comparable subject receiving the cancer therapy, but not the dietary product.

In some embodiments, disclosed herein is method of treating a cancer in a subject in need thereof, the method comprising administering to the subject a therapeutically-effective amount of a dietary product, wherein the dietary product comprises at most about 0.5% (w/w) of cysteine or cystine, wherein the cancer has downregulated 5-methylthioadenosine phosphorylase (MTAP) expression, and wherein the administering of the dietary product to the subject reduces cancer cell proliferation by at least about 20% as compared to a reduction in cancer cell proliferation in a comparable subject who has not been administered the dietary product.

In some embodiments, disclosed herein is a method of treating a condition in a subject in need thereof, the method comprising: a) determining a level of a metabolite in a biological sample from the subject; and b) administering a therapeutically-effective amount of a dietary product to the subject based at least on the level of the metabolite, wherein the dietary product comprises at most about 0.5% (w/w) of at least one non-essential amino acid selected from the group consisting of: glycine, serine, alanine, proline, glutamine, glutamic acid, asparagine, aspartic acid, cysteine, tyrosine, and arginine.

In some embodiments, disclosed herein is a method of treating a cancer in a subject in need thereof, the method comprising administering a therapeutically-effective amount of a dietary product to the subject, wherein the dietary product comprises at most about 0.5% (w/w) cysteine or cystine, wherein the therapeutically-effective amount of the dietary product is lower for a treatment of the cancer as compared to at least one of: a) a therapeutically-effective amount of a dietary product devoid of glucose; b) a therapeutically-effective amount of a dietary product devoid of serine and glycine; and c) a therapeutically-effective amount of a dietary product devoid of lysine.

BRIEF DESCRIPTION OF THE DRAWINGS

FIG. 1 shows the effect of cysteine starvation (−Cysteine; RIGHT PANEL) on cell proliferation compared to fully fed conditions (Control; LEFT PANEL).

FIG. 7 PANEL A shows that addition of 0.2 mM homocysteine (HC) or 0.2 mM cystathionine (CTH) produced a substantial rescue to survival and proliferation in SW480 and MDA-MB-231 cell lines. PANEL B shows that supplementation with 0.8 mM homocysteine (HC) restored cell proliferation, but supplementation with 0.8 mM methionine provided no rescue.

FIG. 9 PANEL A shows that extracellular MTA levels were strongly correlated to sensitivity to starvation. PANEL B shows that MTAP protein expression was correlated to cysteine starvation response.

FIG. 18 PANEL A shows the effect of cysteine starvation and rescue with ferrostatin on MTAP-deletion. PANEL B shows that treatment of cells with an AMD1 inhibitor restored cell survival in response to cysteine starvation. PANEL C shows that the response of NTC- and MTAP-deleted cells to cysteine limitation in vivo differed significantly.

FIG. 27 shows correlation coefficients ($R^2$) for a range of biological parameters versus sensitivity of 11 cell lines to cysteine starvation.

FIG. 32 PANEL A shows cells grown in complete medium with or without 0.1 mM MTOB for 16 h, then either grown in complete medium (Ctr) or matched medium lacking cysteine (–Cys) with or without 0.1 mM MTOB for 32 h. PANEL B shows cells grown in complete medium with or without 0.1 mM MTOB for 5 h, with 0.2 mM $^{13}C_5{}^{15}N_1$-methionine substituted for methionine.

PANEL B shows MDA-MB-231 cells (left) and MIAPaCa-2 cells (right) grown in complete medium with or without 20 μM of the AMD1 inhibitor sardomozide for 16 h (with 0.2 mM $^{34}S_1$-methionine substituted for methionine).

Figure 34:
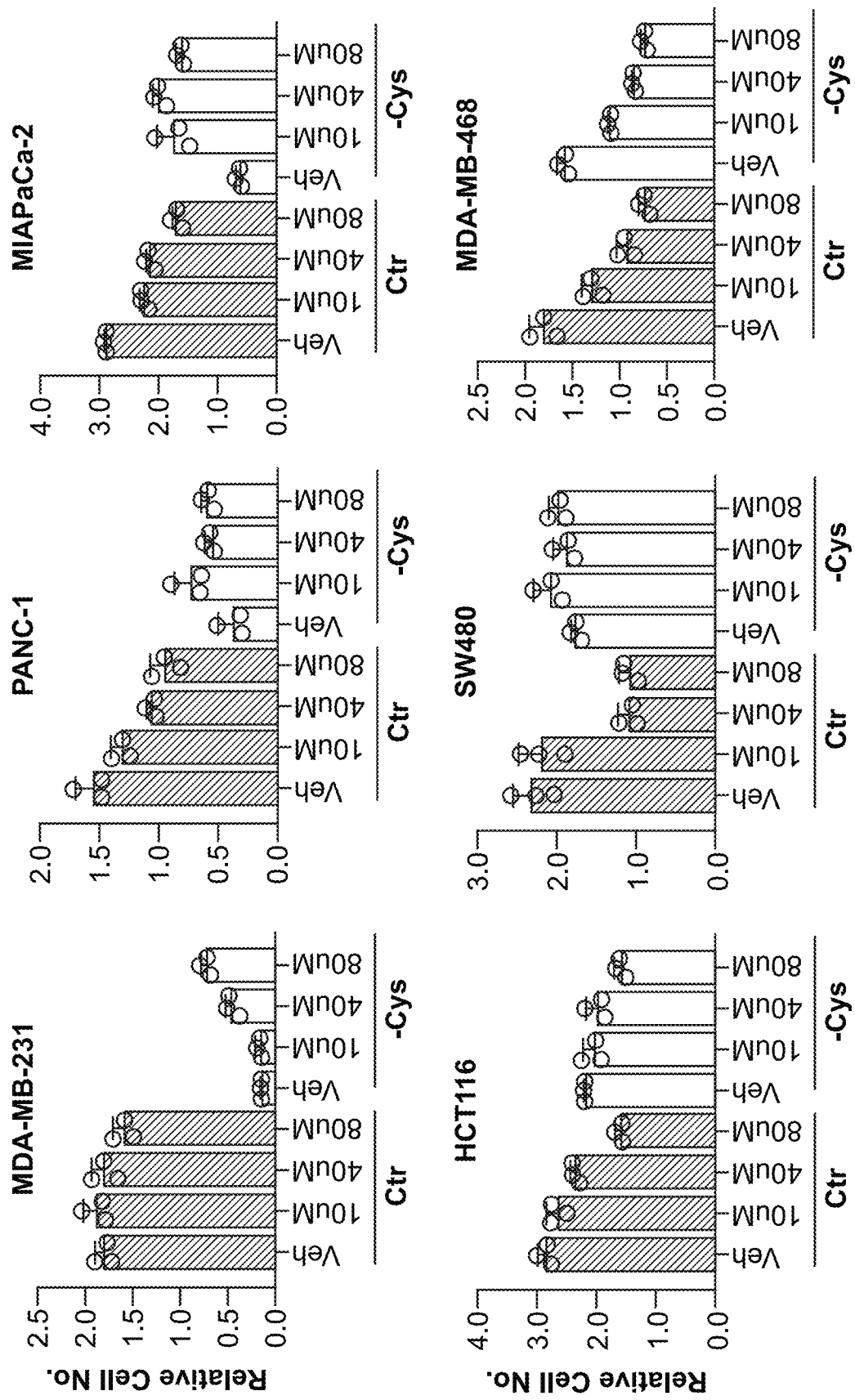

FIG. 34 shows cells grown in complete medium without or with 10 μM, 40 μM, or 80 μM of a PAOX inhibitor for 16 h, then grown in complete medium (Ctr) or matched medium lacking cysteine without or with 10 μM, 40 μM, or 80 μM of a PAOX inhibitor for 24 h.

FIG. 35 PANEL A shows cell lines grown in complete medium with 50 μM of the SMOX inhibitor MDL72527 (+SMOXi) or without (+Vehicle) a SMOX inhibitor, then grown in complete medium (Ctr) or matched medium lacking cysteine (−Cys) with or without 50 μM of the SMOX inhibitor. ROS were detected in real-time by an Operetta automated microscope in live cells treated with CellROX deep red. ROS staining intensity is shown for the 16 h timepoint. PANEL B shows MDA-MB-231 cells grown in either complete medium, medium lacking cysteine under normoxia (Nor) or hypoxia (Hyp); 1% oxygen for stated times. PANEL C shows cell lines grown in complete medium (Ctr) or matched medium lacking cysteine (−Cys) with 20 μM of an AMD1 inhibitor or without an AMD1 inhibitor.

Figure 36:
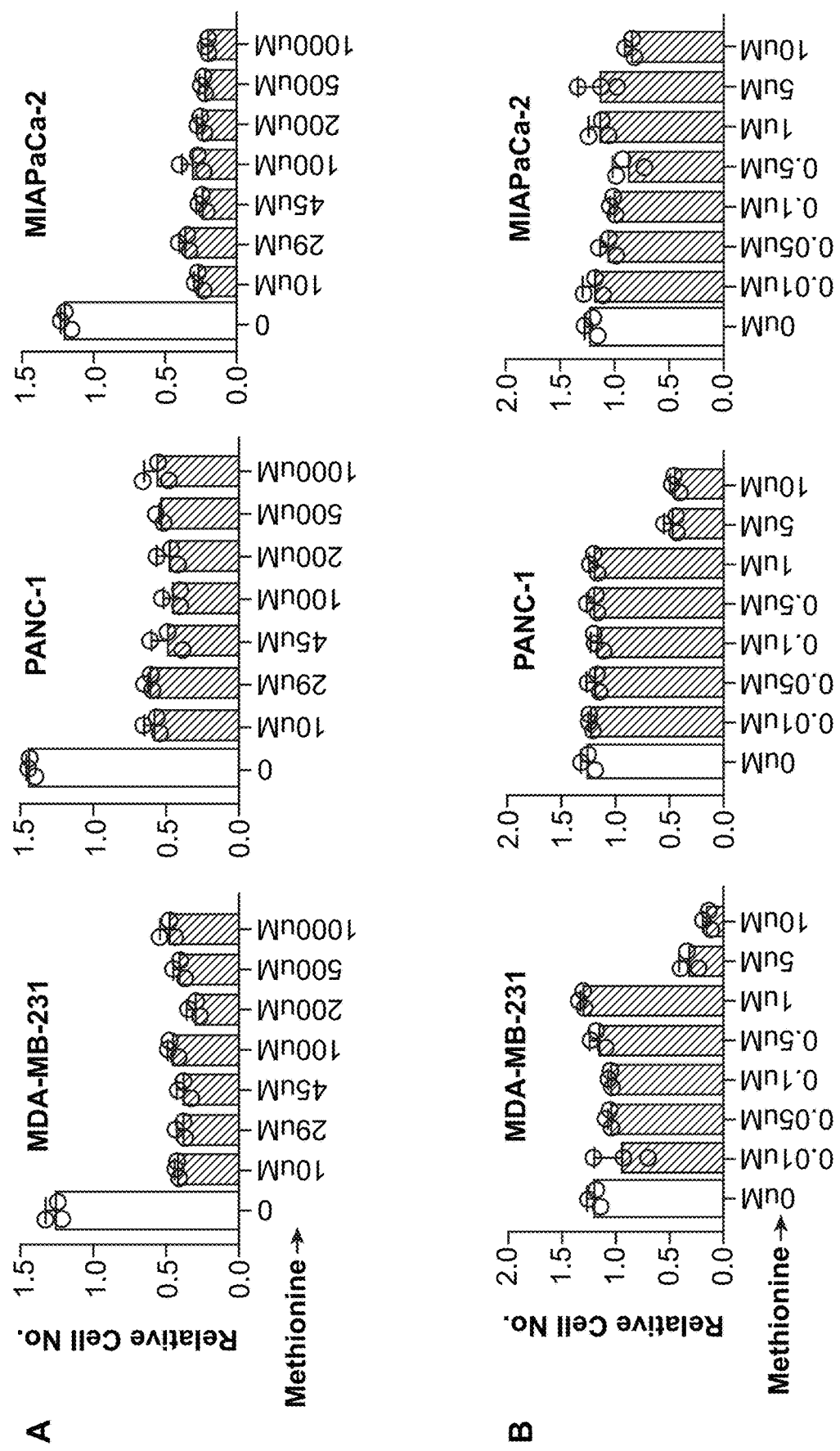
Figure 36:
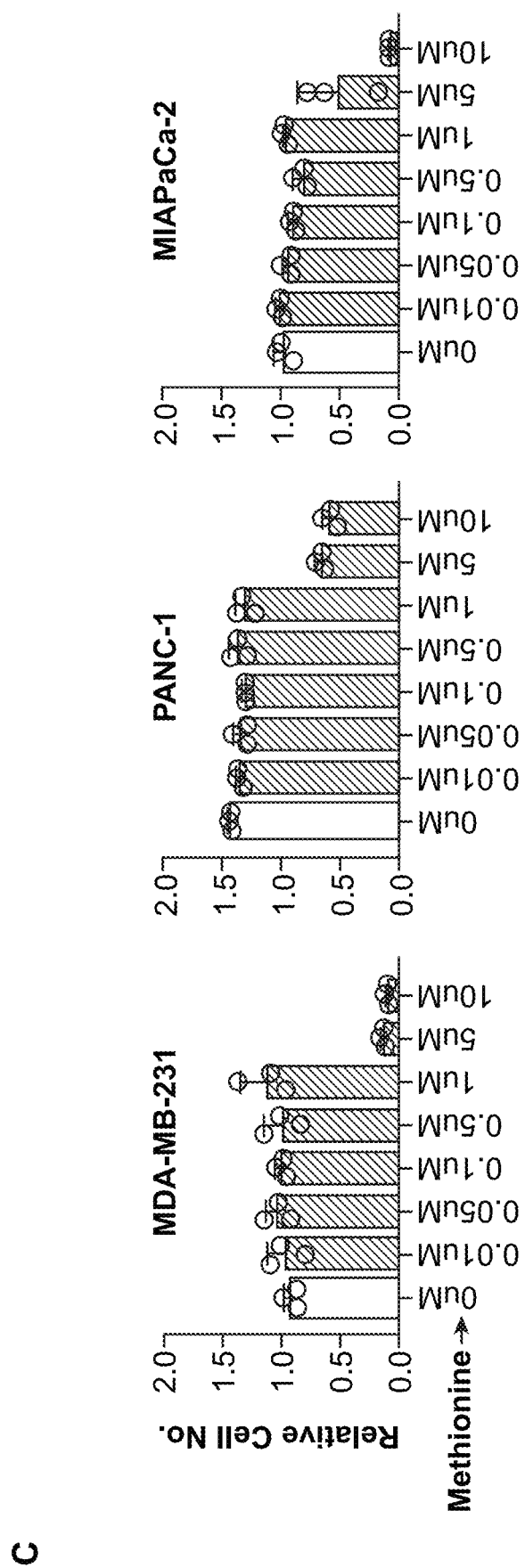

FIG. 36 ROW A shows cell lines highly sensitive to cysteine starvation (MDA-MB-231, PANC-1, and MIAPaCa-2) grown in medium without cysteine containing increasing concentrations of methionine (1 to 1 mM) for 20 h. ROW B shows cell lines sensitive to cysteine starvations (MDA-MB-231, PANC-1, and MIAPaCa-2) grown in medium without cysteine containing increasing concentrations of methionine (0 to 10 μM) for 17 h. ROW C shows cell lines sensitive to cysteine starvations (MDA-MB-231, PANC-1, and MIAPaCa-2) grown in medium without cysteine containing increasing concentrations of methionine (0 to 10 μM) for 41 h.

Figure 37:
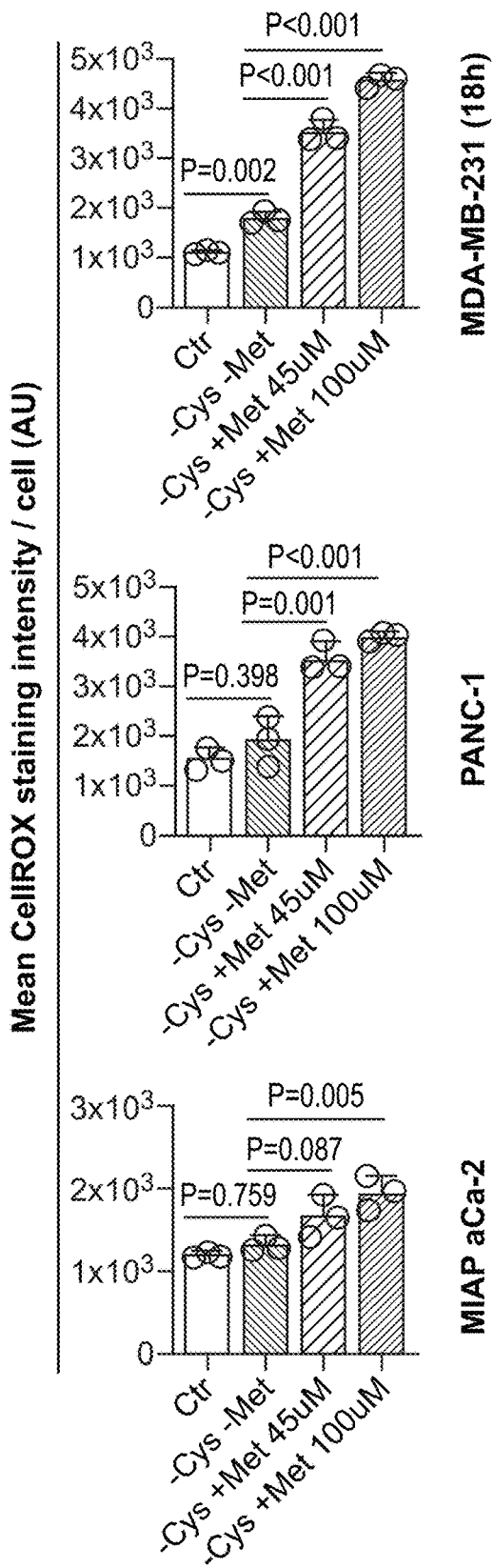

FIG. 37 shows cell lines grown in complete medium (Ctr) or matched medium lacking cysteine (−Cys) with or without methionine (Met) at the stated concentrations.

Figure 38:
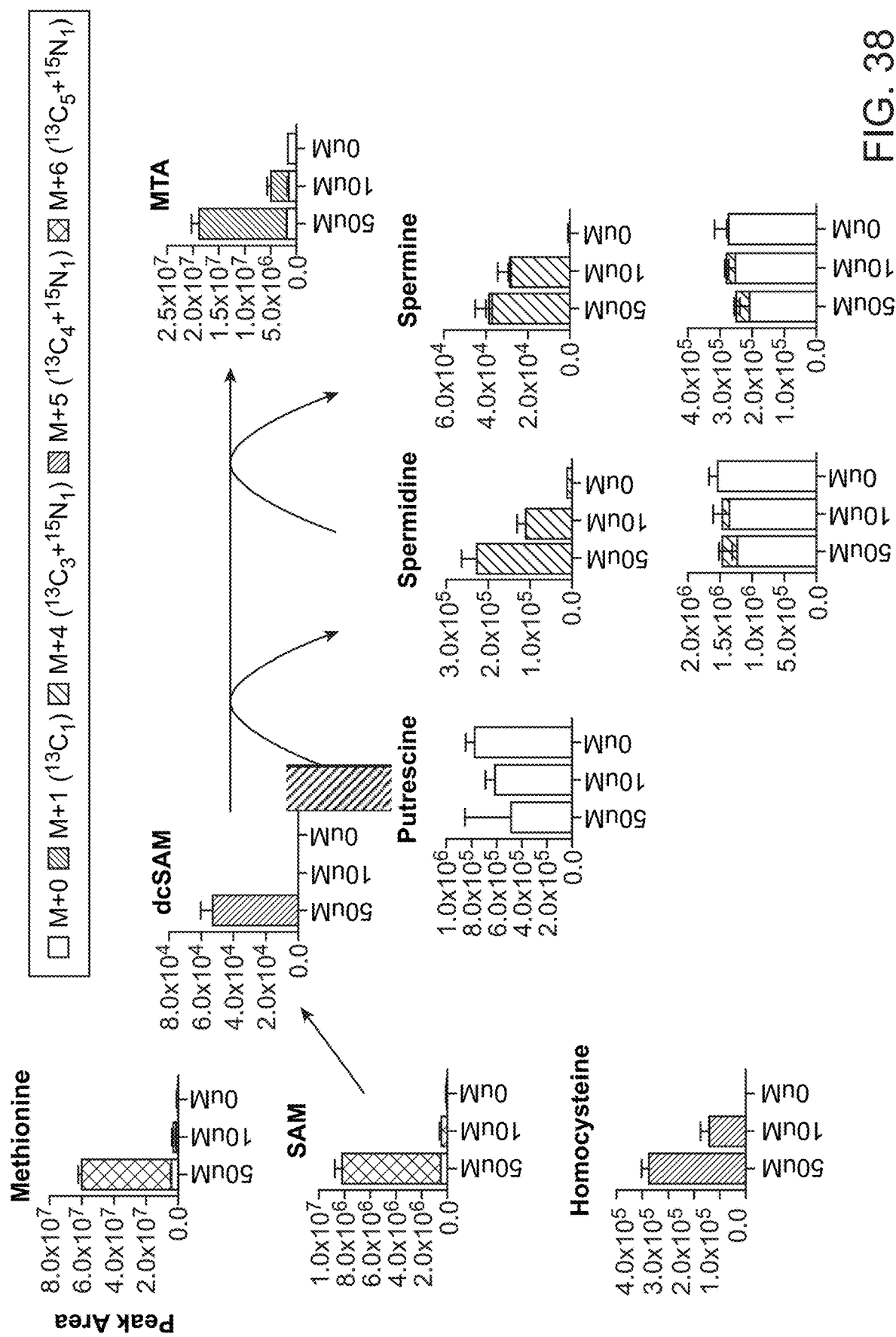
Figure 38:
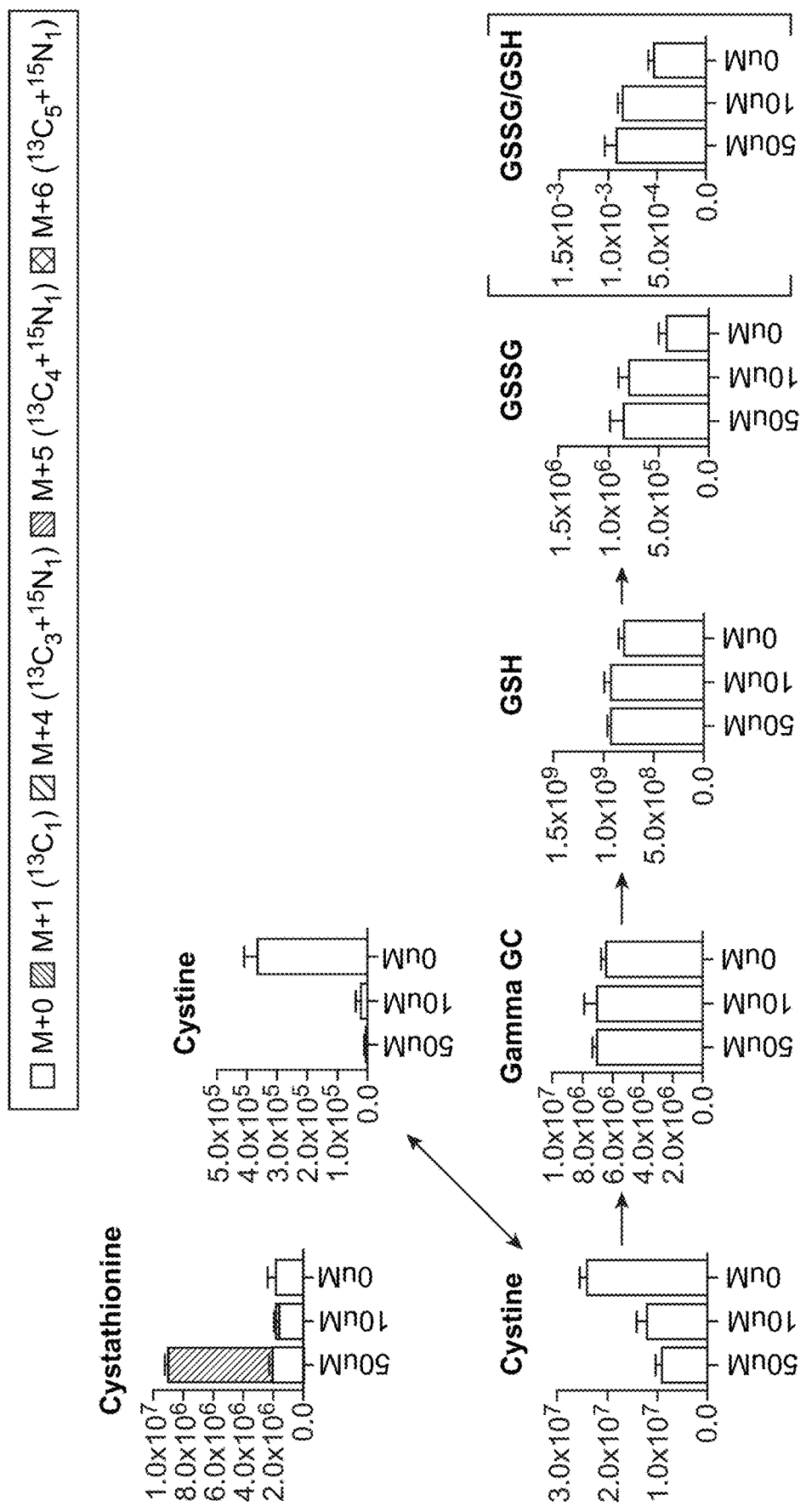

FIG. 38 shows PANC-1 cells grown in medium lacking methionine supplemented with varying levels of $^{13}C_5^{15}N_1$-methionine for 5 h. Metabolites were extracted and analyzed by LC-MS.

Figure 17:
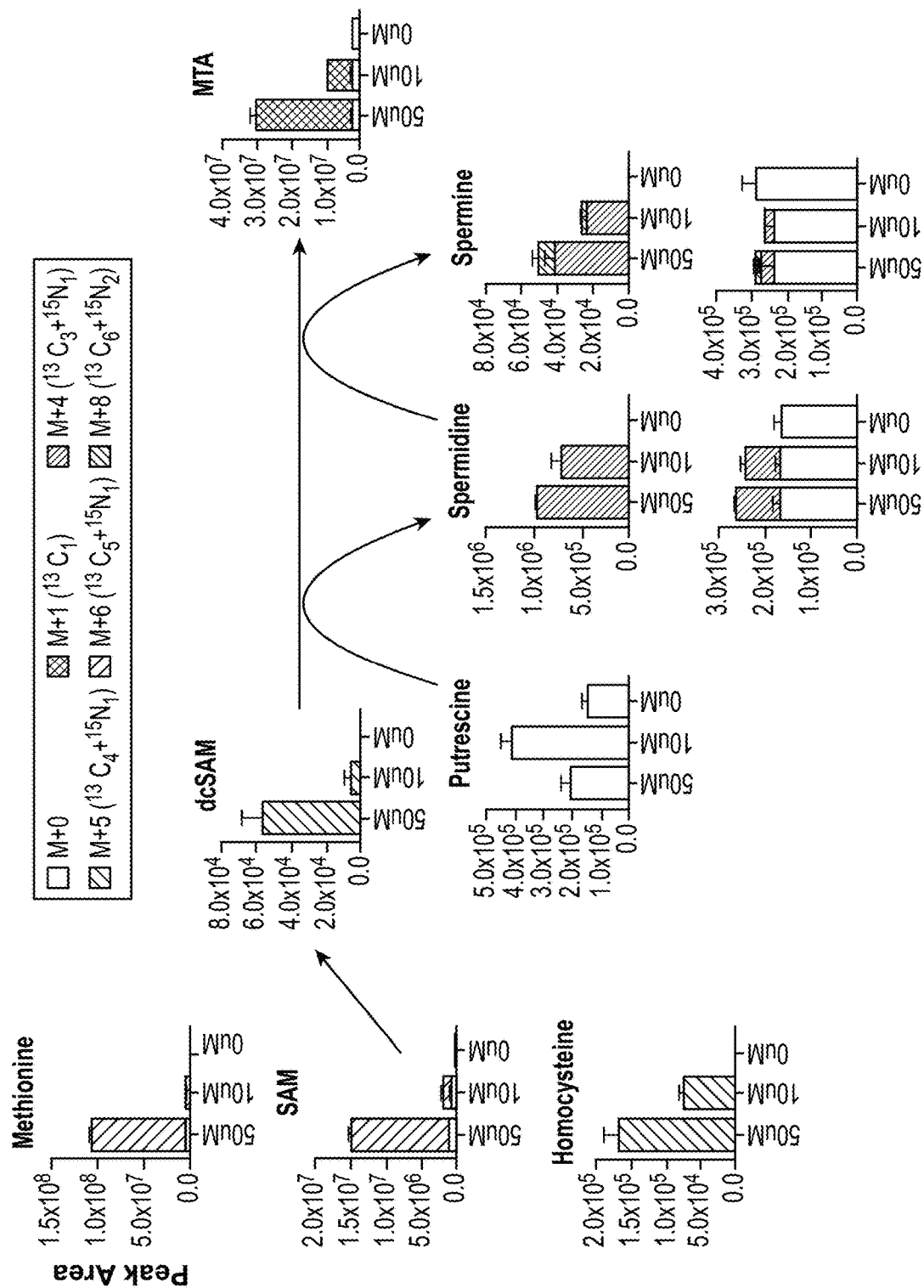
FIG. 17 shows an LC-MS analysis of cysteine starvation-sensitive cell line to examine the impact of methionine withdrawal on cysteine metabolism.
Figure 17:
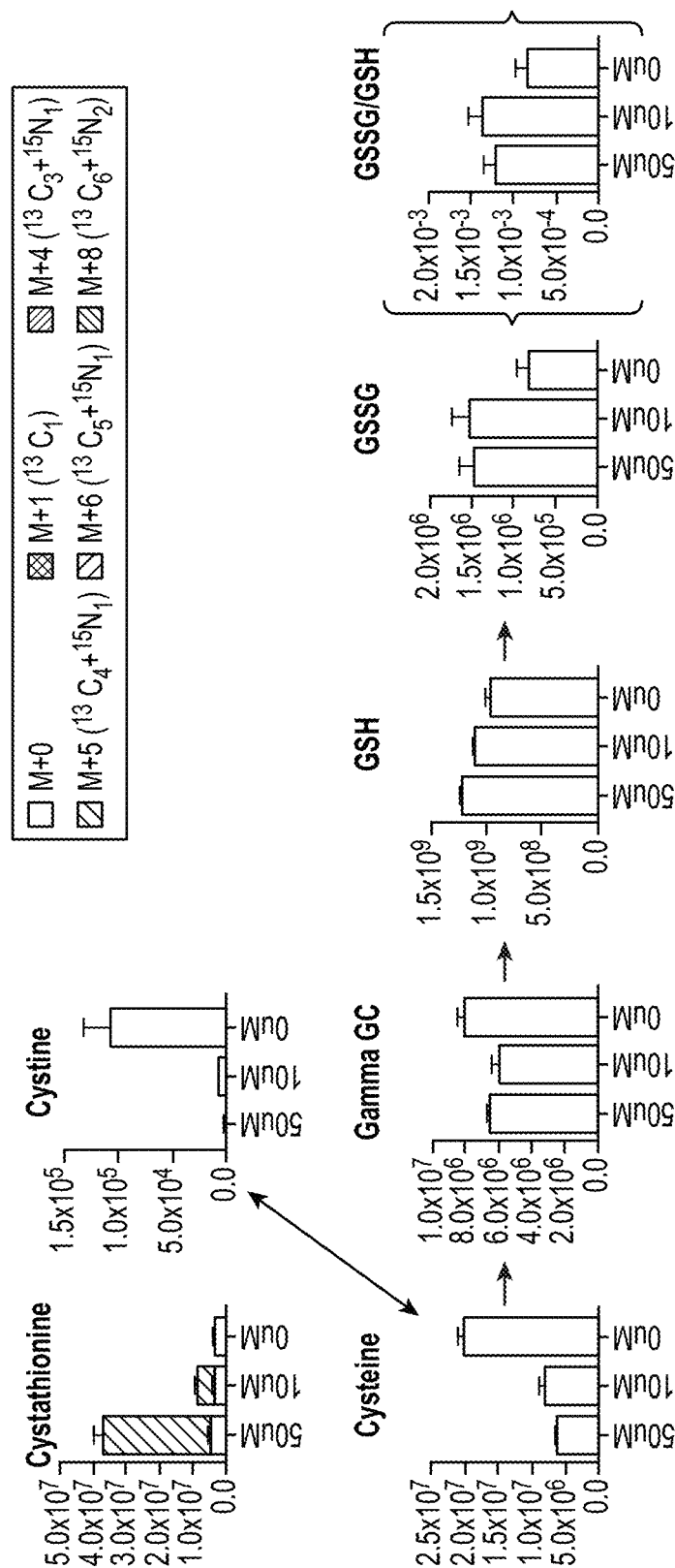

FIG. 39 PANEL A shows levels of amino acid assessed using LC-MS data from the experiments shown in FIG. 17 and FIG. 38. PANEL B shows MIAPaCa-2 cells cultured in either DMEM or RPMI for two weeks.

Figure 40:
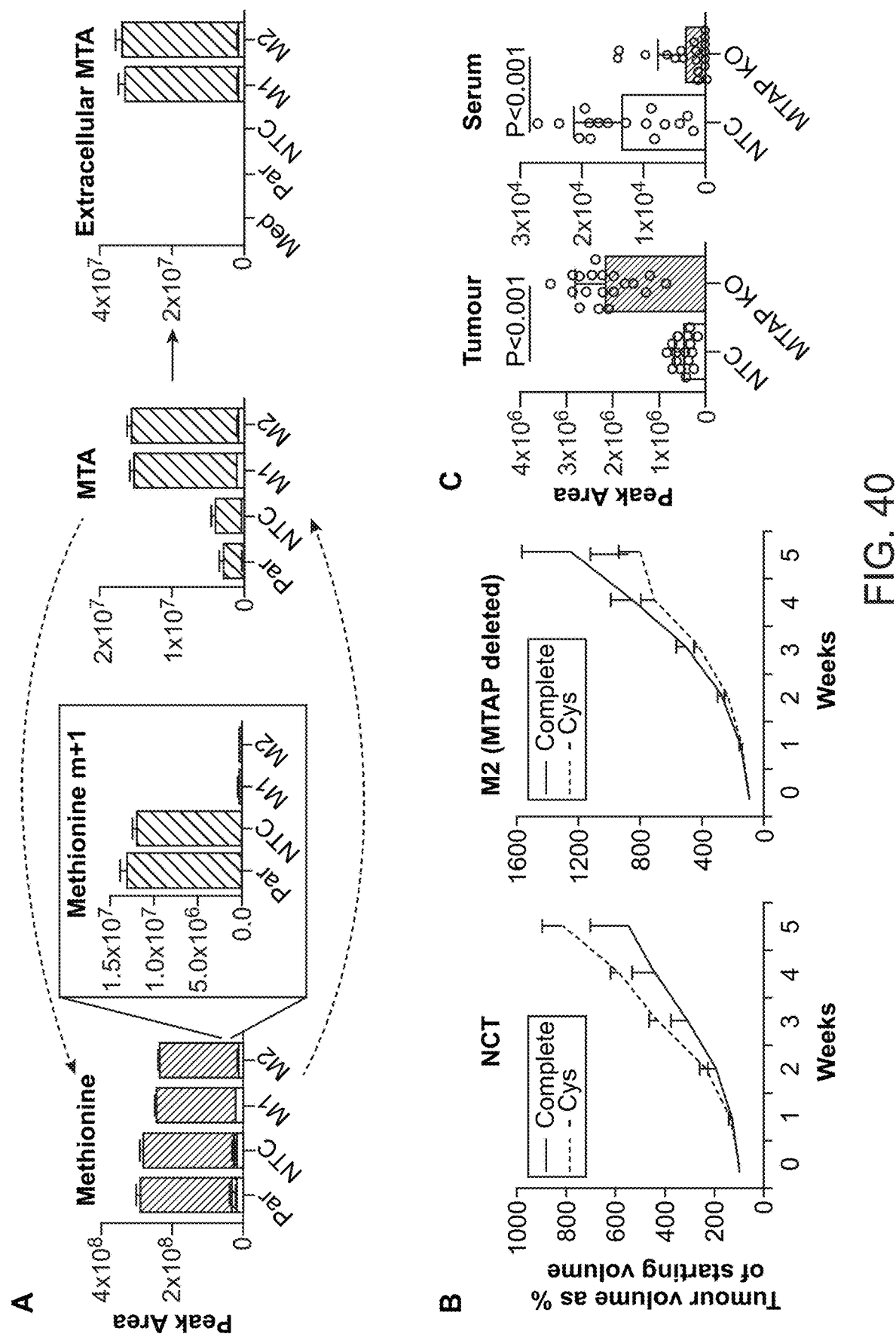

FIG. 40 PANEL A shows MTAP-positive (parental/Par, NTC) and negative (M1, M2) HCT116 cells grown in complete medium with 0.2 mM $^{13}C_5^{15}N_1$-methionine substituted for methionine) for 30 h Metabolites were extracted and analyzed by LC-MS. PANEL B shows data obtained from CD-1 nude mice injected with MTAP-positive (NTC) and MTAP-depleted (M2) HCT116 cells. PANEL C shows metabolites extracted from xenograft tumors and serum, which were subjected to LC-MS analysis for MTA levels.

Figure 41:
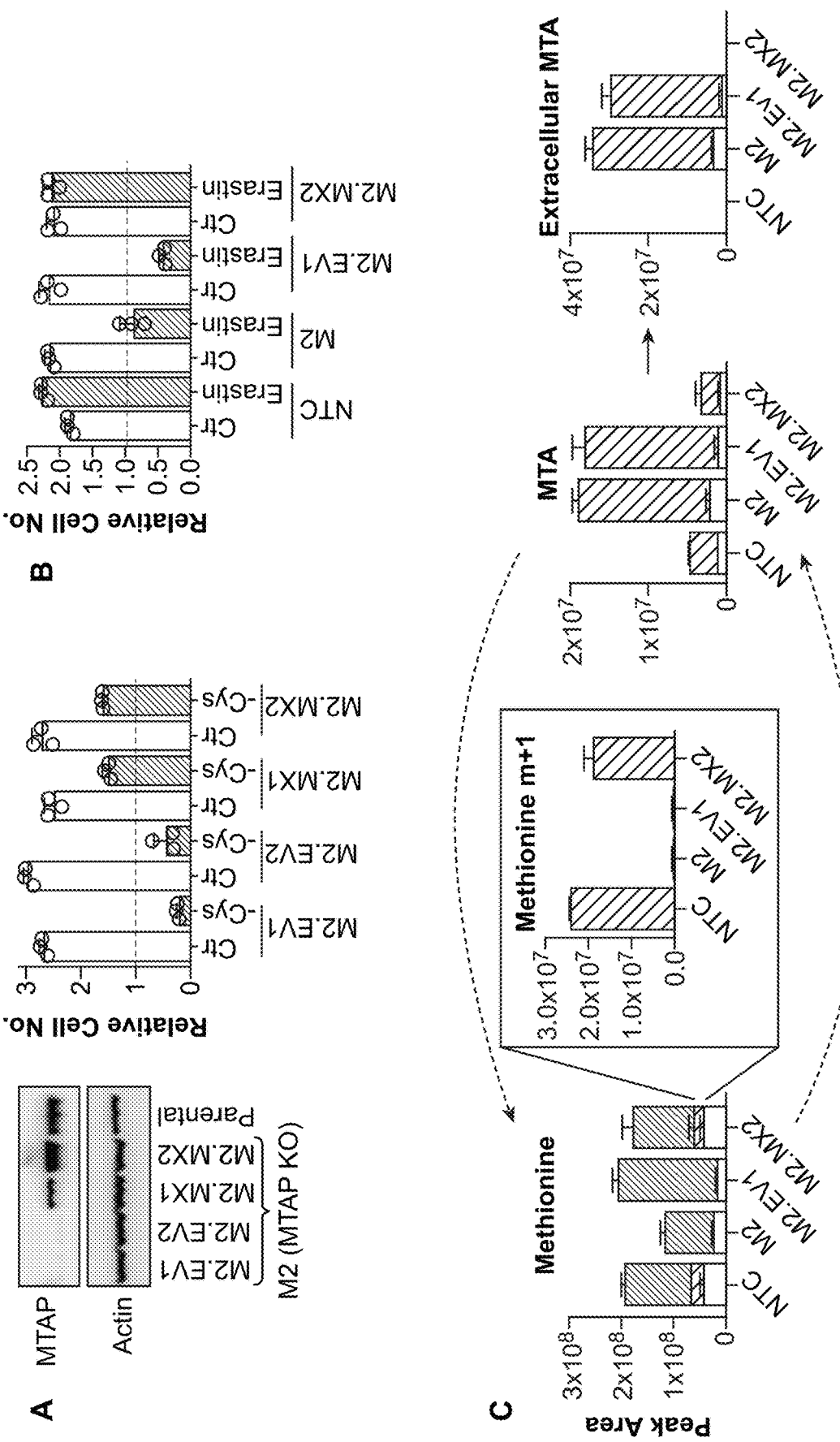

FIG. 41 PANEL A shows HCT116 cells in which MTAP was deleted by CRISPR/Cas9 (M2) that were stably transfected with an empty vector (clones M2.EV1 and M2.EV2) or a plasmid for MTAP expression (clones M2.MX1 and M2.MX2). PANEL B shows the HCT116 clones grown in complete medium with or without the xCT inhibitor and 10 μM ferroptosis inducer erastin for 18 h. PANEL C shows MTAP-expressing (NTC and M2.MX2) and MTAP-deleted (M2 and M2.EV1) HCT116 cells grown in complete medium (with 0.2 mM $^{13}C_5^{15}N_1$-methionine substituted for methionine) for 30 h.

Figure 42:
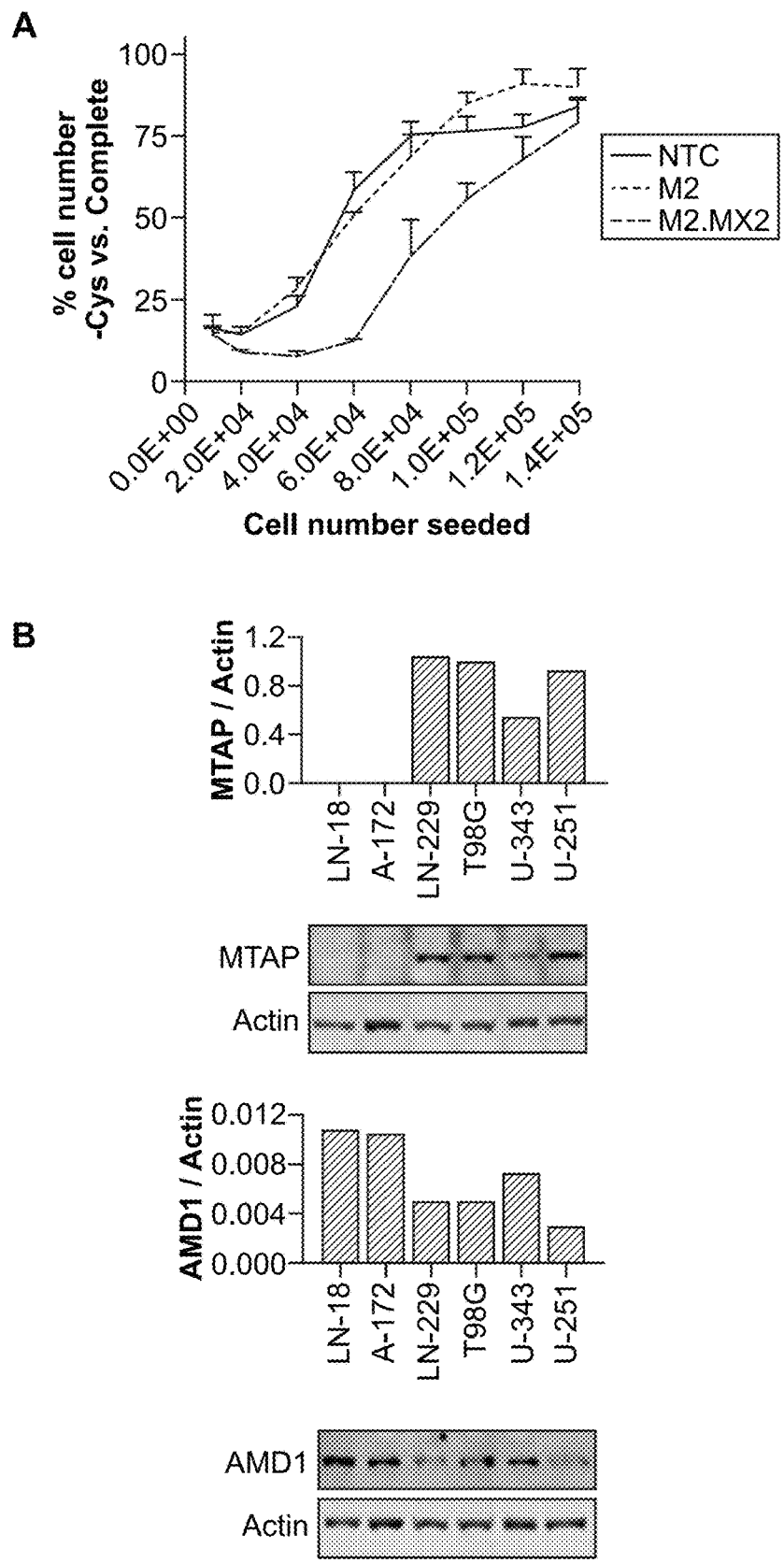

FIG. 42 PANEL A shows MTAP-expressing (NTC and M2.MX2) and MTAP-deleted (M2) HCT116 cells seeded at a range of cell densities in complete medium in 24-well plates. PANEL B shows glioblastoma (GBM) cell lines grown in complete medium for 24 h. Cell lysates were probed for MTAP, AMD1, and actin expression by western blot and quantified with a LiCor scanner.

Figure 43:
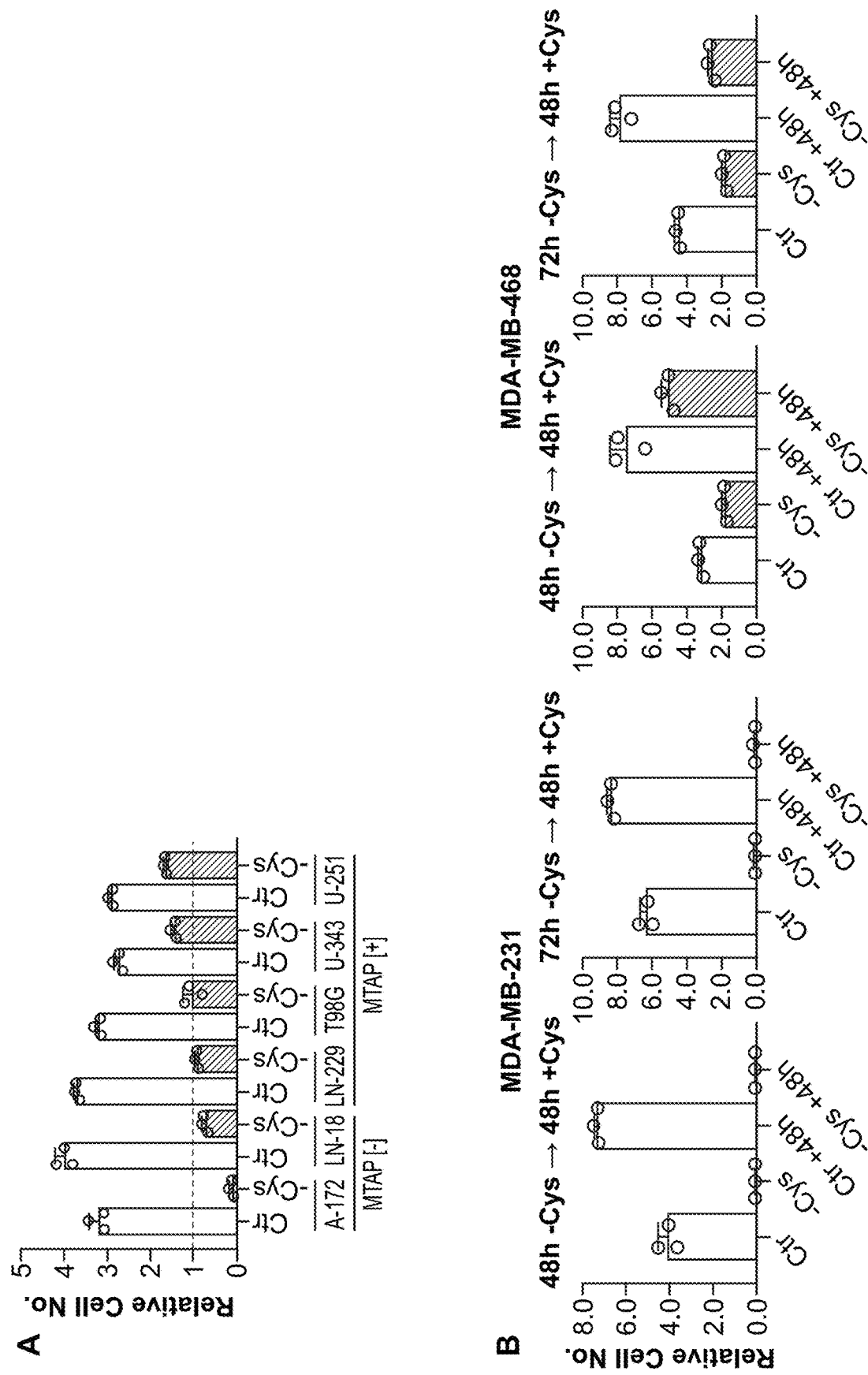

FIG. 43 PANEL A shows GBM cell lines grown in either complete medium (Ctr) or medium lacking cysteine (−Cys) for 48 h. PANEL B shows breast cancer cell lines MDA-MB-231 (highly sensitive) and MDA-MB-468 (resistant) were grown in either control (Ctr) or medium lacking cysteine (−Cys) for 48 h or 72 h.

DETAILED DESCRIPTION OF THE INVENTION

Cancer cells acquire metabolic adaptations that support enhanced rates of growth and proliferation of the cancer cells. While the metabolic adaptations help tune metabolism to support higher anabolic output and bolster anti-oxidant defenses, the metabolic adaptations can also decrease metabolic flexibility and impose increased dependence on nutrient uptake versus de novo synthesis. Cancer cells have high demands for non-essential amino acids (NEAA), which NEAAs are precursors for anabolic and anti-oxidant pathways that support cell survival and proliferation.

Cysteine, which can exist as the homo-dimer cystine, is a NEAA that is required as an essential exogenous nutrient to support cancer cell growth and proliferation. Cancer cells consume cysteine, and cysteine deprivation can induce cell death. Cysteine withdrawal in certain contexts does not simply impede cancer cell proliferation, but can trigger a distinct iron-dependent form of cell death involving lipid peroxidation termed ferroptosis. Oncogene expression can promote sensitivity to cysteine limitation, and enzymatic depletion of cysteine can limit tumor growth in murine cancer models. Inhibition of cystine uptake via the xCT transporter, which is up-regulated in tumors, can also induce ferroptosis.

Cysteine, glycine, and glutamate are important in cancer cell metabolism because cysteine, glycine, and glutamate are used to synthesize the major cellular anti-oxidant glutathione (GSH). In cancer cells, the up-regulated metabolic processes that support uncontrolled proliferation generate elevated levels of reactive oxygen species (ROS), which put increased demands on cellular anti-oxidant pathways. Adequate levels of GSH synthesis and turnover are vital in supporting cancer cell survival and proliferation. Activation of the NRF2 pathway is commonly seen in cancer and drives anti-oxidant responses, including increased cystine uptake and metabolic adaptation to elevated cellular cysteine. An important corollary of elevated cystine uptake is an increased dependency on glutaminolysis. Additionally, cysteine is also essential for the synthesis of proteins and protein co-factors such as iron-sulphur clusters, which are important for ROS-sensing in cancer cells.

Cancer cells can impair expression of enzymes for de novo cysteine synthesis via the transsulfuration pathway (TsP), also known as reverse transsulfuration. Certain cancer cells can up-regulate TsP enzymes to improve survival during cysteine limitation. The ultimate upstream precursor of the TsP is the essential amino acid methionine. Methionine, via conversion to S-adenosylmethionine (SAM) and S-adenosylhomocysteine (SAH), supplies homocysteine to the TsP.

In some embodiments, disclosed herein is a method for treating a cancer in a subject in need thereof, the method comprising administering to the subject a therapeutically-effective amount of a dietary product, wherein the dietary product comprises at most about 0.5% (w/w) of cysteine or cystine, and wherein the dietary product comprises at least about 7.5% (w/w) of at least one essential amino acid selected from the group consisting of: methionine, histidine, isoleucine, leucine, lysine, phenylalanine, threonine, tryptophan, and valine, wherein the subject is undergoing a cancer therapy, wherein the administering the dietary product to the subject increases efficacy of the cancer therapy in the subject by at least about 10% as compared to an efficacy of the cancer therapy in a comparable subject receiving the cancer therapy, but not the dietary product.

In some embodiments, disclosed herein is method of treating a cancer in a subject in need thereof, the method comprising administering to the subject a therapeutically-effective amount of a dietary product, wherein the dietary product comprises at most about 0.5% (w/w) of cysteine or cystine, wherein the cancer has downregulated 5-methylthioadenosine phosphorylase (MTAP) expression, and wherein the administering of the dietary product to the subject reduces cancer cell proliferation by at least about 20% as compared to a reduction in cancer cell proliferation in a subject who has not been administered the dietary product.

In some embodiments, disclosed herein is a method of treating a condition in a subject in need of a dietary product, the method comprising: a) determining a level of a metabolite in a biological sample from the subject; and b) administering a therapeutically-effective amount of a dietary product to the subject based at least on the level of the metabolite, wherein the dietary product comprises at most about 0.5% (w/w) of at least one non-essential amino acid selected from the group consisting of: glycine, serine, alanine, proline, glutamine, glutamic acid, asparagine, aspartic acid, cysteine, tyrosine, and arginine.

In some embodiments, disclosed herein is a method of treating a cancer in a subject in need thereof, the method comprising administering a therapeutically-effective amount of a dietary product to the subject, wherein the dietary product comprises at most about 0.5% (w/w) cysteine or cystine, wherein the therapeutically-effective amount of the dietary product is lower for a treatment of the cancer as compared to at least one of: a) a therapeutically-effective amount of a dietary product devoid of glucose; b) a therapeutically-effective amount of a dietary product devoid of serine and glycine; and c) a therapeutically-effective amount of a dietary product devoid of lysine.

In some embodiments, disclosed herein is a method of identifying a subject in need of a dietary product, the method comprising: a) determining a level of methylthioadenosine (MTA) in a biological sample from the subject; b) identifying the subject as being in need of the dietary product, if the level of MTA in the biological sample is above a reference level; and c) administering the dietary product to the subject, wherein the dietary product comprises at most about 0.5% cysteine or cystine.

Amino Acid Compositions

Disclosed herein are methods of using amino acid compositions to treat a condition. In some embodiments, the composition is used as a dietary product. A composition of the disclosure can comprise at least ten amino acids or a salt of any amino acid thereof. In some embodiments, a composition of the disclosure comprises 10, 11, 12, 13, 14, 15, 16, 17, 18, or 19 amino acids or a salt thereof. In some embodiments, a composition of the disclosure comprises 10 amino acids or a salt thereof. In some embodiments, a composition of the disclosure comprises 14 amino acids or a salt thereof. In some embodiments, a composition of the disclosure comprises 18 amino acids or a salt thereof. In some embodiments, a composition of the disclosure comprises 19 amino acids or a salt thereof. A salt of an amino acid disclosed herein can be a pharmaceutically acceptable salt. In some embodiments, a composition disclosed herein is substantially devoid of at least cysteine. In some embodiments, a composition disclosed herein is substantially devoid of at least cystine. In some embodiments, a composition disclosed herein is substantially devoid of at least cysteine, cytstine, and serine. In some embodiments, a composition disclosed herein is substantially devoid of at least cysteine, cystine, serine, and glycine. In some embodiments, a composition disclosed herein is substantially devoid of at least cysteine, cystine, serine, glycine, and proline.

In some embodiments, a composition of the disclosure comprises 1, 2, 3, 4, 5, 6, 7, 8, or 9 essential amino acids or a salt of any amino acid thereof. In some embodiments, a composition of the disclosure comprises 7, 8, or 9 essential amino acids or a salt of any amino acid thereof. In some embodiments, a composition of the disclosure comprises 8 essential amino acids or a salt of any amino acid thereof. In some embodiments, a composition of the disclosure comprises 9 essential amino acids or a salt of any amino acid thereof. A salt of an amino acid disclosed herein can be a pharmaceutically acceptable salt. In some embodiments, a composition disclosed herein is devoid of at least histidine. In some embodiments, a composition disclosed herein is devoid of at least isoleucine. In some embodiments, a composition disclosed herein is devoid of at least leucine. In some embodiments, a composition disclosed herein is devoid of at least lysine. In some embodiments, a composition disclosed herein is devoid of at least methionine. In some embodiments, a composition disclosed herein is devoid of at least phenylalanine. In some embodiments, a composition disclosed herein is devoid of at least threonine. In some embodiments, a composition disclosed herein is devoid of at least tryptophan. In some embodiments, a composition disclosed herein is devoid of at least valine. Any composition disclosed herein can use cysteine, L-cysteine, cystine, or L-cystine. Any composition disclosed herein can use cystine in place of cysteine. Any composition disclosed herein can use L-cystine in place of L-cysteine.

In some embodiments, a composition of the disclosure comprises 1, 2, 3, 4, 5, 6, 7, 8, 9, 10, or 11 non-essential amino acids or a salt of any amino acid thereof. In some embodiments, a composition of the disclosure comprises 7, 8, 9, 10, or 11 non-essential amino acids or a salt of any amino acid thereof. In some embodiments, a composition of the disclosure comprises 7 non-essential amino acids or a salt of any amino acid thereof. In some embodiments, a composition of the disclosure comprises 8 non-essential amino acids or a salt of any amino acid thereof. In some embodiments, a composition of the disclosure comprises 9 non-essential amino acids or a salt of any amino acid thereof. A salt of an amino acid disclosed herein can be a pharmaceutically acceptable salt. In some embodiments, a composition disclosed herein is devoid of at least alanine, arginine, asparagine, aspartic acid, cystine, or cysteine. In some embodiments, a composition disclosed herein is devoid of at least glutamic acid, glutamine, glycine, or proline. In some embodiments, a composition disclosed herein is devoid of at least serine or tyrosine. In some embodiments, a composition disclosed herein is devoid of at least cysteine. In some embodiments, a composition disclosed herein is devoid of at least cystine. In some embodiments, a composition disclosed herein is devoid of at least cysteine and serine. In some embodiments, a composition disclosed herein is devoid of at least cystine and serine. In some embodiments, a composition disclosed herein is devoid of at least cysteine, serine, and glycine. In some embodiments, a composition disclosed herein is devoid of at least cystine, serine, and glycine. In some embodiments, a composition disclosed herein is devoid of at least cysteine, serine, glycine, and proline. In some embodiments, a composition disclosed herein is devoid of at least cystine, serine, glycine, and proline.

A composition of the disclosure can comprise essential amino acids or a salt of any amino acid thereof and non-essential amino acids or a salt of any amino acid thereof. In some embodiments, a composition of the disclosure comprises 1, 2, 3, 4, 5, 6, 7, 8, or 9 essential amino acids or a salt of any amino acid thereof and 1, 2, 3, 4, 5, 6, 7, 8, 9, 10, or 11 non-essential amino acids or a salt of any amino acid thereof. In some embodiments, a composition of the disclosure comprises 7, 8, or 9 essential amino acids or a salt of any amino acid thereof and 6, 7, 8, or 9 non-essential amino acids or a salt of any amino acid thereof. In some embodiments, a composition of the disclosure comprises 8 or 9 essential amino acids or a salt of any amino acid thereof and 8 or 9 non-essential amino acids or a salt of any amino acid thereof. In some embodiments, a composition of the disclosure comprises 9 essential amino acids or a salt of any amino acid thereof and 7 non-essential amino acids or a salt of any amino acid thereof. In some embodiments, a composition of the disclosure comprises 9 essential amino acids or a salt of any amino acid thereof and 8 non-essential amino acids or a salt of any amino acid thereof. In some embodiments, a composition of the disclosure comprises 9 essential amino acids or a salt of any amino acid thereof and 9 non-essential amino acids or a salt of any amino acid thereof. A salt of an amino acid disclosed herein can be a pharmaceutically acceptable salt.

In some embodiments, a composition of the disclosure comprises histidine, isoleucine, leucine, lysine, methionine, cysteine, phenylalanine, tyrosine, threonine, tryptophan, valine, arginine, glutamine, alanine, aspartic acid, asparagine, glutamic acid or proline. In some embodiments, a composition of the disclosure comprises L-histidine, L-isoleucine, L-leucine, L-lysine, L-methionine, L-cysteine, L-phenylalanine, L-tyrosine, L-threonine, L-tryptophan, L-valine, L-arginine, L-glutamine, L-alanine, L-aspartic acid, L-asparagine, L-glutamic acid, or L-proline. Any amino acid disclosed herein can be a hydrate thereof or a salt thereof.

In some embodiments, a composition comprises histidine or a salt thereof, such as L-histidine or L-histidine hydrochloride. In some embodiments, a composition of the disclosure comprises isoleucine or a salt thereof, such as L-isoleucine, L-isoleucine methyl ester hydrochloride, or L-isoleucine ethyl ester hydrochloride. A salt of an amino acid disclosed herein can be a pharmaceutically acceptable salt. In some embodiments, a composition of the disclosure comprises leucine or a salt thereof, such as L-leucine, L-leucine methyl ester hydrochloride, or L-leucine ethyl ester hydrochloride. A salt of an amino acid disclosed herein can be a pharmaceutically acceptable salt. In some embodiments, a composition of the disclosure comprises lysine or a salt thereof, such as L-lysine, L-lysine hydrochloride, or L-lysine dihydrochloride. A salt of an amino acid disclosed herein can be a pharmaceutically acceptable salt. In some embodiments, a composition of the disclosure comprises methionine or a salt thereof, such as L-methionine, L-methionine methyl ester hydrochloride, or L-methionine hydrochloride. A salt of an amino acid disclosed herein can be a pharmaceutically acceptable salt. Any amino acid disclosed herein can be a hydrate thereof or a salt thereof.

In some embodiments, a composition of the disclosure comprises cysteine or a salt thereof, such as L-cysteine, L-cysteine hydrochloride, L-cysteine methyl ester hydrochloride, or L-cysteine ethyl ester hydrochloride. Any composition disclosed herein can use cysteine, L-cysteine, cystine, or L-cystine. Any composition disclosed herein can use cystine in place of cysteine. Any composition disclosed herein can use L-cystine in place of L-cysteine. In some embodiments, a composition discloses cystine or a salt thereof, such as L-cystine. A salt of an amino acid disclosed herein can be a pharmaceutically acceptable salt. In some embodiments, a composition of the disclosure comprises phenylalanine or a salt thereof, such as L-phenylalanine, DL-phenylalanine, or L-phenylalanine methyl ester hydrochloride. In some embodiments, a composition of the disclosure comprises tyrosine or a salt thereof, such as L-tyrosine or L-tyrosine hydrochloride. In some embodiments, a composition of the disclosure comprises threonine or a salt thereof, such as L-threonine or L-threonine methyl ester hydrochloride. In some embodiments, a composition of the disclosure comprises L-tryptophan. In some embodiments, a composition of the disclosure comprises valine or a salt thereof, such as L-valine, L-valine methyl ester hydrochloride, or L-valine ethyl ester hydrochloride. A salt of an amino acid disclosed herein can be a pharmaceutically acceptable salt. Any amino acid disclosed herein can be a hydrate thereof or a salt thereof.

In some embodiments, a composition of the disclosure comprises arginine or a salt thereof, such as L-arginine or L-arginine hydrochloride. In some embodiments, a composition of the disclosure comprises glutamine or a salt thereof, such as L-glutamine or L-glutamine hydrochloride. In some embodiments, a composition of the disclosure comprises alanine or a salt thereof, such as L-alanine or β-alanine. In some embodiments, a composition of the disclosure comprises aspartic acid or a salt thereof, such as L-aspartic acid, D-aspartic acid, L- or D-aspartic acid potassium salt, L- or D-aspartic acid hydrochloride salt; L- or D-aspartic acid magnesium salt, or L- or D-aspartic acid calcium salt. In some embodiments, a composition of the disclosure comprises L-asparagine. In some embodiments, a composition of the disclosure comprises glutamic acid or a salt thereof, such as L-glutamic acid or L-glutamic acid hydrochloride. In some embodiments, a composition of the disclosure comprises proline or a salt thereof, such as L-proline, L-proline hydrochloride, L-proline methyl ester hydrochloride, or L-proline ethyl ester hydrochloride. A salt of an amino acid disclosed herein can be a pharmaceutically acceptable salt.

A composition of the disclosure can be substantially devoid of at least cysteine. In some embodiments, a composition of the disclosure can comprise at most about 2%, at most about 1.8%, at most about 1.6%, at most about 1.4%, at most about 1.2%, at most about 1.0%, at most about 0.8%, at most about 0.7%, at most about 0.6%, at most about 0.5%, at most about 0.4%, at most about 0.3%, at most about 0.2%, or at most about 0.1% of cysteine or a salt thereof. In some embodiments, a composition of the disclosure can comprise at most about 0.5% of cysteine or a salt thereof. In some embodiments, a composition of the disclosure can comprise at most about 0.4% of cysteine or a salt thereof. In some embodiments, a composition of the disclosure can comprise at most about 0.3% of cysteine or a salt thereof. In some embodiments, a composition of the disclosure can comprise at most about 0.2% of cysteine or a salt thereof. In some embodiments, a composition of the disclosure can comprise at most about 0.1% of cysteine or a salt thereof. In some embodiments, a composition of the disclosure does not comprise any cysteine or a salt thereof.

In some embodiments, a composition of the disclosure can further comprise at most about 2%, at most about 1.8%, at most about 1.6%, at most about 1.4%, at most about 1.2%, at most about 1.0%, at most about 0.8%, at most about 0.7%, at most about 0.6%, at most about 0.5%, at most about 0.4%, at most about 0.3%, at most about 0.2%, or at most about 0.1% of glycine or a salt thereof. In some embodiments, a composition of the disclosure can further comprise at most about 0.5% (w/w) of glycine or a salt thereof. In some embodiments, a composition of the disclosure is devoid of glycine. In some embodiments, a composition of the disclosure can further comprise at most about 2%, at most about 1.8%, at most about 1.6%, at most about 1.4%, at most about 1.2%, at most about 1.0%, at most about 0.8%, at most about 0.7%, at most about 0.6%, at most about 0.5%, at most about 0.4%, at most about 0.3%, at most about 0.2%, or at most about 0.1% of serine or a salt thereof. In some embodiments, a composition of the disclosure can further comprise at most about 0.5% (w/w) of serine or a salt thereof. In some embodiments, a composition of the disclosure is devoid of serine. In some embodiments, a composition of the disclosure can further comprise at most about 2%, at most about 1.8%, at most about 1.6%, at most about 1.4%, at most about 1.2%, at most about 1.0%, at most about 0.8%, at most about 0.7%, at most about 0.6%, at most about 0.5%, at most about 0.4%, at most about 0.3%, at most about 0.2%, or at most about 0.1% of proline or a salt thereof. In some embodiments, a composition of the disclosure can further comprise at most about 0.5% (w/w) of proline or a salt thereof. In some embodiments, a composition of the disclosure is devoid of proline.

In some embodiments, a composition of the disclosure comprises at most about 0.5% cysteine and at most about 0.5% glycine. In some embodiments, a composition of the disclosure is devoid of cysteine and glycine. In some embodiments, a composition of the disclosure comprises at most about 0.5% cysteine and at most about 0.5% serine. In some embodiments, a composition of the disclosure is devoid of cysteine and serine. In some embodiments, a composition of the disclosure comprises at most about 0.5% cysteine, at most about 0.5% glycine, and at most about 0.5% (w/w) serine. In some embodiments, a composition of the disclosure is devoid of cysteine, serine, and glycine. In some embodiments, a composition of the disclosure comprises at most about 0.5% cysteine, at most about 0.5% glycine, at most about 0.5% (w/w) serine, and at most about 0.5% (w/w) proline. In some embodiments, a composition of the disclosure is devoid of cysteine, serine, glycine, and proline. Any composition disclosed herein can use cysteine, L-cysteine, cystine, or L-cystine. Any composition disclosed herein can use cystine in place of cysteine. Any composition disclosed herein can use L-cystine in place of L-cysteine.

A composition of the disclosure can have an increased amount of at least one essential amino acid selected from the group consisting of: methionine, histidine, isoleucine, leucine, lysine, phenylalanine, threonine, tryptophan, and valine. In some embodiments, a composition of the disclosure comprises at least about 7.5% (w/w) of at least one essential amino acid selected from the group consisting of: methionine, histidine, isoleucine, leucine, lysine, phenylalanine, threonine, tryptophan, and valine. In some embodiments, a composition of the disclosure can have an increased amount of methionine. In some embodiments, a composition of the disclosure can comprise at least about 5%, at least about 5.5%, at least about 6.0%, at least about 6.5%, at least about 7.0%, at least about 7.5%, at least about 8.0%, at least about 8.5%, at least about 9.0%, at least about 9.5%, or at least about 10.0% of methionine. In some embodiments, a composition of the disclosure can comprise at least about 7.5% of methionine.

In some embodiments, a composition of the disclosure has at most about 0.5% cysteine and at least about 7.5% (w/w) of at least one essential amino acid selected from the group consisting of: methionine, histidine, isoleucine, leucine, lysine, phenylalanine, threonine, tryptophan, and valine. In some embodiments, a composition of the disclosure has at most about 0.5% cysteine and at least about 7.5% (w/w) of methionine. In some embodiments, a composition of the disclosure is devoid of cysteine and comprises at least about 7.5% (w/w) of methionine. In some embodiments, a composition of the disclosure has at most about 0.5% cysteine, at most about 0.5% (w/w) serine, and at least about 7.5% (w/w) of methionine. In some embodiments, a composition of the disclosure is devoid of cysteine and serine and comprises at least about 7.5% (w/w) of methionine. In some embodiments, a composition of the disclosure has at most about 0.5% cysteine, at most about 0.5% (w/w) glycine, and at least about 7.5% (w/w) of methionine. In some embodiments, a composition of the disclosure is devoid of cysteine and glycine and comprises at least about 7.5% (w/w) of methionine. In some embodiments, a composition of the disclosure has at most about 0.5% cysteine, at most about 0.5% (w/w) glycine, at most about 0.5% (w/w) serine, and at least about 7.5% (w/w) of methionine. In some embodiments, a composition of the disclosure is devoid of cysteine, glycine, and serine; and comprises at least about 7.5% (w/w) of methionine. In some embodiments, a composition of the disclosure has at most about 0.5% cysteine, at most about 0.5% (w/w) glycine, at most about 0.5% (w/w) serine, at most about 0.5% (w/w) proline, and at least about 7.5% (w/w) of methionine. In some embodiments, a composition of the disclosure is devoid of cysteine, glycine, serine, and proline; and comprises at least about 7.5% (w/w) of methionine or salts thereof. Any composition disclosed herein can use cysteine, L-cysteine, cystine, or L-cystine. Any composition disclosed herein can use cystine in place of cysteine. Any composition disclosed herein can use L-cystine in place of L-cysteine.

Pharmaceutical Compositions

A pharmaceutical composition of the disclosure can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

A pharmaceutical composition of the disclosure can be a combination of any compositions or dietary products described herein with other chemical components, such as carriers, stabilizers, diluents, dispersing agents, suspending agents, thickening agents, and/or excipients. The pharmaceutical composition facilitates administration of the dietary product to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration. In some embodiments, the composition or dietary product of the disclosure is administered orally.

A pharmaceutical composition can be administered in a local manner, for example, via injection of the dietary product directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compositions or dietary products of the disclosure with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremophor, DMSO, and potassium phosphate buffer.

Pharmaceutical compositions can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical compositions for parenteral administration include aqueous solutions of the active dietary products in water-soluble form. Suspensions of the active dietary products can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the dietary products to allow for the preparation of highly concentrated solutions. Alternatively, the active ingredient can be in powder form for constitution with a suitable vehicle, e.g., sterile pyrogen-free water, before use.

In practicing a method of treatment or use provided herein, therapeutically-effective amounts of the dietary products described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the dietary products used, and other factors. The dietary products can be used singly or in combination with one or more therapeutic agents as components of mixtures.

Pharmaceutical compositions can be formulated using one or more physiologically-acceptable carriers comprising excipients and auxiliaries, which facilitate processing of the active dietary products into preparations that can be used pharmaceutically. Formulations can be modified depending upon the route of administration chosen. Pharmaceutical compositions comprising a dietary product described herein can be manufactured, for example, by mixing, dissolving, emulsifying, encapsulating, entrapping, or compression processes.

The pharmaceutical compositions can include at least one pharmaceutically-acceptable carrier, diluent, or excipient and dietary products described herein as free-base or pharmaceutically-acceptable salt form. Pharmaceutical compositions can contain solubilizers, stabilizers, tonicity enhancing agents, buffers and preservatives.

Methods for the preparation of compositions comprising the dietary products described herein include formulating the dietary products with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a dietary product is dissolved, emulsions comprising a dietary product, or a solution containing liposomes, micelles, or nanoparticles comprising a dietary product as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, powder, gel, nanosuspension, nanoparticle, microgel, aqueous or oily suspensions, emulsion, and any combination thereof.

Non-limiting examples of pharmaceutically-acceptable excipients suitable for use in the disclosure include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

Anti-adherent: A composition of the disclosure can comprise an anti-adherent. In some embodiments, a composition of the disclosure can comprise an anti-adherent, such as magnesium stearate.

Binding agent: A composition of the disclosure can comprise at least one binding agent to hold the composition together. In some embodiments, a composition of the disclosure can comprise a binding agent, such as a saccharide, protein, or synthetic polymer. In some embodiments, a composition of the disclosure can comprise a disaccharide (e.g., sucrose or lactose), a polysaccharide or polysaccharide derivative (e.g., starch, cellulose, modified cellulose, cellulose ether), or a sugar alcohol (e.g., xylitol, sorbitol, or mannitol). In some embodiments, a composition of the disclosure can comprise a protein binder, such as gelatin. In some embodiments, a composition of the disclosure can comprise a synthetic polymer binder, such as polyvinylpyrrolidone (PVP) or polyethylene glycol (PEG).

Preservative: A composition of the disclosure can comprise at least one preservative. In some embodiments, a composition of the disclosure can comprise an antioxidant or an antimicrobial. Antioxidant agents delay or prevent the deterioration of the composition by oxidative mechanisms. Antimicrobial agents inhibit the growth of spoilage or pathogenic microorganisms in the composition.

Antioxidant: In some embodiments, an antioxidant agent is added to the composition to delay or prevent autoxidation of unsaturated fatty acids or enzyme-catalyzed oxidation. In some embodiments, a composition of the disclosure comprises at least one of ascorbic acid, butylated hydroxyanisole (BHA), butylated hydroxytoluene (BHT), citric acid, a sulfite, tertiary butylhydroquinone (TBHQ), or a tocopherol. In some embodiments, a composition of the disclosure comprises ascorbic acid. In some embodiments, a composition of the disclosure comprises BHT. In some embodiments, a composition of the disclosure comprises citric acid.

In some embodiments, a composition of the disclosure comprises about 100 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg of an antioxidant agent. In some embodiments, a composition of the disclosure comprises up to about 100 mg/kg, up to about 200 mg/kg, up to about 300 mg/kg, up to about 400 mg/kg, up to about 500 mg/kg, up to about 600 mg/kg, up to about 700 mg/kg, up to about 800 mg/kg, up to about 900 mg/kg, or up to about 1000 mg/kg of an antioxidant agent.

Antimicrobial agent: In some embodiments, an antimicrobial agent is added to the composition to delay or prevent growth of spoilage or pathogenic microorganisms in the composition. In some embodiments, a composition of the disclosure comprises at least one of acetic acid, benzoic acid, natamycin, nisin, a nitrate, a nitrite, propionic acid, sorbic acid, a sulfite, or sulfur dioxide.

In some embodiments, a composition of the disclosure comprises about 100 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg of an antimicrobial agent. In some embodiments, a composition of the disclosure comprises up to about 100 mg/kg, up to about 200 mg/kg, up to about 300 mg/kg, up to about 400 mg/kg, up to about 500 mg/kg, up to about 600 mg/kg, up to about 700 mg/kg, up to about 800 mg/kg, up to about 900 mg/kg, or up to about 1000 mg/kg of an antimicrobial agent.

Colorants: A composition of the disclosure can comprise at least one colorant. In some embodiments, a composition of the disclosure comprises a natural colorant or a synthetic colorant. In some embodiments, a composition of the disclosure comprises a natural colorant. In some embodiments, a composition of the disclosure comprises an anthocyanin. In some embodiments, a composition of the disclosure comprises an anthocyanin, such as pelargonidin-3-glucoside obtained from strawberries (*Fragaria* species) or malvidin-3-glucoside obtained from grapes (*Vitis* species). In some embodiments, a composition of the disclosure comprises a betacyanin. In some embodiments, a composition of the disclosure comprises a betacyanin, such as betanin obtained from beet root (*Beta vulgaris*). In some embodiments, a composition of the disclosure comprises a carotenoid. In some embodiments, a composition of the disclosure comprises a carotenoid, such as bixin obtained from annatto (*Bixa Orellana*); crocin obtained from saffron (*Crocus sativus*); capsanthin obtained from paprika (*Capsicum annuum*); beta-carotene obtained from carrot (*Daucus carota*); or canthaxanthin obtained from mushrooms (*Cantharellus cinnabarinus*). In some embodiments, a composition of the disclosure comprises a phenolic. In some embodiments, a composition of the disclosure comprises a phenolic, such as curcumin obtained from turmeric (*Cuycuma longa*).

In some embodiments, a composition of the disclosure comprises a synthetic colorant. In some embodiments, a composition of the disclosure comprises allura red AC, brilliant blue FCF, erythrosine, fast green FCF, indico carmine, sunset yellow FCF, or tartrazine. In some embodiments, a composition of the disclosure comprises FD&C red no. 40, FD&C blue no. 1, FD&C red no. 3, FD&C green no. 3, FD&C blue no. 2, FD&C yellow no. 6, or FD&C yellow no. 5. In some embodiments, a composition of the disclosure comprises E133, E127, E132, E110, or E102.

Flavorants: A composition of the disclosure can comprise at least one flavoring agent. In some embodiments, a composition of the disclosure can comprise a natural flavoring substance, a nature-identical flavoring substance, or an artificial flavoring substance. In some embodiments, a composition of the disclosure can comprise a natural flavoring substance, such as a spice, fruit juice, or vegetable juice. In some embodiments, a composition of the disclosure can comprise a nature-identical flavoring substance, such as vanillin.

In some embodiments, a composition of the disclosure can comprise an artificial flavoring substance, such as allylpyrazine, methoxypyrazine, 2-iso-butyl-3-methoxypyrazine, acetyl-L-pyrazine, 2-acetoxy pyrazine, aldehydes, alcohols, esters, ketones, pyrazines, phenolics, or terpenoids.

Sweetener: A composition of the disclosure can comprise at least one sweetener. In some embodiments, a composition of the disclosure comprises sucrose, glucose, fructose, corn syrup, high-fructose corn syrup, or a sugar alcohol. In some embodiments, a composition of the disclosure comprises a sugar alcohol, such as sorbitol, mannitol, or xylitol. In some embodiments, a composition of the disclosure comprises fructose. In some embodiments, a composition of the disclosure comprises a synthetic sweetener. In some embodiments, a composition of the disclosure comprises saccharin, a cyclamate, aspartame, or acesulfame K. In some embodiments, a composition of the disclosure comprises aspartame.

In some embodiments, a composition of the disclosure can comprise a sweetener in an amount of about 0.5 g/serving, about 1 g/serving, about 1.5 g/serving, about 2 g/serving, about 2.5 g/serving, about 3 g/serving, about 3.5 g/serving, about 4 g/serving, about 4.5 g/serving, about 5 g/serving, about 5.5 g/serving, about 6 g/serving, about 6.5 g/serving, about 7 g/serving, about 7.5 g/serving, about 8 g/serving, about 8.5 g/serving, about 9 g/serving, about 9.5 g/serving, or about 10 g/serving. In some embodiments, a composition of the disclosure can comprise about 1 g/serving of a sweetener. In some embodiments, a composition of the disclosure can comprise about 2.5 g/serving of a sweetener. In some embodiments, a composition of the disclosure can comprise about 5 g/serving of a sweetener.

Processing agents: A composition of the disclosure can comprise at least one processing additive. In some embodiments, a composition of the disclosure can comprise an anticaking agent, a bleaching agent, a chelating agent, a clarifying agent, conditioning agent, emulsifying agent, a humectant, a pH control agent, a stabilizing agent, or a thickening agent. In some embodiments, a composition of the disclosure can comprise an anticaking agent such as sodium aluminosilicate, a chelating agent such as ethylenediaminetetraacetic acid (EDTA), a conditioning agent such as potassium bromate, or a pH control agent such as citric acid or lactic acid. In some embodiments, a composition of the disclosure can comprise a humectant such as glycerol, or a stabilizing and thickening agent such as pectin, gelatin, carrageenan, or guar gum.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

A composition of the disclosure can be, for example, an immediate release form or a controlled release formulation. An immediate release formulation can be formulated to allow the dietary products to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a dietary product's action for an extended period of time. A delayed release form can be formulated to delay the release of an effective dose of one or more dietary products, for example, for about 4, about 8, about 12, about 16, or about 24 h.

A controlled release formulation can be a sustained release form. A sustained release form can be formulated to sustain, for example, the dietary product's action over an extended period of time. A sustained release form can be formulated to provide an effective dose of any dietary product described herein (e.g., provide a physiologically-effective blood profile) over about 4, about 8, about 12, about 16 or about 24 h.

Pharmaceutical compositions described herein can be in unit dosage forms suitable for single administration of precise dosages. In unit dosage form, the formulation is divided into unit doses containing appropriate quantities of one or more dietary products. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

A composition of the disclosure can comprise at least one pharmaceutical excipient, such as an anti-adherent, a binder, coating, colorant, disintegrant, flavorant, preservative, sorbent, sweetener, or vehicle. In some embodiment, a composition of the disclosure comprises a colorant and a flavorant. In some embodiment, a composition of the disclosure comprises a colorant, flavorant, and sweetener. In some embodiment, a composition of the disclosure comprises a flavorant, sweetener, and a preservative.

Supplements: A composition of the disclosure can be administered to a subject that is administered at least one supplement. In some embodiments, a composition of the disclosure is administered to the subject with an energy supplement. In some embodiments, a composition of the disclosure is administered to the subject with an energy supplement, such as caffeine, guarana, Asian ginseng, vitamin B12, or coenzyme Q10. In some embodiments, a composition of the disclosure is administered to the subject with an energy supplement, such as caffeine, tyrosine, pyrroloquinoline quinone (PQQ), theanine, coenzyme Q10, acetyl-L-carnitine (ALCAR), alpha-lipoic acid (ALA), citicoline, creatine, citrulline, beetroot powder, Ashwagandha, or *Rhodiola rosea*. In some embodiments, a composition of the disclosure is administered to the subject with coenzyme Q10.

In some embodiments, a composition of the disclosure is administered to the subject with a micronutrient supplement. In some embodiments, a composition of the disclosure is administered to the subject with a multivitamin. In some embodiments, a composition of the disclosure is administered to the subject with a vitamin supplement, such as vitamin C or vitamin D supplement. In some embodiments, a composition of the disclosure is administered to the subject with a mineral supplement, such as an iron or zinc supplement.

In some embodiments, a composition of the disclosure is administered to the subject with an energy supplement and a micronutrient supplement. In some embodiments, a composition of the disclosure is administered to a subject with coenzyme Q10 and a multivitamin. In some embodiments, a composition of the disclosure is administered to a subject with coenzyme Q10 and a mineral supplement.

Vitamins: A composition of the disclosure can comprise one or more essential vitamins. In some embodiments, a composition of the disclosure can comprise vitamin A, vitamin C, vitamin D, vitamin E, vitamin K, and vitamin B. In some embodiments, a composition of the disclosure can comprise thiamine (vitamin B1), riboflavin (vitamin B2), niacin (vitamin B3), pantothenic acid (vitamin B5), pyroxidine (vitamin B6), biotin (vitamin B7), folate (vitamin B9), or cobalamin (vitamin B12). In some embodiments, a composition of the disclosure can comprise a fat-soluble vitamin, such as vitamin A, vitamin D, vitamin E, or vitamin K. In some embodiments, a composition of the disclosure can comprise a water-soluble vitamin, such as vitamin C and vitamin B. In some embodiments, a composition of the disclosure can comprise a water-soluble vitamin, such as vitamin B, such as thiamine (vitamin B1), riboflavin (vitamin B2), niacin (vitamin B3), pantothenic acid (vitamin B5), pyroxidine (vitamin B6), biotin (vitamin B7), folate (vitamin B9), or cobalamin (vitamin B12).

In some embodiments, a composition of the disclosure can comprise vitamin A, vitamin B, vitamin C, vitamin D, and vitamin E. In some embodiments, a composition of the disclosure can comprise vitamin A, vitamin C, vitamin D, vitamin E, thiamine (vitamin B1), riboflavin (vitamin B2), niacin (vitamin B3), pantothenic acid (vitamin B5), pyroxidine (vitamin B6), biotin (vitamin B7), folate (vitamin B9), and cobalamin (vitamin B12).

A composition of the disclosure can comprise the recommended dietary allowance of vitamins in a male adult. In some embodiments, a composition of the disclosure comprises the recommended dietary allowance of vitamins in a male adult: vitamin A, 900 µg; vitamin C, 90 mg; vitamin D, 15 µg; vitamin E, 15 mg; vitamin K, 120 µg; thiamine, 1.2 mg; riboflavin, 1.3 mg; niacin, 16 mg; pantothenic acid, 5 mg; pyroxidine, 1.3 mg; biotin, 30 µg; folate, 400 µg; and choline, 550 mg. A composition of the disclosure can comprise the recommended dietary allowance of vitamins in a female adult. In some embodiments, a composition of the disclosure comprises the recommended dietary allowance of vitamins in a female adult: vitamin A, 700 µg; vitamin C, 75 mg; vitamin D, 15 µg; vitamin E, 15 mg; vitamin K, 90 µg; thiamine, 1.1 mg; riboflavin, 1.1 mg; niacin, 14 mg; pantothenic acid, 5 mg; pyroxidine, 1.3 mg; biotin, 30 µg; folate, 400 µg; and choline, 425 mg.

A composition of the disclosure can comprise about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of any of the recommended dietary allowance of vitamins in a male or female adult. In some embodiments, a composition of the disclosure can comprise about 20%, about 30%, about 40%, about 50%, or about 60% of any of the recommended dietary allowance of vitamins in a male or female adult. In some embodiments, a composition of the disclosure can comprise about 30% of any of the recommended dietary allowance of vitamins in a male or female adult. In some embodiments, a composition of the disclosure can comprise about 50% of any of the recommended dietary allowance of vitamins in a male or female adult.

Minerals: A composition of the disclosure can comprise one or more minerals or elements. In some embodiments, a composition of the disclosure can comprise calcium, chromium, copper, fluoride, iodide, iron, magnesium, manganese, molybdenum, phosphorous, selenium, zinc, potassium, sodium, or chloride.

A composition of the disclosure can comprise the recommended daily allowance of elements or minerals in a male adult. In some embodiments, a composition of the disclosure comprises a recommended daily allowance of elements or minerals in a male adult: calcium, 1000 mg; chromium, 35 µg; copper, 900 µg; fluoride, 4 mg; iodide, 150 µg; iron, 8 mg; magnesium, 400 mg; manganese, 2.3 mg; molybdenum, 45 µg; phosphorous, 700 mg; selenium, 55 µg; zinc, 11 mg; potassium, 3400 mg; sodium, 1500 mg; or chloride, 2.3 g. A composition of the disclosure can comprise the recommended daily allowance of elements or minerals in a female adult. In some embodiments, a composition of the disclosure comprises a recommended daily allowance of elements or minerals in a female adult: calcium, 1000 mg; chromium, 25 µg; copper, 900 µg; fluoride, 3 mg; iodide, 150 µg; iron, 18 mg; magnesium, 310 mg; manganese, 1.8 mg; molybdenum, 45 µg; phosphorous, 700 mg; selenium, 55 µg; zinc, 8 mg; potassium, 2600 mg; sodium, 1500 mg; or chloride, 2.3 g.

A composition of the disclosure can comprise about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of any of the recommended dietary allowance of elements or minerals in a male or female adult. In some embodiments, a composition of the disclosure can comprise about 20%, about 30%, about 40%, about 50%, or about 60% of any of the recommended dietary allowance of elements or minerals in a male or female adult. In some embodiments, a composition of the disclosure can comprise about 30% of any of the recommended dietary allowance of elements or minerals in a male or female adult. In some embodiments, a composition of the disclosure can comprise about 50% of any of the recommended dietary allowance of elements or minerals in a male or female adult.

Lipids: A composition of the disclosure can comprise fat. In some embodiments, a pharmaceutical composition of the disclosure can comprise saturated fat, trans fat, polyunsaturated fat, or monounsaturated fat. In some embodiments, a composition of the disclosure can comprise saturated fat, trans fat, polyunsaturated fat, and monounsaturated fat. In some embodiments, a composition of the disclosure can comprise about 1 g, about 2 g, about 3 g, about 4 g, about 5 g, about 6 g, about 7 g, about 8 g, about 9 g, or about 10 g of combined fat content. In some embodiments, a composition of the disclosure can comprise about 5 g of combined fat content.

In some embodiments, a composition of the disclosure comprises cholesterol. In some embodiments, a composition of the disclosure comprises about 100 mg/serving of cholesterol. In some embodiments, a composition of the disclosure comprises about 50 mg/serving of cholesterol.

Carbohydrates: In some embodiments, a composition of the disclosure comprises a carbohydrate, such as a sugar, starch, or complex carbohydrate. In some embodiments, a composition of the disclosure comprises a sugar, such as corn syrup, fructose, galactose, glucose, high fructose corn syrup, lactose, maltose, or sucrose. In some embodiments, a composition of the disclosure comprises a sugar alcohol. In some embodiments, a composition of the disclosure comprises a starch. In some embodiments, a composition of the disclosure comprises a resistant starch, such as oats, rice, legumes, raw potato starch, green bananas, or Hi-Maize® flour.

In some embodiments, a composition of the disclosure comprises a complex carbohydrate, such as fiber. In some embodiments, a composition of the disclosure comprises a soluble fiber. In some embodiments, a composition of the disclosure comprises soluble fiber obtained from a food source, such as oatmeal, flax seed, barley, dried peas, apples, or carrots. In some embodiments, a composition of the disclosure comprises a insoluble fiber. In some embodiments, a composition of the disclosure comprises insoluble fiber obtained from a food source, such as seeds, nuts, dark green leafy vegetables, or wheat bran. In some embodiments, a composition of the disclosure comprises fiber, such as inulin, methylcellulose, psyllium, or wheat dextrin.

In some embodiments, a composition of the disclosure is administered to a subject as a nutritionally complete product. In some embodiments, the composition is administered as a meal replacement shake or powder. In some embodiments, the composition is administered via an enteral feeding tube. In some embodiments, the composition is administered as an intravenous topiramate.

Dosing

Pharmaceutical compositions described herein can be in unit dosage forms suitable for single administration of precise dosages. In unit dosage form, the formulation is divided into unit doses containing appropriate quantities of one or more dietary products. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A dose can be expressed in terms of an amount of the drug divided by the mass of the subject, for example, milligrams of drug per kilograms of subject body mass.

A composition described herein can be given to supplement a meal consumed by a subject. A composition described herein can be given as a meal replacement. A composition described herein can be given immediately before or immediately after a meal. A composition described here can be given within about 5 minutes, about 10 minutes, about 15 minutes, about 20 minutes, about 25 minutes, about 30 minutes, about 40 minutes, about one hour, about 2 hours, about 3 hours, about 4 hours, about 5 hours, or about 6 hours before or after a meal.

A composition described herein can be in unit dosage forms suitable for single administration of precise dosages. In unit dosage form, the formulation is divided into unit doses containing appropriate quantities of the composition. In some embodiments, the unit dosage can be in the form of a package containing discrete quantities of the formulation. In some embodiments, formulations of the disclosure can be presented in unit dosage form in single-serving sachet. In some embodiments, formulations of the disclosure can be presented in a single-dose non-reclosable container. In some embodiments, a formulation of the disclosure can be presented in a reclosable container, and the subject can obtain a single-dose serving of the formulation using a scoop or spoon designed to distribute a single-dose serving. In some embodiments, a formulation of the disclosure can be presented in a reclosable container, and the subject can obtain a single-dose serving of the formulation using a scoop or spoon designed to distribute a half-dose serving (i.e., two scoops to distribute one serving).

A composition described herein can be present in a unit dose serving in a range from about 1 g to about 2 g, from about 2 g to about 3 g, from about 3 g to about 4 g, from about 4 g to about 5 g, from about 5 g to about 6 g, from about 6 g to about 7 g, from about 7 g to about 8 g, from about 8 g to about 9 g, from about 9 g to about 10 g, from about 10 g to about 11 g, from about 11 g to about 12 g, from about 12 g to about 13 g, from about 13 g to about 14 g, from about 14 g to about 15 g, from about 15 g to about 16 g, from about 16 g to about 17 g, from about 17 g to about 18 g, from about 18 g to about 19 g, from about 19 g to about 20 g, from about 20 g to about 21 g, from about 21 g to about 22 g, from about 22 g to about 23 g, from about 23 g to about 24 g, or from about 24 g to about 25 g.

A composition described herein can be present in a unit dose serving in an amount of about 1 g, about 2 g, about 3 g, about 4 g, about 5 g, about 6 g, about 7 g, about 8 g, about 9 g, about 10 g, about 11 g, about 12 g, about 13 g, about 14 g, about 15 g, about 16 g, about 17 g, about 18 g, about 19 g, about 20 g, about 21 g, about 22 g, about 23 g, about 24 g, or about 25 g. In some embodiments, a composition described herein is present in a unit dose serving in an amount of about 10 g, 12 g, 15 g, 20 g, or 24 g.

In some embodiments, a composition described herein is present in a unit dose serving in an amount of about 12 g. In some embodiments, a composition described herein is present in a unit dose serving in a sachet in an amount of about 12 g. In some embodiments, a composition described herein is present in a unit dose serving in an amount of about 15 g. In some embodiments, a composition described herein is present in a unit dose serving in a sachet in an amount of about 15 g. In some embodiments, a composition described herein is present in a unit dose serving in an amount of about 24 g. In some embodiments, a composition described herein is present in a unit dose serving in a sachet in an amount of about 24 g.

In some embodiments, a dose of a composition of the disclosure can be expressed in terms of an amount of the drug divided by the mass of the subject, for example, grams of drug per kilograms of subject body mass. In some embodiments, a therapeutically-effective amount of a composition of the disclosure is from about 0.1 g/kg/day to about 0.2 g/kg/day, from about 0.2 g/kg/day to about 0.3 g/kg/day, from about 0.3 g/kg/day to about 0.4 g/kg/day, from about 0.4 g/kg/day to about 0.5 g/kg/day, from about 0.5 g/kg/day to about 0.6 g/kg/day, from about 0.6 g/kg/day to about 0.7 g/kg/day, from about 0.7 g/kg/day to about 0.8 g/kg/day, from about 0.8 g/kg/day to about 0.9 g/kg/day, from about 0.9 g/kg/day to about 1.0 g/kg/day, from about 1.0 g/kg/day to about 1.1 g/kg/day, from about 1.1 g/kg/day to about 1.2 g/kg/day, from about 1.2 g/kg/day to about 1.3 g/kg/day, from about 1.3 g/kg/day to about 1.4 g/kg/day, or from about 1.4 g/kg/day to about 1.5 g/kg/day. In some embodiments, a therapeutically-effective amount of a composition of the disclosure is from about 0.4 g/kg/day to about 0.5 g/kg/day. In some embodiments, a therapeutically-effective amount of a composition of the disclosure is from about 0.6 g/kg/day to about 0.7 g/kg/day. In some embodiments, a therapeutically-effective amount of a composition of the disclosure is from about 0.8 g/kg/day to about 0.9 g/kg/day.

In some embodiments, a therapeutically-effective amount of a composition of the disclosure is about 0.1 g/kg/day, about 0.2 g/kg/day, about 0.3 g/kg/day, about 0.4 g/kg/day, about 0.5 g/kg/day, about 0.6 g/kg/day, about 0.7 g/kg/day, about 0.8 g/kg/day, about 0.9 g/kg/day, about 1.0 g/kg/day, about 1.1 g/kg/day, about 1.2 g/kg/day, about 1.3 g/kg/day, about 1.4 g/kg/day, about 1.5 g/kg/day, about 1.6 g/kg/day, about 1.7 g/kg/day, about 1.8 g/kg/day, about 1.9 g/kg/day, or about 2.0 g/kg/day. In some embodiments, a therapeutically-effective amount of a composition of the disclosure is about 0.6 g/kg/day. In some embodiments, a therapeutically-effective amount of a composition of the disclosure is about 0.7 g/kg/day. In some embodiments, a therapeutically-effective amount of a composition of the disclosure is about 0.8 g/kg/day. In some embodiments, a therapeutically-effective amount of a composition of the disclosure is about 0.9 g/kg/day.

A composition described herein can be provided to a subject to achieve an amount of protein per body weight of the subject. In some embodiments, a composition described herein can be provided to a subject to achieve a range from about 0.2 g protein/kg to about 0.4 g protein/kg, about 0.4 g protein/kg to about 0.6 g protein/kg, about 0.6 g protein/kg to about 0.8 g protein/kg, or about 0.8 g protein/kg to about 1 g protein/kg of body weight of the subject. In some embodiments, a composition described herein can be provided to a subject to achieve a range from about 0.6 g protein/kg to about 0.8 g protein/kg of body weight of the subject.

A composition described herein can be provided to a subject in one or more servings per day. In some embodiments, 1 serving, 2 servings, 3 servings, 4 servings, 5 servings, 6 servings, 7 servings, 8 servings, 9 servings, 10 servings, 11 servings, or 12 servings of a composition described herein is provided to a subject in one day. In some embodiments, 3 servings of a composition described herein is provided to a subject in one day. In some embodiments, 6 servings of a composition described herein is provided to a subject in one day. In some embodiments, 9 servings of a composition described herein is provided to a subject in one day.

Methods of Administration

A composition of the disclosure can be administered to a subject, and the administration can be accompanied by a food-based diet low in or substantially devoid of at least one amino acid. In some embodiments, administration of a composition of the disclosure is accompanied by a food-based diet low in or substantially devoid of one amino acid. In some embodiments, administration of a composition of the disclosure is accompanied by a food-based diet low in or substantially devoid of serine. In some embodiments, administration of a composition of the disclosure is accompanied by a food-based diet low in or substantially devoid of glycine. In some embodiments, administration of a composition of the disclosure is accompanied by a food-based diet low in or substantially devoid of cysteine.

In some embodiments, administration of a composition of the disclosure is accompanied by a food-based diet low in or substantially devoid of at least two amino acids or a salt of any amino acid thereof. In some embodiments, administration of a composition of the disclosure is accompanied by a food-based diet low in or substantially devoid of at least cysteine and glycine. In some embodiments, administration of a composition of the disclosure is accompanied by a food-based diet low in or substantially devoid of at least cysteine and serine. In some embodiments, administration of a composition of the disclosure is accompanied by a food-based diet low in or substantially devoid of at least cysteine and proline.

In some embodiments, administration of a composition of the disclosure is accompanied by a food-based diet low in or substantially devoid of at least three amino acids or a salt of any amino acid thereof. In some embodiments, administration of a composition of the disclosure is accompanied by a food-based diet low in or substantially devoid of at least serine, glycine, and cysteine. In some embodiments, administration of a composition of the disclosure is accompanied by a food-based diet low in or substantially devoid of at least four amino acids or a salt of any amino acid thereof. In some embodiments, administration of a composition of the disclosure is accompanied by a food-based diet low in or substantially devoid of at least cysteine, serine, glycine, and proline. A salt of an amino acid disclosed herein can be a pharmaceutically acceptable salt.

A composition of the disclosure can be administered to a subject that is on a diet. In some embodiments, a composition of the disclosure is administered to the subject, and the subject is on a diet that is low in protein. In some embodiments, a composition of the disclosure is administered to the subject, and the subject is on a low carbohydrate diet. In some embodiments, a composition of the disclosure is administered to the subject, and the subject is on a high-fat, and low-carbohydrate (e.g. ketogenic type diet). In some embodiments, a composition of the disclosure is administered to the subject, and the subject is on a vegetarian diet. In some embodiments, a composition of the disclosure is administered to the subject, and the subject is on a vegan diet. In some embodiments, a composition of the disclosure is administered with a high-methionine diet.

In some embodiments, a composition of the disclosure is administered with a low-cysteine or a low-cystine diet. In some embodiments, a low-cysteine or low-cystine diet provides at most about 50 mg/day, at most about 100 mg/day, at most about 150 mg/day, at most about 200 mg/day, at most about 250 mg/day, at most about 300 mg/day, at most about 350 mg/day, at most about 400 mg/day, at most about 450 mg/day, at most about 500 mg/day, at most about 550 mg/day, at most about 600 mg/day, at most about 650 mg/day, at most about 700 mg/day, at most about 750 mg/day, at most about 800 mg/day, at most about 850 mg/day, at most about 900 mg/day, at most about 950 mg/day, or at most about 1000 mg/day of cysteine or cystine. In some embodiments, a low-cysteine or low-cystine diet provides at most about 250 mg/day of cysteine or cystine. In some embodiments, a low-cysteine or low-cystine diet provides at most about 500 mg/day of cysteine or cystine.

In some embodiments, a composition of the disclosure is administered with a high-methionine diet. In some embodiments, a high-methionine diet provides at least about 100 mg/day, at least about 250 mg/day, at least about 500 mg/day, at least about 750 mg/day, at least about 1000 mg/day, at least about 1250 mg/day, at least about 1500 mg/day, at least about 1750 mg/day, at least about 2000 mg/day, at least about 5 g/day, at least about 10 g/day, at least about 15 g/day, or at least about 20 g/day of methionine or a salt thereof. In some embodiments, a high-methionine diet provides at least about 500 mg/day of methionine or a salt thereof. In some embodiments, a high-methionine diet provides at least about 2 g/day of methionine or a salt thereof. In some embodiments, a high-methionine diet provides at least about 5 g/day of methionine or a salt thereof.

In some embodiments, a composition of the disclosure is administered with a low-cysteine and high-methionine diet. In some embodiments, a composition of the disclosure can be administered with a diet that provides at most about 50 mg/day, at most about 100 mg/day, at most about 150 mg/day, at most about 200 mg/day, at most about 250 mg/day, at most about 300 mg/day, at most about 350 mg/day, at most about 400 mg/day, at most about 450 mg/day, at most about 500 mg/day, at most about 550 mg/day, at most about 600 mg/day, at most about 650 mg/day, at most about 700 mg/day, at most about 750 mg/day, at most about 800 mg/day, at most about 850 mg/day, at most about 900 mg/day, at most about 950 mg/day, or at most about 1000 mg/day of cysteine or cystine; and a diet that provides at least about 100 mg/day, at least about 250 mg/day, at least about 500 mg/day, at least about 750 mg/day, at least about 1000 mg/day, at least about 1250 mg/day, at least about 1500 mg/day, at least about 1750 mg/day, at least about 2000 mg/day, at least about 5 g/day, at least about 10 g/day, at least about 15 g/day, or at least about 20 g/day of methionine or a salt thereof. In some embodiments, a composition of the disclosure can be administered with a diet that provides at most about 300 mg/day of cysteine or cystine; and at least about 500 mg/day of methionine or a salt thereof. In some embodiments, a composition of the disclosure can be administered with a diet that provides at most about 500 mg/day of cysteine or cystine; and at least about 5 g/day of methionine or a salt thereof.

In some embodiments, a composition of the disclosure is administered with a methionine supplement. In some embodiments, a methionine supplement can provide from about 100 mg to about 2000 mg of methionine or a salt thereof. In some embodiments, a methionine supplement can provide from about 100 mg to about 250 mg, from about 250 mg to about 500 mg, from about 500 mg to about 750 mg, from about 750 mg to about 1000 mg, from about 1000 mg to about 1250 mg, from about 1250 mg to about 1500 mg, from about 1500 mg to about 1750 mg, or from about 1750 mg to about 2000 mg of methionine or a salt thereof. In some embodiments, a methionine supplement can provide about 100 mg, about 250 mg, about 500 mg, about 750 mg, about 1000 mg, about 1250 mg, about 1500 mg, about 1750 mg, or about 2000 mg of methionine or a salt thereof. In some embodiments, a methionine supplement can provide about 500 mg of methionine or a salt thereof. In some embodiments, a methionine supplement can provide about 1000 mg of methionine or a salt thereof. In some embodiments, a methionine supplement can provide about 2000 mg of methionine or a salt thereof.

In some embodiments, disclosed herein is a method of treating cancer comprising administering a composition of the disclosure to a subject in need thereof with a diet high in polyamines. In some embodiments, disclosed herein is a method of treating cancer comprising administering a composition of the disclosure to a subject in need thereof with a diet comprising a whole food product with at least about 100 nmol/g, at least about 150 nmol/g, at least about 200 nmol/g, at least about 250 nmol/g, at least about 300 nmol/g, at least about 350 nmol/g, at least about 400 nmol/g, at least about 450 nmol/g, at least about 500 nmol/g, at least about 550 nmol/g, at least about 600 nmol/g, at least about 650 nmol/g, at least about 700 nmol/g, at least about 750 nmol/g, at least about 800 nmol/g, at least about 850 nmol/g, at least about 900 nmol/g, at least about 950 nmol/g, at least about 1000 nmol/g, at least about 1100 nmol/g, at least about 1200 nmol/g, at least about 1300 nmol/g, at least about 1400 nmol/g, at least about 1500 nmol/g, at least about 1600 nmol/g, at least about 1700 nmol/g, at least about 1800 nmol/g, at least about 1900 nmol/g, or at least about 2000 nmol/g of a polyamine, a precursor, or an analog thereof. In some embodiments, disclosed herein is a method of treating cancer comprising administering a composition of the disclosure to a subject in need thereof with a diet comprising a whole food product with at least about 300 nmol/g of a polyamine, a precursor, or an analog thereof. In some embodiments, disclosed herein is a method of treating cancer comprising administering a composition of the disclosure to a subject in need thereof with a diet comprising a whole food product with at least about 500 nmol/g of a polyamine, a precursor, or an analog thereof. In some embodiments, disclosed herein is a method of treating cancer comprising administering a composition of the disclosure to a subject in need thereof with a diet comprising a whole food product with at least about 750 nmol/g of a polyamine, a precursor, or an analog thereof. In some embodiments, disclosed herein is a method of treating cancer comprising administering a composition of the disclosure to a subject in need thereof with a diet comprising a whole food product with at least about 1000 nmol/g of a polyamine, a precursor, or an analog thereof. In some embodiments, disclosed herein is a method of treating cancer comprising administering a composition of the disclosure to a subject in need thereof with a diet comprising a whole food product with at least about 1500 nmol/g of a polyamine, a precursor, or an analog thereof.

In some embodiments, a composition of the disclosure is administered to a subject that is on a low protein diet designed to be low in at least one non-essential amino acid. In some embodiments, a composition of the disclosure is administered to a subject that is on a low protein diet designed to be low in serine and glycine. In some embodiments, a composition of the disclosure is administered to a subject that is on a low protein diet with less than about 2 g/day, about 1.75 g/day, about 1.5 g/day, about 1.25 g/day, about 1 g/day, about 0.75 g/day, or about 0.5 g/day. In some embodiments, a composition of the disclosure is administered to a subject that is on a low protein diet with less than about 500 mg/day, about 450 mg/day, about 400 mg/day, about 350 mg/day, about 300 mg/day, about 250 mg/day, about 200 mg/day, about 150 mg/day, about 100 mg/day, or about 50 mg/day.

Multiple therapeutic agents can be administered in any order or simultaneously. In some embodiments, a composition of the disclosure is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms.

A composition disclosed herein can be administered as soon as is practical after the onset of a disease or condition is detected or suspected, and for a length of time necessary for the treatment of the disease. In some embodiments, the length of time necessary for the treatment of disease is about 12 hours, about 24 hours, about 36 hours, or about 48 hours. In some embodiments, the length of time necessary for the treatment of disease is about 1 day, about 2 days, about 3 days, about 4 days, about 5 days, about 6 days, about 7 days, about 8 days, about 9 days, about 10 days, about 11 days, about 12 days, about 13 days, about 14 days, or about 15 days. In some embodiments, the length of time necessary for the treatment of disease is about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, or about 20 weeks. In some embodiments, the length of time necessary for the treatment of disease is about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months.

In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

A composition of the disclosure can be administered alone continuously throughout a treatment period. In some embodiments, a composition of the disclosure can be administered simultaneously with administration of a therapeutic agent, for example, radiotherapy or chemotherapy. In some embodiments, a composition of the disclosure alone can be administered at least one time a day for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, or 21 days. In some embodiments, a composition of the disclosure alone can be administered at least one time a day for about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, or about 1 year. In some embodiments, a composition of the disclosure can be administered at least one time a day for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, or 21 days, and a therapeutic agent can be administered throughout the treatment period following an appropriate treatment regimen. In some embodiments, a composition of the disclosure can be administered at least one time a day for about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, or about 1 year, and a therapeutic agent can be administered throughout the treatment period following an appropriate treatment regimen.

A composition of the disclosure can be administered intermittently throughout a treatment period. In some embodiments, a subject can be treated with a composition of the disclosure during a treatment period, then go off treatment for an off-treatment period. In some embodiments, the length of the treatment period and off-treatment period are identical. In some embodiments, the length of the treatment period and off-treatment period are different. In some embodiments, the length of the treatment period is longer than the off-treatment period. In some embodiments, the length of the treatment period is shorter than the off-treatment period.

In some embodiments, the length of the treatment period is 5 days, and the length of the off-treatment period is 2 days. In some embodiments, the length of the treatment period is 4 days, and the length of the off-treatment period is 3 days. In some embodiments, the length of the treatment period is 3 days, and the length of the off-treatment period is 4 days. In some embodiments, the length of the treatment period is 2 days, and the length of the off-treatment period is 5 days. In some embodiments, a cycle of a treatment period and an off-treatment period is repeated for 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks.

In some embodiments, a subject can be treated with a composition of the disclosure and a therapeutic agent, then go off treatment before beginning a subsequent treatment cycle with the composition and the therapeutic agent. In some embodiments, the therapeutic agent is radiotherapy. In some embodiments, the therapeutic agent is radiotherapy. In some embodiments, the length of the treatment period and off-treatment period are identical. In some embodiments, the length of the treatment period and off-treatment period are different. In some embodiments, the length of the treatment period is longer than the off-treatment period. In some embodiments, the length of the treatment period is shorter than the off-treatment period. In some embodiments, the length of the treatment period is 5 days, and the length of the off-treatment period is 2 days. In some embodiments, the length of the treatment period is 4 days, and the length of the off-treatment period is 3 days. In some embodiments, the length of the treatment period is 3 days, and the length of the off-treatment period is 4 days. In some embodiments, the length of the treatment period is 2 days, and the length of the off-treatment period is 5 days. In some embodiments, a cycle of a treatment period and an off-treatment period is repeated for 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks.

A composition described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Aqueous suspension compositions can be packaged in single-dose non-reclosable containers. Multiple-dose reclosable containers can be used, for example, in combination with or without a preservative.

In some embodiments, a composition is administered to a subject throughout a day. In some embodiments, a composition is administered to a subject with a meal. In some embodiments, a composition is administered to a subject with a snack. In some embodiments, a composition is administered to a subject without a meal. In some embodiments, a composition is administered to a subject through the day in equal intervals. In some embodiments, a first serving is administered before breakfast, a second serving is administered with breakfast, a third serving is administered with lunch, a fourth and fifth serving is administered with dinner, and a sixth serving is administered before bed.

A composition provided herein can be administered in conjunction with other therapies, for example, chemotherapy, radiation, surgery, anti-inflammatory agents, immunotherapy, biologicals, and selected vitamins. The other agents can be administered prior to, after, or concomitantly with the pharmaceutical compositions.

In some embodiments, a composition of the disclosure can be administered with a high fat diet. In some embodiments, the high fat diet is a diet that has greater than about 50%, about 60%, about 70%, about 80%, or about 90% daily calories from fat. In some embodiments, a composition of the disclosure is administered with a low carbohydrate diet. In some embodiments, the low carbohydrate diet is a diet with less than about 50%, about 40%, about 30%, about 20%, about 10%, or about 5% daily calories from carbohydrates. In some embodiments, a composition of the disclosure is administered with a low protein diet. In some embodiments, the low protein diet is a diet with less than about 15%, about 14%, about 13%, about 12%, about 11%, about 10%, about 9%, about 8%, about 7%, about 6%, about 5%, about 4%, about 3%, about 2%, or about 1% of daily calories from whole protein. In some embodiments, the low protein diet has a whole protein amount of less than about 50 g/day, about 40 g/day, about 30 g/day, about 20 g/day, or about 10 g/day. In some embodiments, a composition of the disclosure is administered with a high fat, low carbohydrate, and low protein diet. In some embodiments, a composition of the disclosure is administered with a normal diet.

In some embodiments, a composition of the disclosure is administered with a diet low in cysteine. In some embodiments, a composition of the disclosure is administered with a diet high in methionine. In some embodiments, a composition of the disclosure is administered with a diet high in polyamines. In some embodiments, a composition of the disclosure is administered with a diet low in cysteine and high in methionine. In some embodiments, a composition of the disclosure is administered with a diet low in cysteine, high in methionine, and high in polyamines.

In some embodiments, disclosed herein is a method of treating cancer comprising administering a composition of the disclosure to a subject in need thereof with a diet low in cysteine, wherein the subject has a cancer that is MTAP-deficient. In some embodiments, disclosed herein is a method of treating cancer comprising administering a composition of the disclosure to a subject in need thereof with a diet high in cysteine, wherein the subject has a cancer that has elevated MTAP levels. In some embodiments, disclosed herein is a method of treating cancer comprising administering a composition of the disclosure to a subject in need thereof with a diet low in cysteine, wherein the subject has a cancer that has dysregulated polyamine metabolism. In some embodiments, disclosed herein is a method of treating cancer comprising administering a composition of the disclosure to a subject in need thereof with a diet low in cysteine and high in methionine, wherein the subject has a cancer that is MTAP-deficient. In some embodiments, disclosed herein is a method of treating cancer comprising administering a composition of the disclosure to a subject in need thereof with a diet low in cysteine and high in methionine, wherein the subject has a cancer that has dysregulated polyamine metabolism.

Combination Therapy

Multiple therapeutic agents can be administered in any order or simultaneously. In some embodiments, a dietary product of the disclosure is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 h of the onset of the symptoms, within the first 24 h of the onset of the symptoms, within the first 6 h of the onset of the symptoms, or within 3 h of the onset of the symptoms. The initial administration can be via any route practical, such as by any route described herein using any formulation described herein.

Polyamines can enhance the ability of a dietary product of the disclosure to treat a condition, for example, a cancer. In some embodiments, a polyamine can be administered to alter polyamine metabolism. In some embodiments, a dietary product of the disclosure can be administered with a polyamine, precursor, or analog thereof. In some embodiments, administering a polyamine, a precursor, or an analog thereof can increase ROS levels in cancer cells. In some embodiments, administering a polyamine, a precursor, or an analog thereof; a dietary product of the disclosure; and a cancer therapy can increase the efficacy of a cancer treatment. In some embodiments, the polyamine is a triamine. In some embodiments, the polyamine is a tetraamine. In some embodiments, the polyamine is spermidine. In some embodiments, the polyamine is spermine. In some embodiments, the polyamine is putrescine. In some embodiments, the polyamine is cadaverine. In some embodiments, the polyamine is a synthetic polyamine, for example, diethylenetriamine (DETA), triethylenetetramine (TETA), tetraethylenepentamine (TEPA), or pentaethylenehyexamine (PEHA). In some embodiments, the polyamine is a macrocyclic polyamine, for example, 1,4,7-triazacyclononane or cyclen. In some embodiments, the polyamine is a branched polyamine, for example, tris(2-aminoethyl)amine.

In some embodiments, a method disclosed herein can administer from about 1 mg to about 25 mg, about 25 mg to about 50 mg, about 50 mg to about 75 mg, about 75 mg to about 100 mg, about 100 mg to about 150 mg, about 150 mg to about 200 mg, about 200 mg to about 250 mg, about 250 mg to about 300 mg, about 300 mg to about 350 mg, about 350 mg to about 400 mg, about 400 mg to about 450 mg, or about 450 mg to about 500 mg of a polyamine, precursor, or analog thereof. In some embodiments, a method disclosed herein can administer from about 1 mg to about 25 mg of a polyamine, precursor, or analog thereof. In some embodiments, a method disclosed herein can administer from about 25 mg to about 50 mg of a polyamine, precursor, or analog thereof. In some embodiments, a method disclosed herein can administer from about 50 mg to about 75 mg of a polyamine, precursor, or analog thereof. In some embodiments, a method disclosed herein can administer from about 75 mg to about 100 mg of a polyamine, precursor, or analog thereof.

In some embodiments, a method disclosed herein can administer about 1 mg, about 5 mg, about 10 mg, about 15 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg of a polyamine, precursor, or analog thereof. In some embodiments, a method disclosed herein can administer about 25 mg of a polyamine, precursor, or analog thereof. In some embodiments, a method disclosed herein can administer about 50 mg of a polyamine, precursor, or analog thereof. In some embodiments, a method disclosed herein can administer about 100 mg of a polyamine, precursor, or analog thereof. In some embodiments, a method disclosed herein can administer about 150 mg of a polyamine, a precursor, or an analog thereof.

In some embodiments, a method disclosed herein can administer about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, about 10 g, about 11 g, about 12 g, about 13 g, about 14 g, about 15 g, about 16 g, about 17 g, about 18 g, about 19 g, about 20 g, about 21 g, about 22 g, about 23 g, about 24 g, about 25 g, about 26 g, about 27 g, about 28 g, about 29 g, or about 30 g of a polyamine, a precursor, or an analog thereof.

Cyst(e)inase is an enzyme that mediates sustained depletion of the extracellular L-cysteine or L-cystine. Treatment with cyst(e)inase selectively causes cell cycle arrest and death in cancer cells due to depletion of intracellular GSH and ensuing elevated ROS. In some embodiments, a dietary product of the disclosure can be administered with a polyamine or analog thereof.

In some embodiments, a method disclosed herein can administer from about 10 mg/kg to about 50 mg/kg, from about 50 mg/kg to about 75 mg/kg, from about 75 mg/kg to about 100 mg/kg, from about 100 mg/kg to about 125 mg/kg, from about 125 mg/kg to about 150 mg/kg, from about 150 mg/kg to about 175 mg/kg, from about 175 mg/kg to about 200 mg/kg, from about 200 mg/kg to about 225 mg/kg, from about 225 mg/kg to about 250 mg/kg, from about 250 mg/kg to about 300 mg/kg, from about 300 mg/kg to about 350 mg/kg, from about 350 mg/kg to about 400 mg/kg, from about 400 mg/kg to about 450 mg/kg, from about 450 mg/kg to about 500 mg/kg, from about 500 mg/kg to about 550 mg/kg, from about 550 mg/kg to about 600 mg/kg, from about 600 mg/kg to about 650 mg/kg, from about 650 mg/kg to about 700 mg/kg, from about 700 mg/kg to about 750 mg/kg, from about 750 mg/kg to about 800 mg/kg, from about 800 mg/kg to about 850 mg/kg, from about 850 mg/kg to about 900 mg/kg, from about 900 mg/kg to about 950 mg/kg, or from about 950 mg/kg to about 1000 mg/kg of a cyst(e)inase. In some embodiments, a method disclosed herein can administer from about 10 mg/kg to about 50 mg/kg of a cyst(e)inase. In some embodiments, a method disclosed herein can administer from about 50 mg/kg to about 100 mg/kg of a cyst(e)inase. In some embodiments, a method disclosed herein can administer from about 100 mg/kg to about 250 mg/kg of a cyst(e)inase.

In some embodiments, a method disclosed herein can administer about 10 mg/kg, about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, about 250 mg/kg, about 275 mg/kg, about 300 mg/kg, about 325 mg/kg, about 350 mg/kg, about 375 mg/kg, about 400 mg/kg, about 425 mg/kg, about 450 mg/kg, about 475 mg/kg, about 500 mg/kg, about 550 mg/kg, about 600 mg/kg, about 650 mg/kg, about 700 mg/kg, about 750 mg/kg, about 800 mg/kg, about 850 mg/kg, about 900 mg/kg, about 950 mg/kg, or about 1000 mg/kg of a cyst(e)inase. In some embodiments, a method disclosed herein can administer about 50 mg/kg of a cyst(e)inase. In some embodiments, a method disclosed herein can administer about 100 mg/kg of a cyst(e)inase. In some embodiments, a method disclosed herein can administer about 150 mg/kg of a cyst(e)inase. In some embodiments, a method disclosed herein can administer about 200 mg/kg of a cyst(e)inase. In some embodiments, a method disclosed herein can administer about 500 mg/kg of a cyst(e)inase.

In some embodiments, a method disclosed herein can administer at least about 5 mg/kg/day, at least about 10 mg/kg/day, at least about 15 mg/kg/day, at least about 20 mg/kg/day, at least about 25 mg/kg/day, at least about 30 mg/kg/day, at least about 35 mg/kg/day, at least about 45 mg/kg/day, or at least about 50 mg/kg/day of methionine or a pharmaceutically acceptable salt thereof. In some embodiments, a method disclosed herein can administer at least about 10 mg/kg/day of methionine or a pharmaceutically acceptable salt thereof. In some embodiments, a method disclosed herein can administer at least about 20 mg/kg/day of methionine or a pharmaceutically acceptable salt thereof. In some embodiments, a method disclosed herein can administer at least about 25 mg/kg/day of methionine or a pharmaceutically acceptable salt thereof.

In some embodiments, a dietary product disclosed herein substantially devoid of at least cysteine is administered with a cysteinase. In some embodiments, a dietary product disclosed herein substantially devoid of at least cysteine is administered with a methionine supplement. In some embodiments, a dietary product disclosed herein substantially devoid of at least cysteine is administered with a methionine supplement and a polyamine. In some embodiments, a dietary product disclosed herein substantially devoid of at least cysteine is administered with a methionine supplement but not a polyamine. In some embodiments, a dietary product disclosed herein substantially devoid of at least cysteine is administered with a methionine supplement, a polyamine, and a cysteinase. In some embodiments, a dietary product disclosed herein substantially devoid of at least cysteine is administered with a polyamine and a cysteinase but not a methionine supplement.

In some embodiments, a dietary product of the disclosure devoid of at least cysteine is administered to a subject with an MTAP-deleted tumor. In some embodiments, a dietary product of the disclosure devoid of at least cysteine and a methionine supplement are administered to a subject with an MTAP-deleted tumor. In some embodiments, a dietary product disclosed herein substantially devoid of at least cysteine is administered to a subject with an MTAP-deleted tumor with a methionine supplement and a polyamine. In some embodiments, a dietary product disclosed herein substantially devoid of at least cysteine is administered to a subject with an MTAP-deleted tumor with a methionine supplement but not a polyamine. In some embodiments, a dietary product disclosed herein substantially devoid of at least cysteine is administered to a subject with an MTAP-deleted tumor with a methionine supplement, a polyamine, and a cysteinase. In some embodiments, a dietary product disclosed herein substantially devoid of at least cysteine is administered to a subject with an MTAP-deleted tumor with a polyamine and a cysteinase but not a methionine supplement.

In some embodiments, radiotherapy can be used in combination with a method or composition of the disclosure to prevent or reduce the likelihood of tumor recurrence after surgery to remove a primary malignant tumor. In some embodiments, radiotherapy and chemotherapy can be used in combination with a method or composition of the disclosure. In some embodiments, a method and compositions of the disclosure can be administered in combination with radiotherapy to treat a cancer. In some embodiments, a method and compositions of the disclosure can be administered in combination with radiotherapy to reduce symptoms of a cancer. In some embodiments, a method and compositions of the disclosure can be administered in combination with radiotherapy to slow the growth of a cancer.

In some embodiments, the radiotherapy is external beam radiation therapy. External beam radiation therapy uses a machine that locally aims radiation at a cancer. In some embodiments, the radiotherapy is internal beam radiation therapy. In some embodiments, external beam radiation can be used to shrink tumors to treat pain, trouble breathing, or loss of bowel or bladder control. In some embodiments, the external-beam radiation therapy is three-dimensional conformal radiation therapy (3D-CRT). In some embodiments, the external-beam radiation therapy is intensity modulated radiation therapy (IMRT). In some embodiments, the external-beam radiation therapy is proton beam therapy. In some embodiments, the external-beam radiation therapy is image-guided radiation therapy (IGRT). In some embodiments, the external-beam radiation therapy is stereotactic radiation therapy (SRT).

Internal radiation therapy is a treatment that places a source of radiation in the subject's body. In some embodiments, the source of radiation is a liquid. In some embodiments, the source of radiation is a solid. In some embodiments, the internal radiotherapy uses a permanent implant. In some embodiments, the internal radiotherapy is a temporary internal radiotherapy, for example, a needle, tube, or applicator. In some embodiments, the solid source of radiation is used in brachytherapy. In some embodiments, seeds, ribbons, or capsules containing a radiation source are placed in a subject's body. In some embodiments, the radiotherapy is brachytherapy, where a radioactive source is placed inside or next to an area requiring treatment. In some embodiments, the radiotherapy is total body irradiation (TBI) in preparation for a bone marrow transplant.

In some embodiments, the radiotherapy is intraoperative radiation therapy (IORT). In some embodiments, the radiotherapy is systemic radiation therapy. In some embodiments, the radiotherapy is radioimmunotherapy. In some embodiments, the radiotherapy uses a radiosensitizer or a radioprotector.

In some embodiments, brachytherapy is used to treat a cancer of the head, neck, breast, cervix, prostate, or eye. In some embodiments, a systemic radiation therapy such as radioactive iodine, or I-131, can be used to treat thyroid cancer. In some embodiments, targeted radionuclide therapy can be used to treat advanced prostate cancer or a gastroenteropancreatic neuroendocrine tumor (GEP-NET). In some embodiments, shaped radiation beams can be aimed from several angles of exposure to intersect at the tumor while sparing normal tissue. In some embodiments, a tumor absorbs a much larger dose of radiation than does a surrounding healthy tissue.

In some embodiments, an amino acid starvation therapy of the disclosure can be used in combination with a chemotherapeutic regimen. In some embodiments, the chemotherapeutic regimen is an immunotherapy. In some embodiments, the immunotherapy is an antibody therapy. In some embodiments, the antibody therapy is treatment with alemtuzumab, rituximab, ibritumomab tiuxetan, or ofatumumab. In some embodiments, the immunotherapy is an interferon. In some embodiments, the interferon is interferon α. In some embodiments, the immunotherapy is an interleukin, for example, IL-2. In some embodiments, the immunotherapy is an interleukin inhibitor, for example, an IRAK4 inhibitor.

In some embodiments, the immunotherapy is a cancer vaccine. In some embodiments, the cancer vaccine is a prophylactic vaccine. In some embodiments, the cancer vaccine is a treatment vaccine. In some embodiments, the cancer vaccine is an HPV vaccine, for example, Gardisil™ Cervarix, Oncophage, or Sipuleucel-T. In some embodiments, the immunotherapy is gp100. In some embodiments, the immunotherapy is a dendritic cell-based vaccine, for example, Ad.p53 DC. In some embodiments, the immunotherapy is a toll-like receptor modulator, for example, TLR-7 or TLR-9. In some embodiments, the immunotherapy is a PD-1, PD-L1, PD-L2, or CTL4-A modulator, for example, nivolumab. In some embodiments, the immunotherapy is an IDO inhibitor, for example, indoximod. In some embodiments, the immunotherapy is an anti-PD-1 monoclonal antibody, for example, MK3475 or nivolumab. In some embodiments, the immunotherapy is an anti-PD-L1 monoclonal antibody, for example, MEDI-4736 or RG-7446. In some embodiments, the immunotherapy is an anti-PD-L2 monoclonal antibody. In some embodiments, the immunotherapy is an anti-CTL1-4 antibody, for example, ipilumumab.

In some embodiments, a composition or dietary product of the disclosure can be administered with an MTAP inhibitor. In some embodiments, the MTAP inhibitor is MTDIA, also known as MT-DADMe-ImmA or methylthio-DADMe-Immunicillin A.

Therapeutic Effects

Disclosed herein is a method of treating a cancer, the method comprising administering to a subject in need thereof a therapeutically-effective amount of a composition of the disclosure. In some embodiments, a composition of the disclosure can decrease cell proliferation, decrease tumor size, or decrease an amount of at least one amino acid.

A composition of the disclosure can decrease cell proliferation in a subject. In some embodiments, administering a composition of a disclosure can decrease cell proliferation in a subject by from about 5% to about 10%, from about 10% to about 15%, from about 15% to about 20%, from about 20% to about 25%, from about 25% to about 30%, from about 35% to about 40%, from about 40% to about 45%, from about 45% to about 50%, from about 50% to about 75%, from about 75% to about 100%, from about 100% to about 125%, from about 125% to about 150%, from about 150% to about 175%, or from about 175% to about 200% compared to a subject that is not administered the dietary composition. In some embodiments, administering a composition of a disclosure can decrease cell proliferation in a subject by from about 20% to about 25% compared to a subject that is not administered the dietary composition. In some embodiments, administering a composition of a disclosure can decrease cell proliferation in a subject by from about 50% to about 75% compared to a subject that is not administered the dietary composition.

In some embodiments, administering a composition of a disclosure can decrease cell proliferation in a subject by about 5%, about 10%, about 15%, about 20%, about 25%, about 30%, about 35%, about 40%, about 45%, about 50%, about 75%, about 100%, about 125%, about 150%, about 175%, or about 200% compared to a subject that is not administered the dietary composition. In some embodiments, administering a composition of a disclosure can decrease cell proliferation in a subject by about 20% compared to a subject that is not administered the dietary composition. In some embodiments, administering a composition of a disclosure can decrease cell proliferation in a subject by about 30% compared to a subject that is not administered the dietary composition. In some embodiments, administering a composition of a disclosure can decrease cell proliferation in a subject by about 50% compared to a subject that is not administered the dietary composition. In some embodiments, administering a composition of a disclosure can decrease cell proliferation in a subject by about 70% compared to a subject that is not administered the dietary composition.

In some embodiments, administering a composition of the disclosure can decrease a tumor size in a subject by from about 5% to about 10%, from about 10% to about 15%, from about 15% to about 20%, from about 20% to about 25%, from about 25% to about 30%, from about 35% to about 40%, from about 40% to about 45%, from about 45% to about 50%, from about 50% to about 75%, from about 75% to about 100%, from about 100% to about 125%, from about 125% to about 150%, from about 150% to about 175%, or from about 175% to about 200%. In some embodiments, administering a composition of the disclosure can decrease a tumor size in a subject by from about 20% to about 25%. In some embodiments, administering a composition of the disclosure can decrease a tumor size in a subject by from about 45% to about 50%.

In some embodiments, administering a composition of the disclosure can decrease a tumor size in a subject by about 5%, about 10%, about 15%, about 20%, about 25%, about 30%, about 35%, about 40%, about 45%, about 50%, about 75%, about 100%, about 125%, about 150%, about 175%, or about 200%. In some embodiments, administering a composition of the disclosure can decrease a tumor size in a subject by about 20%. In some embodiments, administering a composition of the disclosure can decrease a tumor size in a subject by about 30%. In some embodiments, administering a composition of the disclosure can decrease a tumor size in a subject by about 50%.

In some embodiments, administering a composition of the disclosure devoid of at least cysteine or cystine can decrease an amount of circulating cysteine or cystine in the serum, plasma, or blood of a subject by at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, or at least about 98%. In some embodiments, administering a composition of the disclosure can decrease an amount of circulating cysteine or cystine in the serum, plasma, or blood of a subject by at least about 75%. In some embodiments, administering a composition of the disclosure can decrease an amount of circulating cysteine or cystine in the serum, plasma, or blood of a subject by at least about 80%. In some embodiments, administering a composition of the disclosure can decrease an amount of circulating cysteine or cystine in the serum, plasma, or blood of a subject by at least about 85%.

In some embodiments, administering a composition of the disclosure devoid of at least cysteine or cystine can decrease a level of tissue cysteine or cystine in the subject by at least about 10%, at least about 20%, at least about 30%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, or at least about 98%, as measured by LC-MS analysis of a tissue sample. In some embodiments, administering a composition of the disclosure can decrease a level of tissue cysteine or cystine in the subject by at least about 75%. In some embodiments, administering a composition of the disclosure can decrease a level of tissue cysteine or cystine in the subject by at least about 80%. In some embodiments, administering a composition of the disclosure can decrease a level of tissue cysteine or cystine in the subject by at least about 85%.

In some embodiments, administering a composition of the disclosure devoid of at least cysteine or cystine and at least one additional amino acid can decrease an amount of circulating cysteine or cystine or the at least one additional amino acid in the subject by at least about 10%, at least about 20%, at least about 30%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, or at least about 98%, as measured by LC-MS analysis of a tissue sample. In some embodiments, administering a composition of the disclosure can decrease an amount of circulating cysteine or cystine or the at least one additional amino acid in the subject by at least about 75%. In some embodiments, administering a composition of the disclosure can decrease an amount of circulating cysteine or cystine or the at least one additional amino acid in the subject by at least about 80%. In some embodiments, administering a composition of the disclosure can decrease an amount of circulating cysteine or cystine or the at least one additional amino acid in the subject by at least about 85%.

In some embodiments, administering a composition of the disclosure devoid of at least cysteine or cystine and at least one additional amino acid can decrease a level of tissue cysteine or cystine or the at least one additional amino acid in the subject by at least about 10%, at least about 20%, at least about 30%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, or at least about 98%, as measured by LC-MS analysis of a tissue sample. In some embodiments, administering a composition of the disclosure can decrease a level of tissue cysteine or cystine or the at least one additional amino acid in the subject by at least about 75%. In some embodiments, administering a composition of the disclosure can decrease a level of tissue cysteine or cystine or the at least one additional amino acid in the subject by at least about 80%. In some embodiments, administering a composition of the disclosure can decrease a level of tissue cysteine or cystine or the at least one additional amino acid in the subject by at least about 85%.

In some embodiments, administering a composition of the disclosure devoid of at least cysteine or cystine can decrease an amount of circulating cysteine or cystine in the subject for at least about 2 hours, at least about 4 hours, at least about 6 hours, at least about 8 hours, at least about 10 hours, at least about 12 hours, at least about 14 hours, at least about 16 hours, at least about 18 hours, at least about 20 hours, at least about 22 hours, at least about 24 hours, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, or at least about 14 days, as measured by LC-MS analysis of a tissue sample. In some embodiments, administering a composition of the disclosure devoid of at least cysteine or cystine can decrease an amount of circulating cysteine or cystine in the subject for at least about 8 hours. In some embodiments, administering a composition of the disclosure devoid of at least cysteine or cystine can decrease an amount of circulating cysteine or cystine in the subject for at least about 12 hours. In some embodiments, administering a composition of the disclosure devoid of at least cysteine or cystine can decrease an amount of circulating cysteine or cystine in the subject for at least about 18 hours.

In some embodiments, administering a composition of the disclosure devoid of at least cysteine or cystine can decrease a level of tissue cysteine or cystine in the subject for at least about 2 hours, at least about 4 hours, at least about 6 hours, at least about 8 hours, at least about 10 hours, at least about 12 hours, at least about 14 hours, at least about 16 hours, at least about 18 hours, at least about 20 hours, at least about 22 hours, at least about 24 hours, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, or at least about 14 days, as measured by LC-MS analysis of a tissue sample. In some embodiments, administering a composition of the disclosure devoid of at least cysteine or cystine can decrease a level of tissue cysteine or cystine in the subject for at least about 8 hours. In some embodiments, administering a composition of the disclosure devoid of at least cysteine or cystine can decrease a level of tissue cysteine or cystine in the subject for at least about 12 hours. In some embodiments, administering a composition of the disclosure devoid of at least cysteine or cystine can decrease a level of tissue cysteine or cystine in the subject for at least about 18 hours.

Administering a composition of the disclosure devoid of at least cysteine or cystine can increase overall survival of a subject. In some embodiments, administering a composition of the disclosure devoid of at least cysteine or cystine can increase overall survival of a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, administering a composition of the disclosure devoid of at least cysteine or cystine can increase overall survival of a subject by at least about 10%. In some embodiments, administering a composition of the disclosure devoid of at least cysteine or cystine can increase overall survival of a subject by at least about 20%. In some embodiments, administering a composition of the disclosure devoid of at least cysteine or cystine can increase overall survival of a subject by at least about 30%.

Administering a composition of the disclosure devoid of at least cysteine or cystine can increase progression free survival of a subject. In some embodiments, administering a composition of the disclosure devoid of at least cysteine or cystine can increase progression free survival of a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, administering a composition of the disclosure devoid of at least cysteine or cystine can increase progression free survival of a subject by at least about 10%. In some embodiments, administering a composition of the disclosure devoid of at least cysteine or cystine can increase progression free survival of a subject by at least about 20%. In some embodiments, administering a composition of the disclosure devoid of at least cysteine or cystine can increase progression free survival of a subject by at least about 30%.

Administering a composition of the disclosure devoid of at least cysteine or cystine can increase percentage of cancer cell death. In some embodiments, administering a composition of the disclosure devoid of at least cysteine or cystine can increase percentage of cancer cell death by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, administering a composition of the disclosure devoid of at least cysteine or cystine can increase percentage of cancer cell death by at least about 10%. In some embodiments, administering a composition of the disclosure devoid of at least cysteine or cystine can increase percentage of cancer cell death by at least about 20%. In some embodiments, administering a composition of the disclosure devoid of at least cysteine or cystine can increase percentage of cancer cell death by at least about 30%.

Administering a composition of the disclosure devoid of at least cysteine or cystine can increase ferroptosis in a tumor cell. In some embodiments, administering a composition of the disclosure devoid of at least cysteine or cystine can increase ferroptosis in a tumor cell by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, administering a composition of the disclosure devoid of at least cysteine or cystine can increase ferroptosis in a tumor cell by at least about 10%. In some embodiments, administering a composition of the disclosure devoid of at least cysteine or cystine can increase ferroptosis in a tumor cell by at least about 20%. In some embodiments, administering a composition of the disclosure devoid of at least cysteine or cystine can increase ferroptosis in a tumor cell by at least about 30%.

Administering a composition of the disclosure devoid of at least cysteine or cystine can increase sensitivity to a cancer therapy in a subject. In some embodiments, administering a composition of the disclosure devoid of at least cysteine or cystine can increase sensitivity to a cancer therapy in a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, administering a composition of the disclosure devoid of at least cysteine or cystine can increase sensitivity to a cancer therapy in a subject by at least about 10%. In some embodiments, administering a composition of the disclosure devoid of at least cysteine or cystine can increase sensitivity to a cancer therapy in a subject by at least about 20%. In some embodiments, administering a composition of the disclosure devoid of at least cysteine or cystine can increase sensitivity to a cancer therapy in a subject by at least about 30%.

Administering a composition of the disclosure devoid of at least cysteine or cystine can increase a treatment response rate of a therapeutic agent. In some embodiments, administering a composition of the disclosure devoid of at least cysteine or cystine can increase a treatment response rate of a therapeutic agent by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, administering a composition of the disclosure devoid of at least cysteine or cystine can increase a treatment response rate of a therapeutic agent by at least about 10%. In some embodiments, administering a composition of the disclosure devoid of at least cysteine or cystine can increase a treatment response rate of a therapeutic agent by at least about 20%. In some embodiments, administering a composition of the disclosure devoid of at least cysteine or cystine can increase a treatment response rate of a therapeutic agent by at least about 30%.

Administering a composition of the disclosure devoid of at least cysteine or cystine with a therapeutic agent can increase the efficacy of the therapeutic agent in a subject compared to a subject treated only with the composition of the disclosure. In some embodiments, administering a composition of the disclosure devoid of at least cysteine or cystine with a therapeutic agent can increase the efficacy of the therapeutic agent in a subject by at least about at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to a subject treated only with the composition of the disclosure. In some embodiments, administering a composition of the disclosure devoid of at least cysteine or cystine with a therapeutic agent can increase the efficacy of the therapeutic agent in a subject by at least about at least about 10% compared to a subject treated only with the composition of the disclosure. In some embodiments, administering a composition of the disclosure devoid of at least cysteine or cystine with a therapeutic agent can increase the efficacy of the therapeutic agent in a subject by at least about at least about 20% compared to a subject treated only with the composition of the disclosure. In some embodiments, administering a composition of the disclosure devoid of at least cysteine or cystine with a therapeutic agent can increase the efficacy of the therapeutic agent in a subject by at least about at least about 30% compared to a subject treated only with the composition of the disclosure.

Administering a composition of the disclosure devoid of at least cysteine or cystine with a therapeutic agent to a subject can have a decreased dose of the therapeutic agent compared to a subject treated with the therapeutic agent alone to achieve the same outcome. In some embodiments, administering a composition of the disclosure devoid of at least cysteine or cystine with a therapeutic agent to a subject can decrease the required dose of the therapeutic agent by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to a subject treated with the therapeutic agent alone to achieve the same outcome. In some embodiments, administering a composition of the disclosure devoid of at least cysteine or cystine with a therapeutic agent to a subject can decrease the required dose of the therapeutic agent by at least about 10% compared to a subject treated with the therapeutic agent alone to achieve the same outcome. In some embodiments, administering a composition of the disclosure devoid of at least cysteine or cystine with a therapeutic agent to a subject can decrease the required dose of the therapeutic agent by at least about 20% compared to a subject treated with the therapeutic agent alone to achieve the same outcome. In some embodiments, administering a composition of the disclosure devoid of at least cysteine or cystine with a therapeutic agent to a subject can decrease the required dose of the therapeutic agent by at least about 30% compared to a subject treated with the therapeutic agent alone to achieve the same outcome.

Administering a composition of the disclosure devoid of at least cysteine or cystine with a therapeutic agent to a subject can decrease adverse events associated with an additional therapy compared to a subject treated with the additional therapy alone. In some embodiments, administering a composition of the disclosure devoid of at least cysteine or cystine with a therapeutic agent to a subject can decrease adverse events associated with an additional therapy by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to a subject treated with the additional therapy alone. In some embodiments, administering a composition of the disclosure devoid of at least cysteine or cystine with a therapeutic agent to a subject can decrease adverse events associated with an additional therapy by at least about 10% compared to a subject treated with the additional therapy alone. In some embodiments, administering a composition of the disclosure devoid of at least cysteine or cystine with a therapeutic agent to a subject can decrease adverse events associated with an additional therapy by at least about 20% compared to a subject treated with the additional therapy alone. In some embodiments, administering a composition of the disclosure devoid of at least cysteine or cystine with a therapeutic agent to a subject can decrease adverse events associated with an additional therapy by at least about 30% compared to a subject treated with the additional therapy alone.

Methods of Use

The present disclosure provides methods for treating a subject. A composition disclosed herein can be used in the treatment of any disease. In some embodiments, a composition disclosed herein is used to treat cancer in a subject in need thereof. Altering the diet and nutrient of a subject can have desired health benefits and can be efficacious in the treatment of disease.

Based on the particular disease and/or need of the patient, the present disclosure provides methods for generalized-treatment recommendation for a subject as well as methods for subject-specific treatment recommendation. Methods for treatments can comprise one of the following steps: determining a level of a nutrient in a subject; detecting a presence or absence of a disease in the subject based upon the determining, and recommending to the subject at least one generalized or subject-specific treatment to ameliorate disease symptoms.

In some embodiments, a composition disclosed herein can be used to manage a disease or condition by a dietary intervention. In some embodiments, a composition disclosed herein can be used as part of a treatment plan for a particular disease or condition.

In some embodiments, the subject has cancer. Cancer is caused by uncontrollable growth of neoplastic cells, leading to invasion of adjacent and distant tissues resulting in death. Cancer cells often have underlying genetic or epigenetic abnormalities that affect both coding and regulatory regions of the genome. Genetic abnormalities in cancer cells can change protein structures, dynamic and expression levels, which in turn alter the cellular metabolism of the cancer cells. Changes in cell cycles can make cancer cells proliferate at a much higher speed than normal cells. With the increased metabolic rate and proliferation, cancer tissues have much higher nutrient demands compared to normal tissues.

Cancer cells have nutrient auxotrophy and have a much higher nutrient demand compared to normal cells. As an adaptation to fulfill the increased nutritional demand, cancer cells can upregulate the glucose and amino acid transporters on the cell membrane to obtain more nutrients from circulation. Cancer cells can also rewire metabolic pathways by enhancing glycolysis and glutaminolysis to sustain a higher rate of ATP production or energy supply. Glucose and amino acids are highly demanded nutrients in cancer cells. Some cancer cell types and tumor tissues are known to be auxotrophic to specific amino acids. Cancers' auxotrophy to different amino acids can render the cancer types vulnerable to amino acid starvation treatments.

When mammalian cells experience amino acid starvation, the cells undergo a homeostatic response to amino acid shortage. Amino acid deficiency can trigger a general amino acid control pathway that involves shifting resources and energy of cells to expression of membrane transporters, growth hormones, and metabolic enzymes for amino acid homeostasis. Up-regulation of membrane transporters can enhance amino acid uptake, and up-regulation of metabolic enzymes can enhance amino acid synthesis. The cells can also recycle proteins and organelles to regenerate non-essential amino acids by autophagy. By general amino acid control pathway and autophagy, cells attempt to maintain amino acid homeostasis. Tumor tissues can also overcome amino acid starvation by enhancing angiogenesis to obtain more nutrient supply.

When homeostasis cannot be achieved upon severe amino acid starvation, cancer cells can inhibit protein synthesis, suppress growth, or undergo programmed cell death. The cell death mechanisms of amino acid starvation can be caspase-dependent apoptosis, autophagic cell death, or ferroptotic cell death. Amino acid transporters, metabolic enzymes, autophagy-associated proteins, and amino acid starvation can be used to control cancer growth.

A method disclosed herein can monitor nutrient consumption by a subject. The nutrient consumption can be measured by taking a biological sample from a subject. The biological sample can be for example, whole blood, serum, plasma, mucosa, saliva, cheek swab, urine, stool, cells, tissue, bodily fluid, sweat, breath, lymph fluid, CNS fluid, and lesion exudates. A combination of biological samples can be used with a method of the disclosure.

A method of composition of the disclosure can slow the proliferation of cancer cell lines, or kill cancer cells. Non-limiting examples of cancer that can be treated by a compound of the disclosure include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some embodiments, a method of the disclosure can be used to treat breast cancer. In some embodiments, a method of the disclosure can be used to colorectal cancer. In some embodiments, a method of the disclosure can be used to treat pancreatic cancer.

Kits

Compositions of the disclosure can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Methods of Patient Stratification for Cysteine Depletion

In some embodiments, disclosed herein is a method of stratifying a patient population into groups to determine a patient group likely to respond to cysteine depletion therapy. In some embodiments, the method comprises determining a patient's MTAP status to stratify a patient population into groups to determine a patient group likely to respond to cysteine depletion therapy. In some embodiments, the method comprises determining a patient's AMD1 status to stratify a patient population into groups to determine a patient group likely to respond to cysteine depletion therapy. In some embodiments, the method comprises determining a patient's polyamine metabolism status to stratify a patient population into groups to determine a patient group likely to respond to cysteine depletion therapy.

In some embodiments, disclosed herein is a method of treating a condition in a subject in need of a dietary product, the method comprising: a) determining a level of a metabolite in a biological sample from the subject; and b) administering a therapeutically-effective amount of a dietary product to the subject based at least on the level of the metabolite, wherein the dietary product comprises at most about 0.5% (w/w) of at least one non-essential amino acid selected from the group consisting of: glycine, serine, alanine, proline, glutamine, glutamic acid, asparagine, aspartic acid, cysteine, tyrosine, and arginine. In some embodiments, the metabolite is MTA. In some embodiments, the metabolite is a polyamine. In some embodiments, the metabolite is S-adenosylmethionine, S-adenosylhomocysteine, homocysteine, gamma-glutamyl cysteine, GSH or GSSH. In some embodiments, the metabolite is GSH. In some embodiments, the metabolite is GSSH.

In some embodiments, the method comprises determining a patient's MTAP status, wherein a patient with MTAP-depletion is treated with a composition of the disclosure substantially devoid of at least cysteine. In some embodiments, the method comprises determining a patient's MTAP status, wherein a patient with elevated MTAP levels is treated with a composition high in cysteine. In some embodiments, the method comprises determining a patient's MTAP status, wherein a patient with MTAP-depletion is treated with a cysteine inhibitor. In some embodiments, the method comprises determining a patient's MTAP status, wherein a patient with MTAP-depletion is treated with a cysteinase enzyme.

In some embodiments, a patient with tumor tissue sample comprising a metabolite level that is greater than a metabolite level of a non-tumor tissue or tumor without an MTAP deficiency can be treated with a composition or method disclosed herein. In some embodiments, the metabolite level of an MTAP-deficient tumor tissue sample is at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 60-fold, at least about 70-fold, at least about 80-fold, at least about 90-fold, at least about 100-fold, at least about 150-fold, at least about 200-fold, at least about 250-fold, at least about 300-fold, at least about 350-fold, at least about 400-fold, at least about 450-fold, at least about 500-fold, at least about 550-fold, at least about 600-fold, at least about 700-fold, at least about 800-fold, at least about 900-fold, or at least about 1000-fold higher than the metabolite level of a tissue sample that is non-cancerous or is not MTAP-deficient. In some embodiments, the metabolite level of an MTAP-deficient tumor tissue sample is at least about 2-fold higher than the metabolite level of a tissue sample that is non-cancerous or is not MTAP-deficient. In some embodiments, the metabolite level of an MTAP-deficient tumor tissue sample is at least about 5-fold higher than the metabolite level of a tissue sample that is non-cancerous or is not MTAP-deficient. In some embodiments, the metabolite level of an MTAP-deficient tumor tissue sample is at least about 10-fold higher than the metabolite level of a tissue sample that is non-cancerous or is not MTAP-deficient. In some embodiments, the metabolite level of an MTAP-deficient tumor tissue sample is at least about 20-fold higher than the metabolite level of a tissue sample that is non-cancerous or is not MTAP-deficient. In some embodiments, the metabolite level of an MTAP-deficient tumor tissue sample is at least about 50-fold higher than the metabolite level of a tissue sample that is non-cancerous or is not MTAP-deficient. In some embodiments, the metabolite level of an MTAP-deficient tumor tissue sample is at least about 100-fold higher than the metabolite level of a tissue sample that is non-cancerous or is not MTAP-deficient.

EXAMPLES

Example 1: Experimental Methods a. Cell Culture

HCT116, SW480, MDA-MB-468, MDA-MB-231, AsPC-1, BxPC-3, CFPAC-1, MIAPaCa-2, PANC-1, Panc10.05, SW1990, U-251, LN-18, LN-229, T98G, U-343, A-172 cells were used. Cell lines were authenticated using Short Tandem Repeat (STR) profiling and tested for mycoplasma. Colorectal and breast cancer cell lines were grown in Dulbecco's Modified Eagle Medium (DMEM), pancreatic ductal adenocarcinoma (PDAC) cell lines were grown in Roswell Park Memorial institute (RPMI) 1640. All cell lines were supplemented with penicillin-streptomycin, amphotericin, 2 mM L-glutamine, and 10% fetal bovine serum (FBS). Cells were kept at 37° C. in 5% $CO_2$ in a humidified cell culture incubator. A formulated medium lacking cysteine, cystine, methionine, and serine was used as a base for creating experimental media. The base medium formulation contained 0.2 mM L-histidine, 0.4 mM L-isoleucine, 0.4 mM L-leucine, 0.4 mM L-lysine, 0.2 mM L-phenylalanine, 0.4 mM L-threonine, 0.08 mM L-tryptophan, 0.4 mM L-valine, 0.2 mM L-arginine, 2 mM L-glutamine, 0.2 mM L-tyrosine, 0.4 mM L-alanine, 0.3 mM L-proline, 0.15 mM L-glutamic acid, 0.1 mM L-aspartic acid, 0.2 mM L-asparagine, and 0.4 mM glycine. The base medium was supplemented with 10% dialyzed FBS, penicillin-streptomycin, and amphotericin. To ensure an adequate supply of vitamin B6 (a crucial co-factor for de novo cysteine synthesis), base medium was supplemented with additional 20 µM vitamin B6. The control experimental medium was the base medium supplemented with 0.4 mM L-cysteine, 0.2 mM L-methionine, and 0.4 mM L-serine. The cysteine starvation (–Cys) experimental medium was base medium supplemented with 0.2 mM L-methionine and 0.4 mM L-serine.

b. Generation of MTAP-KO Cells Using CRISPR/Cas9 and MTAP Re-Expression

HCT116 cells were transfected using a lipid-based transfection method with pSpCas9(BB)-2A-puro (PX459) V2.0, which expresses both Cas9 and gRNA [NTC (SEQ ID NO: 1): AAAATAGCAGTAAACTCAAC, MTAP KO seq 1 (SEQ ID NO: 2): GTTTTGCCCCAAAACGAGAG, MTAP KO seq 2 (SEQ ID NO: 3): GCCTGGTAGTTGACCTTTGA]. Successfully transfected cells were selected with puromycin and grown as clonal colonies. Clones were selected based initially on MTA efflux measured by liquid chromatography mass spectrometry (LC-MS). Clones with greatest MTA efflux were selected, and methylthioadenosine phosphorylase knockout (MTAP-KO) was then confirmed by western blot. MTAP-KO HCT116 cells were transfected with pCMV-Hygro-MTAP and pCMV-Hygro-negative control vector, selected using hygromycin B, and grown as clonal colonies. Clones were selected based initially on MTA efflux measured by LC-MS. Clones with low MTA efflux were selected, then MTAP re-expression was confirmed by western blot.

c. Cell Counting Experiments

Cells were seeded at $6 \times 10^4$ cells per well into 24-well plates (triplicate wells per condition) in the relevant complete medium and adhered for a full 24-hour period. A 'time-0' plate was included to record the starting cell number to calculate relative cell numbers. Cells were washed once with phosphate-buffered saline (PBS) before receiving experimental medium containing or lacking the specified amino acids, metabolites, or drugs. At the stated time-points the medium was removed, cells were fixed in a 4% formalin-PBS solution. Cells were then washed and stored in PBS before staining with 4',6-diamidino-2-phenylindole (DAPI)-Triton™ X100-PBS solution for 1 hour, followed by storage in PBS at 4° C. until further analysis. DAPI-stained cell nuclei were detected via microscopy.

Homocysteine, cystathionine, glutathione, putrescine, spermine, spermidine, GPX4 inhibitor ML210, SMOX inhibitor MDL 72527, PAOX inhibitor diminazene aceturate, ferrostatin-1 and erastin were used. AMD1 inhibitor sardomozide/SAM486A, GPX4 inhibitor RSL3, and CSE inhibitor beta-cyano-L-alanine were used. For experiments using sardomozide, cells were seeded as described above. Prior to cysteine starvation, cells were fed complete medium supplemented with the stated concentration of sardomozide. After 16 hours, the medium was removed, and the cells were washed in PBS. Either complete or cysteine-free medium (without any sardomozide) was then added, and the cells were incubated for the stated times before fixing the cells to perform cell counts.

For experiments using spermine oxidase (SMOX) and polyamine oxidase (PAOX) inhibitors or MTOB, cells were pre-treated with stated concentrations for 16 hours in complete medium. After pre-treatment, cells were washed in PBS, and treatment was continued in complete or cysteine-free medium for stated times. After treatment was finished, cells were fixed and stained as described above. For experiments using MTA, polyamines, GPX4 and CSE inhibitors, treatment started at the same time as cysteine starvation. For experiments involving hypoxic conditions, cells were seeded in normoxic conditions and allowed to adhere for 24 hours before control and cysteine starvation medium was added and cells were immediately transferred either to a humidified cell culture incubator set to 37° C. in 20% $O_2$ (normoxia), or a hypoxia chamber set to 37° C. in 1% $O_2$ (hypoxia) for the stated times. Cells were fixed immediately and stained as described above.

Figure 29:
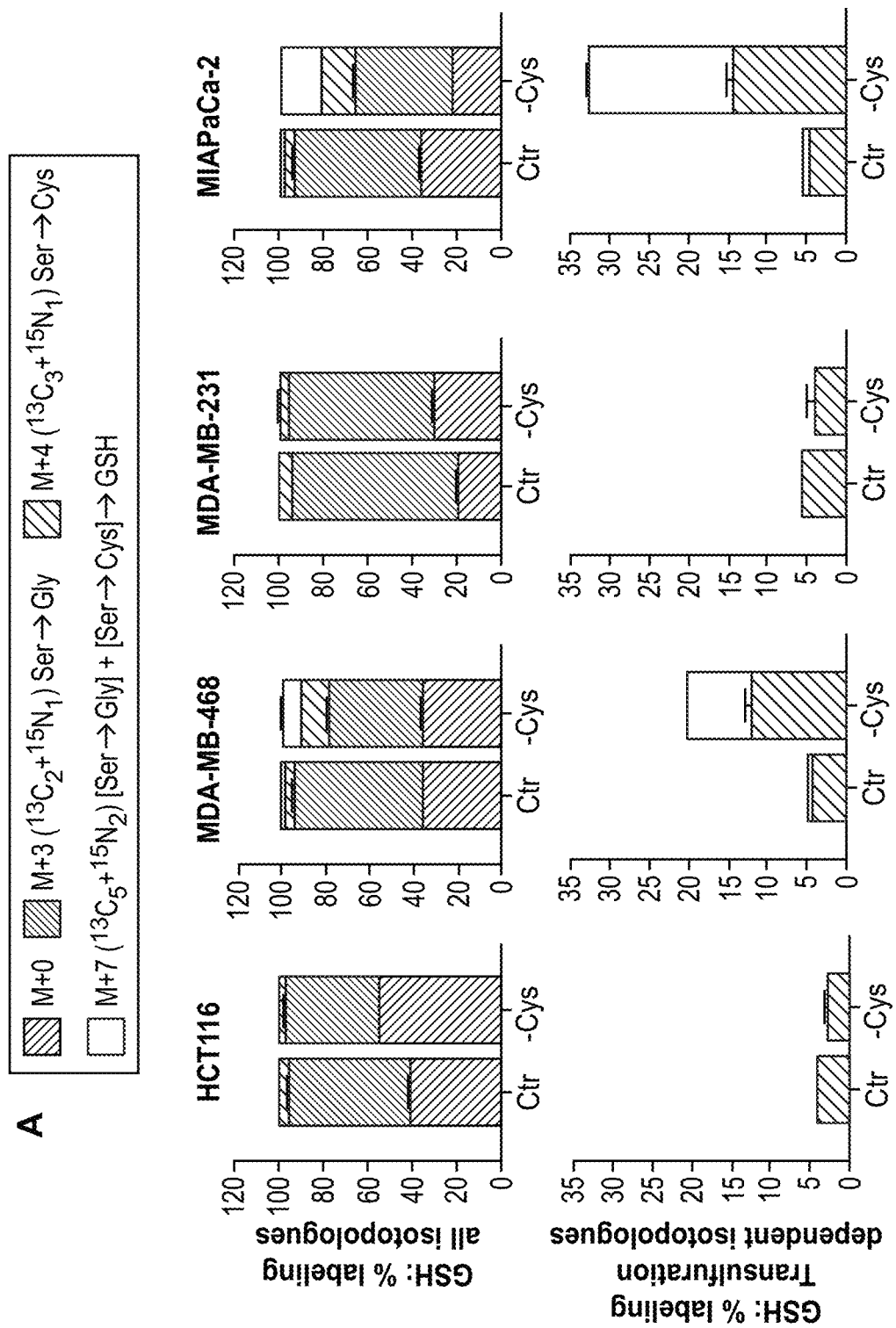
FIG. 29 PANEL A uses peak area data shown in FIG. 28 to show GSH levels as a % total of the total GSH pool. In the top panel, all isotopologues are shown. In the lower panel, only cysteine-derived isotopologues (m+4 and m+7) are shown. PANEL B shows cells grown in complete (Ctr) or medium lacking cysteine (–Cys) without (Veh) or with 0.5 mM or 1 mM of the CSE inhibitor beta-cyano-L-alanine for 48 h.
Figure 29:
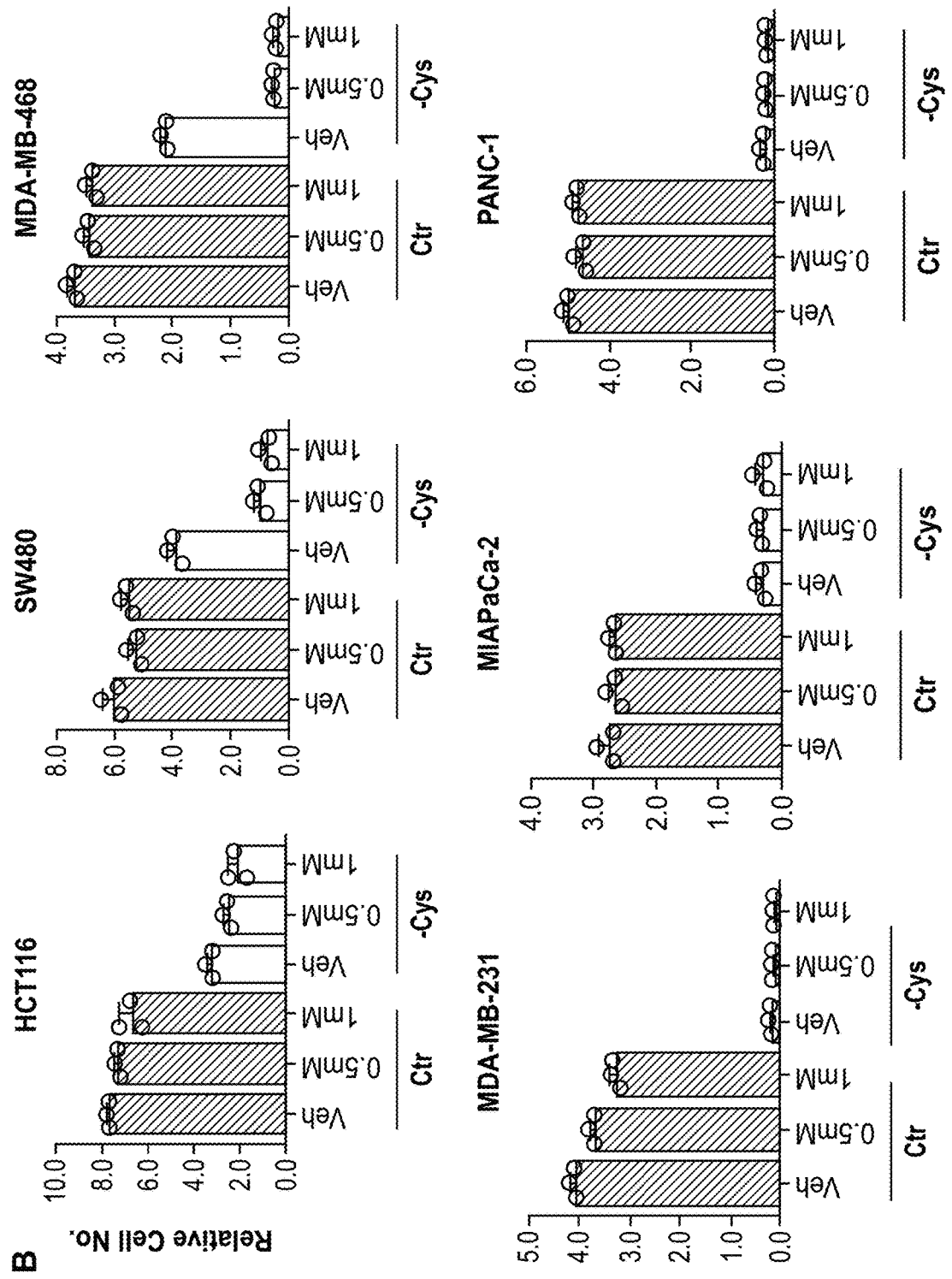

Throughout the cysteine starvation experiments, a correlation of low cell density on susceptibility to nutrient withdrawal was observed (FIG. 42 PANEL A). Low seeding density increased the sensitivity of all cells to cysteine starvation, and high cell density decreased cell sensitivity of all cells to cysteine starvation. For example, cells relatively resistant to cysteine starvation, such as HCT116, became more sensitive at low confluence. More starvation-sensitive cells, such as MIAPaCa-2, became more resistant to cell death at high confluence. To limit the confounding factor in cell counting experiments, cells were seeded to be 20-30% confluent at the time of starvation, i.e. low enough to be in a proliferative state and not suffering substantial contact inhibition, but high enough not to be overtly sensitized to nutrient limitation. For experiments such as LC-MS analysis, cells were intentionally seeded at higher densities to prolong cell survival and allow labelling (e.g. with $^{13}C_3^{15}N_1$-serine into GSH; FIG. 29 PANEL A) to be assessed in cells deprived of cysteine for up to 48 h.

d. Western Blotting

Protein was extracted from whole cells by lysis in RIPA buffer supplemented with a protease and phosphate inhibitor cocktail. Lysates were cleared using centrifugation, resolved on 4-12% bis-tris pre-cast gels, and transferred to nitrocellulose membranes. Primary antibodies used were MTAP, AMD1, ODC1, GPX4, AHCY, CBS, CSE, and actin as a loading control on the same blots. Secondary antibodies used were IRDye800CW anti-mouse, IRDye680RD anti-mouse, IRDye800CW anti-rabbit, and IRDye680RD anti-rabbit. Protein bands were detected and quantified using an infrared scanner and imaging software.

e. CellROX Assay on Live Cells

Cells were seeded as described above. Live cells were stained with Hoechst 33342 nuclear stain for 20 min. The medium was removed, and cells were stained in 100 µl medium containing CellTracker™ Green CMFDA Dye and Hoechst stain for 40 min. The cells were then washed with PBS, and 300 µl of the relevant experimental medium was added for 1 hour. Then, CellROX® Deep Red was spiked into the medium, and the cells were incubated for 40 min. The medium was removed, the cells were washed with PBS, and new relevant experimental medium including CellROX was added. The cells were imaged using an Operetta automated microscope platform set to 37° C. in 5% $CO_2$ every hour for 16-24 hours. I f. Malondialdehyde (MDA) Staining on Fixed Cells Cells were seeded, treated and fixed as described above. Blocking was performed in 5% donkey serum and 0.3% Triton™ X100 in PBS for 1 hour at 4° C. Staining was performed using blocking buffer including an MDA antibody 1:600 overnight at 4° C. on a shaker. Cells were washed with PBS and the secondary antibody Alexa Fluor® 568, goat-anti rabbit, and 0.2 nM Calcein AM in blocking solution was added for 1-2 hours at RT in the dark. Cells were washed with PBS again and imaged using a microscope.

g. Steady State Metabolite Measurements

Metabolomics experiments were performed as follows. Cells were seeded into 6-well plates ($5\times10^5$-$1.5\times10^6$ cells/mL, depending on time-course, triplicate wells per condition) in complete medium and adhered overnight. Cells were washed with PBS, and the relevant experimental media were added for the stated times. Duplicate wells were used for cell counting. Cell counts were used to normalize the volume of lysis solvent prior to metabolite extractions ($2\times10^6$ cells/mL). Cells were washed quickly in PBS, then ice-cold lysis solvent (methanol 50%, acetonitrile 30%, water 20%) was added, and cells were scraped on ice. Lysates were transferred to 1.5 mL tubes on ice, vortexed, then spun by centrifugation at 15,000 rpm at 4° C. for 10 minutes. Supernatants were collected and stored at −80° C. for LC-MS analysis.

For spermine analysis, a Sequant® ZIC®-HILIC column guard (20 mm×2.1 mm) was used to separate spermine with the mobile phase using A=0.1% (v/v) formic acid in water and B=0.1% (v/v) formic acid in acetonitrile. The flow rate was set to 200 L/min, and the injection volume was 20 µL. The separation was performed using an isocratic program of 80% of A and 20% of B, with a total run time of 3 min. The exactive mass spectrometer was operated in full scan mode over a mass range of 50-800 m/z at a resolution of 50,000 in positive mode.

h. Carbon-13 Labeling of Metabolites

For experiments using labelled methionine, the same basic protocol was used as described for the steady state metabolite measurements described above. Experimental media were formulated lacking methionine or serine (described above) and supplemented with the stated concentrations of $^{13}C_5^{15}N_1$-methionine, $^{13}C_3^{15}N_1$-serine or $^{34}S_1$-methionine. Metabolites were extracted as described above.

i. LC-MS Analysis and Data Processing

Prepared samples were analyzed on an LC-MS platform consisting of an Accela™ 600 LC system and an Exactive™ mass spectrometer. A Sequant® ZIC®-HILIC column (4.6 mm×150 mm, 3.5 µm) was used to separate the metabolites with the mobile phase using A=0.1% (v/v) formic acid in water and B=0.1% (v/v) formic acid in acetonitrile. A gradient program starting at 20% of A and linearly increasing to 80% at 30 min was used followed by washing (92% of A for 5 mins) and re-equilibration (20% of A for 10 min) steps. The total run time of the method was 45 min. The LC stream was desolvated and ionized in the HESI probe. The Exactive™ mass spectrometer was operated in full scan mode over a mass range of 70-1,200 m/z at a resolution of 50,000 with polarity switching. The LC-MS raw data was converted into mzML files by using ProteoWizard and imported to MZMine 2.10 for peak extraction and sample alignment. An in-house database including all possible $^{13}C$ and $^{15}N$ isotopic m/z values of the relevant metabolites was used for the assignment of LCMS signals. Finally the peak areas were used for comparative quantification.

j. LC-MS Analysis of Polyunsaturated Phospholipids

Cells were seeded as $3\times10^5$ cells per well into 6-well plates (triplicate wells per condition) and cultured in complete medium for 48 hours. For lipid extraction, the cell samples were prepared as described above except that ice-cold isopropanol (IPA) was used as the lysis solvent. For phospholipid measurement by LC-MS, 20 µl of lysate solution was injected into a LC-MS platform consisting of an Accela™ 600 LC system and an Exactive™ mass spectrometer. An ACE silica gel column (3 mm×150 mm×3 µm) was used to separate the lipids in normal phase mode with the mobile phase using A=20 mM ammonium acetate/IPA (80:20, v/v) and B=ACN/IPA (80:20, v/v). A gradient program with flow rate of 0.3 mL/min was used; starting at 8% of A for 1 min, from 1 to 5 min linearly increasing A to 9% and to 20% from 5 to 10 min, to 25% from 10 to 16 min and to 35% from 16 to 23 min and finally back to 8% of A from 26-40 min for re-equilibration. The Exactive™ mass spectrometer was operated in full scan mode over a mass range of 100-1,200 m/z at a resolution of 50,000 with polarity switching. The LC-MS raw data were converted into mzML files using ProteoWizard and imported to MZMine 2.10 for peak extraction and sample alignment. Phospholipids were identified by an in silico algorithm (Lipid search) in MZMine 2.10 with lipid classification and detailed fatty acyl information including the number of carbons and double bonds. Peak areas were used for comparative analysis.

k. Inductively Coupled Plasma Optical Emission Spectrometry (ICP-OES) Iron Assay Cell lines were seeded in 6-well plates (each line in five wells) with the appropriate media as described above. After 24 hours, two wells of cells were counted, and the average number was used in million/mL as T=0 h. The cells in the remaining three wells were cultured with 1.5 mL of complete media. After 72 hours, 1 mL of used medium was taken and diluted with 4 mL of deionized water for iron measurements using ICP-OES. The cells were counted, and the average number in million/mL was used as T=72 h. The diluted media were analyzed using an Optima® 7300 DV ICP-OES. The iron levels in ppm from triplicate samples of each cell line were averaged and then normalized to the difference in cell number between T=0 h and T=72 h for comparative analysis.

l. Xenograft Experiment

CD1-Nude (Cr1:CD1-Foxn1nu) 6-8 week old female mice were housed in a barrier facility proactive in environmental enrichment. Prior to experimental dietary modifications, mice were fed a normal chow diet and water ad libitum. HCT116-NTC and HCT116-MTAP-KO cells ($4\times10^6$/flank) were implanted by unilateral sub-cutaneous injection. Injection sites were monitored daily until visible, measurable tumors had formed (approximately 5 mm in length). Mice with tumors were given an experimental diet containing all essential amino acids, but lacking all non-essential amino acids. The diet consisted of the following ingredients: Sucrose 15%, Corn starch 49.76%, Corn oil 7.89%, Amino acid premix 16%, Vitamin mix 0.2%, Mineral mix 10%, Sodium bicarbonate 1%, DL-alpha tocopheryl acetate 0.004%, Ethoxyquin (preservative) 0.019%, color dye 0.03%. Amino acid premix (% by weight of total formulation): L-histidine-HCl 1.33%, L-isoleucine 1.78%, L-leucine 2.67%, L-lysine-HCl 3.11% L-Methionine 1.33%, L-Phenylalanine 1.78%, L-Threonine 1.78%, L-Tryptophan 0.44%, and L-valine 1.78%. Drinking water contained or lacked cysteine & cystine, with all other non-essential amino acids added.

Control drinking water (pH 7) contained Glycine, L-alanine, L-asparagine, L-aspartic acid, L-glutamic acid, L-proline, L-serine, L-glutamine, L-arginine, L-cysteine hydrochloride monohydrate (all 16 mM), L-tyrosine disodium salt hydrate (3 mM) and D-glucose (25 mM). Cysteine-free drinking water (pH 7) contained L-alanine, L-asparagine, L-aspartic acid, L-glutamic acid, L-proline, L-glutamine, L-arginine (all 18.3 mM), Glycine and L-serine (16 mM), L-tyrosine disodium salt hydrate (3 mM) and D-glucose (25 mM). Both diet and drinking water were allowed ad libitum.

Tumors were measured three times per week with calipers, and volumes were calculated using the formula: volume=(length×width$^2$)/2. Upon reaching the maximum permitted tumor size (length or width=15 mm) or if tumors became ulcerated, mice were humanely killed.

m. Data Presentation and Statistics

For each set of data, the n-numbers and error bars are shown in the figure legends. Where mean values of individual measurements are shown, bars are standard deviation (SD), where mean of means are shown bars are standard error of mean (SEM). In vitro data are displayed as averages of n=3 biological replicates, noted in each Figure legend. Tumor sizes were measured 3 times per week, and tumor volumes were converted to changes in volume (as percentage) compared to the starting volume when diet was changed. Data are presented as weekly mean tumor volumes with bars showing SEM.

To compare the relative effects of cysteine-free diet on NTC and MTAP-KO cells, the difference in weekly mean tumor volume (as percentage) between individual tumors on the cysteine-free diet and the mean tumor volume on control diet was calculated. Statistical comparison between multiple groups was done by ordinary one-way ANOVA with Sidak's multiple comparison test. For FIG. 40 PANEL C, where only two groups are compared, an unpaired TTEST with two-tails was performed. P-values are shown to 3 decimal places, statistical significance was taken as P<0.05.

Example 2: Cellular Sensitivity to Cysteine Starvation

A panel of cell lines consisting of colorectal (HCT116 and SW480), breast (MDA-MB-231 and MDA-MB-468), and pancreatic cancers (AsPC-1, BxPC-3, CFPAC-1, MIAPaCa-2, PANC-1, Panc10.5, and SW1990) were used to assess the impact of cysteine starvation on a range of cancer cells. In all experiments, where cysteine was removed, the homodimer cystine was also absent.

FIG. 1 shows the effect of cysteine starvation (−Cysteine; RIGHT PANEL) on cell proliferation compared to fully fed conditions (Control; LEFT PANEL). After three days of cysteine starvation, all 11 cell lines showed severely impaired proliferation compared to fully fed conditions. Several cell lines maintained approximately the same cell numbers during starvation (e.g. HCT116, SW480, MDA-MB-468, and AsPC-1), indicating that the cells had survived. Other cell lines, particularly MDA-MB-231, MIAPaCa-2 and PANC-1, had a relative cell number (versus the starting cell number) below one, indicating cell death.

Figure 2:
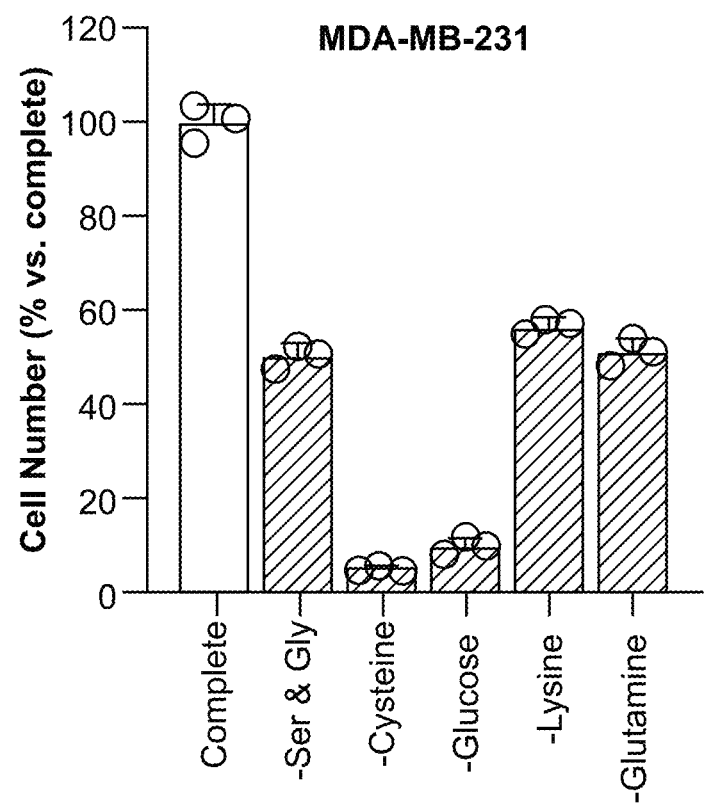
FIG. 2 shows the effect of starving cells of major nutrients in MDA-MB-231 cells.
Figure 22:
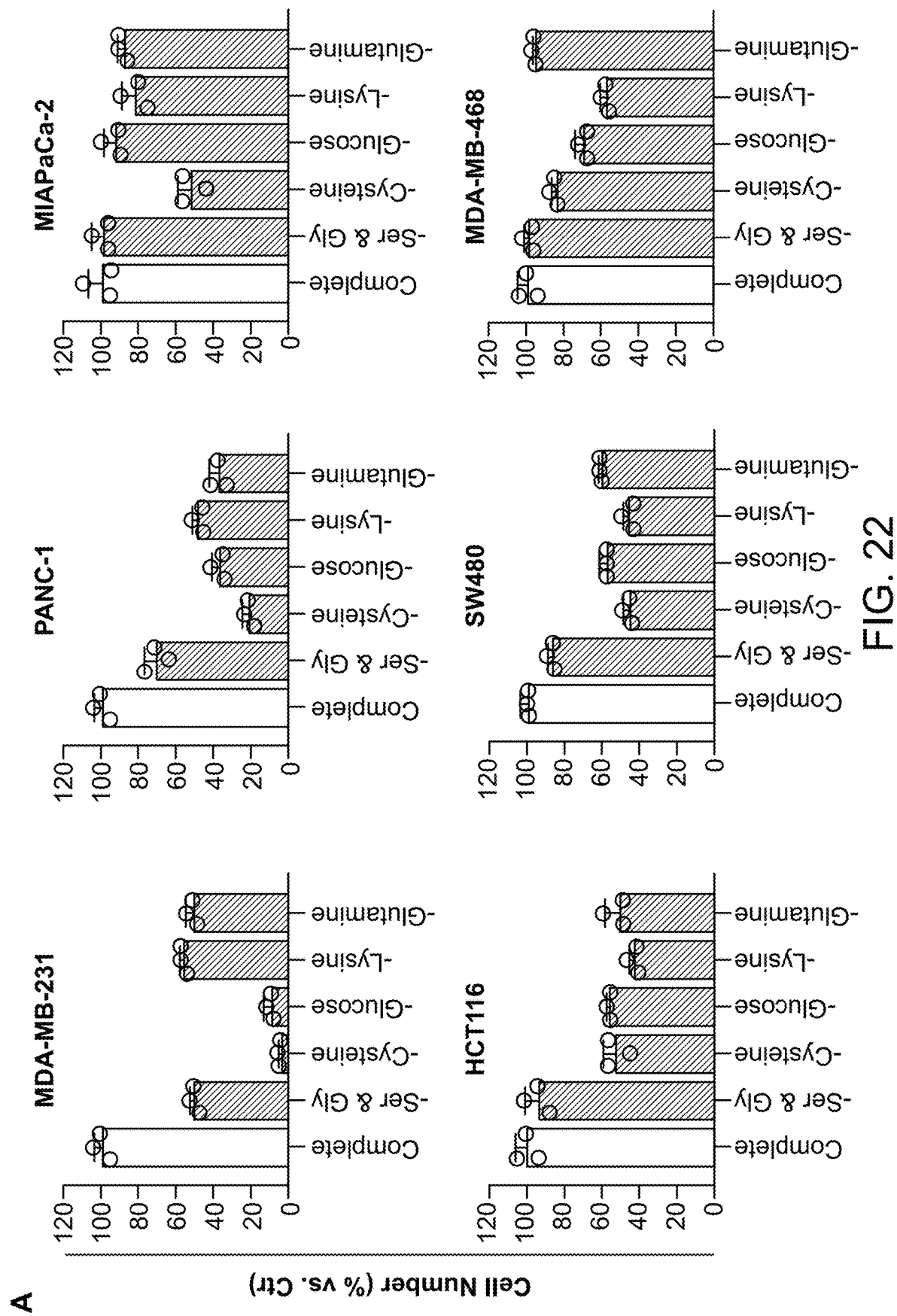
FIG. 22 PANEL A shows cell lines grown in complete medium or matched medium lacking the stated nutrients for 24 hr. MDA-MB-231 data is replicated from FIG. 2 for comparison with other cell lines. PANEL B shows cell lines grown with (Ctr) or without cysteine (–Cys) and ferrostatin (+F) 1 µM for 24 h and 72 h.
Figure 22:
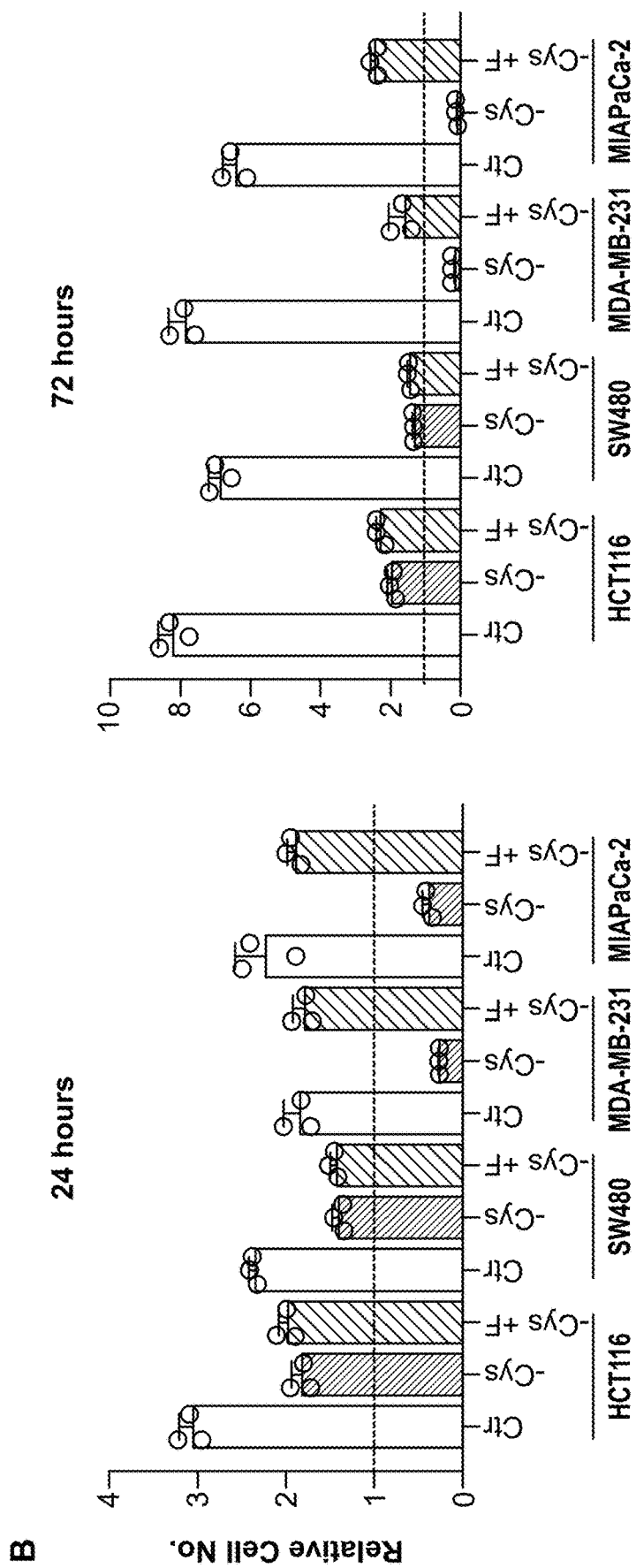

The response of cells to cysteine starvation versus a range of other major nutrients was determined. FIG. 2 shows the effect of starving cells of major nutrients in MDA-MB-231 cells. FIG. 22 PANEL A shows cell lines grown in complete medium or matched medium lacking the stated nutrients for 24 hr. MDA-MB-231 data is replicated from FIG. 2 for comparison with other cell lines. MDA-MB-231, MIAPaCa-2, and PANC-1 cells were more sensitive to cysteine withdrawal than key non-essential amino acids (i.e., serine and glycine; or glutamine), an essential amino acid (lysine), or complete glucose removal. In contrast, HCT116, SW480, and MDA-MB-468 had similar sensitivity to cysteine withdrawal as to other nutrients, such as glucose and lysine.

Figure 3:
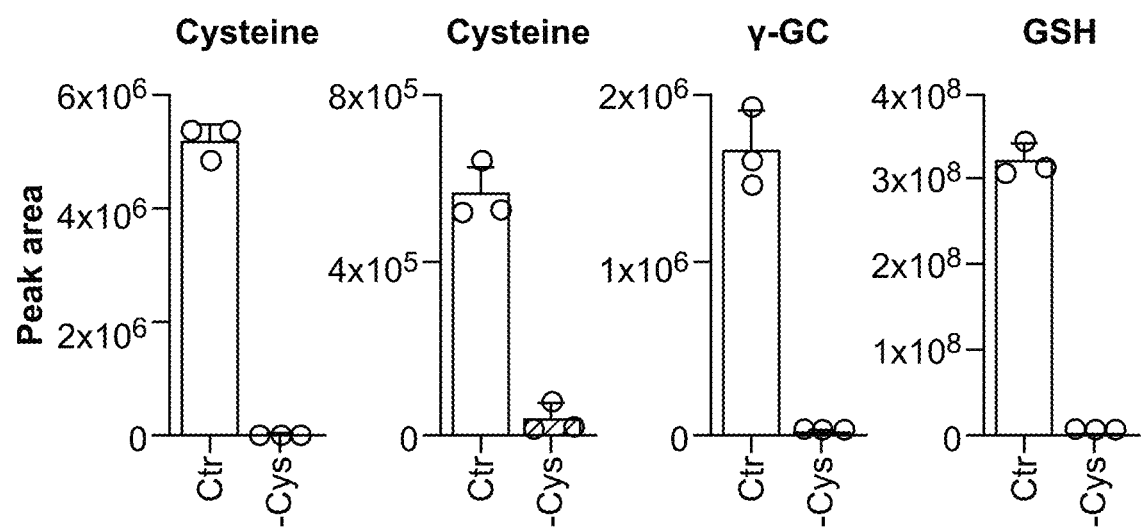
FIG. 3 shows the effect of cysteine starvation on levels of cysteine, cystine, γ-GC, and GSH.

The basic metabolic effects of cysteine starvation were determined using LC-MS analysis. Levels of intracellular cysteine and cystine were substantially depleted on removal of exogenous cysteine. These changes were paralleled by decreases in glutathione (GSH) and the cysteine-derived precursor γ-glutamylcysteine. FIG. 3 shows the effect of cysteine starvation on levels of cysteine, cystine, γ-GC, and GSH.

Figure 4:
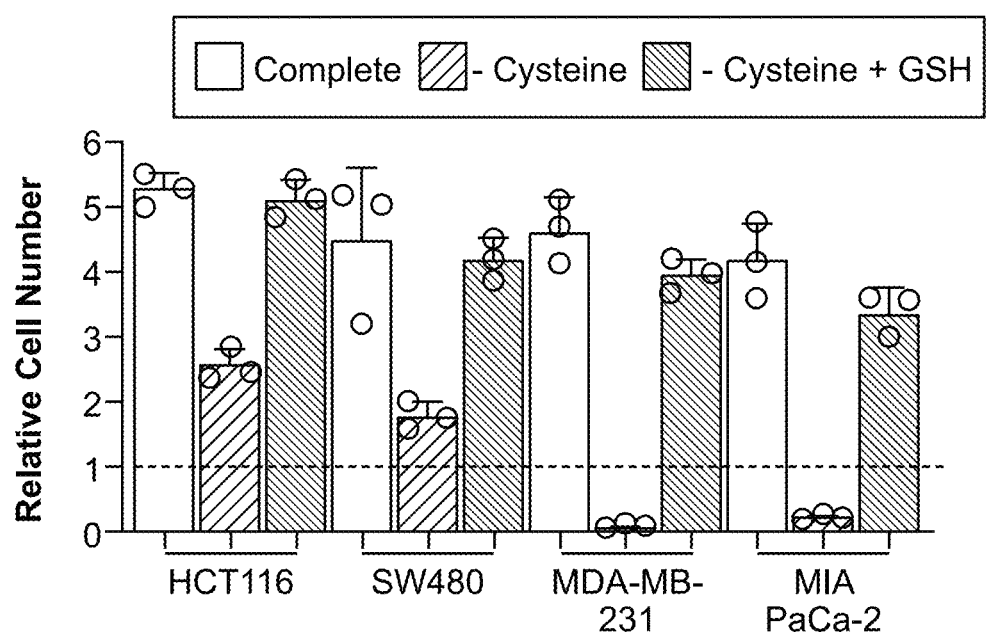
FIG. 4 shows the effect of cysteine starvation and exogenous GSH on cell death in HCT116, SW480, MDA-MB-231, and MIAPaCa-2 cells.
Figure 23:
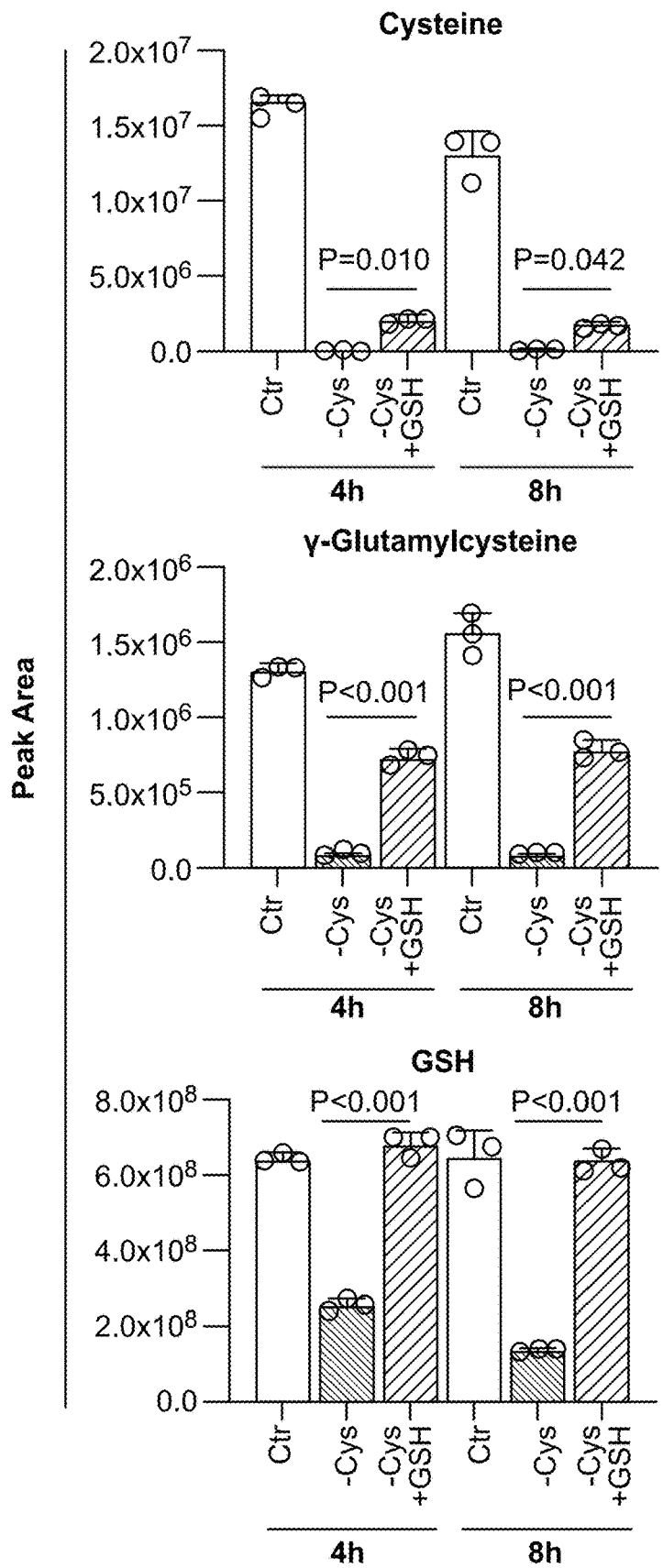
FIG. 23 shows MDA-MB-231 cells either grown in complete medium containing all amino acids (Ctr) or matched medium lacking cysteine with 5 mM glutathione (–Cys+GSH) or without glutathione (–Cys) for the stated times.

FIG. 23 shows MDA-MB-231 cells either grown in complete medium containing all amino acids (Ctr) or matched medium lacking cysteine with 5 mM glutathione (−Cys+GSH) or without glutathione (−Cys) for the stated times. Metabolites were extracted and analyzed using LC-MS. Addition of exogenous GSH fully restored intracellular GSH levels, along with partial rescue of cysteine and γ-glutamylcysteine, which prevented cell death and restored proliferation. FIG. 4 shows the effect of cysteine starvation and exogenous GSH on cell death in HCT116, SW480, MDA-MB-231, and MIAPaCa-2 cells.

Ferrostatin is a potent inhibitor of the iron-dependent cell death caused by cysteine starvation that acts as a radical trapping anti-oxidant that prevents lipid peroxidation. FIG. 22 PANEL B shows cell lines grown with (Ctr) or without cysteine (−Cys) and ferrostatin (+F) 1 µM for 24 h and 72 h. In sensitive cells, ferrostatin prevented cell death in response to cysteine starvation, and had little impact on the more resistant cells. In contrast to GSH, ferrostatin did not restore proliferation, reflecting that, unlike GSH, ferrostatin acts downstream of metabolite changes and cannot directly supplement cysteine dependent metabolic pathways.

Figure 5:
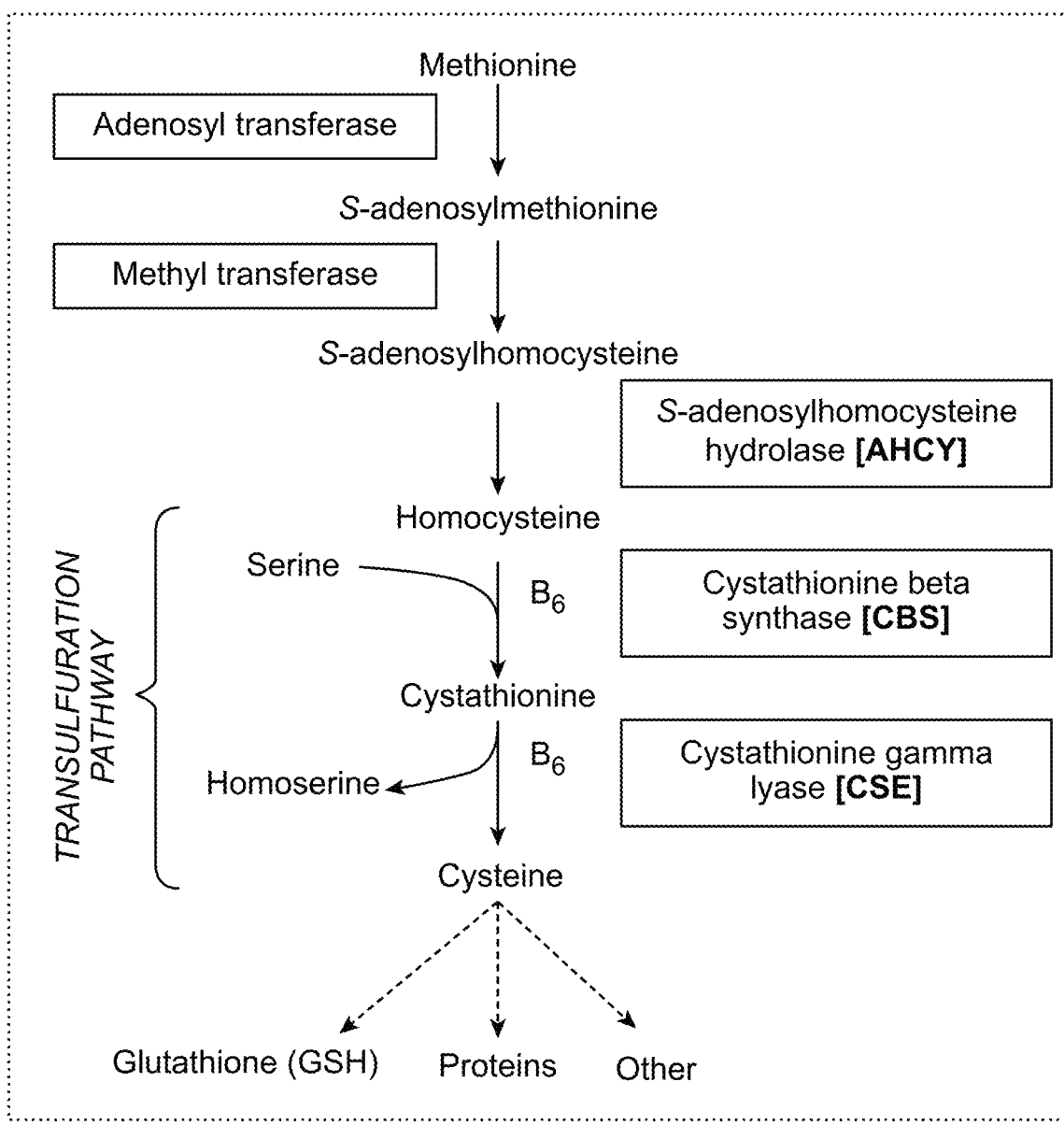
FIG. 5 illustrates the relationship between response to cysteine starvation and expression of TsP enzymes for de novo cysteine synthesis.

Example 3: High Sensitivity to Cysteine Starvation does not Correlate with Transsulfuration Pathway Enzyme Expression, and is not Rescued by Excess Methionine The relationship between response to cysteine starvation and expression of TsP enzymes for de novo cysteine synthesis was investigated (FIG. 5). Scatter plots comparing enzyme expression versus cell number after cysteine starvation show that there was no correlation between starvation response and expression of S-adenosylhomocysteine hydrolase (AHCY), cystathione ß-synthase (CBS), or cystathionine γ-lyase (CSE).

Figure 6:
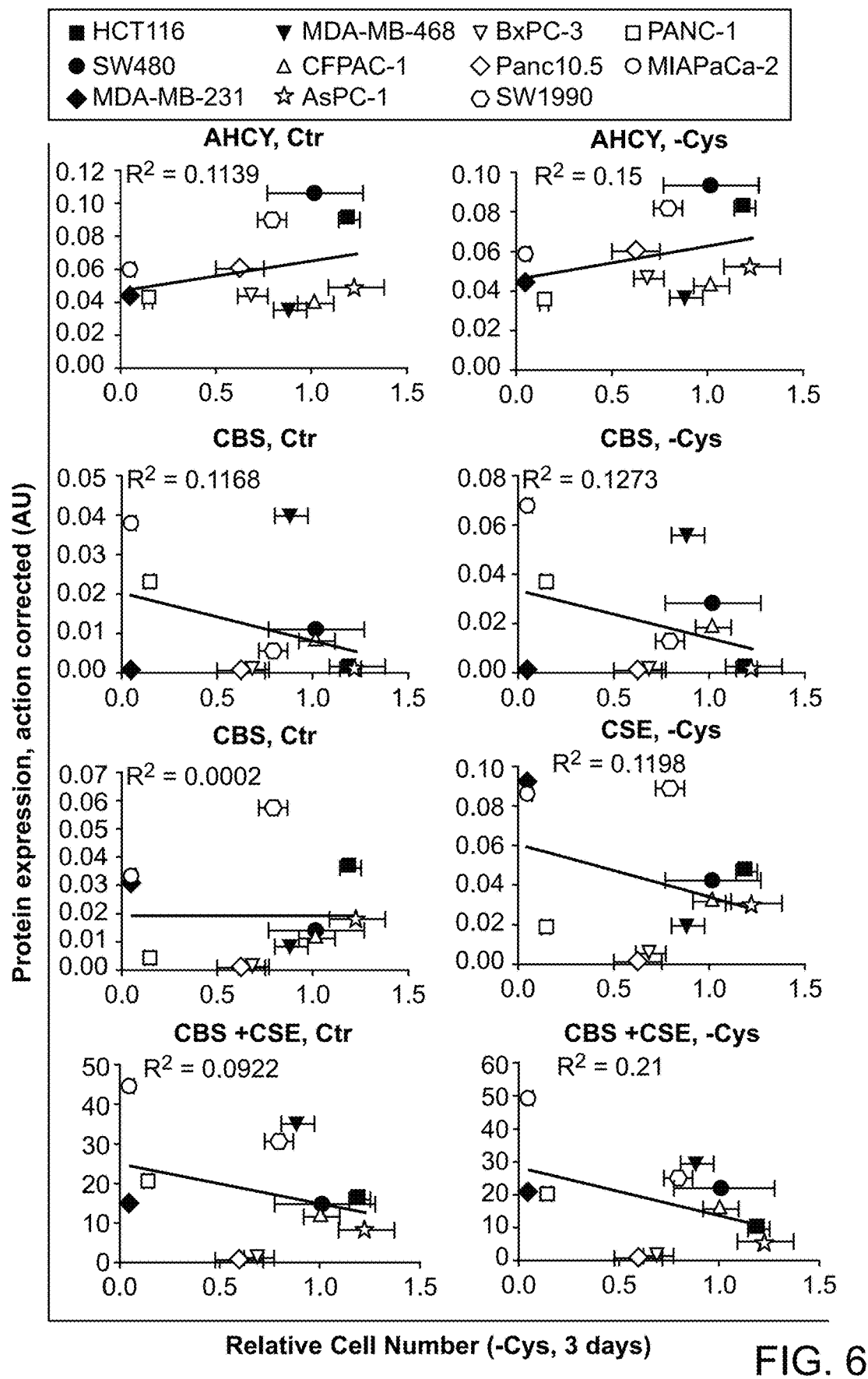
FIG. 6 shows scatter plots comparing enzyme expression of S-adenosylhomocysteine hydrolase (AHCY); cystathione β-synthase (CBS); cystathionine γ-lyase (CSE); or CBS+CSE versus cell number after cysteine starvation.
Figure 24:
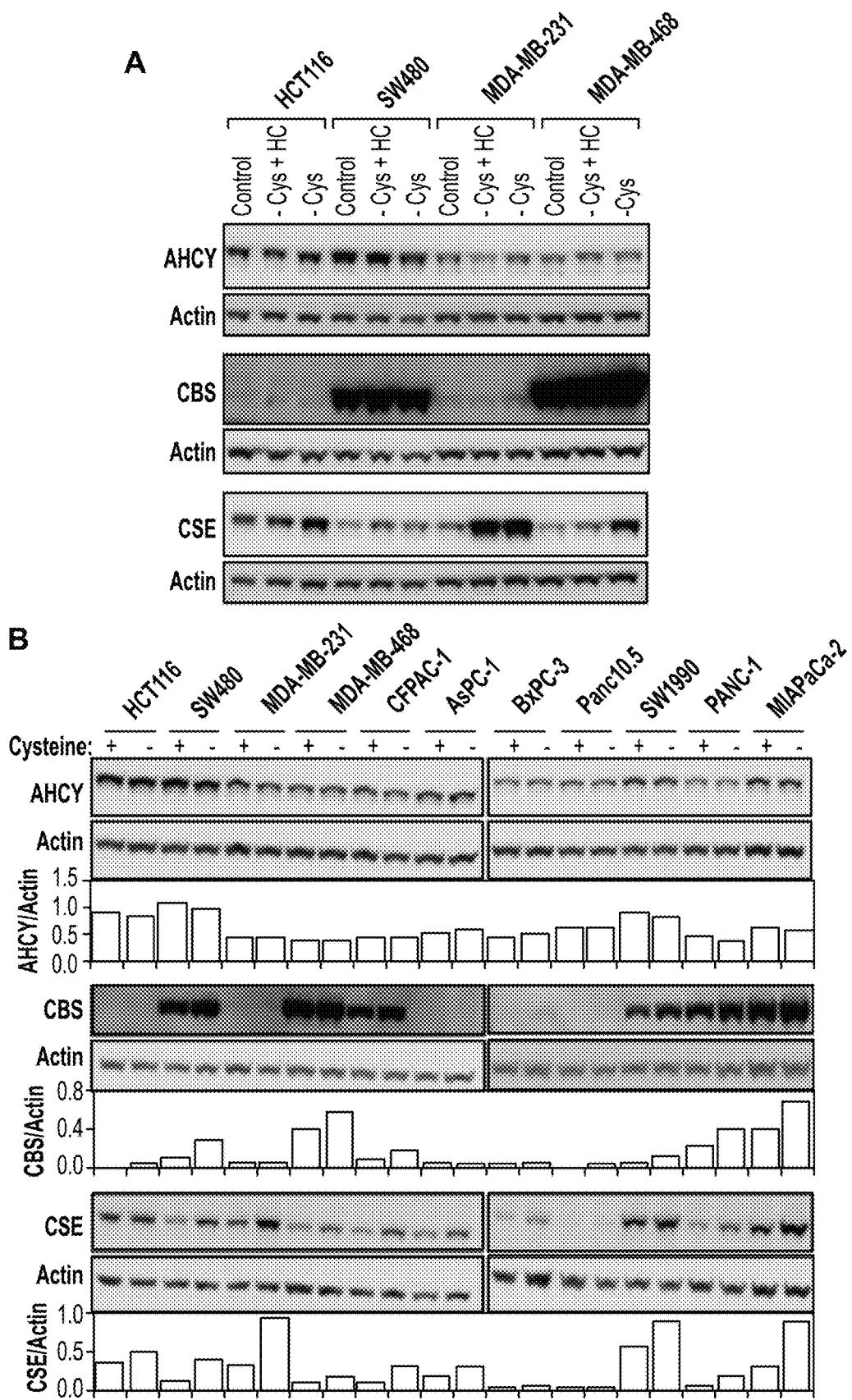
FIG. 24 PANEL A shows colorectal (HCT116 and SW480) and breast (MDA-MB-231 and MDA-MB-468) cancer cells were either grown in complete medium containing all amino acids (Ctr) or matched medium lacking cysteine with 0.8 mM homocysteine (–Cys+HC) or without homocysteine (–Cys) for 24 hr. PANEL B shows cells grown in complete medium containing all amino acids (+) or matched medium lacking cysteine (–) for 24 h.

FIG. 6 shows scatter plots comparing enzyme expression of S-adenosylhomocysteine hydrolase (AHCY); cystathione ß-synthase (CBS); cystathionine γ-lyase (CSE); or CBS+ CSE versus cell number after cysteine starvation. FIG. 24 PANEL A shows colorectal (HCT116 and SW480) and breast (MDA-MB-231 and MDA-MB-468) cancer cells were either grown in complete medium containing all amino acids (Ctr) or matched medium lacking cysteine with 0.8 mM homocysteine (−Cys+HC) or without homocysteine (−Cys) for 24 hr. Cell lysates were probed for transsulfuration pathway enzyme expression by western blot. PANEL B shows cells grown in complete medium containing all amino acids (+) or matched medium lacking cysteine (−) for 24 h. Cell lysates were probed for transsulfuration pathway enzyme expression by western blot. Bands were quantified on a LiCor scanner, and actin-corrected band intensity (arbitrary units) are shown.

To determine whether precursor availability is a limiting factor in achieving de novo cysteine synthesis, cells were supplemented with homocysteine (HC) or cystathionine (CTH) during cysteine starvation. FIG. 7 PANEL A shows that addition of either precursor at 0.2 mM produced a substantial rescue to survival/proliferation either in less sensitive (SW480) or highly sensitive (MDA-MB-231) cell lines. FIG. 7 PANEL B shows that a higher concentration of homocysteine (0.8 mM) was further able to restore proliferation. However, supplementation with the same concentration of methionine (0.8 mM, 4-8 fold higher than normal cell culture medium) provided no rescue.

Figure 25:
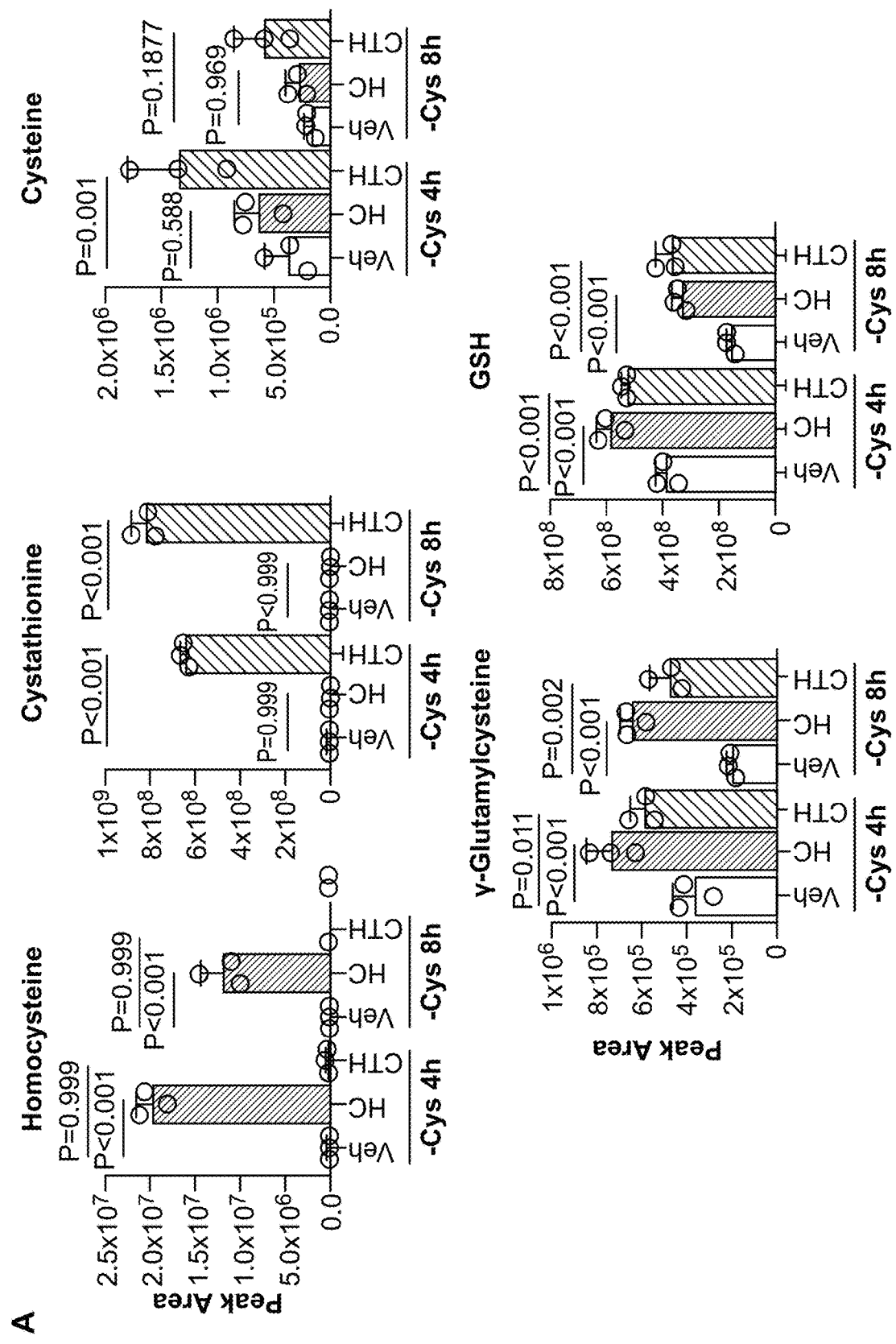
FIG. 25 PANEL A shows MDA-MB-231 cells grown in medium lacking cysteine (–Cys), supplemented with vehicle (Veh), supplemented with 0.2 mM homocysteine (HC), or supplemented with 0.2 mM cystathionine (CTH) for the stated times. PANEL B shows MDA-MB-231 cells grown in medium lacking cysteine, supplemented with vehicle (Veh), or supplemented with 0.2 mM or 0.8 mM homocysteine (HC) for 8 h.
Figure 25:
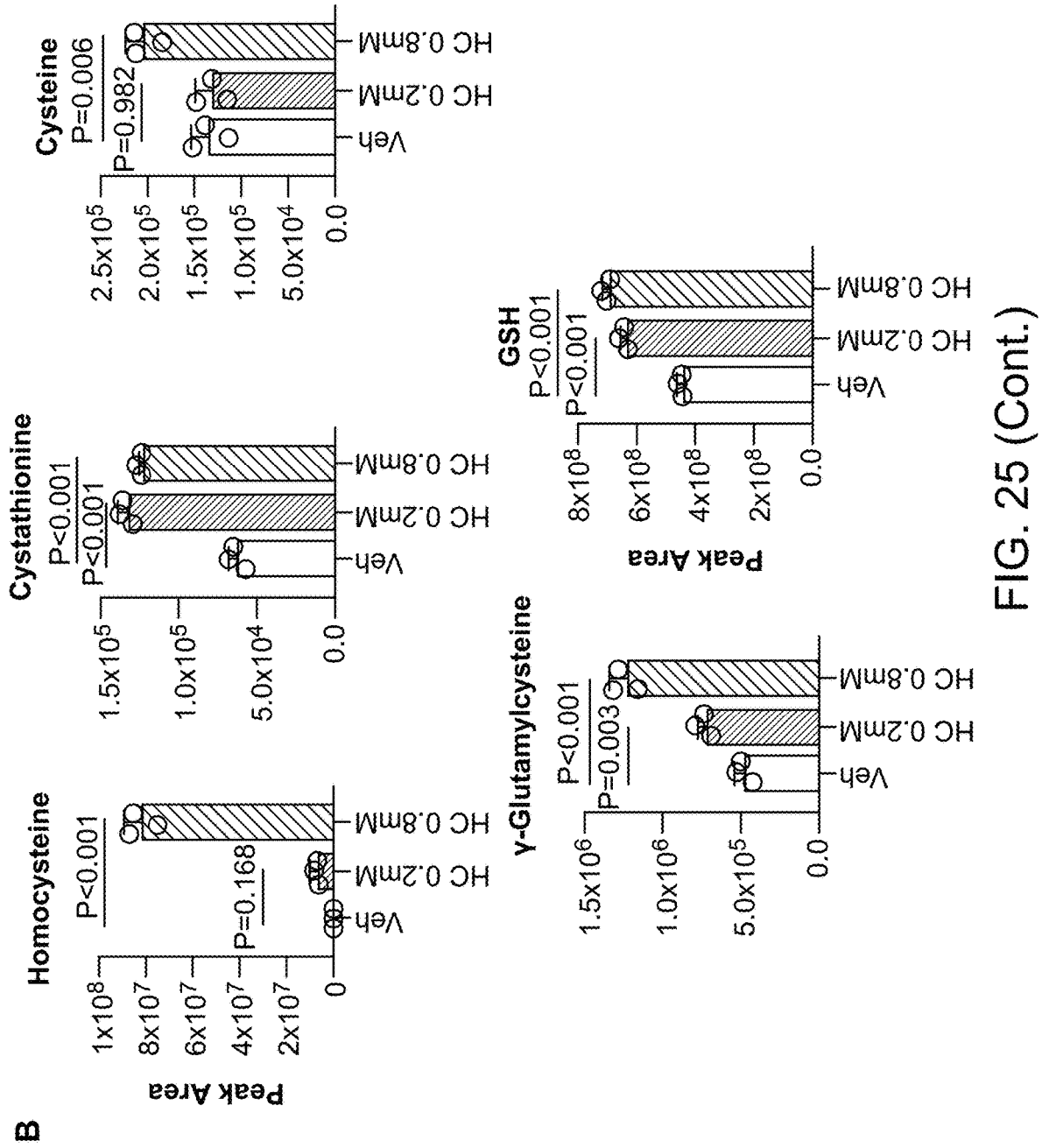

The ability of exogenous homocysteine and cystathionine to augment intracellular levels of transsulfuration intermediates and cysteine, γ-glutamylcysteine, and GSH was assessed using LC-MS analysis. FIG. 25 PANEL A shows MDA-MB-231 cells grown in medium lacking cysteine (−Cys), supplemented with vehicle (Veh), supplemented with 0.2 mM homocysteine (HC), or supplemented with 0.2 mM cystathionine (CTH) for the stated times. Metabolites were extracted and analyzed by LC-MS. PANEL B shows MDA-MB-231 cells grown in medium lacking cysteine, supplemented with vehicle (Veh), or supplemented with 0.2 mM or 0.8 mM homocysteine (HC) for 8 h. Metabolites were extracted and analyzed by LC-MS. Statistical comparisons in FIG. 23 and FIG. 25 PANEL A and PANEL B were done by an ordinary one-way ANOVA with Sidak's multiple comparison test. Other than western blots, all data are averages of n=3 biological replicates. Error bars are in SD.

Intracellular homocysteine and cystathionine levels were significantly increased by addition of 0.2 mM homocysteine or cystathionine to the culture medium, leading to moderate increases in cysteine levels, and more marked increases in γ-glutamylcysteine and GSH. The increases in cysteine, γ-glutamylcysteine, and GSH were not on a scale required to restore metabolite levels to metabolite levels seen under fed conditions (FIG. 3). High pathway turnover in the starved state may prevent metabolite accumulation.

Addition of 0.8 mM homocysteine, which restored proliferation and increased cell survival, provided a significant increase in cysteine levels (unlike 0.2 mM homocysteine). This suggests that increased GSH is required to promote survival by combating ROS. An increase in steady state cysteine levels may be important for allowing cells to proliferate (e.g. by supporting protein synthesis).

FIG. 24 PANEL A shows colorectal (HCT116 and SW480) and breast (MDA-MB-231 and MDA-MB-468) cancer cells were either grown in complete medium containing all amino acids (Ctr) or matched medium lacking cysteine with 0.8 mM homocysteine (−Cys+HC) or without homocysteine (−Cys) for 24 hr. Supplementing cells with homocysteine had little impact on transsulfuration pathway enzyme expression beyond that caused by starvation alone. The ability of exogenous homocysteine and cystathionine to rescue proliferation suggests that while transsulfuration enzyme levels may vary substantially between cell lines, the expression and activity of the transsulfuration enzymes is adequate to make cysteine if the proximal precursors are present in large enough quantities.

Figure 8:
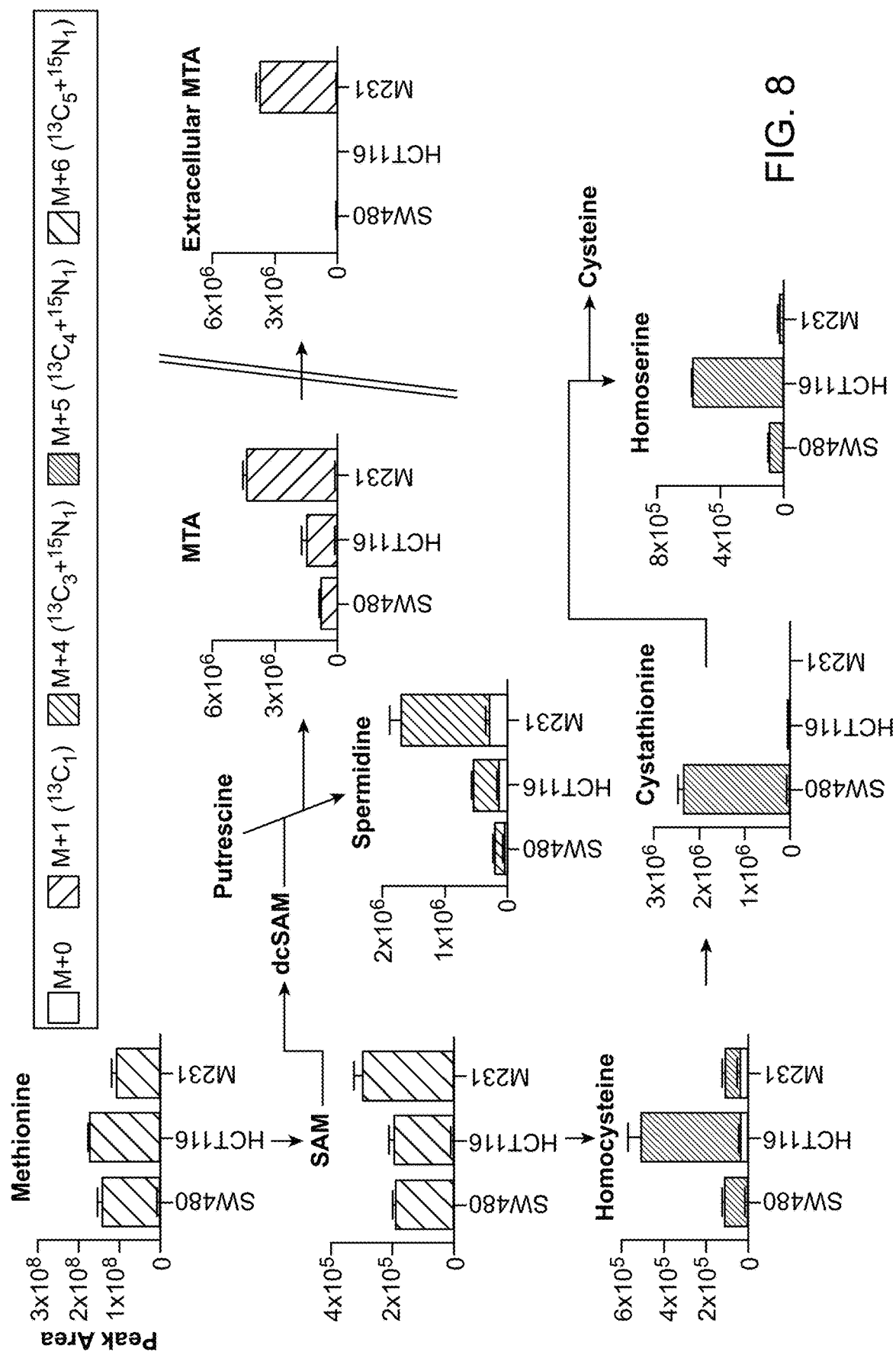
FIG. 8 shows that methionine entered the transsulfuration pathway in HCT116 and SW480 cells, with labelling detected in homocysteine, cystathionine and homoserine. Very little labelling was detected in homocysteine, cystathionine, and homoserine in MDA-MB-231 cells.
Figure 8:
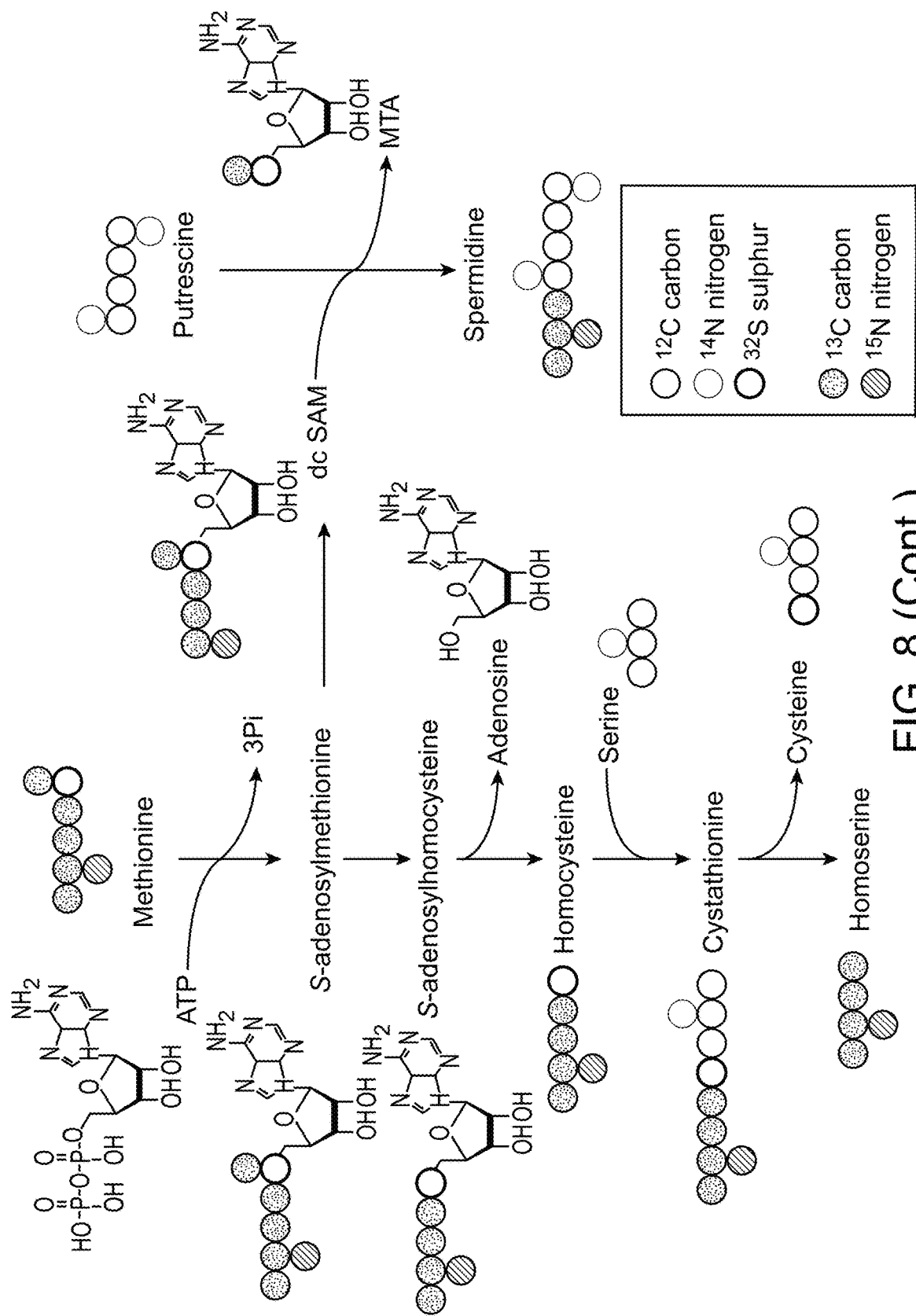

Example 4: Methylthioadenosine Efflux Correlates with Sensitivity to Cysteine Starvation The essential amino acid methionine is the ultimate upstream precursor for cysteine synthesis (FIG. 5), and should supply adequate levels of homocysteine for use in the transsulfuration pathway. The fate of methionine in highly sensitive MDA-MB-231 cells and less sensitive HCT116 and SW480 cells was determined using heavy carbon- and nitrogen-labeled methionine ($^{13}C_5$$^{15}N_1$-methionine). FIG. 8 shows that methionine entered the transsulfuration pathway in HCT116 and SW480 cells, with labelling detected in homocysteine, cystathionine and homoserine. However, very little labelling was detected in homocysteine, cystathionine, and homoserine in MDA-MB-231 cells.

Aside from the transsulfuration pathway, methionine can be used for polyamine synthesis. Polyamines have important and diverse cellular functions, and cancer cells frequently display elevated polyamine pathway activity. The highly cysteine starvation-sensitive MDA-MB-231 cells had comparatively high levels of methionine derived labelling in the polyamine spermidine. The polyamine pathway by-product 5-methylthioadenosine (MTA, derived from S-adenosylmethionine) also showed increased levels and labelling in MDA-MB-231 cells. Unlike the HCT116 and SW480 cells, MDA-MB-231 cells had a substantial exogenous pool of methionine derived labelled MTA.

MTA efflux is a functional measure of both MTAP expression and polyamine pathway activity. Levels of extracellular MTA across the cell line panel were examined using LC-MS and by plotting MTA levels versus ability to survive cysteine starvation. Unlike transsulfuration enzyme expression. FIG. 6 shows scatter plots comparing enzyme expression of S-adenosylhomocysteine hydrolase (AHCY); cystathione ß-synthase (CBS); cystathionine γ-lyase (CSE); or CBS+ CSE versus cell number after cysteine starvation.

Figure 26:
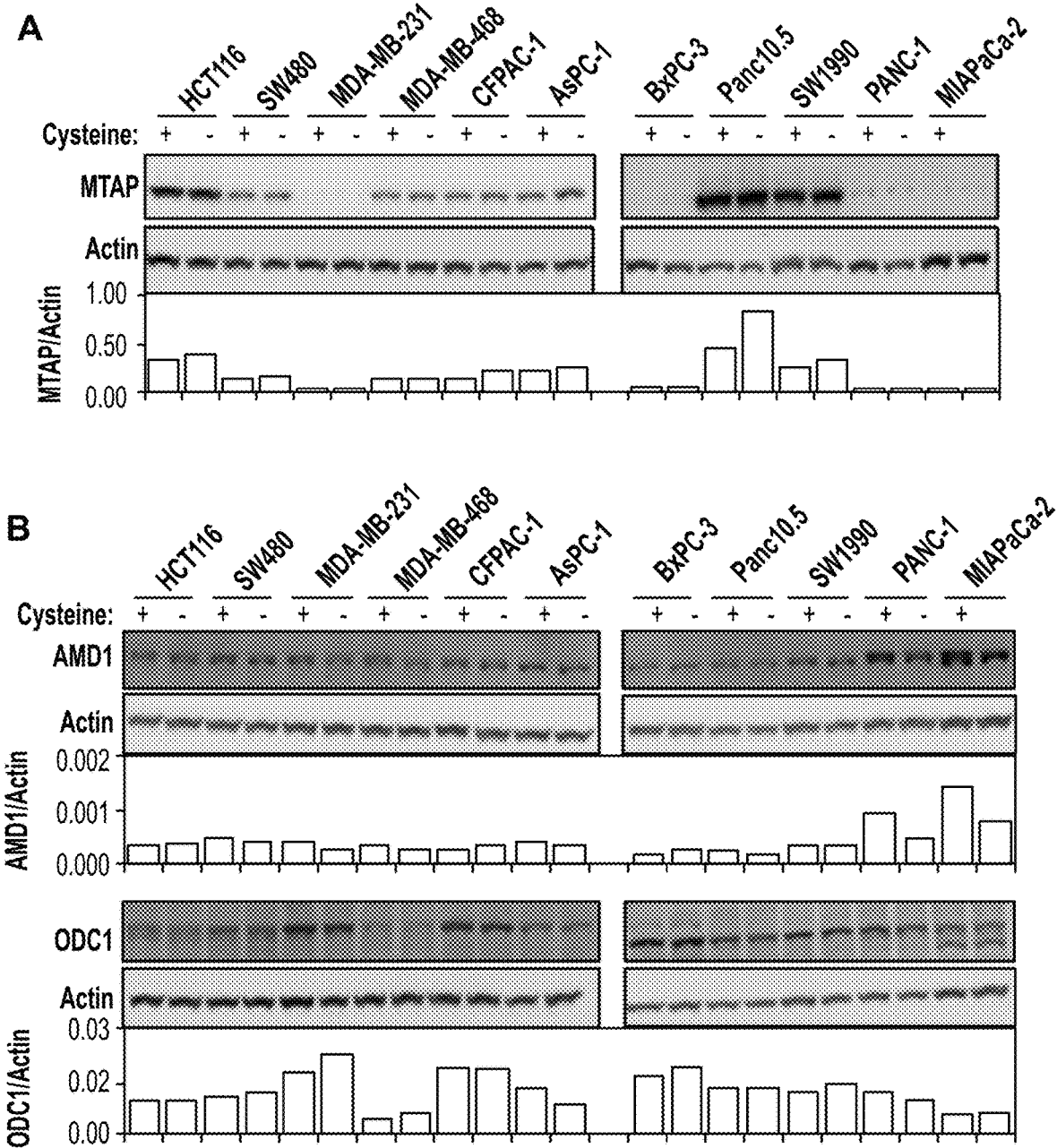
FIG. 26 PANEL A shows the impact of cells grown with (+) or without (–) cysteine for 24 hr on MTAP deletion. PANEL B shows cells grown with (+) or without (–) cysteine for 24 h. Cell lysates were probed for AMD1 and OCD1 enzyme expression by western blot and quantified with a LiCor scanner.

FIG. 9 PANEL A shows that there was a clear correlation between extracellular MTA levels and sensitivity to starvation. Cells that showed highest MTA efflux were consistently the most sensitive to cysteine starvation. MTA is the direct substrate of MTAP, a key enzyme in the methionine salvage pathway. FIG. 9 PANEL B shows that MTAP protein expression showed a correlation with cysteine starvation response, though to a lesser degree than MTA efflux. FIG. 26 PANEL A shows cells grown with (+) or without (−) cysteine for 24 hr. Cell lysates were probed for MTAP expression by western blot and quantified with a LiCor scanner.

Example 5: Polyamine Pathway Activity Correlates with Sensitivity to Cysteine Starvation Numerous cellular processes have the capacity to influence sensitivity to cysteine starvation. A wide range of additional cellular factors were tested for their correlation with cysteine starvation sensitivity in the cell line panel. The following were included in the analysis: metabolite levels for cysteine; methionine; SAM; decarboxy-SAM (dc-SAM); MTA; cystathionine; homocysteine; γ-glutamylcysteine; GSH; GSSG; NADP+ and NADPH; metabolite ratios for GSH/GSSG and NADP+/NADPH; enzyme expression for GPX4, CBS, CSE, AHCY, combined CBS+CSE, AMD1, ODC1, and combined AMD1+ODC1; lipid ROS levels (malonyldialdehyde-MDA staining); levels of phospholipids with polyunsaturated fatty acyls (PUFA-PLs; targets of ROS/Fe2+ dependent lipid peroxidation) detected by LC-MS; steady state ROS levels (CellROX staining); cellular iron uptake determined by Inductively Coupled Plasma-Optical Emission Spectrometry; and GPX4 inhibitor $IC_{50}$ values.

Of the >60 factors tested, the six factors with highest correlation (extracellular MTA [Ctr], cellular MTA [Ctr], combined ODC1+AMD1 expression [Ctr], cellular MTA [−Cys], decarboxy-SAM [Ctr] and AMD1 expression [Ctr] ($R^2$ values=0.65356 to 0.39630) are all indicators of polyamine pathway activity.

FIG. 26 PANEL B shows cells grown with (+) or without (−) cysteine for 24 h. Cell lysates were probed for AMD1 and OCD1 enzyme expression by western blot and quantified with a LiCor scanner. FIG. 27 shows correlation coefficients ($R^2$) for a range of biological parameters versus sensitivity of 11 cell lines to cysteine starvation. Metabolite levels are all intracellular, except for 'Extracellular MTA'. Multiple parameters were assessed under fed (Ctr) and cysteine-starved (−Cys) conditions. All metabolite levels are normalized to cell number. Protein expression was quantified by western blot using a LiCor scanner, and are all normalized to actin. Iron uptake was assessed by ICP-OES. Steady state ROS levels were detected by live cell imaging of CellROX stain, steady state lipid peroxidation levels were evaluated by immunocytochemistry staining for malonyldialdehyde (MDA) and were both quantified using an automated microscope.

Combined expression of CBS and CSE during cysteine starvation (CBS+CSE expression [−Cys]), was present within the top 15 of the list, supporting a role for TsP activity, but with a markedly lower correlation ($R^2$=0.20996), than for polyamine pathway activity. Also represented in the top 15 of the list are GPX4 inhibitor $IC_{50}$ values. The predictable correlation is indicative that cysteine starvation and GPX4 inhibition kills cells by the same mechanism—i.e. ferroptosis. While cysteine starvation-sensitive cells could be primed for sensitivity by having low GPX4 levels, GPX4 expression showed little correlation to cysteine starvation sensitivity [$R^2$ GPX4 Ctr=0.03213, $R^2$ GPX4−Cys=0.05780]. The data demonstrate a correlation between polyamine pathway activity and cellular sensitivity to cysteine starvation.

Figure 28:
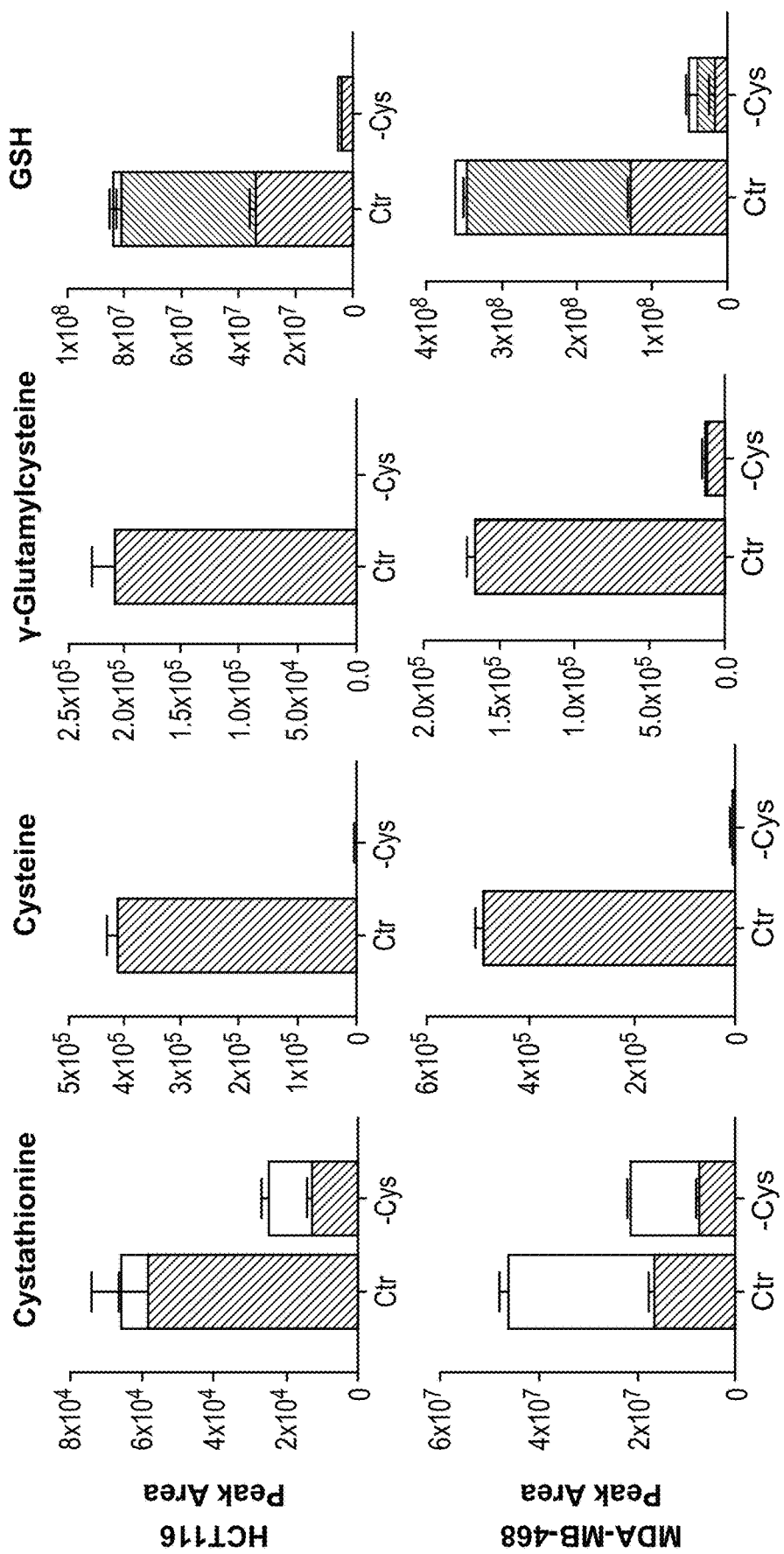
FIG. 28 shows cells grown in complete medium (0.4 mM with $^{13}C_3{}^{15}N_1$-serine substituted for serine) for 48 h.
Figure 28:
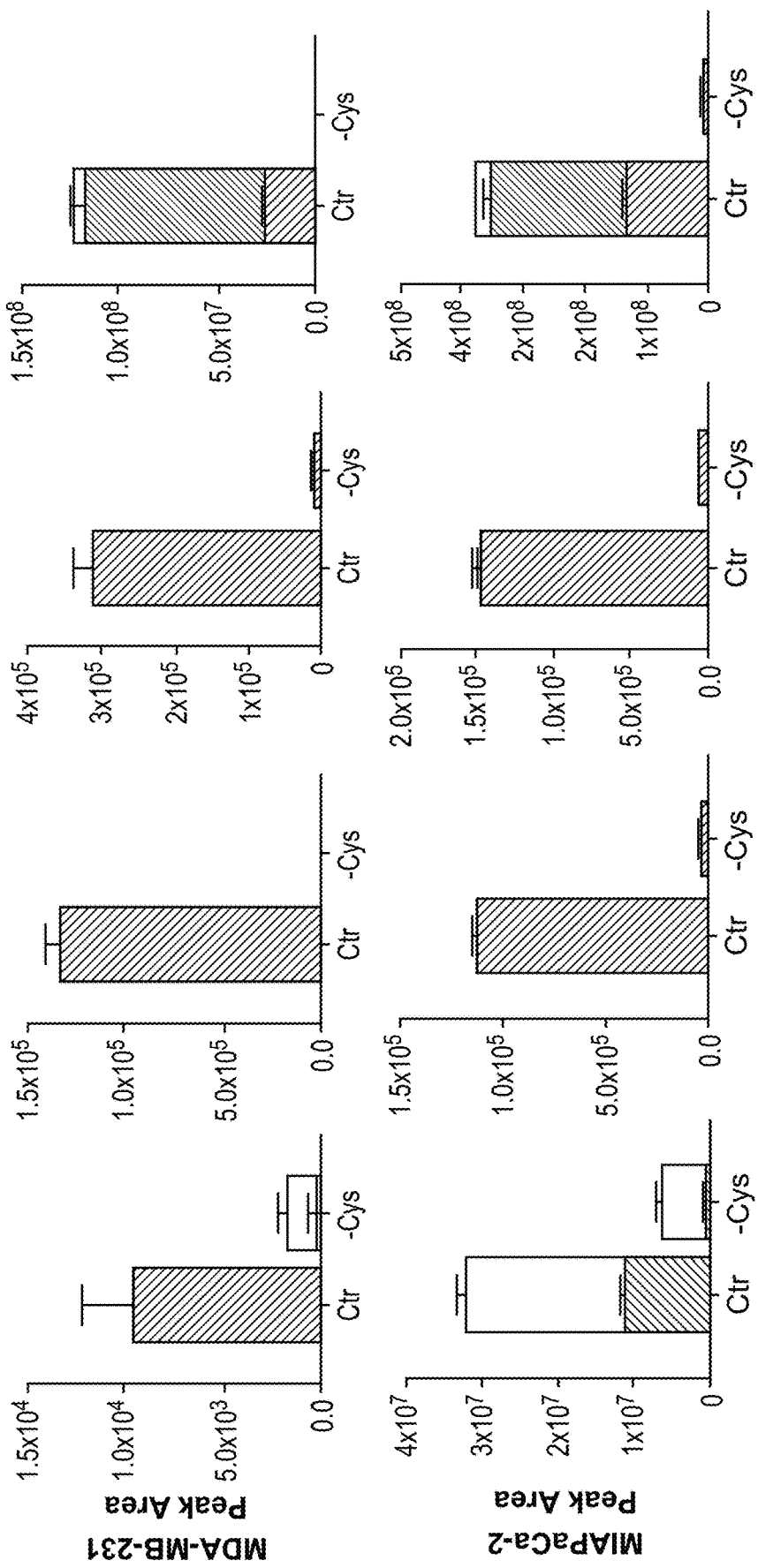

Example 6: Lack of Correlation Between De Novo Cysteine Synthesis and High Sensitivity to Cysteine Starvation To more closely scrutinize TsP activity and de novo cysteine synthesis, cells were supplemented with $^{13}C_3^{15}N_1$-serine, which, unlike $^{13}C_5^{15}N_1$-methionine, gives rise to labelled cysteine when utilized by TsP (FIG. 8). It can be difficult to detect measurable intracellular steady state levels of a highly cell permeable nutrients when removed from the medium. Under starvation conditions, newly synthesized high-demand nutrients, such as serine and cysteine, are rapidly converted into downstream metabolites, making detectable steady state levels difficult to accumulate. FIG. 28 shows cells grown in complete medium (0.4 mM with $^{13}C_3^{15}N_1$-serine substituted for serine) for 48 h. Metabolites were extracted and analyzed by LC-MS.

Labelling in the downstream metabolites into which the labelled metabolite is converted is possible to detect. In the case of cysteine, the downstream metabolite GSH can be detected. There are two possible routes of incorporation of serine-derived carbon and nitrogen into GSH: via glycine synthesis and via cysteine synthesis. Mass+3 (m+3, $^{13}C_2^{15}N_1$) GSH indicates serine>glycine>GSH labelling, whereas m+4 ($^{13}C_3^{15}N_1$) GSH indicates serine>cysteine>GSH labelling. An m+7 GSH peak indicates serine derived glycine (m+3) and serine derived cysteine (m+4) are simultaneously incorporated into GSH.

De novo cysteine synthesis did not correlate with a response to cysteine starvation. FIG. 29 PANEL A uses peak area data shown in FIG. 28 to show GSH levels as a % total of the total GSH pool. In the top panel, all isotopologues are shown. In the lower panel, only cysteine-derived isotopologues (m+4 and m+7) are shown. All data are averages of n=3 biological replicates. Error bars are in SD. While HCT116, MDA-MB-468, MDA-MB-231, and MIAPaCa-2 cells all showed evidence of de novo cysteine synthesis after 48 h of starvation, cysteine synthesis was not higher in the more resistant cells. HCT116 (more resistant) and MDA-MB-231 (more sensitive) had comparable low levels of de novo cysteine synthesis during cysteine starvation, and MDA-MB-468 (more resistant) and MIAPaCa-2 (more sensitive) had comparable high levels of de novo cysteine synthesis during cysteine starvation.

The protein expression and LC-MS data suggested that de novo cysteine synthesis was not the dominant determinant of sensitivity to cysteine starvation. The basic underlying importance of de novo cysteine synthesis was confirmed by treating cells with a CSE inhibitor, beta-cyano-L-Alanine. FIG. 29 PANEL B shows cells grown in complete (Ctr) or medium lacking cysteine (−Cys) without (Veh) or with 0.5 mM or 1 mM of the CSE inhibitor beta-cyano-L-alanine for 48 h. The data contains analysis underlying correlation coefficients in FIG. 27. All data are averages of n=3 biological replicates. Error bars are in SD. As expected, CSE inhibitor treatment increased the sensitivity to cysteine starvation of the resistant cell lines SW480 and MDA-MB-468, validating the basic role of TsP in making cysteine. HCT116 cells had only a modest response to CSE inhibition, reflecting low levels of TsP activity shown in FIG. 29 PANEL A. The data disclosed herein show that while TsP activity has a clear functional role in helping cells adapt to cysteine starvation, TsP activity is not necessarily the dominant factor in determining which cell lines have the highest degree of sensitivity.

Figure 30:
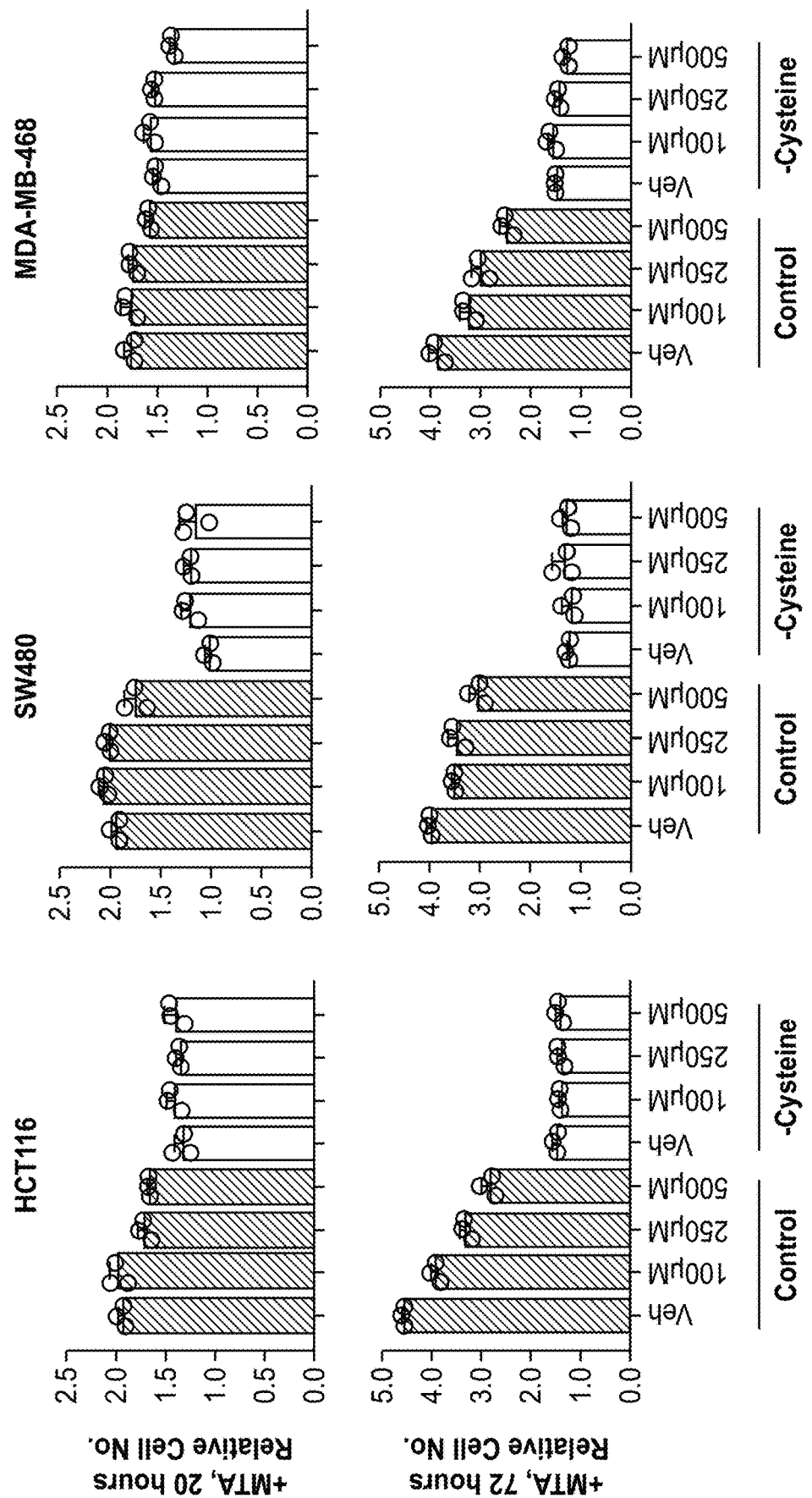
FIG. 30 shows cells grown in complete medium containing all amino acids (Ctr) or matched medium lacking cysteine (–Cys) with increasing amounts of MTA for 20 hr and 72 h.
Figure 30:
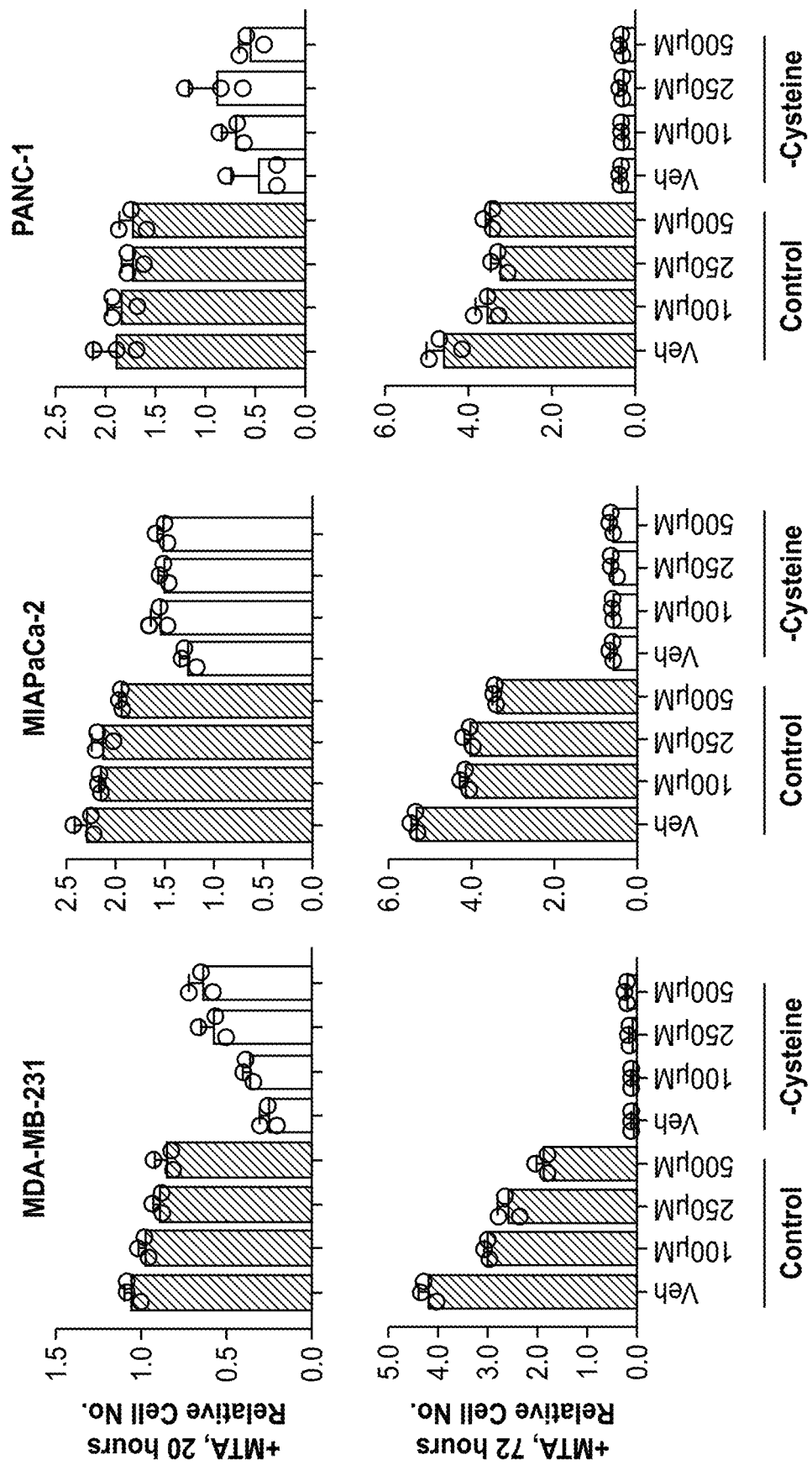
Figure 31:
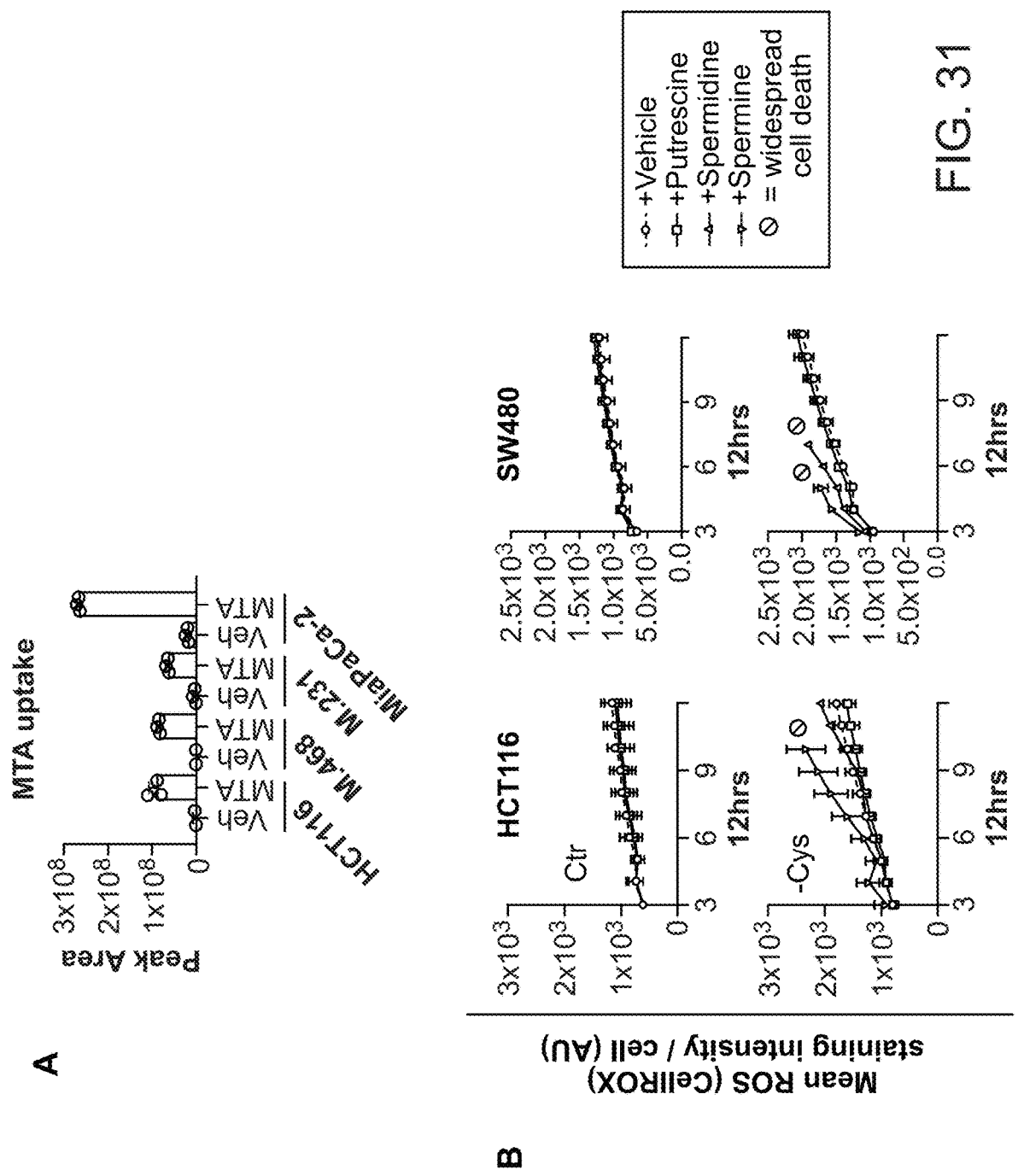
FIG. 31 PANEL A shows cells grown in complete medium with vehicle or 500 µM MTA for 24 h. Metabolites were extracted and analyzed by LC-MS. PANEL B TOP ROW shows cells grown in complete medium containing either 20 µM putrescine (+Putrescine), 20 µM spermidine (+Spermidine), or 20 UM spermine (+Spermine) or without the agents (+Vehicle). PANEL B BOTTOM ROW shows cells grown in medium without cysteine containing 20 µM putrescine (+Putrescine), 20 µM spermidine (+Spermidine), or 20 UM spermine (+Spermine) or without the agents (+Vehicle).
Figure 31:
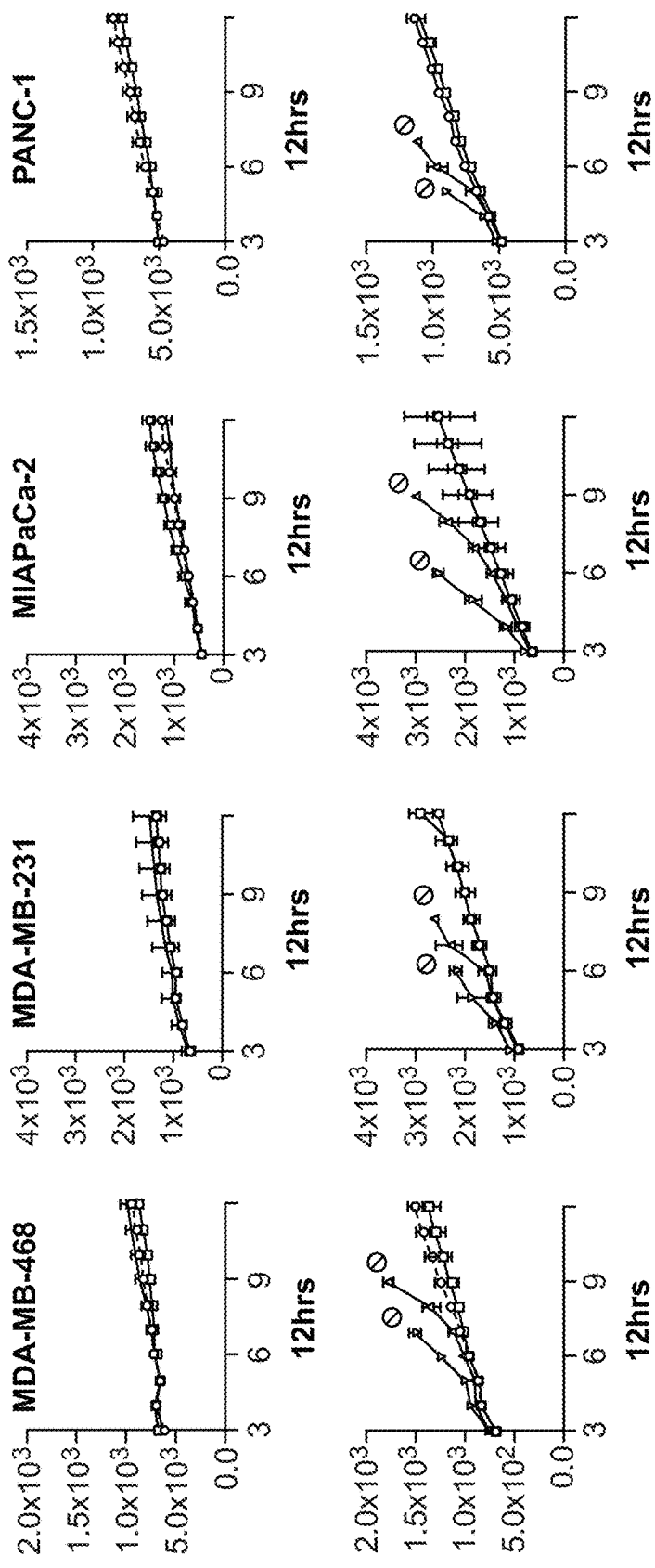

Due to the lack of correlation between de novo synthesis and cysteine starvation sensitivity, the effect of polyamine metabolism on cysteine starvation sensitivity was investigated by supplementing cells with polyamine pathway metabolites. FIG. 30 shows cells grown in complete medium containing all amino acids (Ctr) or matched medium lacking cysteine (−Cys) with increasing amounts of MTA for 20 hr and 72 h. FIG. 31 PANEL A shows cells grown in complete medium with vehicle or 500 μM MTA for 24 h. Metabolites were extracted and analyzed by LC-MS. While high levels of MTA decreased the proliferation of fed cells, MTA did not sensitize cells to cysteine starvation. MTA also showed a trend in at least one of the sensitive cell lines (MDA-MB-231) to give short-term protection from cysteine starvation. The results indicated that MTA does not sensitize cells to cysteine starvation.

Figure 10:
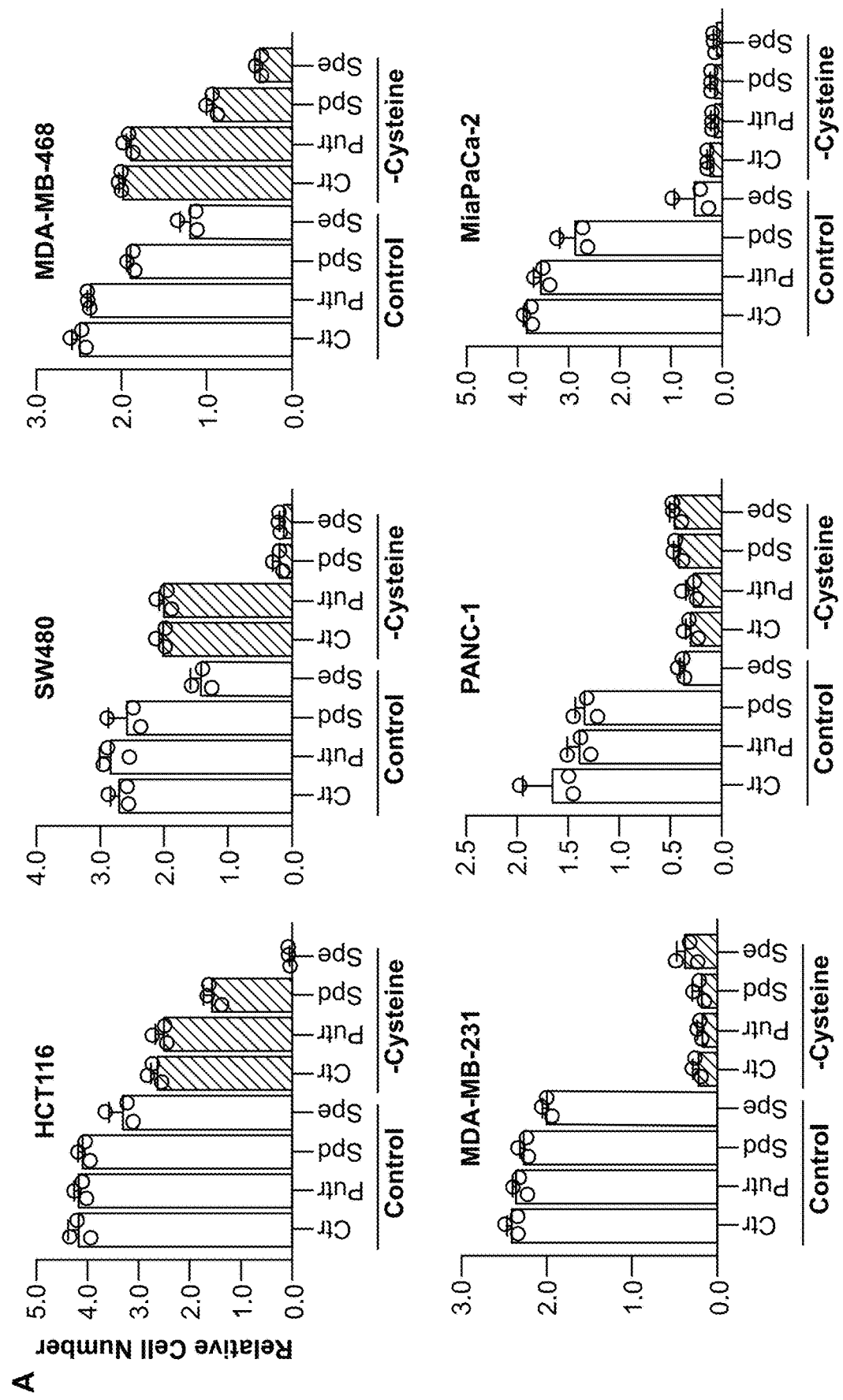
FIG. 10 ROW A shows that resistant cell lines HCT116, SW480, and MDA-MB-468 became highly sensitized in the presence of the polyamines. ROW B shows a consistent trend for lower putrescine concurrent with higher spermidine and spermine in the more sensitive cells (MDA-MB-231, PANC-1 and MIAPaCa-2).
Figure 10:
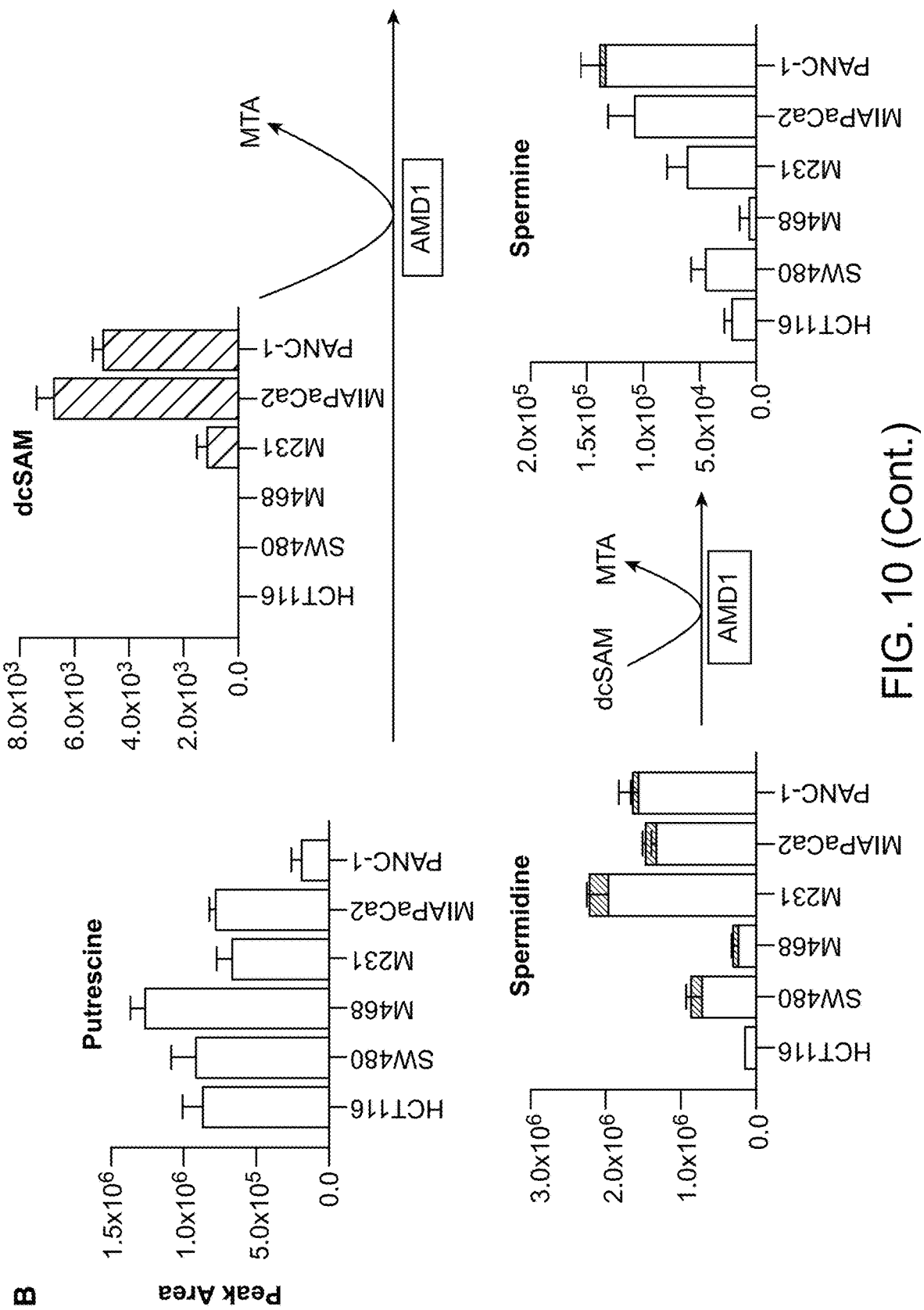

Next, cells were supplemented directly with the polyamines putrescine, spermidine and spermine. In contrast to MTA and putrescine, spermidine and spermine had a dramatic impact on cysteine starvation sensitivity. FIG. 10 ROW A shows that resistant cell lines HCT116, SW480, and MDA-MB-468 became highly sensitized in the presence of the polyamines. PANEL B TOP ROW shows cells grown in complete medium containing either 20 μM putrescine (+Putrescine), 20 μM spermidine (+Spermidine), or 20 UM spermine (+Spermine) or without the agents (+Vehicle). PANEL B BOTTOM ROW shows cells grown in medium without cysteine containing 20 μM putrescine (+Putrescine), 20 μM spermidine (+Spermidine), or 20 μM spermine (+Spermine) or without the agents (+Vehicle). Reactive oxygen species (ROS) were detected in real-time by an Operetta automated microscope in live cells treated with CellROX deep red. Staining for ROS levels in live cells supplemented with polyamines showed that spermidine and spermine caused a rapid increase in ROS levels in cysteine starved cells with very rapid, widespread cell death. LC-MS analysis was used to directly assess polyamine levels in cells under control conditions. FIG. 10 ROW B shows that there was a consistent trend for lower putrescine concurrent with higher spermidine and spermine in the more sensitive cells (MDA-MB-231, PANC-1 and MIAPaCa-2), suggesting higher rates of de novo spermidine/spermine synthesis. A short (3 h) labelling period with $^{13}C_5^{15}N_1$-methionine generally showed limited labelling in spermidine and spermine, and there was clear labelling upstream in dc-SAM, but only in the MTAP deficient, cysteine starvation sensitive cell lines. dc-SAM is produced from SAM by AMD1-catalysed decarboxylation, and is required for the synthesis of spermidine and spermine, during which dc-SAM is converted to MTA. The results show that MTAP-deleted cell lines have higher production of dc-SAM, leading to increased synthesis of polyamines such as spermidine and spermine, which may contribute to cysteine starvation sensitivity.

Figure 11:
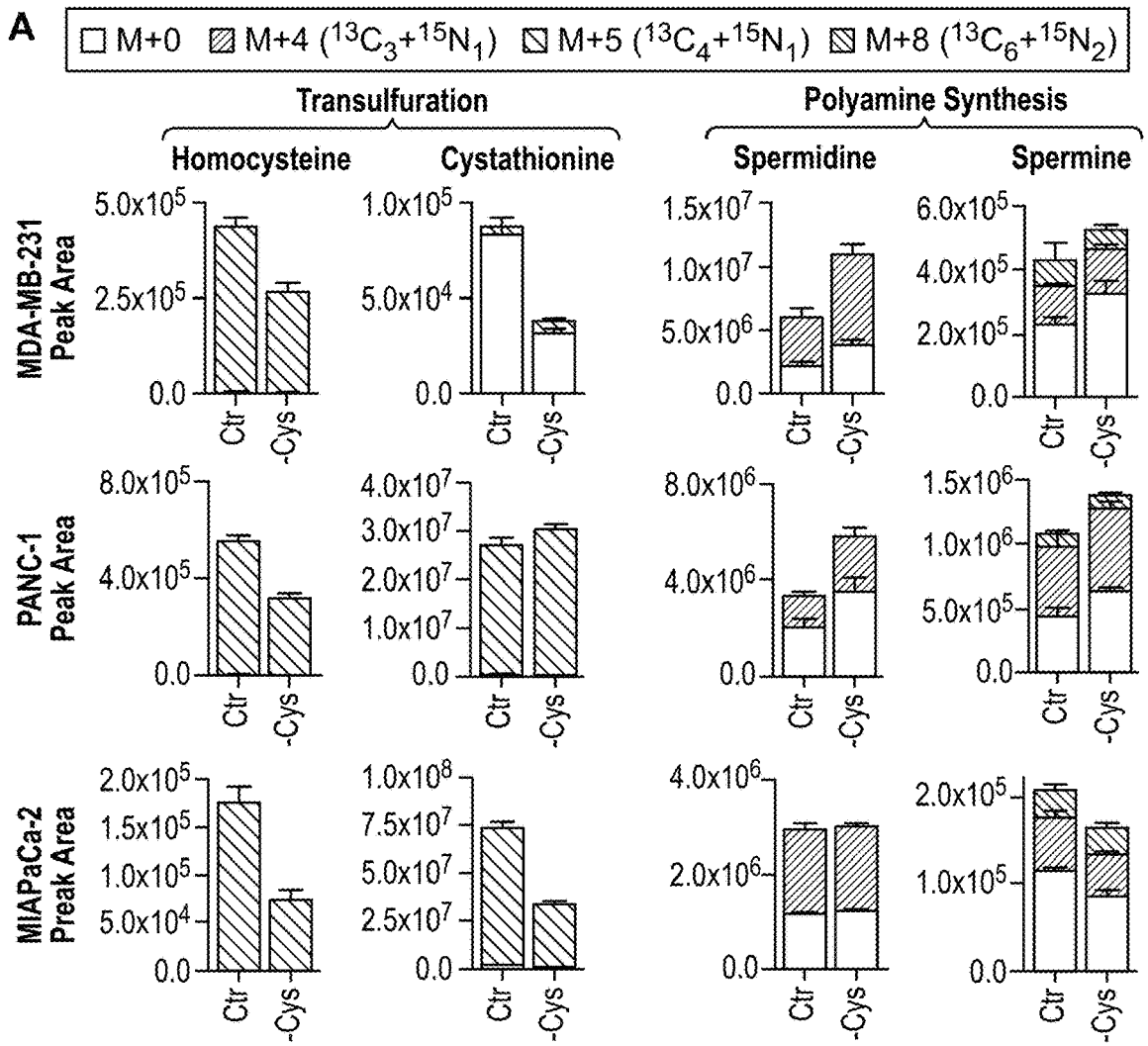
FIG. 11 PANEL A shows LC-MS analyses of MDA-MB-231, PANC-1, and MIAPaCa-2 cells supplemented with homocysteine, cystathionine, spermidine, or spermine to assess the activity of the polyamine pathway versus TsP during cysteine starvation. PANEL B shows that treating cells with an AMD1 inhibitor (sardomozide) prevented cell death in response to cysteine starvation.

FIG. 11 PANEL A shows LC-MS analyses of MDA-MB-231, PANC-1, and MIAPaCa-2 cells supplemented with homocysteine, cystathionine, spermidine, or spermine to assess the activity of the polyamine pathway versus TsP during cysteine starvation. Longer (16 h) incubation times with $^{13}C_5^{15}N_1$-methionine resulted in a high proportion of polyamines and TsP intermediates being labelled. Polyamine labelling was generally maintained or even increased during starvation, suggesting that polyamine synthesis remains active during starvation.

To assess whether diminished polyamine pathway activity could rescue cells from starvation, two methods were employed to inhibit the pathway. As the decarboxylase responsible for SAM to dc-SAM conversion, AMD1 has an important role in regulating polyamine synthesis. FIG. 11 PANEL B shows that treating cells with an AMD1 inhibitor (sardomozide) prevented cell death in response to cysteine starvation.

FIG. 32 PANEL A shows cells grown in complete medium with or without 0.1 mM MTOB for 16 h, then either grown in complete medium (Ctr) or matched medium lacking cysteine (−Cys) with or without 0.1 mM MTOB for 32 h. FIG. 32 PANEL B shows cells grown in complete medium with or without 0.1 mM MTOB for 5 h, with 0.2 mM $^{13}C_5^{15}N_1$-methionine substituted for methionine). Similar to AMD1 inhibition, 4-methylthio-2-oxobutanoic acid (MTOB) supplementation rescued cells from cysteine starvation. Rescue with either method (AMD1 inhibitor/MTOB supplementation) was temporary, especially with the AMD1 inhibitor.

Figure 12:
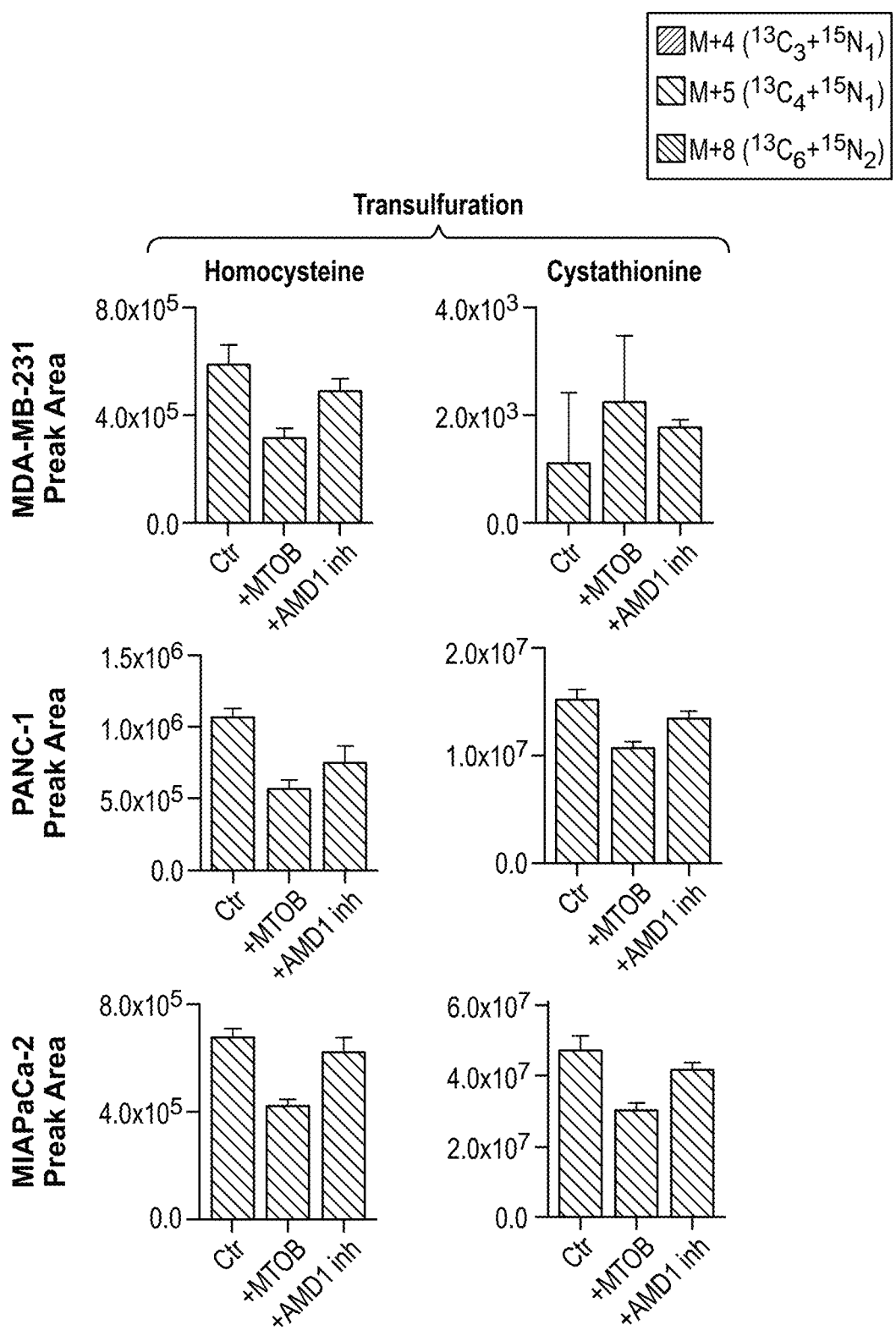
FIG. 12 shows LC-MS analyses of MDA-MB-231, PANC-1, and MIAPaCa-2 cells starved of cysteine and grown with $^{13}C_5{}^{15}N_1$-methionine or $^{34}S_1$-methionine.
Figure 12:
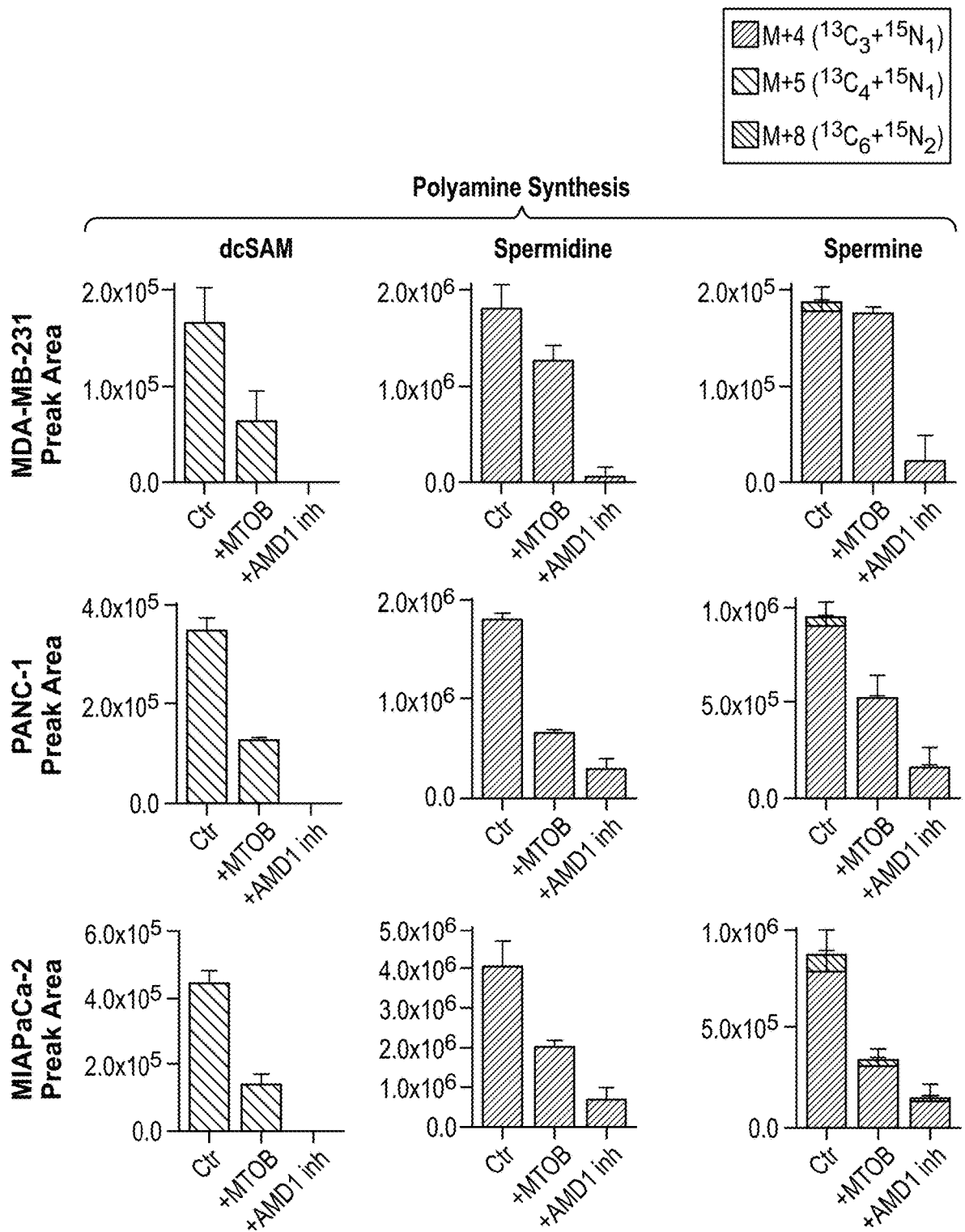
Figure 33:
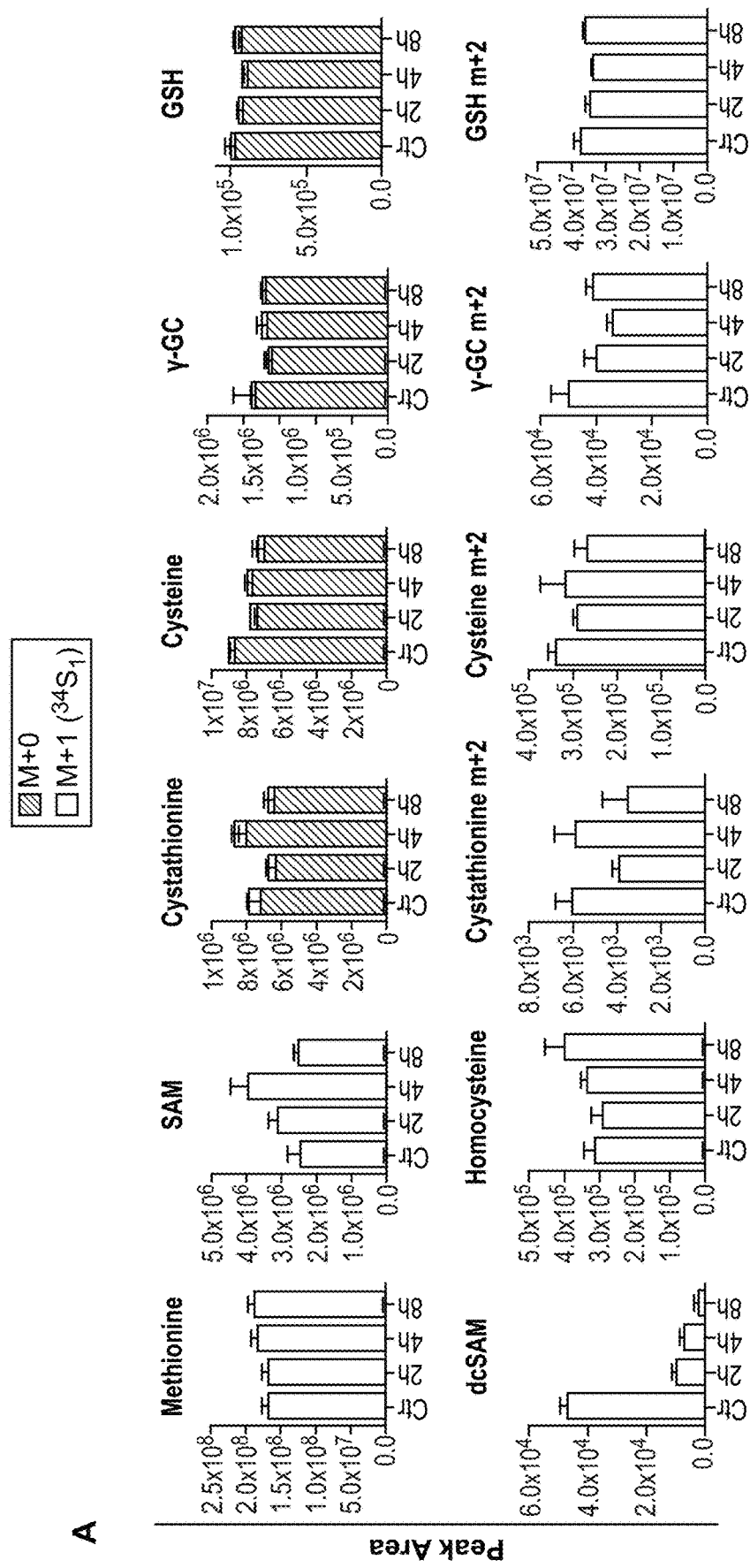
FIG. 33 PANEL A shows MDA-MB-231 cells grown in complete medium (with 0.2 mM $^{23}S_1$-methionine substituted for methionine) for 24 h, then treated with 20 µM of the AMD1 inhibitor sardomozide for 2 h, 4 h, and 8 h.

FIG. 12 shows LC-MS analyses of MDA-MB-231, PANC-1, and MIAPaCa-2 cells starved of cysteine and grown with $^{13}C_5^{15}N_1$-methionine or $^{34}S_1$-methionine. FIG. 33 PANEL A shows MDA-MB-231 cells grown in complete medium (with 0.2 mM $^{23}S_1$-methionine substituted for methionine) for 24 h, then treated with 20 μM of the AMD1 inhibitor sardomozide for 2 h, 4 h, and 8 h. PANEL B shows MDA-MB-231 cells (left) and MIAPaCa-2 cells (right) grown in complete medium with or without 20 μM of the AMD1 inhibitor sardomozide for 16 h (with 0.2 mM $^{34}S_1$-methionine substituted for methionine). All data are averages of n=3 biological replicates. Error bars are SD. The data disclosed herein show that AMD1 inhibition and MTOB supplementation caused a marked inhibition of polyamine synthesis, displayed as decreased dc-SAM and polyamine labelling, which was particularly strong for the AMD1 inhibitor. The data disclosed herein also show that preventing entry of methionine into the polyamine pathway did not appreciably increase the levels of TsP intermediates.

Figure 13:
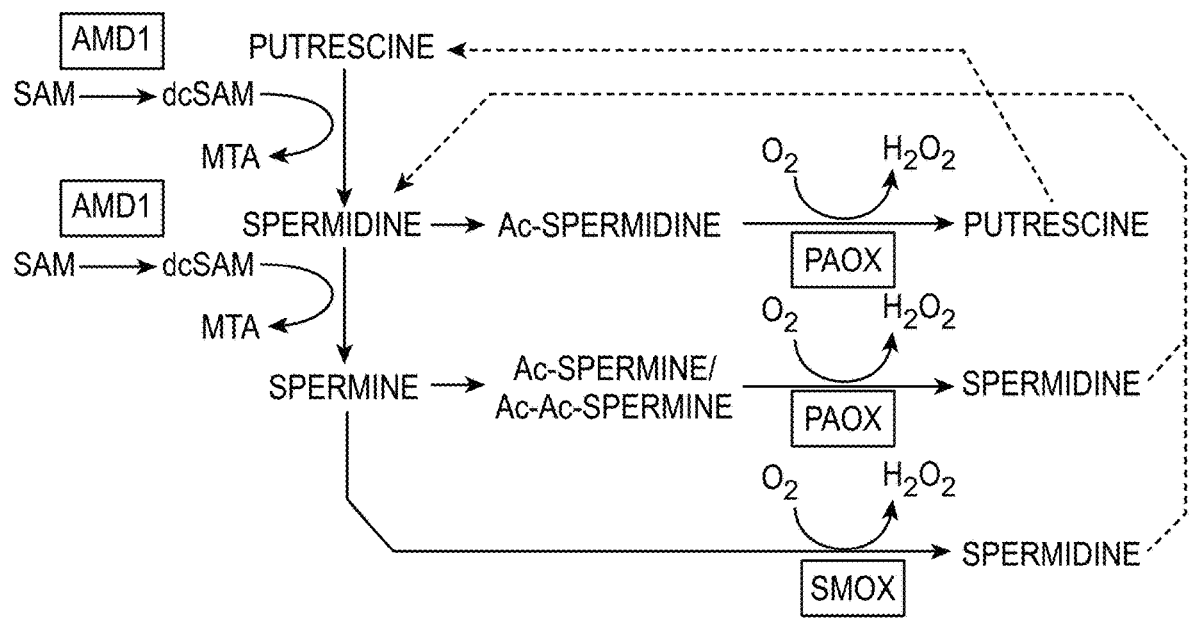
FIG. 13 illustrates the reactions of polyamine metabolism that generate the reactive oxygen species (ROS) hydrogen peroxide ($H_2O_2$).
Figure 14:
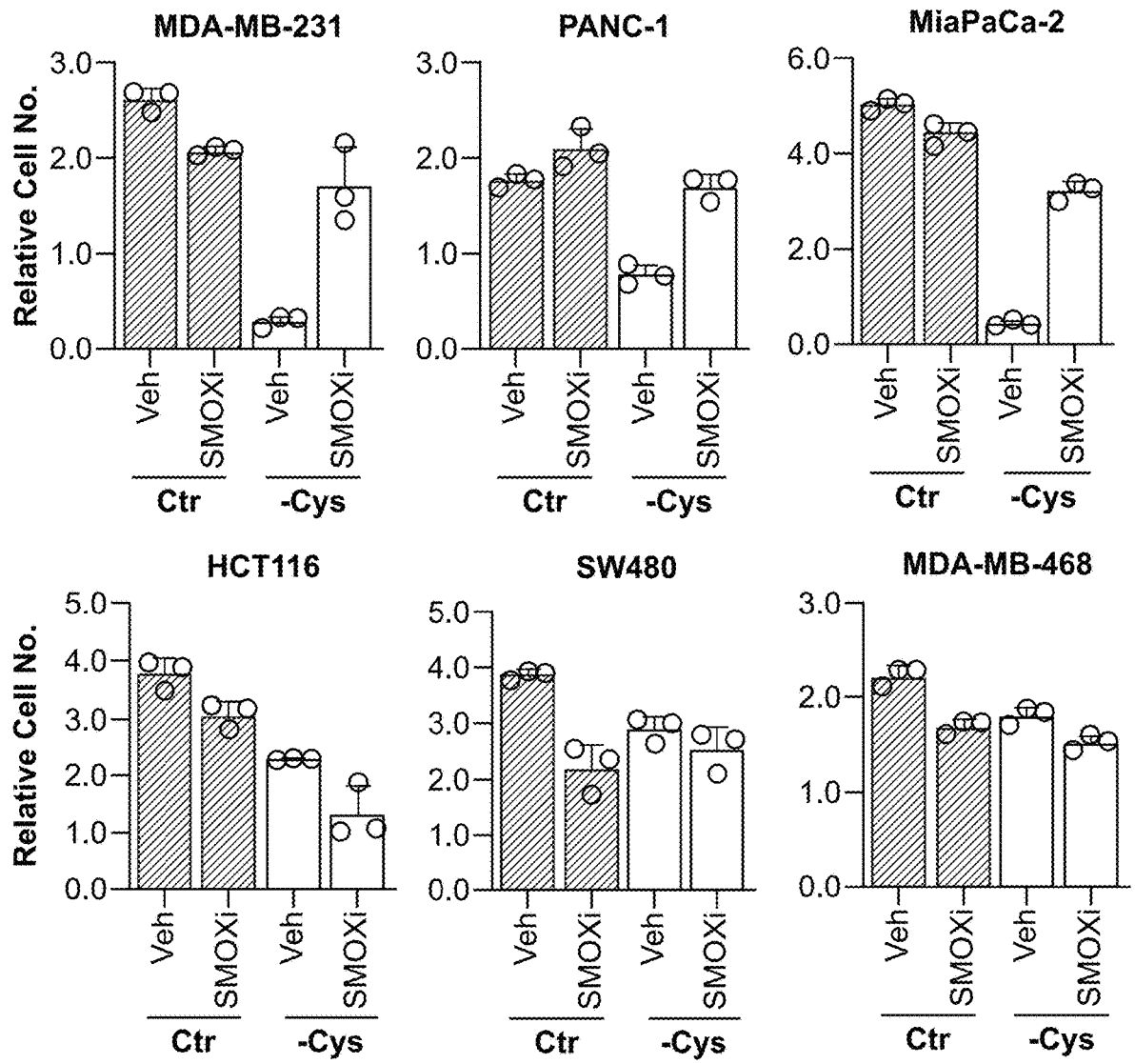
FIG. 14 shows the effect of treating MDA-MB-231, PANC-1, MIAPaCa-2, HCT116, SW480, and MDA-MB-468 cells with a SMOX inhibitor to assess the impact of these ROS-generating reactions on the response of cells to cysteine starvation.

Example 7: Inhibiting Polyamine Metabolism Protects Highly Sensitive Cells from Cysteine Starvation There are multiple reactions of polyamine metabolism that generate the reactive oxygen species hydrogen peroxide ($H_2O_2$), potentially explaining the ability of spermidine and spermine to increase ROS levels and sensitize cells to starvation (FIG. 13). These reactions are mediated by spermine oxidase (SMOX) and polyamine oxidase (PAOX). FIG. 14 shows the effect of treating MDA-MB-231, PANC-1, MIAPaCa-2, HCT116, SW480, and MDA-MB-468 cells with a SMOX inhibitor to assess the impact of these ROS-generating reactions on the response of cells to cysteine starvation. FIG. 34 shows cells grown in complete medium without or with 10 μM, 40 μM, or 80 μM of a PAOX inhibitor for 16 h, then grown in complete medium (Ctr) or matched medium lacking cysteine without or with 10 μM, 40 μM, or 80 μM of a PAOX inhibitor for 24 h. Inhibition of SMOX and PAOX prevented cell death in starvation sensitive cell lines (MDA-MB-231, MIAPaCa-2, and PANC-1). In starvation resistant cell lines (HCT116, SW480, and MDA-MB-468), SMOX and PAOX inhibitors gave little or no additional advantage during cysteine starvation.

Figure 15:
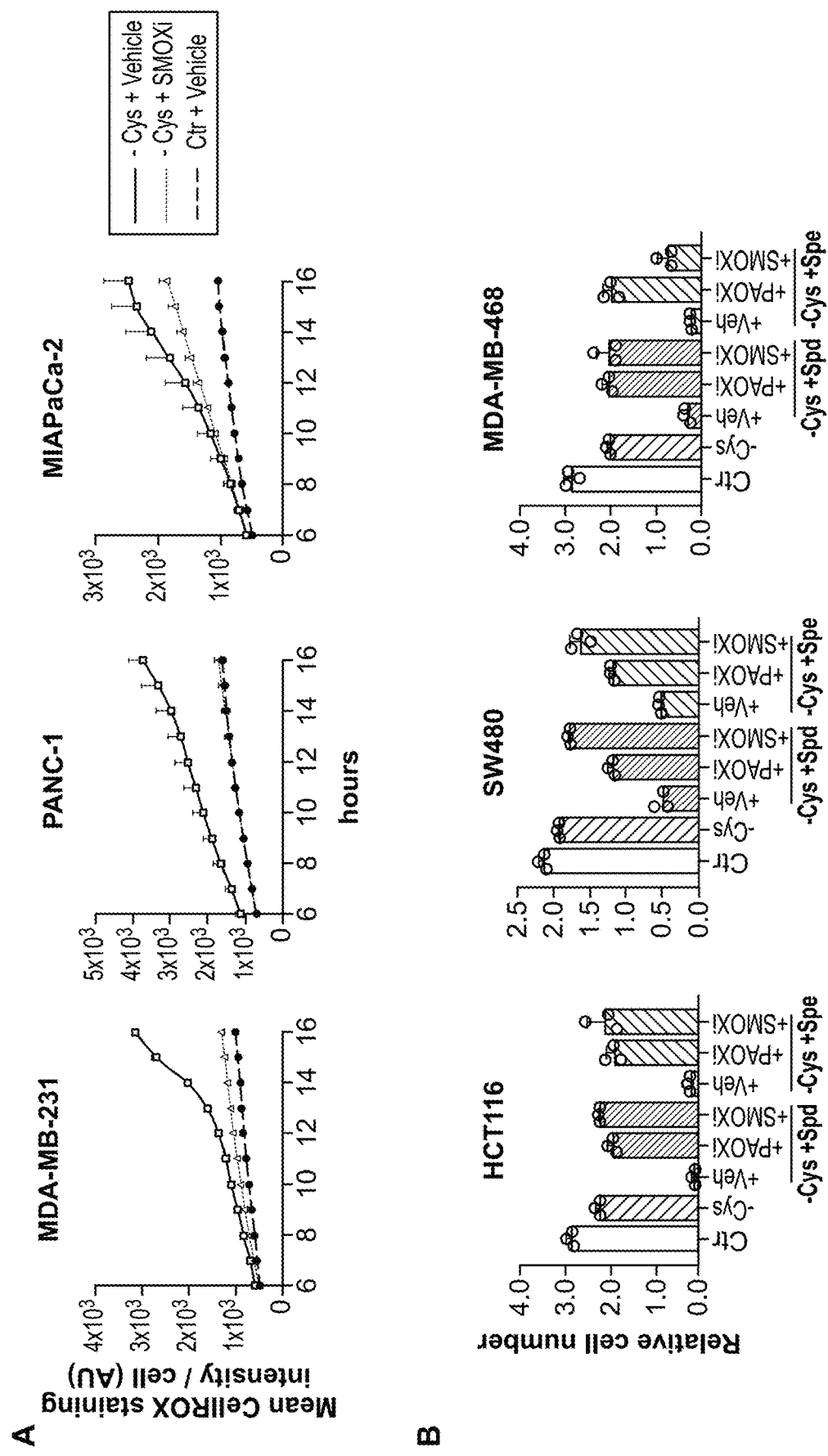
FIG. 15 ROW A shows the effects of cysteine starvation and/or treatment with a SMOX inhibitor on MDA-MB-231, PANC-1, and MIAPaCa-2 cells on mean CellROX staining intensities. ROW B shows the effect of cysteine starvation, treatment with SMOX and PAOX inhibitors, spermidine or spermine on HCT116, SW480, and MDA-MB-468 cells. ROW C shows the effect of cysteine starvation and/or AMD1 inhibition on mean CellROX staining intensity in MDA-MB-231, PANC-1, and MIAPaCa-2 cells.
Figure 15:
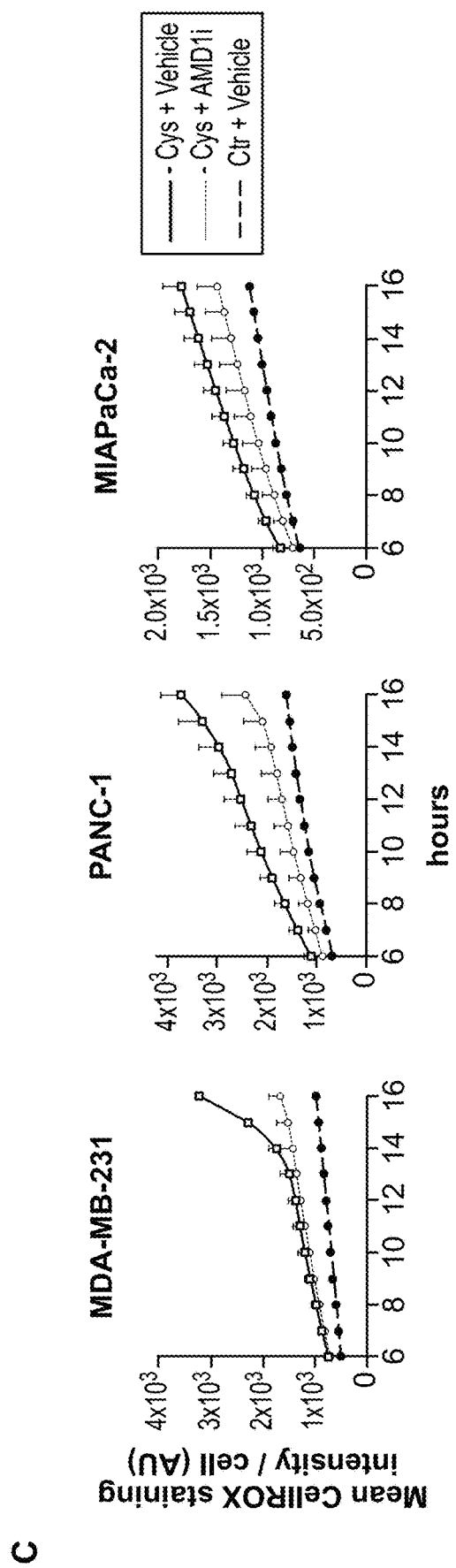

FIG. 15 ROW A shows the effects of cysteine starvation and/or treatment with a SMOX inhibitor on MDA-MB-231, PANC-1, and MIAPaCa-2 cells on mean CellROX staining intensities. FIG. 35 PANEL A shows cell lines grown in complete medium with 50 UM of the SMOX inhibitor MDL72527 (+SMOXi) or without (+Vehicle) a SMOX inhibitor, then grown in complete medium (Ctr) or matched medium lacking cysteine (−Cys) with or without 50 μM of the SMOX inhibitor. ROS were detected in real-time by an Operetta automated microscope in live cells treated with CellROX deep red. ROS staining intensity is shown for the 16 h timepoint. Analysis of ROS levels confirmed that inhibiting SMOX during cysteine starvation allowed cells to maintain lower ROS levels.

Given that SMOX and PAOX reactions require oxygen ($O_2$), whether oxygen levels could modulate the response to cysteine starvation was investigated. FIG. 35 PANEL B shows MDA-MB-231 cells grown in either complete medium, medium lacking cysteine under normoxia (Nor) or hypoxia (Hyp); 1% oxygen for stated times. Growth in hypoxic conditions (1% $O_2$) prevented cell death after 24 h cysteine starvation. However, this rescue was temporary with cell death occurring by 32 h.

Next, whether SMOX and PAOX inhibition could rescue starvation resistant cells from the sensitizing effects of spermidine and spermine treatment was tested. FIG. 15 ROW B shows the effect of cysteine starvation, treatment with SMOX and PAOX inhibitors, spermidine or spermine on HCT116, SW480, and MDA-MB-468 cells. SMOX and PAOX inhibitors restored HCT116, SW480, and MDA-MB-468 cell survival and growth under polyamine treatment concurrent with cysteine starvation. FIG. 15 ROW C shows the effect of cysteine starvation and/or AMD1 inhibition on mean CellROX staining intensity in MDA-MB-231, PANC-1, and MIAPaCa-2 cells. FIG. 35 PANEL C shows cell lines grown in complete medium (Ctr) or matched medium lacking cysteine (−Cys) with 20 μM of an AMD1 inhibitor or without an AMD1 inhibitor. ROS were detected in real-time by a microscope in live cells treated with CellROX deep red. ROS staining intensity is shown for the 16 h timepoint. Similar to SMOX inhibition, AMD1 inhibition diminished ROS levels, demonstrating that polyamine metabolism increases ROS during cysteine starvation.

Figure 16:
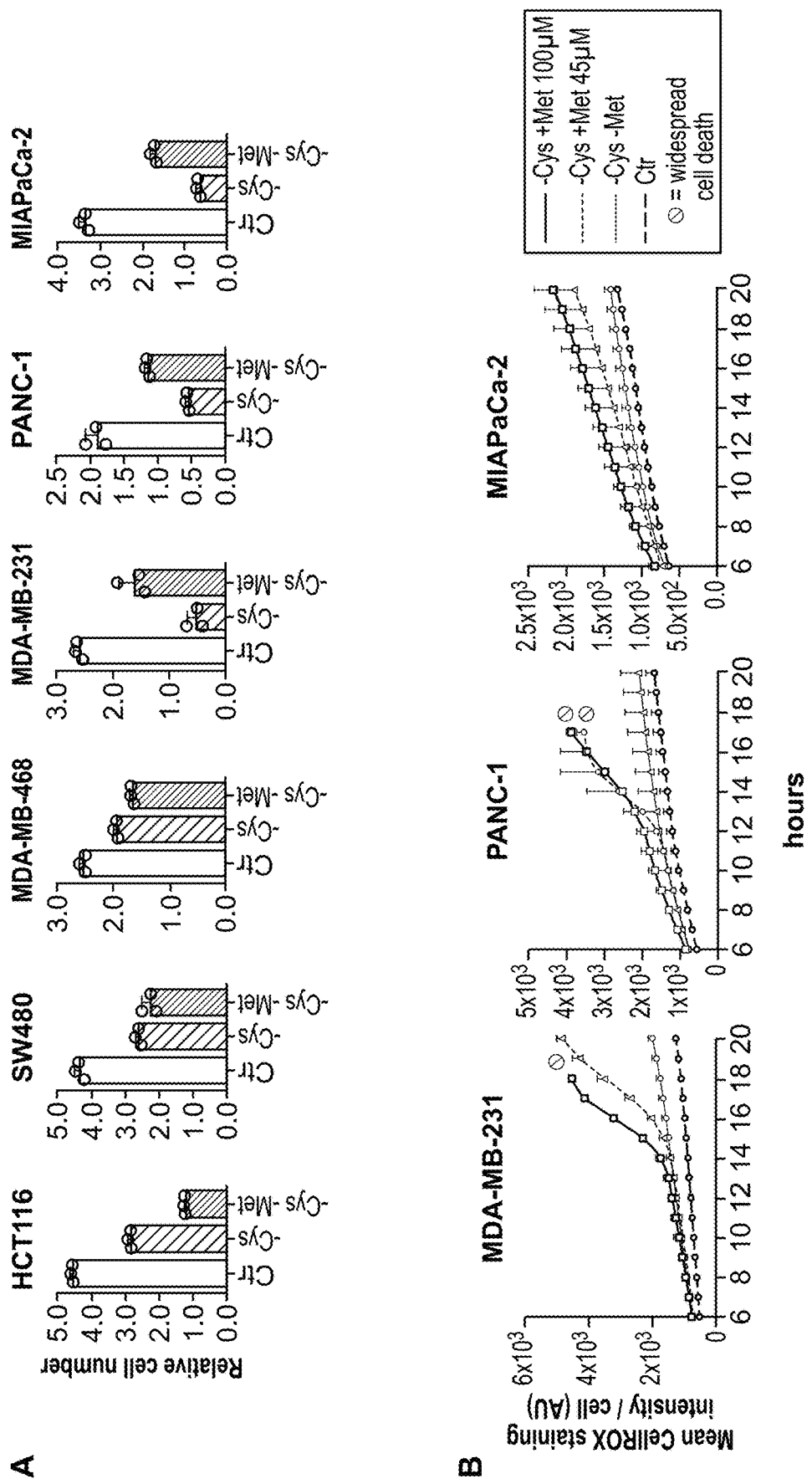
FIG. 16 ROW A shows the effect of cysteine starvation and combined methionine and cysteine starvation on cell survival of HCT116, SW480, MDA-MB-468, MDA-MB-231, PANC-1, and MIAPaCa-2 cells. ROW B shows the effect of cysteine starvation with or without exogenous methionine in MDA-MB-231, PANC-1, and MIAPaCa-2 cell survival.

Example 8: Methionine Withdrawal Protects Highly Sensitive Cells from Cysteine Starvation Methionine is a precursor for both polyamine and cysteine synthesis. Whether modulating methionine levels directly could influence the response to cysteine starvation was tested, with the assumption that methionine withdrawal would further sensitize cells to starvation. FIG. 16 ROW A shows the effect of cysteine starvation and combined methionine and cysteine starvation on cell survival of HCT116, SW480, MDA-MB-468, MDA-MB-231, PANC-1, and MIAPaCa-2 cells. In cell lines more resistant to cysteine starvation, combined methionine and cysteine starvation mildly (SW480 and MIAPaCa-2) or strongly (HCT116) inhibited cell growth. Combined methionine and cysteine starvation was much better tolerated than cysteine starvation alone in more sensitive cell lines. MDA-MB-231, MIAPaCa-2, and PANC-1 cells all displayed a lack of cell death and even a degree of proliferation under methionine and cysteine free conditions. These results show that polyamine metabolism dominates over de novo cysteine synthesis in determining whether a cell line is highly sensitive to cysteine starvation.

Cell culture media contain supra-physiological methionine levels (100 µM-200 µM). The effect of lower, more physiological methionine levels on cysteine starvation sensitivity was investigated. In adult humans, the concentration of methionine in the blood ranges from 10 µM-45 µM, with a mean value of 29 µM. FIG. 36 ROW A shows cell lines highly sensitive to cysteine starvation (MDA-MB-231, PANC-1, and MIAPaCa-2) grown in medium without cysteine containing increasing concentrations of methionine (1 to 1 mM) for 20 h. ROW B shows cell lines sensitive to cysteine starvations (MDA-MB-231, PANC-1, and MIAPaCa-2) grown in medium without cysteine containing increasing concentrations of methionine (0 to 10 µM) for 17 h. ROW C shows cell lines sensitive to cysteine starvations (MDA-MB-231, PANC-1, and MIAPaCa-2) grown in medium without cysteine containing increasing concentrations of methionine (0 to 10 µM) for 41 h. MDA-MB-231, MIAPaCa-2, and PANC-1 cells all remained highly sensitive to cysteine starvation in the range 10 µM-1000 µM. A further decrease in methionine concentration showed that the cells remained sensitive to cysteine starvation down to 5 µM methionine. While sustainable cell survival and proliferation in the complete absence of cysteine and methionine is not possible, the rescue provided by methionine removal was durable, lasting over 40 h.

FIG. 16 ROW B shows the effect of cysteine starvation with or without exogenous methionine in MDA-MB-231, PANC-1, and MIAPaCa-2 cell survival. FIG. 37 shows cell lines grown in complete medium (Ctr) or matched medium lacking cysteine (−Cys) with or without methionine (Met) at the stated concentrations. ROS were detected in real time by an automated microscope in live cells treated with CellROX deep red. ROS staining intensity is shown for the 18 h standpoint. Statistical comparisons in FIG. 35 PANEL A, PANEL B, PANEL C, and FIG. 37 were done by an ordinary one-way ANOVA with Sidak's multiple comparison test. All data are averages of n=3 biological replicates. Error bars are in SD. Under cysteine starved conditions, in MTAP deleted cells, ROS levels increased in a dose-dependent manner in response to methionine concentration.

FIG. 17 shows an LC-MS analysis of cysteine starvation-sensitive cell line to examine the impact of methionine withdrawal on cysteine metabolism. FIG. 38 shows PANC-1 cells grown in medium lacking methionine supplemented with varying levels of $^{13}C_5{}^{15}N_1$-methionine for 5 h. Metabolites were extracted and analyzed by LC-MS. Methionine starvation dramatically decreased entry of precursors into the TsP and polyamine synthesis pathways. These changes were accompanied by increased cysteine and cystine levels, as well as decreased GSSG levels and decreased GSSG/GSH ratio.

To assess whether the changes were specific to cysteine or a generic impact of methionine withdrawal on amino acids, changes across all other amino acids were analyzed.

FIG. 39 PANEL A shows levels of amino acid assessed using LC-MS data from the experiments shown in FIG. 17 and FIG. 38. Relative quantity (peak area, relative to 50 µM condition) is shown for each amino acid. PANEL B shows MIAPaCa-2 cells cultured in either DMEM or RPMI for two weeks. Experiments were performed by growing cells either in complete medium (Ctr) or matched medium lacking cysteine (−Cys) for 32 h and 48 h. Methionine restriction increased the total cellular levels of amino acids. The effect was most dramatic in cysteine, glycine, and serine (all precursors of GSH); and asparagine (used in protein synthesis and as an uptake exchange factor of serine). The paradoxical increase in cysteine levels and accompanying decrease in GSSG in response to methionine starvation further supports the hypothesis that decreased polyamine pathway activity alleviates the oxidative burden on MTAP deleted cells. Given differences in methionine levels between different cell culture media (e.g. DMEM ~200 µm, RPMI1640~100 µM), the effect of maintaining cells in different media on sensitivity to cysteine starvation was determined. No difference in sensitivity was observed based on the maintenance medium.

Example 9: Acute MTAP Deletion and Restoration can Modulate Polyamine Pathway Activity and Cellular Sensitivity to Cysteine Starvation FIG. 26 PANEL A shows the effect of cells grown with (+) or without (−) cysteine for 24 hr on MTAP deletion. HCT116 cells expressed relatively high levels of MTAP and were sensitive to cysteine starvation. The HCT116 cells were more resistant to cell death than other cell lines (FIG. 1). To assess the impact of MTAP deletion, CRISPR/Cas9 was used to delete MTAP from HCT116 cells. FIG. 18 PANEL A shows the effect of cysteine starvation and rescue with ferrostatin on MTAP-deletion. MTAP-deletion increased the sensitivity of the cells to cysteine starvation, which was rescued by treatment with the ferroptosis inhibitor ferrostatin.

FIG. 40 PANEL A shows MTAP-positive (parental/Par, NTC) and negative (M1, M2) HCT116 cells grown in complete medium with 0.2 mM $^{13}C_5{}^{15}N_1$-methionine substituted for methionine) for 30 h Metabolites were extracted and analyzed by LC-MS. PANEL B shows data obtained from CD-1 nude mice injected with MTAP-positive (NTC) and MTAP-depleted (M2) HCT116 cells. Once measurable xenograft tumors had formed, mice were transferred to a diet and drinking water regimen containing all amino acids (Complete) or lacking cysteine and cystine but containing all other amino acids (−Cys). Data are averages, bars are SEM. NTC control diet n=8; NTC-Cys diet n=7, MTAP-KO2 Control diet n=9; MTAP-KO2−Cys n=10. PANEL C shows metabolites extracted from xenograft tumors and serum, which were subjected to LC-MS analysis for MTA levels. Data are averages, bars are SD, unpaired T-test, 2-tails. NTC n=16; MTAP KO n=19. All data, except for FIG. 40 PANEL B and PANEL C are averages of n=3 biological replicates. Error bars show SD. LC-MS analysis confirmed that MTAP deletion prevented methionine salvage (signified by m+1 methionine) and caused intracellular accumulation and efflux of MTA. Similar to cell lines with endogenous MTAP deletion, FIG. 18 PANEL B shows that treatment of cells with an AMD1 inhibitor restored cell survival in response to cysteine starvation.

To test whether the in vitro observations could be translated in vivo, a xenograft experiment with non-targeting control and MTAP-deleted HCT116 cells was performed. FIG. 18 PANEL C shows that the response of NTC- and MTAP-deleted cells to cysteine limitation in vivo differed significantly. FIG. 40 PANEL B shows data obtained from CD-1 nude mice injected with MTAP-positive (NTC) and MTAP-depleted (M2) HCT116 cells. While the MTAP-expressing NTC cells generally showed increased tumor growth in response to cysteine starvation, the MTAP-deleted cells displayed decreased tumor volume compared to NTC cells. LC-MS analysis of MTA levels confirmed that MTAP-deleted tumor tissue was significantly higher in MTA versus NTC tumors. FIG. 40 PANEL C shows metabolites extracted from xenograft tumors and serum, which were subjected to LC-MS analysis for MTA levels. The increase of MTA in MTAP-deleted tumor tissue did not translate to higher serum MTA. The results suggest that analysis of MTA levels in tumor biopsy tissue, but not in serum, may be a viable biomarker to detect MTAP deletion.

FIG. 41 PANEL A shows HCT116 cells in which MTAP was deleted by CRISPR/Cas9 (M2) that were stably transfected with an empty vector (clones M2.EV1 and M2.EV2) or a plasmid for MTAP expression (clones M2.MX1 and M2.MX2). MTAP expression was validated by western blot. Cells were grown in complete medium containing all amino acids (Ctr), or matched medium lacking cysteine (-Cys). After 20 h, cells were fixed, stained, and counted. PANEL B shows the HCT116 clones grown in complete medium with or without the xCT inhibitor and 10 μM ferroptosis inducer erastin for 18 h. PANEL C shows MTAP-expressing (NTC and M2.MX2) and MTAP-deleted (M2 and M2.EV1) HCT116 cells grown in complete medium (with 0.2 mM $^{13}C_5^{15}N_1$-methionine substituted for methionine) for 30 h. Metabolites were extracted and analyzed by LC-MS. Stable re-expression of MTAP in MTAP-deleted HCT116 cells restored the ability of the cells to survive during cysteine starvation and treatment with the cysteine-uptake inhibitor Erastin (a system xCT inhibitor and ferroptosis inducing agent). In MDA-MB-231 cells (endogenous MTAP deletion), overexpression of MTAP did not rescue sensitivity (not shown), suggesting that an adaptive process occurs that confers an inability to acutely re-adapt to MTAP expression in cells suffering long-term MTAP deletion. LC-MS analysis confirmed that MTAP re-expression in MTAP-deleted HCT116 cells prevented MTA efflux and restored the ability of these cells to salvage methionine from MTA.

FIG. 42 PANEL A shows MTAP-expressing (NTC and M2.MX2) and MTAP-deleted (M2) HCT116 cells seeded at a range of cell densities in complete medium in 24-well plates. After 24 h, cells were washed with PBS, and the medium was changed to medium lacking cysteine or complete medium containing all amino acids. After 20 h, cells were fixed, stained, and counted. Cell confluence consistently showed an impact on response to starvation. Sparsely seeded cells were more sensitive than confluent cells, but the effect of MTAP deletion/restoration was consistent across a broad range of cell densities.

Figure 19:
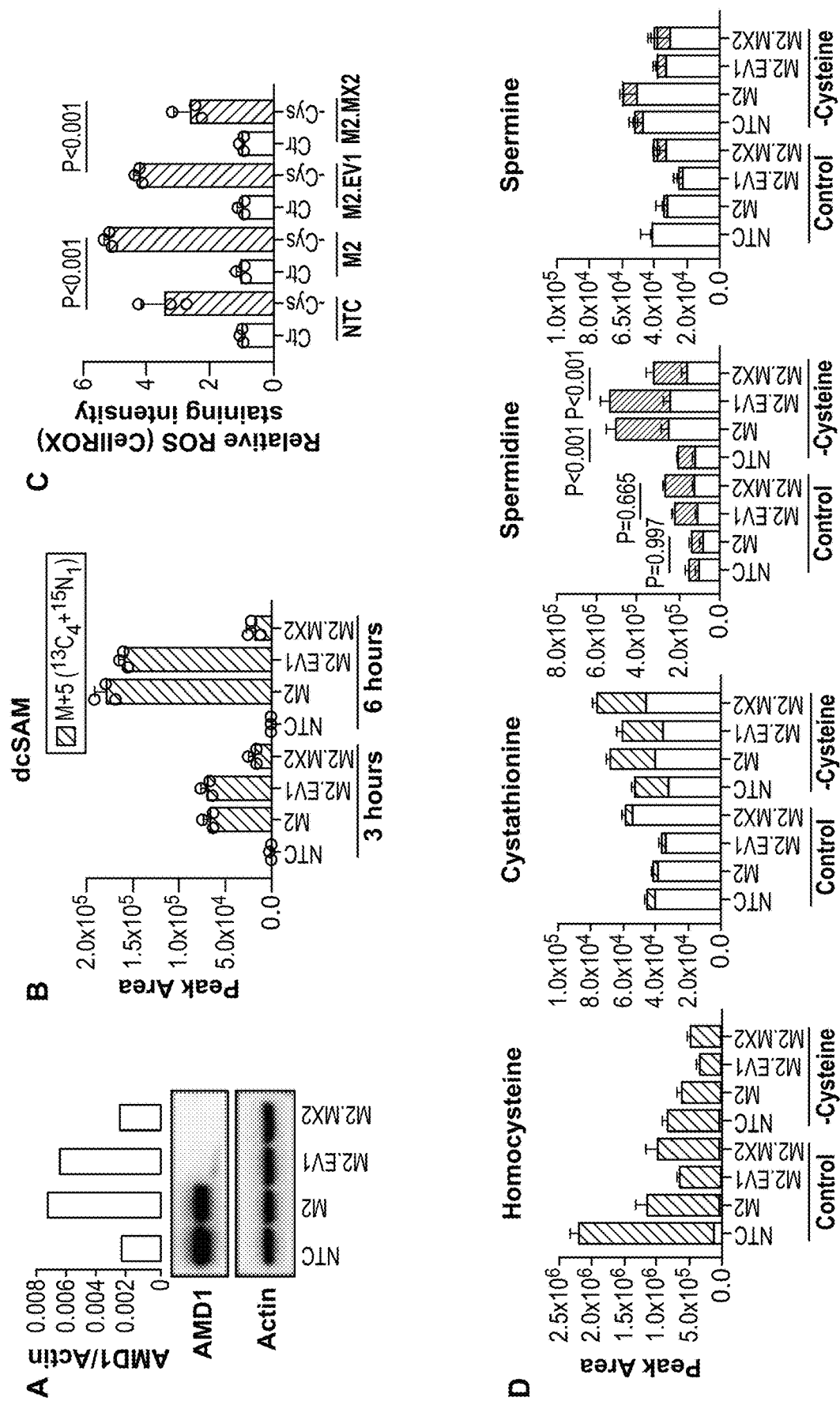
FIG. 19 PANEL A shows a western blot demonstrating the effect of MTAP loss in AMD1 expression. PANEL B shows an LC-MS analysis of AMD1 up-regulation leading to a dramatic increase in methionine-dependent dc-SAM labelling, indicative of increased polyamine pathway activity. PANEL C shows that MTAP-deleted HCT116 cells showed increased elevation of cellular ROS levels in response to cysteine starvation versus MTAP-expressing cells. PANEL D shows an LC-MS analysis indicating that MTAP-deleted cells had substantially higher methionine-dependent labelling in the polyamine spermidine and no consistent difference in labelling of TsP intermediates.

FIG. 19 PANEL A shows a western blot demonstrating the effect of MTAP loss in AMD1 expression. The western blot shows that MTAP loss promoted a three-fold increase in AMD1 expression, whereas MTAP restoration decreased AMD1 to basal levels. FIG. 19 PANEL B shows an LC-MS analysis of AMD1 up-regulation leading to a dramatic increase in methionine-dependent dc-SAM labelling, indicative of increased polyamine pathway activity. FIG. 19 PANEL C shows that MTAP-deleted HCT116 cells showed increased elevation of cellular ROS levels in response to cysteine starvation versus MTAP-expressing cells.

FIG. 19 PANEL D shows an LC-MS analysis indicating that, in line with increased dc-SAM labelling, MTAP-deleted cells had substantially higher methionine-dependent labelling in the polyamine spermidine and no consistent difference in labelling of TsP intermediates.

Figure 20:
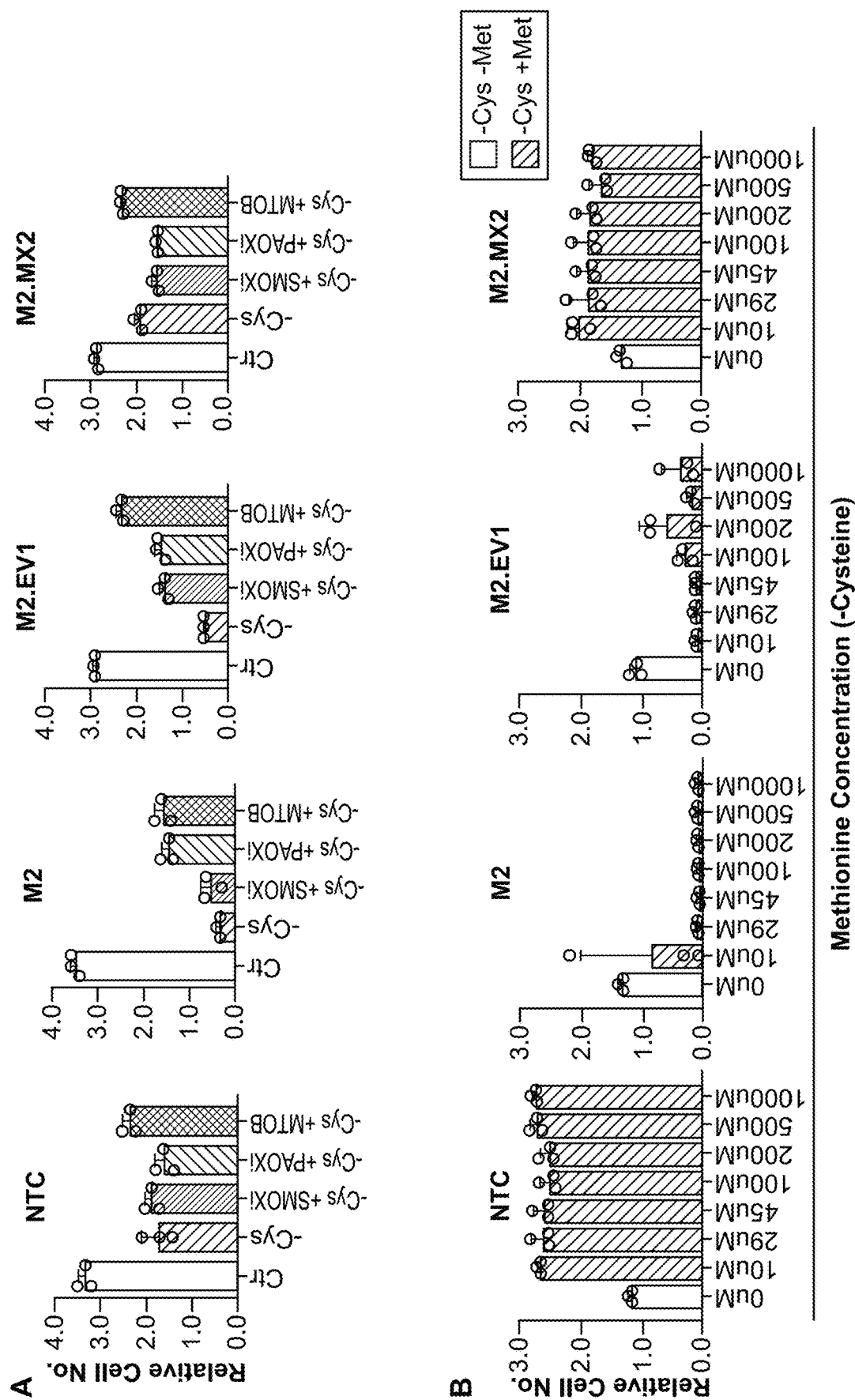
FIG. 20 ROW A shows that inhibition of polyamine metabolism with a SMOX inhibitor, PAOX inhibitor, and MTOB supplementation had little impact on MTAP expressing cells, but rescued cell survival in MTAP-deleted cells during cysteine starvation. ROW B shows that the presence of methionine was advantageous to MTAP expressing cells during cysteine starvation, and even low levels of methionine inhibited the ability of MTAP deleted cells to survive.

SMOX and PAOX inhibitors and MTOB supplementation were used to further assess the relationship between polyamine synthesis and sensitivity to cysteine starvation in MTAP-deleted/restored HCT116 cells. FIG. 20 ROW A shows that inhibition of polyamine metabolism with a SMOX inhibitor, PAOX inhibitor, and MTOB supplementation had little impact on MTAP expressing cells, but rescued cell survival in MTAP-deleted cells during cysteine starvation. A dramatic contrast in the effect of methionine withdrawal on MTAP-deleted versus restored HCT116 cells was observed. FIG. 20 ROW B shows that the presence of methionine was advantageous to MTAP expressing cells during cysteine starvation, and even low levels of methionine inhibited the ability of MTAP deleted cells to survive.

Glioblastomas (GBM) have a relatively high frequency of MTAP deletion. A panel of GBM cell lines were tested for sensitivity to cysteine starvation. FIG. 43 PANEL A shows GBM cell lines grown in either complete medium (Ctr) or medium lacking cysteine (-Cys) for 48 h. PANEL B shows breast cancer cell lines MDA-MB-231 (highly sensitive) and MDA-MB-468 (resistant) were grown in either control (Ctr) or medium lacking cysteine (-Cys) for 48 h or 72 h. Cells for the time point were fixed and counted. Other cells treated the same way were re-fed with complete medium for an additional 48 h (Ctr+48 h, -Cys 48 h) before cells were counted. All data except western blots are averages of n=3 biological replicates. Error bars are SD. MTAP-deleted lines showed highest expression of AMD1 and were the most sensitive to starvation. The ability of cells to recover from and proliferate post-cysteine starvation was also tested. Highly cysteine starvation sensitive MDA-MB-231 cells did not survive or recover, whereas more resistant MDA-MB-468 cells were able to survive and grow.

The in vivo data suggest that dietary cysteine limitation can promote or diminish tumor formation depending on the tumor genotype. Cysteine uptake (as cystine) may cause significant efflux of glutamate, an important metabolic precursor, a process which can confer decreased metabolic flexibility.

Example 10: Discussion of Results

Exogenous cysteine was vital to support maximal proliferation across a range of breast, colorectal and pancreas cancer cell lines. A sub-set of cancer cells were found to be susceptible to cysteine starvation, which could be even more damaging than complete glucose withdrawal. In the panel of cells tested, TsP enzyme expression did not correlate with the ability to survive during cysteine starvation. Even cells with relatively low expression of CBS or CSE were rescued from starvation-induced cell death by supplementation with their enzymatic substrates homocysteine and cystathionine. Furthermore, cells with high CBS and CSE expression, and competent for de novo cysteine synthesis, such as MIAPaCa-2, underwent cell death in response to cysteine starvation.

Given the ability of homocysteine and cystathionine to rescue cells from cysteine starvation, excess methionine, the ultimate precursor for these metabolites, was unable to provide rescue. Based on this result, the initial hypothesis was that methionine was diverted to an alternative metabolic pathway that effectively competes with the TsP. The polyamine synthesis pathway uses the methionine-derived precursor dc-SAM to produce the polyamines spermine and spermidine. Polyamines are essential for growth in eukaryotic cells, where they are present at millimolar concentrations, and have varied roles including DNA stabilization, regulation of gene expression and in membranes and microtubules. Up-regulated polyamine synthesis can be observed in cancer cells, with the formation of putrescine catalyzed by the classic myc-target ODC1. The fate of carbon-13 labelled methionine was traced using LC-MA analysis, and carbon-13-labelled methionine was found to readily enter the polyamine pathway, labelling polyamines and the methionine-derived by-product MTA. Whereas MTA can be recycled back to methionine via the methionine salvage pathway, LC-MS analysis revealed that certain cells displayed a significant MTA efflux, illustrating a lack of methionine salvage.

Genetic deletion of the MTA metabolizing enzyme MTAP, which is chromosomally co-located with the tumor suppressor p16, is a common event in cancer, occurring as a 'bystander/passenger' gene deletion. Loss of MTAP prevents methionine recycling, meaning that a constant supply of new methionine is required to enter polyamine synthesis in MTAP deleted cells. Levels of exogenous MTA (a combined measure of polyamine synthesis and MTAP status) correlated strongly with sensitivity to cysteine starvation. Labelling experiments with $^{13}C_3^{15}N_1$-serine showed that starvation sensitive MTAP-deleted cells did not necessarily have lower cysteine synthesis than the more resistant MTAP positive cells. Inhibition of the polyamine pathway, which rescued MTAP-deleted cells from cysteine starvation, did not increase entry of methionine-derived precursors into the TsP.

LC-MS analysis revealed that MTAP-deleted cells had much higher methionine-derived labelling in the polyamine synthesis precursor dc-SAM along with higher polyamine steady state levels and higher methionine-derived polyamine labelling. Supplementing with the polyamines spermidine or spermine increased cellular ROS levels and dramatically sensitized cells to cysteine starvation. Inhibition of polyamine synthesis or inhibition of polyamine inter-conversion (mediated by SMOX and PAOX) decreased cellular ROS levels and rescued MTAP-deleted cells from cysteine starvation. Given the cyclical nature of polyamine metabolism (FIG. 13), the potential for SMOX/PAOX dependent ROS production in the context of elevated dc-SAM levels seems theoretically very high.

Methionine withdrawal rescued rather than sensitized cells from cysteine starvation. The data disclosed herein show that cancer cells have a paucity of methionine-derived precursors available for cysteine synthesis, and that TsP activity is important to allow cells to survive cysteine withdrawal. The data disclosed herein also show that polyamine metabolism can override these factors and acutely sensitize cancer cells to cysteine starvation induced cell death.

The ability of cells to effectively up-regulate TsP enzyme expression and activity in response to cysteine starvation can improve cell survival. The data show that TsP enzyme expression was up-regulated in response to cysteine starvation, and that direct inhibition of TsP activity sensitized cells to cysteine starvation. However, the influence of polyamine metabolism was dominant over TsP enzyme expression in determining acute cysteine starvation sensitivity in the cell lines tested here. Notably, MDA-MB-231 cells, displaying both low expression of TsP enzymes and MTAP-deletion, showed the highest degree of sensitivity to cysteine starvation.

Figure 21:
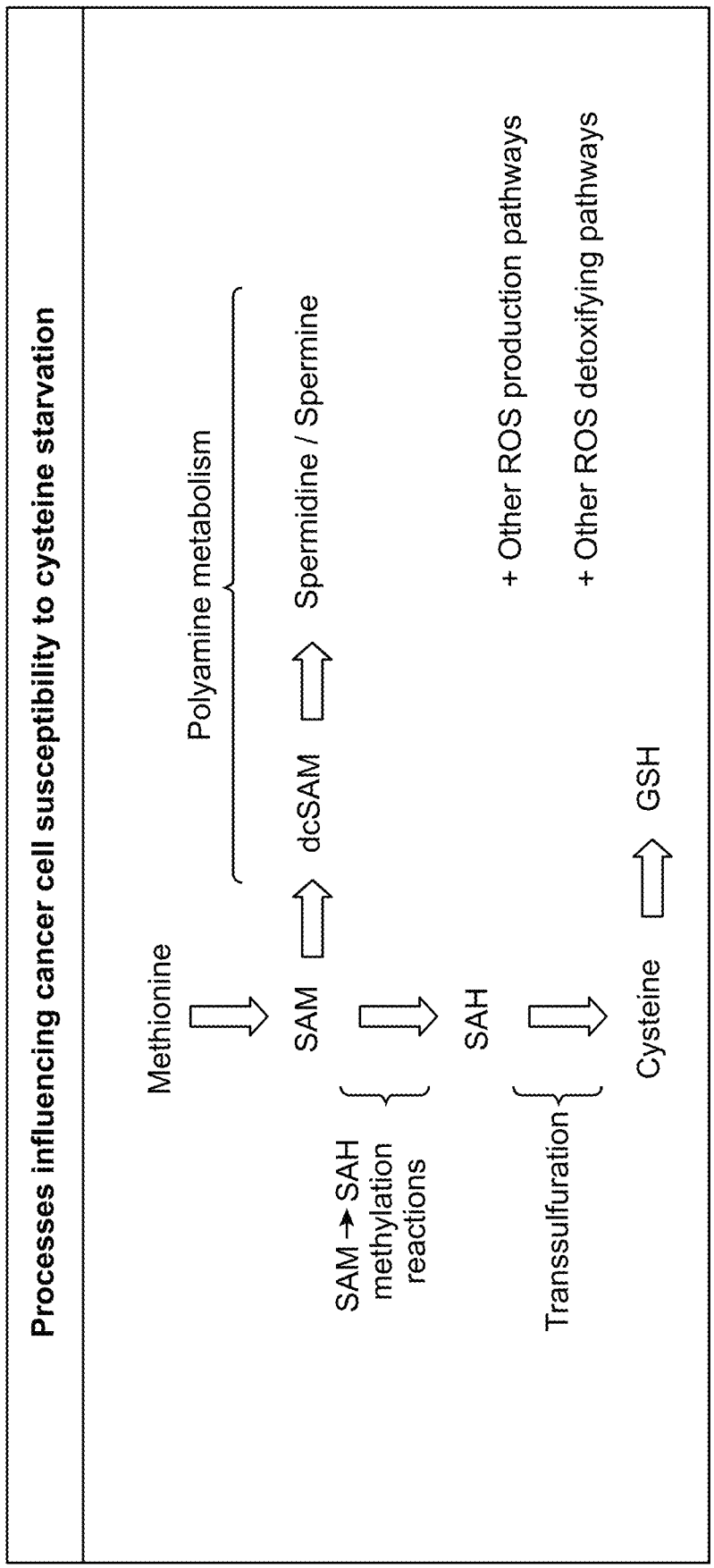
FIG. 21 illustrates processes influencing cancer cell susceptibility to cysteine starvation.

The current disclosure shows that, in a panel of cancer cell lines including breast, colorectal and pancreatic cancer, that TsP enzyme expression did not predict which cells where most sensitive to cysteine starvation. While exogenous homocysteine was able to rescue cells from cysteine starvation, methionine did not. The data of this disclosure show that there is limited entry of methionine to the TsP, but that polyamine metabolism can inform why cancer cells can display acute sensitivity to cysteine starvation. FIG. 21 illustrates processes influencing cancer cell susceptibility to cysteine starvation.

An alternative fate for methionine is utilization for polyamine synthesis. The current disclosure shows that much of the methionine taken up by cancer cells enters the polyamine synthesis pathway, which, through synthesis of spermidine and spermine, consumes SAM and produces 5-methylthioadenosine (MTA). A strong correlation was observed between cellular efflux of MTA (a metabolic consequence of MTAP deletion) and cysteine starvation sensitivity. Cells with MTAP deletion (a frequent occurrence in cancer) had increased polyamine pathway activity. A detailed metabolic analysis revealed that elevated polyamine metabolism can be metabolic liability during cysteine starvation, independent of the TsP.

The current disclosure shows that neither expression of enzymes for cysteine synthesis nor availability of the primary precursor methionine correlated with sensitivity to cysteine starvation. A strong correlation was observed between efflux of the methionine-derived metabolite methylthioadenosine (MTA), and cysteine starvation sensitivity. MTA efflux resulted from genetic deletion of methylthioadenosine phosphorylase (MTAP, frequently deleted in cancer). MTAP loss up-regulated polyamine metabolism which, concurrent with cysteine withdrawal, promoted elevated ROS and prevented cell survival.

Example 11: Dietary Product Low in Cysteine and High in Methionine

TABLE 1 shows Formulation 1 comprising an amino acid mixture that is devoid of cystine, serine, and glycine.

TABLE 1

| | Amino Acids | mg/sachet | % of AA composition |
|---|---|---|---|
| 1 | L-Histidine | 445 | 4.09 |
| 2 | L-Isoleucine | 600 | 5.77 |
| 3 | L-Leucine | 1,150.00 | 11.06 |
| 4 | L-Lysine Monohydrate | 995 | 9.57 |
| 5 | L-Methionine | 300 | 2.89 |
| 6 | L-Phenylalanine | 750 | 7.22 |
| 7 | L-Threonine | 600 | 5.77 |
| 8 | L-Tryptophan | 220 | 2.12 |
| 9 | L-Valine | 600 | 5.77 |
| 10 | L-Cystine/L-cystine | 0 | 0.00 |
| 11 | L-Tyrosine | 330 | 3.17 |
| 12 | L-Glutamine | 300 | 2.89 |
| 13 | L-Arginine Base | 246 | 2.37 |
| 14 | L-Alanine | 600 | 5.77 |
| 15 | L-Aspartic Acid | 508.7 | 4.89 |
| 16 | L-Asparagine Hydrate | 600 | 5.77 |
| 17 | L-Arginine-L-Glutamate Salt | 1,300.00 | 12.51 |

TABLE 1-continued

|  | Amino Acids | mg/sachet | % of AA composition |
|---|---|---|---|
| 18 | L-Serine | 0 | 0.00 |
| 19 | Glycine | 0 | 0.00 |
| 20 | L-Proline | 800 | 7.70 |
| 21 | Taurine | 50 | 0.48 |
|  | Total Amino Acids | 10,394.70 | 99.81 |
|  | Other Materials |  | Extra aspartate |
| 22 | L-Aspartic Acid Potassium Salt | 380 | 294 |
| 23 | L-Aspartic Acid Magnesium Salt | 211 | 179 |
| 24 | D-Glucose | 0 |  |
|  | Total Materials | 10,323.70 |  |

TABLE 2 shows Formulation 2 comprising an amino acid mixture devoid of serine, glycine, and cysteine with normal methionine levels.

TABLE 2

|  | Amino acids | mg/sachet | % of AA in product | Example daily intake (g/day) for 70 kg person |
|---|---|---|---|---|
| 1 | L-Histidine HCl | 550 | 4.93 | 2.75 |
| 2 | L-Isoleucine | 600 | 5.38 | 3.00 |
| 3 | L-Leucine | 1,150.00 | 10.31 | 5.75 |
| 4 | L-Lysine HCl | 1,100.00 | 9.87 | 5.50 |
| 5 | L-Methionine | 300 | 2.69 | 1.50 |
| 6 | L-Phenylalanine | 750 | 6.73 | 3.75 |
| 7 | L-Threonine | 600 | 5.38 | 3.00 |
| 8 | L-Tryptophan | 220 | 1.97 | 1.10 |
| 9 | L-Valine | 600 | 5.38 | 3.00 |
| 10 | L-Cysteine HCl | 0 | 0.00 | 0.00 |
| 11 | L-Tyrosine | 330 | 2.96 | 1.65 |
| 12 | L-Glutamine | 300 | 2.69 | 1.50 |
| 13 | L-Arginine Base | 950 | 8.52 | 4.75 |
| 14 | L-Alanine | 600 | 5.38 | 3.00 |
| 15 | L-Aspartic Acid | 1,000.00 | 8.97 | 5.00 |
| 16 | L-Asparagine Hydrate | 600 | 5.38 | 3.00 |
| 17 | L-Glutamic Acid | 600 | 5.38 | 3.00 |
| 18 | L-Serine | 0 | 0.00 | 0.00 |
| 19 | Glycine | 0 | 0.00 | 0.00 |
| 20 | L-Proline | 900 | 8.07 | 4.50 |
|  | Total | 11150 | 100 | 55.75 |

TABLE 3 shows Formulation 3 comprising an amino acid mixture devoid of serine, glycine, and cysteine with high methionine levels.

TABLE 3

|  |  | mg/sachet | % of AA in product | Example daily intake (g/day) for 70 kg person |
|---|---|---|---|---|
| 1 | L-Histidine HCl | 550 | 4.68 | 2.75 |
| 2 | L-Isoleucine | 600 | 5.11 | 3.00 |
| 3 | L-Leucine | 1,150.00 | 9.79 | 5.75 |
| 4 | L-Lysine HCl | 1,100.00 | 9.36 | 5.50 |
| 5 | L-Methionine | 900 | 7.66 | 4.50 |
| 6 | L-Phenylalanine | 750 | 6.38 | 3.75 |
| 7 | L-Threonine | 600 | 5.11 | 3.00 |
| 8 | L-Tryptophan | 220 | 1.87 | 1.10 |
| 9 | L-Valine | 600 | 5.11 | 3.00 |
| 10 | L-Cysteine HCl | 0 | 0.00 | 0.00 |
| 11 | L-Tyrosine | 330 | 2.81 | 1.65 |
| 12 | L-Glutamine | 300 | 2.55 | 1.50 |
| 13 | L-Arginine Base | 950 | 8.09 | 4.75 |
| 14 | L-Alanine | 600 | 5.11 | 3.00 |
| 15 | L-Aspartic Acid | 1,000.00 | 8.51 | 5.00 |

TABLE 3-continued

|  |  | mg/sachet | % of AA in product | Example daily intake (g/day) for 70 kg person |
|---|---|---|---|---|
| 16 | L-Asparagine Hydrate | 600 | 5.11 | 3.00 |
| 17 | L-Glutamic Acid | 600 | 5.11 | 3.00 |
| 18 | L-Serine | 0 | 0.00 | 0.00 |
| 19 | Glycine | 0 | 0.00 | 0.00 |
| 20 | L-Proline | 900 | 7.66 | 4.50 |
|  | Total | 11750 | 100 | 58.75 |

TABLE 4 shows Formulation 4 comprising an amino acid mixture devoid of cysteine with normal methionine levels.

TABLE 4

|  |  | mg/sachet | % of AA in product | Example daily intake (g/day) for 70 kg person |
|---|---|---|---|---|
| 1 | L-Histidine HCl | 550 | 4.93 | 2.75 |
| 2 | L-Isoleucine | 600 | 5.38 | 3.00 |
| 3 | L-Leucine | 1,150.00 | 10.31 | 5.75 |
| 4 | L-Lysine HCl | 1,100.00 | 9.87 | 5.50 |
| 5 | L-Methionine | 300 | 2.69 | 1.50 |
| 6 | L-Phenylalanine | 750 | 6.73 | 3.75 |
| 7 | L-Threonine | 600 | 5.38 | 3.00 |
| 8 | L-Tryptophan | 220 | 1.97 | 1.10 |
| 9 | L-Valine | 600 | 5.38 | 3.00 |
| 10 | L-Cysteine HCl | 0 | 0.00 | 0.00 |
| 11 | L-Tyrosine | 330 | 2.96 | 1.65 |
| 12 | L-Glutamine | 300 | 2.69 | 1.50 |
| 13 | L-Arginine Base | 950 | 8.52 | 4.75 |
| 14 | L-Alanine | 600 | 5.38 | 3.00 |
| 15 | L-Aspartic Acid | 1,000.00 | 8.97 | 5.00 |
| 16 | L-Asparagine Hydrate | 600 | 5.38 | 3.00 |
| 17 | L-Glutamic Acid | 600 | 5.38 | 3.00 |
| 18 | L-Serine | 330 | 2.96 | 1.65 |
| 19 | Glycine | 550 | 4.93 | 2.75 |
| 20 | L-Proline | 900 | 8.07 | 4.50 |
|  | Total | 12030 | 107.8923767 | 60.15 |

TABLE 5 shows Formulation 5 comprising an amino acid mixture devoid of cysteine with high methionine levels.

TABLE 5

|  |  | mg/sachet | % of AA in product | Example daily intake (g/day) for 70 kg person |
|---|---|---|---|---|
| 1 | L-Histidine HCl | 550 | 4.68 | 2.75 |
| 2 | L-Isoleucine | 600 | 5.11 | 3.00 |
| 3 | L-Leucine | 1,150.00 | 9.79 | 5.75 |
| 4 | L-Lysine HCl | 1,100.00 | 9.36 | 5.50 |
| 5 | L-Methionine | 900 | 7.66 | 4.50 |
| 6 | L-Phenylalanine | 750 | 6.38 | 3.75 |
| 7 | L-Threonine | 600 | 5.11 | 3.00 |
| 8 | L-Tryptophan | 220 | 1.87 | 1.10 |
| 9 | L-Valine | 600 | 5.11 | 3.00 |
| 10 | L-Cysteine HCl | 0 | 0.00 | 0.00 |
| 11 | L-Tyrosine | 330 | 2.81 | 1.65 |
| 12 | L-Glutamine | 300 | 2.55 | 1.50 |
| 13 | L-Arginine Base | 950 | 8.09 | 4.75 |
| 14 | L-Alanine | 600 | 5.11 | 3.00 |
| 15 | L-Aspartic Acid | 1,000.00 | 8.51 | 5.00 |
| 16 | L-Asparagine Hydrate | 600 | 5.11 | 3.00 |
| 17 | L-Glutamic Acid | 600 | 5.11 | 3.00 |

TABLE 5-continued

|  |  | mg/sachet | % of AA in product | Example daily intake (g/day) for 70 kg person |
|---|---|---|---|---|
| 18 | L-Serine | 330 | 2.81 | 1.65 |
| 19 | Glycine | 550 | 4.68 | 2.75 |
| 20 | L-Proline | 900 | 7.66 | 4.50 |
|  | Total | 12630 | 107.4893617 | 63.15 |

Example 12: Use of Radiotherapy to Treat a Cancer

A first subject with a cancer is treated with a short course of radiotherapy to treat the cancer. The first subject is placed on a diet substantially devoid of cysteine with at least one of a methionine supplement and a polyamine, a precursor, or an analog two days before starting radiotherapy treatment (i.e., day-2). The amino acid-depleted diet is administered for a total of 10 days, starting 2 days before treatment through 4 days post-treatment (i.e., day-2 through day 8). The first subject is treated with 5 Gy a day for 5 days. The first subject returns to a normal, habitual diet after day 8, or 4 days post-radiation treatment. If the first subject is treated with chemotherapy after the radiotherapy, the first subject is placed on a cycled diet throughout the chemotherapy. The cycle diet places the first subject on an alternating 5 day amino acid-depleted diet (e.g., Monday-Friday) followed by a 2 day habitual diet (e.g., Saturday, Sunday) throughout the chemotherapy treatment period. TABLE 6 shows a short course radiotherapy to treat a cancer.

TABLE 6

| Day number | Day of week | Radiotherapy dose | Diet |
|---|---|---|---|
| −3 | Fri | 0 Gy | Habitual |
| −2 | Sat | 0 Gy | AA depleted Day 1 |
| −1 | Sun | 0 Gy | AA depleted Day 2 |
| 0 | Mon | 5 Gy | AA depleted Day 3 |
| 1 | Tue | 5 Gy | AA depleted Day 4 |
| 2 | Wed | 5 Gy | AA depleted Day 5 |
| 3 | Thu | 5 Gy | AA depleted Day 6 |
| 4 | Fri | 5 Gy | AA depleted Day 7 |
| 5 | Sat | 0 Gy | AA depleted Day 8 |
| 6 | Sun | 0 Gy | AA depleted Day 9 |
| 7 | Mon | 0 Gy | AA depleted Day 10 |
| 8 | Tue | 0 Gy | Habitual |
| Chemotherapy | Ongoing | n/a | Cycle 5 days of AA depleted diet + 2 days habitual diet throughout Chemotherapy treatment |

A second subject with a cancer is treated with a long course of radiotherapy to treat the cancer. The second subject is placed on a diet substantially devoid cysteine with at least one of a methionine supplement and a polyamine, a precursor, or an analog two days before starting radiotherapy treatment (i.e., day-2). The amino acid-depleted diet is administered for a total of 7 days, starting 2 days before treatment through the course of treatment (i.e., day-2 through day 4). The second subject is treated with 2 Gy a day for 5 days. The second subject returns to a normal, habitual diet for two days before starting an additional round of radiotherapy. Subsequent radiation therapy cycles administer 5 days of an amino-acid depleted diet with 2 Gy of radiation for 5 days, followed by 2 days of a habitual diet. The cycle is repeated as needed.

If the second subject is treated with chemotherapy after the radiotherapy, the second subject is placed on a cycled diet throughout the chemotherapy. The cycle diet places the second subject on an alternating 5 day amino acid-depleted diet (e.g., Monday-Friday) followed by a 2 day habitual diet (e.g., Saturday, Sunday) throughout the chemotherapy treatment period. TABLE 7 shows a long course radiotherapy treatment to treat a cancer.

TABLE 7

| Day number | Day of week | Radiotherapy dose | Diet |
|---|---|---|---|
| −3 | Fri | 0 Gy | Habitual |
| −2 | Sat | 0 Gy | AA depleted Day 1 |
| −1 | Sun | 0 Gy | AA depleted Day 2 |
| 0 | Mon | 2 Gy | AA depleted Day 3 |
| 1 | Tue | 2 Gy | AA depleted Day 4 |
| 2 | Wed | 2 Gy | AA depleted Day 5 |
| 3 | Thu | 2 Gy | AA depleted Day 6 |
| 4 | Fri | 2 Gy | AA depleted Day 7 |
| 5 | Sat | 0 Gy | Habitual |
| 6 | Sun | 0 Gy | Habitual |
| 7 | Mon | 2 Gy | AA depleted Day 1 |
| 8 | Tue | 2 Gy | AA depleted Day 2 |
| 9 | Wed | 2 Gy | AA depleted Day 3 |
| 10 | Thu | 2 Gy | AA depleted Day 4 |
| 11 | Fri | 2 Gy | AA depleted Day 5 |
| 12 | Sat | 0 Gy | Habitual |
| 13 | Sun | 0 Gy | Habitual |
| 14 | Mon | 2 Gy | AA depleted Day 1 |
| 15 | Tue | 2 Gy | AA depleted Day 2 |
| 16 | Wed | 2 Gy | AA depleted Day 3 |
| 17 | Thu | 2 Gy | AA depleted Day 4 |
| 18 | Fri | 2 Gy | AA depleted Day 5 |
| 19 | Sat | 0 Gy | Habitual |
| 20 | Sun | 0 Gy | Habitual |
| 21 | Mon | 2 Gy | AA depleted Day 1 |
| 22 | Tue | 2 Gy | AA depleted Day 2 |
| 23 | Wed | 2 Gy | AA depleted Day 3 |
| 24 | Thu | 2 Gy | AA depleted Day 4 |
| 25 | Fri | 2 Gy | AA depleted Day 5 |
| 26 | Sat | 0 Gy | Habitual |
| 27 | Sun | 0 Gy | Habitual |
| 28 | Mon | 2 Gy | AA depleted Day 1 |
| 29 | Tue | 2 Gy | AA depleted Day 2 |
| 30 | Wed | 2 Gy | AA depleted Day 3 |
| 31 | Thu | 2 Gy | AA depleted Day 4 |
| 32 | Fri | 2 Gy | AA depleted Day 5 |
| 33 | Sat | 0 Gy | Habitual |
| 34 | Sun | 0 Gy | Habitual |
| Chemotherapy | Ongoing | n/a | Cycle 5 days of AA depleted diet + 2 days habitual diet throughout Chemotherapy treatment |

Embodiments

The following non-limiting embodiments provide illustrative examples of the disclosure, but do not limit the scope of the disclosure.

Embodiment 1. A method for treating a cancer in a subject in need thereof, the method comprising administering to the subject a therapeutically-effective amount of a dietary product, wherein the dietary product comprises at most about 0.5% (w/w) of cysteine or cystine, and wherein the dietary product comprises at least about 7.5% (w/w) of at least one essential amino acid selected from the group consisting of: methionine, histidine, isoleucine, leucine, lysine, phenylalanine, threonine, tryptophan, and valine, wherein the subject is undergoing a cancer therapy for the cancer, wherein the administering the dietary product to the subject increases efficacy of the cancer therapy in the subject by at least about 10% as compared to an efficacy of the cancer therapy in a comparable subject receiving the cancer therapy, but not the dietary product.

Embodiment 2. The method of embodiment 1, wherein the cancer is breast cancer.

Embodiment 3. The method of embodiment 1, wherein the cancer is colorectal cancer.

Embodiment 4. The method of embodiment 1, wherein the cancer is pancreatic cancer.

Embodiment 5. The method of any one of embodiments 1-4, wherein the cancer has downregulated 5-methylthioadenosine phosphorylase (MTAP) expression.

Embodiment 6. The method of any one of embodiments 1-4, wherein the cancer has upregulated adenosylmethionine decarboxylase 1 (AMD1) expression.

Embodiment 7. The method of any one of embodiments 1-4, wherein the cancer exhibits dysregulated polyamine metabolism.

Embodiment 8. The method of any one of embodiments 1-7, wherein the administering is oral.

Embodiment 9. The method of any one of embodiments 1-8, wherein the therapeutically-effective amount of the dietary product is from about 0.5 g/kg/day to about 1 g/kg/day.

Embodiment 10. The method of any one of embodiments 1-9, wherein the therapeutically-effective amount of the dietary product is about 0.8 g/kg/day.

Embodiment 11. The method of any one of embodiments 1-10, wherein the dietary product is devoid of cysteine or cystine.

Embodiment 12. The method of any one of embodiments 1-11, wherein the dietary product further comprises at most about 0.5% (w/w) of glycine.

Embodiment 13. The method of any one of embodiments 1-12, wherein the dietary product is devoid of glycine.

Embodiment 14. The method of any one of embodiments 1-13, wherein the dietary product further comprises at most about 0.5% (w/w) of serine.

Embodiment 15. The method of any one of embodiments 1-14, wherein the dietary product is devoid of glycine.

Embodiment 16. The method of any one of embodiments 1-10, wherein the dietary product comprises at most about 0.5% (w/w) of cysteine or cystine, at most about 0.5% (w/w) of serine, and at most about 0.5% (w/w) of glycine.

Embodiment 17. The method of any one of embodiments 1-16, wherein the dietary product is devoid of cysteine or cystine, serine, and glycine.

Embodiment 18. The method of any one of embodiments 1-17, wherein the dietary product is further devoid of tyrosine.

Embodiment 19. The method of any one of embodiments 1-18, wherein the dietary product is further devoid of arginine.

Embodiment 20. The method of any one of embodiments 1-19, wherein the dietary product is further devoid of tyrosine and arginine.

Embodiment 21. The method of any one of embodiments 1-20, wherein the dietary product comprises more than about 7.5% (w/w) of methionine.

Embodiment 22. The method of any one of embodiments 1-21, wherein the dietary product further comprises from about 1% to about 10% (w/w) of a polyamine, a precursor, or an analog thereof.

Embodiment 23. The method of any one of embodiments 1-22, wherein the cancer therapy is radiotherapy.

Embodiment 24. The method of any one of embodiments 1-22, wherein the cancer therapy is chemotherapy.

Embodiment 25. The method of any one of embodiments 1-22, wherein the cancer therapy is immunotherapy.

Embodiment 26. The method of any one of embodiments 1-22, wherein the cancer therapy comprises administration of an anti-cancer agent to the subject.

Embodiment 27. The method of embodiment 26, wherein the anti-cancer agent is a polyamine, or a precursor, or an analog thereof.

Embodiment 28. The method of embodiment 27, wherein the polyamine, the precursor, or the analog thereof is putrescine.

Embodiment 29. The method of embodiment 27, wherein the polyamine, the precursor, or the analog thereof is spermidine.

Embodiment 30. The method of embodiment 27, wherein the polyamine, the precursor, or the analog thereof is spermine.

Embodiment 31. The method of embodiment 27, wherein the administering of the therapeutically-effective amount of the dietary product and the administering a therapeutically-effective amount of the polyamine, the precursor, or the analog thereof results in a greater reduction of cancer cell proliferation in a biological sample from the subject as compared to a reduction of cancer cell proliferation in a comparable biological sample from a comparable subject who has been administered the dietary product but not the polyamine, the precursor, or the analog thereof.

Embodiment 32. The method of embodiment 31, wherein the biological sample is a tumor biopsy sample.

Embodiment 33. The method of embodiment 31, wherein the therapeutically-effective amount of the polyamine, the precursor, or the analog thereof is from about 100 mg to about 5000 mg.

Embodiment 34. The method of any one of embodiments 1-33, further comprising administering a methylthioadenosine phosphorylase (MTAP) inhibitor.

Embodiment 35. The method of any one of embodiments 1-34, further comprising administering from about 100 mg to about 2000 mg of methionine or a salt thereof.

Embodiment 36. The method of any one of embodiments 1-35, further comprising administering a low-cysteine or low-cystine diet to the subject, wherein the low-cysteine or the low-cystine diet provides at most about 500 mg/day of cysteine or cystine or salts thereof.

Embodiment 37. The method of any one of embodiments 1-36, further comprising administering a diet that provides at least about 500 mg/day of methionine or a salt thereof.

Embodiment 38. The method of any one of embodiments 1-37, further comprising administering a low-cysteine or a low-cystine diet, wherein the low-cysteine or the low-cystine diet provides at most about 500 mg/day of cysteine or cystine or salts thereof; and diet that provides at least about 500 mg/day of methionine or a salt thereof to the subject.

Embodiment 39. The method of any one of embodiments 1-38, wherein the therapeutically-effective amount of the dietary product is lower for a treatment of cancer as compared to a therapeutically-effective amount of a comparable dietary product that does not comprise at most about 0.5% (w/w) cysteine or cystine and at least about 7.5% (w/w) of at least one essential amino acid selected from the group consisting of: methionine, histidine, isoleucine, leucine, lysine, phenylalanine, threonine, tryptophan, and valine.

Embodiment 40. The method of embodiment 1, wherein the therapeutically-effective amount of the dietary product is lower for the method as compared to administering the dietary product and not the cancer therapy.

Embodiment 41. The method of embodiment 40, wherein the therapeutically-effective amount of the dietary product is lower for the method as compared to administering the dietary product and not a polyamine, a precursor, or an analog thereof.

Embodiment 42. The method of embodiment 40, wherein the therapeutically-effective amount of the dietary product is at least about 15% lower for the method as compared to administering the dietary product and not the cancer therapy.

Embodiment 43. The method of embodiment 40, wherein the therapeutically-effective amount of the dietary product is at least about 30% lower for the method as compared to administering the dietary product and not the cancer therapy.

Embodiment 44. A method of treating a cancer in a subject in need thereof, the method comprising administering to the subject a therapeutically-effective amount of a dietary product, wherein the dietary product comprises at most about 0.5% (w/w) of cysteine or cystine, wherein the cancer has downregulated 5-methylthioadenosine phosphorylase (MTAP) expression, and wherein the administering of the dietary product to the subject reduces cancer cell proliferation by at least about 20% as compared to a reduction in cancer cell proliferation in a comparable subject who has not been administered the dietary product.

Embodiment 45. The method of embodiment 44, wherein the cancer is breast cancer.

Embodiment 46. The method of embodiment 44, wherein the cancer is colorectal cancer.

Embodiment 47. The method of embodiment 44, wherein the cancer is pancreatic cancer.

Embodiment 48. The method of any one of embodiments 44-47, wherein the cancer has upregulated adenosylmethionine decarboxylase 1 (AMD1) expression.

Embodiment 49. The method of any one of embodiments 44-47, wherein the cancer exhibits dysregulated polyamine metabolism.

Embodiment 50. The method of any one of embodiments 44-49, wherein the administering is oral.

Embodiment 51. The method of any one of embodiments 44-50, wherein the therapeutically-effective amount of the dietary product is from about 0.5 g/kg/day to about 1 g/kg/day.

Embodiment 52. The method of any one of embodiments 44-51, wherein the therapeutically-effective amount of the dietary product is about 0.8 g/kg/day.

Embodiment 53. The method of any one of embodiments 44-52, wherein the dietary product is devoid of cysteine or cystine.

Embodiment 54. The method of any one of embodiments 44-53, wherein the dietary product further comprises at most about 0.5% (w/w) of glycine.

Embodiment 55. The method of any one of embodiments 44-54, wherein the dietary product is devoid of glycine.

Embodiment 56. The method of any one of embodiments 44-55, wherein the dietary product further comprises at most about 0.5% (w/w) of serine.

Embodiment 57. The method of any one of embodiments 44-56, wherein the dietary product is devoid of serine.

Embodiment 58. The method of any one of embodiments 44-57, wherein the dietary product comprises at most about 0.5% (w/w) of cysteine or cystine, at most about 0.5% (w/w) of serine, and at most about 0.5% (w/w) of glycine.

Embodiment 59. The method of any one of embodiments 44-58, wherein the dietary product is devoid of cysteine or cystine, serine, and glycine.

Embodiment 60. The method of any one of embodiments 44-59, wherein the dietary product is further devoid of tyrosine.

Embodiment 61. The method of any one of embodiments 44-60, wherein the dietary product is further devoid of arginine.

Embodiment 62. The method of any one of embodiments 44-61, wherein the dietary product is further devoid of tyrosine and arginine.

Embodiment 63. The method of any one of embodiments 44-62, wherein the dietary product further comprises more than about 7.5% (w/w) of methionine.

Embodiment 64. The method of any one of embodiments 44-63, wherein the dietary product further comprises from about 1% to about 10% (w/w) of a polyamine, a precursor, or an analog thereof.

Embodiment 65. The method of any one of embodiments 44-64, wherein the administering of the dietary product reduces cancer cell proliferation by at least about 30%.

Embodiment 66. The method of any one of embodiments 44-65, further comprising administering a cancer therapy.

Embodiment 67. The method of embodiment 66, wherein the cancer therapy is radiotherapy.

Embodiment 68. The method of embodiment 66, wherein the cancer therapy is chemotherapy.

Embodiment 69. The method of embodiment 66, wherein the cancer therapy is immunotherapy.

Embodiment 70. The method of embodiment 66, wherein the cancer therapy is an anti-cancer agent.

Embodiment 71. The method of embodiment 70, wherein the anti-cancer agent is a polyamine, or a precursor, or an analog thereof.

Embodiment 72. The method of embodiment 71, wherein the polyamine, the precursor, or the analog thereof is putrescine.

Embodiment 73. The method of embodiment 71, wherein the polyamine, the precursor, or the analog thereof is spermidine.

Embodiment 74. The method of embodiment 71, wherein the polyamine, the precursor, or the analog thereof is spermine.

Embodiment 75. The method of embodiment 71, wherein the administering of the therapeutically-effective amount of the dietary product and the administering a therapeutically-effective amount of the polyamine, the precursor, or the analog thereof results in a greater reduction of cancer cell proliferation in a biological sample from the subject as compared to a reduction of cancer cell proliferation in a comparable biological sample from a comparable subject who has been administered the dietary product but not the polyamine, the precursor, or the analog thereof.

Embodiment 76. The method of embodiment 75, wherein the biological sample is a tumor biopsy sample.

Embodiment 77. The method of embodiment 75, wherein the therapeutically-effective amount of the polyamine, the precursor, or the analog thereof is from about 100 mg to about 5000 mg.

Embodiment 78. The method of any one of embodiments 44-77, further comprising administering a methylthioadenosine phosphorylase (MTAP) inhibitor.

Embodiment 79. The method of any one of embodiments 44-78, further comprising administering from about 100 mg to about 2000 mg of methionine or a salt thereof.

Embodiment 80. The method of any one of embodiments 44-79, further comprising administering a low-cysteine or a low-cystine diet to the subject, wherein the low-cysteine or the low-cystine diet provides at most about 500 mg/day of cysteine or cystine or salts thereof.

Embodiment 81. The method of any one of embodiments 44-80, further comprising administering a diet that provides at least about 500 mg/day of methionine or a salt thereof.

Embodiment 82. The method of any one of embodiments 44-81, further comprising administering a low-cysteine or a low-cystine diet, wherein the low-cysteine diet provides at most about 500 mg/day of cysteine or cystine or salts thereof; and diet that provides at least about 500 mg/day of methionine or a salt thereof to the subject.

Embodiment 83. A method of treating a condition in a subject in need thereof, the method comprising: a) determining a level of a metabolite in a biological sample from the subject; and b) administering a therapeutically-effective amount of a dietary product to the subject based at least on the level of the metabolite, wherein the dietary product comprises at most about 0.5% (w/w) of at least one non-essential amino acid selected from the group consisting of: glycine, serine, alanine, proline, glutamine, glutamic acid, asparagine, aspartic acid, cysteine, tyrosine, and arginine.

Embodiment 84. The method of embodiment 83, wherein the condition is a cancer.

Embodiment 85. The method of embodiment 84, wherein the cancer is breast cancer.

Embodiment 86. The method of embodiment 84, wherein the cancer is colorectal cancer.

Embodiment 87. The method of embodiment 84, wherein the cancer is pancreatic cancer.

Embodiment 88. The method of any one of embodiments 84-87, wherein the cancer exhibits downregulated 5-methylthioadenosine phosphorylase (MTAP) expression.

Embodiment 89. The method of any one of embodiments 84-88, wherein the cancer has upregulated adenosylmethionine decarboxylase 1 (AMD1) expression.

Embodiment 90. The method of any one of embodiments 84-89, wherein the cancer exhibits dysregulated polyamine metabolism.

Embodiment 91. The method of any one of embodiments 83-90, wherein the metabolite is methylthioadenosine (MTA).

Embodiment 92. The method of any one of embodiments 83-90, wherein the metabolite is a polyamine, a precursor, or an analog thereof.

Embodiment 93. The method of any one of embodiments 83-92, wherein the biological sample is a tumor.

Embodiment 94. The method of embodiment 93, wherein the tumor is a solid tumor.

Embodiment 95. The method of embodiment 93, wherein the tumor is a liquid tumor.

Embodiment 96. The method of any one of embodiments 83-92, wherein the biological sample is blood.

Embodiment 97. The method of any one of embodiments 83-96, wherein the therapeutically-effective amount of the dietary product is from about 0.5 g/kg/day to about 1 g/kg/day.

Embodiment 98. The method of embodiment 97, wherein the therapeutically-effective amount of the dietary product is about 0.8 g/kg/day.

Embodiment 99. The method of any one of embodiments 83-98, wherein the biological sample is a MTAP-deficient tumor, wherein the level of the metabolite is at least about 2-fold higher than a level of a metabolite in a biological sample that is not an MTAP-deficient tumor.

Embodiment 100. The method of any one of embodiments 83-99, wherein the dietary product comprises at most about 0.5% (w/w) of cysteine or cystine.

Embodiment 101. The method of any one of embodiments 83-100, wherein the dietary product is devoid of cysteine or cystine.

Embodiment 102. The method of any one of embodiments 83-101, wherein the dietary product comprises at most about 0.5% (w/w) of glycine.

Embodiment 103. The method of any one of embodiments 83-102, wherein the dietary product is devoid of glycine.

Embodiment 104. The method of any one of embodiments 83-103, wherein the dietary product comprises at most about 0.5% (w/w) of serine.

Embodiment 105. The method of any one of embodiments 83-104, wherein the dietary product is devoid of serine.

Embodiment 106. The method of any one of embodiments 83-105, wherein the dietary product comprises at most about 0.5% (w/w) of cysteine or cystine, at most about 0.5% (w/w) of serine, and at most about 0.5% (w/w) of glycine.

Embodiment 107. The method of any one of embodiments 83-106, wherein the dietary product is devoid of cysteine or cystine, serine, and glycine.

Embodiment 108. The method of any one of embodiments 83-107, wherein the dietary product is further devoid of tyrosine.

Embodiment 109. The method of any one of embodiments 83-107, wherein the dietary product is further devoid of arginine.

Embodiment 110. The method of any one of embodiments 83-109, wherein the dietary product is further devoid of tyrosine and arginine.

Embodiment 111. The method of any one of embodiments 83-110, wherein the dietary product further comprises more than about 7.5% (w/w) of methionine.

Embodiment 112. The method of any one of embodiments 83-111, wherein the dietary product further comprises from about 1% to about 10% (w/w) of a polyamine, a precursor, or an analog thereof.

Embodiment 113. The method of any one of embodiments 83-112, further comprising administering a cancer therapy.

Embodiment 114. The method of embodiment 113, wherein the cancer therapy is radiotherapy.

Embodiment 115. The method of embodiment 113, wherein the cancer therapy is chemotherapy.

Embodiment 116. The method of embodiment 113, wherein the cancer therapy is immunotherapy.

Embodiment 117. The method of embodiment 113, wherein the cancer therapy is an anti-cancer agent.

Embodiment 118. The method of embodiment 117, wherein the anti-cancer agent is a polyamine, or a precursor, or an analog thereof.

Embodiment 119. The method of embodiment 118, wherein the polyamine, the precursor, or the analog thereof is putrescine.

Embodiment 120. The method of embodiment 118, wherein the polyamine, the precursor, or the analog thereof is spermidine.

Embodiment 121. The method of embodiment 118, wherein the polyamine, the precursor, or the analog thereof is spermine.

Embodiment 122. The method of embodiment 118, wherein the administering of the therapeutically-effective amount of the dietary product and the administering a therapeutically-effective amount of the polyamine, the precursor, or the analog thereof results in a greater reduction of cancer cell proliferation in a biological sample from the subject as compared to a reduction of cancer cell proliferation in a comparable biological sample from a comparable subject who has been administered the dietary product but not the polyamine, the precursor, or the analog thereof.

Embodiment 123. The method of embodiment 122, wherein the biological sample is a tumor biopsy sample.

Embodiment 124. The method of embodiment 122, wherein the therapeutically-effective amount of the polyamine, the precursor, or the analog thereof is from about 100 mg to about 5000 mg.

Embodiment 125. The method of any one of embodiments 83-124, further comprising administering a methylthioadenosine phosphorylase (MTAP) inhibitor.

Embodiment 126. The method of any one of embodiments 83-125, further comprising administering from about 100 mg to about 2000 mg of methionine or a salt thereof.

Embodiment 127. The method of any one of embodiments 83-126, further comprising administering a low-cysteine or a low-cystine diet to the subject, wherein the low-cysteine or the low-cystine diet provides at most about 500 mg/day of cysteine or cystine or salts thereof.

Embodiment 128. The method of any one of embodiments 83-127, further comprising administering a diet that provides at least about 500 mg/day of methionine or a salt thereof.

Embodiment 129. The method of any one of embodiments 83-128, further comprising administering a low-cysteine or a low-cystine diet, wherein the low-cysteine or the low-cystine diet provides at most about 500 mg/day of cysteine or cystine or salts thereof; and diet that provides at least about 500 mg/day of methionine or a salt thereof to the subject.

Embodiment 130. A method of treating a cancer in a subject in need thereof, the method comprising administering a therapeutically-effective amount of a dietary product to the subject, wherein the dietary product comprises at most about 0.5% (w/w) cysteine or cystine, wherein the therapeutically-effective amount of the dietary product is lower for a treatment of the cancer as compared to at least one of: a) a therapeutically-effective amount of a dietary product devoid of glucose; b) a therapeutically-effective amount of a dietary product devoid of serine and glycine; and c) a therapeutically-effective amount of a dietary product devoid of lysine.

Embodiment 131. The method of embodiment 130, wherein the cancer is breast cancer.

Embodiment 132. The method of embodiment 130, wherein the cancer is colorectal cancer.

Embodiment 133. The method of embodiment 130, wherein the cancer is pancreatic cancer.

Embodiment 134. The method of any one of embodiments 130-133, wherein the cancer exhibits downregulated 5-methylthioadenosine phosphorylase (MTAP) expression.

Embodiment 135. The method of any one of embodiments 130-134, wherein the cancer has upregulated adenosylmethionine decarboxylase 1 (AMD1) expression.

Embodiment 136. The method of any one of embodiments 130-135, wherein the cancer exhibits dysregulated polyamine metabolism.

Embodiment 137. The method of any one of embodiments 130-136, wherein the administering is oral.

Embodiment 138. The method of any one of embodiments 130-137, wherein the therapeutically-effective amount of the dietary product is from about 0.5 g/kg/day to about 1 g/kg/day.

Embodiment 139. The method of any one of embodiments 130-138, wherein the therapeutically-effective amount of the dietary product is about 0.8 g/kg/day.

Embodiment 140. The method of any one of embodiments 130-139, wherein the dietary product is devoid of cysteine or cystine.

Embodiment 141. The method of any one of embodiments 130-140, wherein the dietary product comprises at most about 0.5% (w/w) of glycine.

Embodiment 142. The method of any one of embodiments 130-141, wherein the dietary product is devoid of glycine.

Embodiment 143. The method of any one of embodiments 130-142, wherein the dietary product comprises at most about 0.5% (w/w) of serine.

Embodiment 144. The method of any one of embodiments 130-143, wherein the dietary product is devoid of serine.

Embodiment 145. The method of any one of embodiments 130-144, wherein the dietary product comprises at most about 0.5% (w/w) of cysteine or cystine, at most about 0.5% (w/w) of serine, and at most about 0.5% (w/w) of glycine.

Embodiment 146. The method of any one of embodiments 130-145, wherein the dietary product is devoid of cysteine or cystine, serine, and glycine.

Embodiment 147. The method of any one of embodiments 130-146, wherein the dietary product is further devoid of tyrosine.

Embodiment 148. The method of any one of embodiments 130-147, wherein the dietary product is further devoid of arginine.

Embodiment 149. The method of any one of embodiments 130-148, wherein the dietary product is further devoid of tyrosine and arginine.

Embodiment 150. The method of any one of embodiments 130-149, wherein the dietary product further comprises more than about 7.5% (w/w) of methionine.

Embodiment 151. The method of any one of embodiments 130-150, wherein the dietary product further comprises from about 1% to about 10% (w/w) of a polyamine, a precursor, or an analog thereof.

Embodiment 152. The method of any one of embodiments 130-151, further comprising administering a cancer therapy.

Embodiment 153. The method of embodiment 151, wherein the cancer therapy is radiotherapy.

Embodiment 154. The method of embodiment 151, wherein the cancer therapy is chemotherapy.

Embodiment 155. The method of embodiment 151, wherein the cancer therapy is immunotherapy.

Embodiment 156. The method of embodiment 151, wherein the cancer therapy comprises administration of an anti-cancer agent.

Embodiment 157. The method of embodiment 155, wherein the anti-cancer agent is a polyamine, or a precursor, or an analog thereof.

Embodiment 158. The method of embodiment 156, wherein the polyamine, the precursor, or the analog thereof is putrescine.

Embodiment 159. The method of embodiment 156, wherein the polyamine, the precursor, or the analog thereof is spermidine.

Embodiment 160. The method of embodiment 156, wherein the polyamine, the precursor, or the analog thereof is spermine.

Embodiment 161. The method of embodiment 130, wherein administering of the therapeutically-effective amount of the dietary product and administering a therapeutically-effective amount of the polyamine, the precursor, or the analog thereof results in a greater reduction of cancer cell proliferation in a biological sample from the subject as compared to a reduction of cancer cell proliferation in a comparable biological sample from a comparable subject who has been administered the dietary product but not the polyamine, the precursor, or the analog thereof.

Embodiment 162. The method of embodiment 157, wherein the biological sample is a tumor biopsy sample.

Embodiment 163. The method of embodiment 157, wherein the therapeutically-effective amount of the polyamine, the precursor, or the analog thereof is from about 100 mg to about 5000 mg.

Embodiment 164. The method of any one of embodiments 130-163, further comprising administering a methylthioadenosine phosphorylase (MTAP) inhibitor.

Embodiment 165. The method of any one of embodiments 130-164, further comprising administering from about 100 mg to about 2000 mg of methionine or a salt thereof.

Embodiment 166. The method of any one of embodiments 130-165, further comprising administering a low-cysteine or a low-cystine diet to the subject, wherein the low-cysteine or the low-cystine diet provides at most about 500 mg/day of cysteine or cystine or salts thereof.

Embodiment 167. The method of any one of embodiments 130-166, further comprising administering a diet that provides at least about 500 mg/day of methionine or a salt thereof.

Embodiment 168. The method of any one of embodiments 130-167, further comprising administering a low-cysteine or a low-cystine diet, wherein the low-cysteine diet provides at most about 500 mg/day of cysteine or cystine or salts thereof, and diet that provides at least about 500 mg/day of methionine or a salt thereof to the subject.

What is claimed is:

1. A method for treating a cancer having dysregulated polyamine metabolism in a subject in need thereof, wherein the cancer having dysregulated polyamine metabolism is breast cancer, colorectal cancer, pancreatic cancer, or brain cancer, the method comprising administering to the subject a therapeutically effective amount of a dietary product, wherein:
    the dietary product comprises at most about 0.5% (w/w) of cysteine or cystine; the dietary product comprises at least about 7.5% (w/w) of methionine;
    the therapeutically effective amount of the dietary product is from about 0.5 g/kg/day to about 1 g/kg/day; and
    the subject is undergoing a cancer therapy for the cancer having dysregulated polyamine metabolism.

2. The method of claim 1, wherein the cancer having dysregulated polyamine metabolism is breast cancer.

3. The method of claim 1, wherein the cancer having dysregulated polyamine metabolism is colorectal cancer.

4. The method of claim 1, wherein the cancer having dysregulated polyamine metabolism is pancreatic cancer.

5. The method of claim 1, wherein the cancer having dysregulated polyamine metabolism has downregulated 5-methylthioadenosine phosphorylase (MTAP) expression.

6. The method of claim 1, wherein the cancer having dysregulated polyamine metabolism has upregulated adenosylmethionine decarboxylase 1 (AMD1) expression.

7. The method of claim 1, wherein the administering is oral.

---

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaatagcag taaactcaac                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gttttgcccc aaaacgagag                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcctggtagt tgacctttga                                                   20

8. The method of claim 1, wherein the dietary product is devoid of cysteine or cystine.

9. The method of claim 8, wherein the dietary product is devoid of cysteine or cystine, serine, and glycine.

10. The method of claim 9, wherein the dietary product is further devoid of tyrosine and arginine.

11. The method of claim 1, wherein the dietary product comprises more than about 10% (w/w) of methionine.

12. The method of claim 1, wherein the cancer therapy is radiotherapy.

13. The method of claim 1, wherein the cancer therapy is chemotherapy.

14. The method of claim 1, wherein the cancer therapy further comprises administration of a therapeutically effective amount of a polyamine, a precursor of the polyamine, or an analog of the polyamine to the subject.

15. The method of claim 14, wherein the therapeutically effective amount of the polyamine, the precursor of the polyamine, or the analog of the polyamine is from about 100 mg to about 5000 mg.

16. The method of claim 1, comprising administering from about 100 mg to about 2000 mg of the methionine.

17. The method of claim 1, comprising administering at most about 500 mg/day of the cysteine or cystine.

18. The method of claim 1, wherein administering the dietary product to the subject increases efficacy of the cancer therapy in the subject by at least about 10% as compared to an efficacy of the cancer therapy in a comparable subject receiving the cancer therapy but not the dietary product.

19. The method of claim 1, wherein administering the dietary product elevates cellular reactive oxygen species (ROS) levels.

* * * * *